(12) United States Patent
Zhao et al.

(10) Patent No.: US 11,414,497 B2
(45) Date of Patent: Aug. 16, 2022

(54) ANTI-PSMA ANTIBODIES AND USE THEREOF

(71) Applicant: ORIMABS LTD., Wallingford, PA (US)

(72) Inventors: Aizhi Zhao, Wallingford, PA (US); Weihong Wen, Xi'an (CN); Yueheng Han, Wallingford, PA (US)

(73) Assignee: OriMabs Ltd., Wallingford, PA (US)

( * ) Notice: Subject to any disclaimer, the term of this patent is extended or adjusted under 35 U.S.C. 154(b) by 908 days.

(21) Appl. No.: 16/093,246

(22) PCT Filed: Apr. 12, 2017

(86) PCT No.: PCT/US2017/027154
§ 371 (c)(1),
(2) Date: Oct. 12, 2018

(87) PCT Pub. No.: WO2017/180713
PCT Pub. Date: Oct. 19, 2017

(65) Prior Publication Data
US 2021/0277141 A1    Sep. 9, 2021

Related U.S. Application Data

(60) Provisional application No. 62/321,975, filed on Apr. 13, 2016.

(51) Int. Cl.
| | | |
|---|---|---|
| A61K 49/00 | (2006.01) |
| G01N 33/53 | (2006.01) |
| C07K 16/00 | (2006.01) |
| C07K 16/46 | (2006.01) |
| C07H 21/04 | (2006.01) |
| C12N 5/20 | (2006.01) |
| C12N 1/20 | (2006.01) |
| C12N 15/00 | (2006.01) |
| C07K 16/30 | (2006.01) |
| A61K 47/68 | (2017.01) |
| A61P 35/00 | (2006.01) |
| G01N 33/574 | (2006.01) |
| A61K 38/00 | (2006.01) |
| A61K 39/00 | (2006.01) |

(52) U.S. Cl.
CPC ...... *C07K 16/3069* (2013.01); *A61K 47/6869* (2017.08); *A61K 49/0058* (2013.01); *A61P 35/00* (2018.01); *G01N 33/57434* (2013.01); *A61K 38/00* (2013.01); *A61K 2039/505* (2013.01); *C07K 2317/21* (2013.01); *C07K 2317/24* (2013.01); *C07K 2317/31* (2013.01); *C07K 2317/565* (2013.01); *C07K 2317/567* (2013.01); *C07K 2317/622* (2013.01); *C07K 2317/73* (2013.01); *C07K 2317/77* (2013.01); *C07K 2317/92* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 10,179,819 B2 | 1/2019 | Kirshner et al. | |
| 2003/0027253 A1* | 2/2003 | Presnell | A61P 25/00 435/69.1 |
| 2003/0124129 A1* | 7/2003 | Oliner | A61P 19/02 424/155.1 |
| 2003/0148463 A1* | 8/2003 | Kufer | C07K 16/00 435/69.1 |
| 2004/0033229 A1 | 2/2004 | Maddon et al. | |
| 2005/0186214 A1 | 8/2005 | Liu et al. | |
| 2010/0196265 A1 | 8/2010 | Adams et al. | |
| 2011/0236390 A1* | 9/2011 | Almagro | A61P 17/00 424/139.1 |
| 2012/0213771 A1* | 8/2012 | Keler | A61P 35/00 424/133.1 |
| 2013/0089516 A1 | 4/2013 | Frelinger et al. | |
| 2014/0030269 A1 | 1/2014 | Coljee | |
| 2015/0322137 A1 | 11/2015 | Takada et al. | |

FOREIGN PATENT DOCUMENTS

| | | | |
|---|---|---|---|
| JP | 2008529556 A | 8/2008 | |
| JP | 2008530243 A | 8/2008 | |
| KR | 100733933 B1 | 7/2007 | |
| WO | 2001009192 A1 | 2/2001 | |
| WO | 2006/089230 A2 | 8/2006 | |
| WO | 2006/089231 A2 | 8/2006 | |
| WO | 2011121110 A1 | 4/2011 | |
| WO | WO-2015155412 A1 * | 10/2015 | ....... G01N 33/56961 |

OTHER PUBLICATIONS

Brown et al. Tolerance of single, but not multiple, amino acid replacements in antibody VH CDR2: a means of minimizing B cell wastage from somatic hypermutation? J. Immuno. May 1996, 3285-91. (Year: 1996).*

Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*

Schulke, N. et al., "The Homodimer of Prostate-Specific Membrane Antigen is a Functional Target for Cancer Therapy"; PNAS (2003); vol. 100:22; pp. 12590-12595.

(Continued)

*Primary Examiner* — Maher M Haddad
(74) *Attorney, Agent, or Firm* — Fox Rothschild LLP

(57) ABSTRACT

The present invention relates to compositions and methods related to antibody or antibody fragments that specifically bind PSMA.

19 Claims, 39 Drawing Sheets
Specification includes a Sequence Listing.

(56) References Cited

OTHER PUBLICATIONS

Crawford, A. et al., "Fully Human Bispecific Antibodies Induce Potent Anti-Tumor Effects Against Prostate Tumors in Mice"; Molecular Cancer Therapeutics (2015); vol. 14:12, SUPPL. 2. Abstract No. A193) 5 pgs.
Kiess et al., "Prostate-specific membrane antigen as a target for cancer imaging and therapy," Q J Nucl Med Mol Imaging (Sep. 2015); 59(3):241-268.
Han et al., "A novel anti-PSMA human scFv has the potential to be used as a diagnostic tool in prostate cancer," Oncotarget (Jul. 2016); 7(37):59471-59481.
Likar et al., "A New Human-Derived Reporter Gene Suitable for Clinical PET Imaging of T-Cell Trafficking," Molecular Therapy (May 1, 2004); (Abstract 185-S71).
Brown et al., "Tolerance to Single, but not multiple, amino acid replacements in antibody V-H CDR2: A means of minimizing B cell wastage from somatic hypermutation," The Journal of Immunology (Jan. 1, 1996); 156(9):3285-3291.
Barderas et al., "Affinity maturation of antibodies assisted by in silico modeling," PNAS (Jul. 1, 2008); 105(26):9029-9034.
Winkler et al.,"Changing the Antigen Binding Specificity by Single Point Mutations of an Anti-p24 (HIV-1) Antibody," The Journal of Immunology (Oct. 15, 2000); 165(8):4505-4514.
Maynard et al., "Protection against anthrax toxin by recombinant antibody fragments correlates with antigen affinity," Nature (Jun. 2002); 20:597-601.

\* cited by examiner

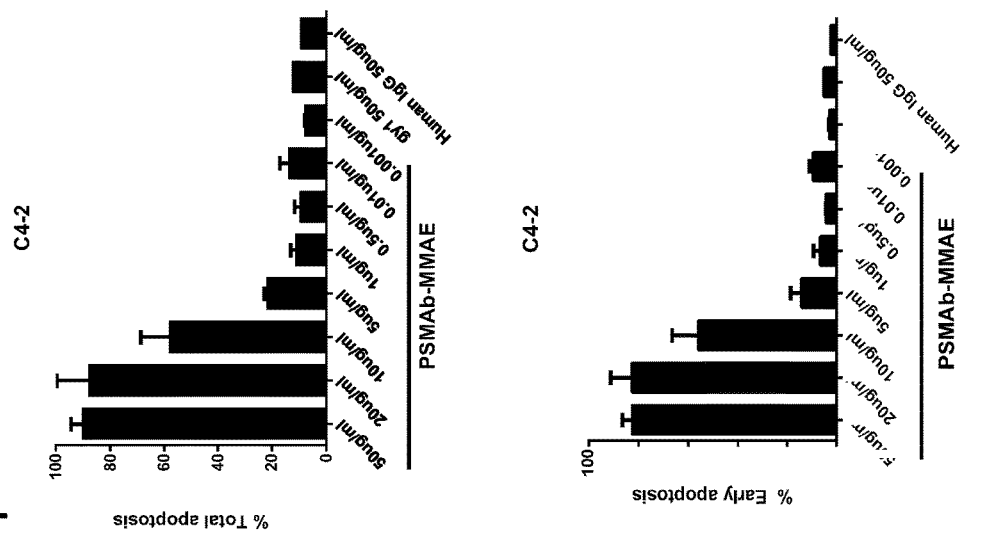
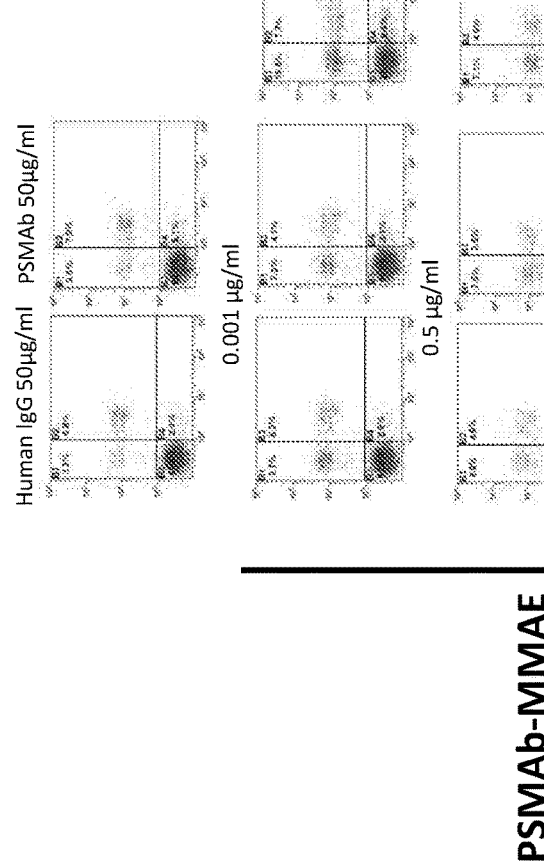
Figure 24G – Figure 24I

ANTI-PSMA ANTIBODIES AND USE
THEREOF

CROSS REFERENCE TO RELATED
APPLICATION

This application is a U.S. National Phase of International Application No.: PCT/US2017/027154, filed Apr. 13, 2017, which claims the benefit of priority to U.S. Provisional Application No. 62/321,975 filed on Apr. 13, 2016. The contents of the applications are incorporated herein by reference in their entirety.

BACKGROUND OF THE INVENTION

It has been shown that 14% males have been diagnosed with prostate cancer at in their life span; and as many as 2.8 million prostate cancers have been diagnosed in 2012 with a mortality rate of 21.4 per 100 thousand people. However, the current approaches, such as surgery, radiotherapy, chemotherapy, and androgen deprivation therapy, have limited effect for those late stage cancers. Thus far, radical surgery is still the major treatment of prostate cancer. Therefore, the emerging precision medicine, especially the ones based on tumor targeting antibodies, is expected to improve the outcome of prostate treatment.

Prostate specific membrane antigen (PSMA) has been confirmed as a specific marker for prostate epithelial cells (Horoszewicz, J. S. et al. (1987) Anticancer Res, 7(5B): 927-35; Israeli, R. S., et al. (1993) Cancer Res, 53(2): 227-30; Israeli, R. S., et al. (1994) Cancer Res, 54(7): 1807-11; Wright, G. L., Jr., et al. (1995) Urol Oncol, 1(1): 18-28; Troyer, J. K. et al. (1995) Int J Cancer, 62(5): 552-8; Sokoloff, R. L., et al. (2000) Prostate, 43(2): 150-7), which laid the foundation for development of prostate cancer targeted precision medicine. Histological study indicated that almost all prostate cancers express PSMA (Bostwick, D. G., et al. (1998) Cancer, 82(11): 2256-61; Kusumi, T., et al. (2008) Pathol Int, 58(11): 687-94; Mannweiler, S., et al. (2009) Pathol Oncol Res, 15(2): 167-72; Ananias, H. J., et al. (2009) Prostate, 69(10): 1101-8) and cancers with higher malignancy, or metastasis, or resistant to androgen deprivation therapy, usually express much higher PSMA (Ananias, H. J., et al. (2009) Prostate, 69(10): 1101-8; Wright, G. L., Jr., et al. (1995) Urol Oncol, 1(1): 18-28; Wright, G. L., Jr., et al. (1996) Urology, 48(2): 326-34; Sweat, S. D., et al. (1998) Urology, 52(4): 637-40). Although PSMA was thought to be a prostate-specific marker, later studies have indicated that intestine cells, renal proximal tubule and salivary gland also express low level PSMA (Troyer, J. K. et al. (1995) Int J Cancer, 62(5): 552-8). It is of note that the PSMA expression levels in normal tissues are 100-1000 times lower than in tumor (Sokoloff, R. L., et al. (2000) Prostate, 43(2): 150-7) and these normal tissues are usually not easily accessible to circulating antibodies (Troyer, J. K. et al. (1995) Int J Cancer, 62(5): 552-8), which further assured the safety of PSMA targeted imaging and therapy.

PSMA is a glutamate carboxypeptidase (Pinto, J. T., et al. (1996) Clin Cancer Res, 2(9): 1445-51) and its function in prostate cancer is unclear. However, it is revealed that high PSMA expression is related to high infiltration of cancer. Therefore, PSMA targeted imaging and therapies will considerably improve the diagnosis and treatment outcome of prostate cancers. In addition to prostate, PSMA is also highly expressed in neovasculature in many solid tumors while is absent in normal vessels (Sokoloff, R. L., et al. (2000) Prostate, 43(2): 150-7). Therefore, PSMA is an ideal marker not only for prostate cancer, but also for neovasculature targeted therapy for other solid tumors.

Antibodies are the most efficient tool for tumor targeting in that they can specifically recognize tumor-related or tumor-specific antigens expressed on tumor cells, which opens avenues for antibody based precision medicine, including tumor targeted imaging and therapy, such as optical, PET, SPECT, or MRI imaging for early tumor detection, antibody drug conjugate, and radiotherapy, chimeric antigen receptor T cell or NK cell therapies for cancer treatment. Unfortunately, there are no PSMA antibodies currently on the market.

Thus, there is a need in the art for compositions and methods targeting PSMA for the treatment of cancer. The present invention satisfies this unmet need.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4, comprising FIG. 4A: SDS-PAGE shows soluble gy1 expression in induced *E. coli*. Lane 1: Marker; Lane 2: uninduced whole cell lysis; Lane 3-5: induced cell lysis, whole cell (3), supernatant (4) and precipitation (5). FIG. 4B: SDS-PAGE shows purified gy1 protein. Lane 1: Marker; Lane 2: uninduced supernatant of cell lysis; Lane 3: induced supernatant of cell lysis; and Lane 4: purified gy1 scFv. FIG. 4C: Western blot analysis confirms the purified gy1 recombinant protein by anti-His6 Ab. Lane 1: uninduced supernatant of cell lysis; Lane 2: induced supernatant of cell lysis; and Lane 3: purified gy1 scFv.

FIG. 8, comprising FIG. 8A: C4-2 cells were incubated with gy1 scFv for 4 h and then detected with anti-6His IgG and FITC-conjugated secondary antibody. Different cellular organelle markers (RFP-labeled, red) for endosome, lysosome, ER and Golgi apparatus and DAPI (blue) were used to co-stain the organelles and nucleus. FIG. 8B: Co-localization of gy1 and markers for Golgi apparatus and ER were further studied for different period of incubation times of 1 hour, 2 hours, 4 hours and 6 hours.

FIG. 13, comprising FIG. 13A: Twelve hours post injection, mice were sacrificed and tissue and organs were harvested. Biodistribution of IRDye800cw-labeled gy1 in different mouse organs were analyzed using Xenogen IVIS Kinetic imaging system. 1, brain; 2, lung; 3, heart; 4, liver; 5, spleen; 6, kidney; 7, small intestine; 8, bone; 9, PC3-PSMA$^+$ or PC3-PSMA" tumor tissue; 10, muscle. FIG. 13B: Fluorescence quantification of different organs were studied using the IRDye800cw signal intensity in tumor and different organs measured by IVIS software. Bar, mean values; Error bar, SD; n=5; **$P<0.01$.

FIG. 14, comprising FIG. 14A: SDS-GAGE of purified PSMAb. Lane 1: CHO cell supernatant before antibody purification; Lane 2: denatured purified PSMAb; and Lane 3: non-denatured purified PSMAb. FIG. 14B: Affinity measurement of PSMAb. PSMAb affinity was measured on PSMA positive cell line C4-2. Briefly, C4-2 cultured in 96-well plate were fixed with 4% paraformaldehyde, blocked with 3% $H_2O_2$ and 6% bovine serum albumin sequentially. Cells were then incubated with three-fold serially diluted PSMAb, from 100 nM down to 0.19 pM, for 1h at 37° C. Cell binding was detected with HRP-conjugated mouse anti-human IgG Fc Ab and Colorimetric signals were developed by TMB and stopped by STOP buffer. The absorbance at 450 nm was used to calculate affinity using GraphPad Prism 5.0 software.

FIG. 17, comprising

FIG. 18, comprising

FIG. 22, comprising

FIG. 23, comprising

FIG. 25, comprising

DETAILED DESCRIPTION

Figure 1:
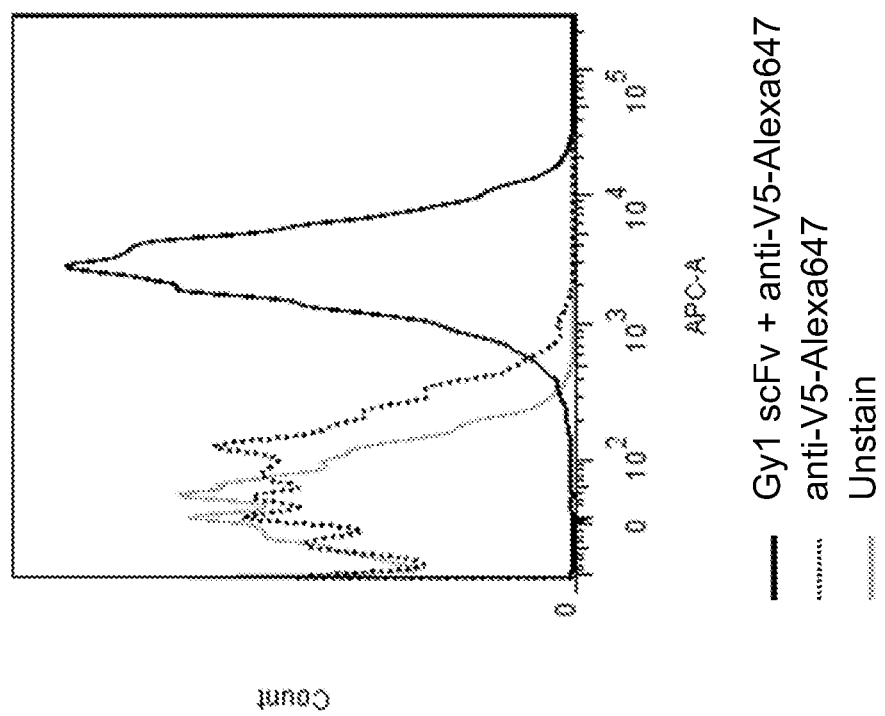
FIG. 1 is a graph demonstrating that gy1 scFv specifically binds PSMA+ cells. ScFv gy1 binding on PSMA was studied on LNCap FGC cells using flow cytometry. Briefly, LNCap FGC cells were detached with versene solution, washed with PBS and incubated on ice for 1 hour with gy1-containing yeast supernatant that was diluted 3-fold with FACS buffer. Cells were washed three time with cold PBS and then incubated with 1:200 diluted anti-V5-Alexa647 in FACS buffer on ice for 1 hour in darkness. Non-bound anti-V5-Alexa647 was removed by three time washes with cold PBS and then cells were resuspended in 300 µl FACS containing 8 µl via-probe (BD biosciences). Gy1 binding on LNCap FGC cells were detected using flow cytometry where only living cells were gated and analyzed. Flow cytometry controls include: (1) unstained cells; and (2) cells stained with anti-V5-Alexa647. Solid gray line represents unstained cells; dotted black line represents anti-V5-Alexa647 stained cells; while solid black line represents cells stained with gy1 scFv and then anti-V5-Alexa647.

The present invention is related to compositions and methods for treating cancer. The present invention is based in part upon the discovery of antibody fragments that specifically bind to extracellular domain of PSMA. The present invention thus provides compositions comprising an antibody or antibody fragment that binds to PSMA. Exemplary compositions of the invention include an antibody, antibody fragment, bispecific antibody, an antibody-drug conjugate, a PSMA-targeting imaging agent, chimeric antigen receptor, a cell expressing a chimeric antigen receptor, and the like.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for treating and preventing cancer. In certain embodiments, the composition comprises an antibody or antibody fragment that specifically binds to the extracellular domain of PSMA. The present invention is based upon the discovery of antibody fragments that bind to PSMA. The fragments were identified in yeast-display system expressing an antibody library. As described herein, the antibody fragments provided in the present invention are used to formulate therapeutic and diagnostic compositions that target PSMA found in prostate cancer and in the neovasculature of other solid tumors. In one embodiment, the composition is an antibody-drug conjugate (ADC), wherein the antibody or antibody fragment targets the drug to the tumor location. In one embodiment, the composition is a bispecific antibody, wherein the bispecific antibody comprise the antibody or antibody fragment that specifically binds to PSMA and a second antibody or antibody fragment that binds to a T-cell antigen, (e.g. CD3). In one embodiment, the composition is a chimeric antigen receptor that comprises the antibody or antibody fragment that specifically binds to PSMA. In one embodiment, the invention comprises an isolated nucleic acid encoding an antibody or antibody fragment, bispecific antibody, or chimeric antigen receptor. In one embodiment, the invention comprises a cell that is modified to express an antibody or antibody fragment, bispecific antibody, or chimeric antigen receptor. The present invention provides a method for treating or preventing cancer, including but not limited to prostate cancer. In certain embodiments, the method comprises administering to a subject an effective amount of a composition comprising an antibody or antibody fragment that specifically binds to PSMA. For example, in one embodiment, the method comprises administering to the subject an antibody or antibody fragment, bispecific antibody, or chimeric antigen receptor. In one embodiment, the method comprises administering to a subject an effective amount of a composition comprising an isolated nucleic acid encoding an antibody or antibody fragment, bispecific antibody, or chimeric antigen receptor. In one embodiment, the method comprises administering to a subject a cell modified to express an antibody or antibody fragment, bispecific antibody, or chimeric antigen receptor.

The present invention provides a method for detecting cancer in a subject, comprising administering to the subject a targeted imaging agent comprising an antibody or antibody fragment that specifically binds to PSMA. The antibody or antibody fragment can be conjugated to any imaging agent to provide for a targeted imaging agent used in various imaging modalities, including but not limited to PET, SPECT, MRI, or optical imaging.

Compositions

As described herein, the present invention provides a composition comprising an antibody or antibody fragment that specifically binds to PSMA. The present invention is based upon the construction of a large yeast display human scFv library and isolation of a high affinity anti-PSMA scFv. The affinity of the isolated scFv to PSMA was measured to be $9 \times 10^{-10}$ nM. Further, several mutations of the scFv were generated which increased its functionality. The conversion of an scFv to a full-length antibody increased its affinity to $1 \times 10^{-10}$ nM.

Hybridoma technology is well developed traditional way for monoclonal antibody preparation. However, the murine origin of the antibody greatly impedes its application in human beings. Although humanization could partially reduce the immunogenicity of murine antibodies and humanized antibodies are widely used currently in clinic, the immunogenicity related side effects still raise in around 50% patients because humanization could never reach 100% because certain level of murine amino acids need to be remained to keep the antigen binding activity for the antibodies. J591, with an affinity around 3 nM, is a humanized PSMA antibody that has been widely used in research and some clinical trials (McDevitt, M. R., et al. (2000) Cancer Res, 60(21): 6095-100). Therefore, fully human antibodies are the most desirable ones for clinical applications.

Transgenic mice humab-mouse and xenomouse have been developed by Medarex/GenPharm International and Abgenix for development of fully human antibodies via traditionally hybridoma method. PSMA Development Company, LLC (Progenics Pharmaceuticals, Inc.) has used xenomouse to develop four fully human anti-PSMA antibodies with affinities of $1 \times 10^{"9}$ nM, $7.9 \times 10^{-10}$ nM, $5.1 \times 10^{-10}$ nM, and $2.1 \times 10^{-10}$ nM respectively (U.S. Pat. No. 8,470,330).

Compared to the transgenic mice, an antibody library is a more convenient and equally efficient for fully human antibody preparation. The rationale is to isolate peripheral blood mononuclear cells (PBMC) from healthy or particular donors, extract mRNA and amplify variable regions of antibody, assemble into single chain antibody (scFv) or Fab format and display on phage or yeast surface via molecular biological strategies. The advantage of the antibody library is that as long as the library size is large enough, high affinity antibodies could be readily isolated. If the library is constructed from human B cells, the derived antibody will be 100% human origin and will not have immunogenicity issues for clinical applications.

Due to the complicated conformation and structure that has 4 inter chain disulfide bonds, a full-length antibody is difficult to be expressed by E. coli or yeast. Therefore, the most often displayed antibody format are scFv and Fab. scFv contains only the variable regions of heavy and light chain, while Fab also contain the light chain constant region and the first constant region of heavy chain. In certain instances, compared to the small antibody fragments, such as Fv, scFv, Fab or scFv-Fc, a full-length antibody has the most stable structure, longest circulation time, highest affinity, best tolerance to labeling or modification, and could mediate antibody-dependent cellular cytotoxicity (ADCC) and antibody-dependent cellular cytotoxicity (ADCC). Full-length antibodies are therefore is the most popular format in clinic.

The strategy for using an antibody library is to first discover the antibody fragment, such as scFv or Fab, then convert them into full-length antibody. Although many scFv or Fab could be successfully converted to a full-length antibody without compromising function, some fragment antibodies will lose their affinity once converted to full-length antibody (Schirrmann, T., et al. Molecules, (2011) 16(1): 412-26; Baker, K. P., et al. (2003) Arthritis Rheum, 48(11): 3253-65; Thie, H., et al. (2011) PLoS One, 6(1): e15921), which might be due to the conformation change of binding site as a result of the addition of constant regions. In terms of the scFv, the inter chain linker may contribute to the antigen binding confirmation in some scFvs, which will be removed when being converted into full-length antibody and therefore impairs the antigen binding affinity. A high affinity scFv or Fab therefore may not ensure a high affinity full antibody derivative. Each conversion should be deemed as a unique case and need to be confirmed by experiments.

In one embodiment, the present invention provides a composition comprising an antibody drug conjugate (ADC). ADCs are a platform strategy to arm antibodies for antigen specific toxicity delivery. The rationale is to conjugate antibodies, usually tumor targeting antibodies, with super toxic drugs to selectively kill tumor cells in a targeted manner while normal tissue be spared. Drugs used in ADC mainly fall into two types, one is microtubulin inhibitor, such as auristatin (MMAE, MMAF) (Stephan, J. P., et al. (2008) Bioconjug Chem, 19(8): 1673-83; Younes, A., et al. (2010) N Engl J Med, 363(19): 1812-21; Okeley, N. M., et al. (2010) Clin Cancer Res, 16(3): 888-970) and maytansinoid (DM1 and DM4) (Lambert, J. M. et al. (2014). J Med Chem, 57(16): 6949-64; Bender, B., et al. (2014) AAPS J, 16(5): 994-1008; Raufi, A., A. S. Ebrahim et al. (2013) Cancer Manag Res, 5: 225-33); the other type is double strand DNA cleavage agent, such as calicheamicin. Due to the supertoxicity, certain drugs could not be used alone as chemotherapy agents, but rather they have to be conjugated to antibodies to reduce the side effects and improve the therapeutic efficacy.

In one embodiment, the present invention provides a composition comprising a bispecific antibody. Bispecific monoclonal antibody (BsMAb, BsAb) is another strategy to make powerful anti-tumor weapons using novel antibodies. BsAb is an artificial protein that is composed of fragments of two different monoclonal antibodies and consequently binds to two different types of antigen. The most widely used application of this approach is in cancer immunotherapy, where BsMAbs are engineered that simultaneously bind to a cytotoxic cell (using a receptor like CD3) and a target like a tumor cell to be destroyed (Muller D et al. (2010) BioDrugs, 24(2):89-98; Chames P1 et al. (2009) MAbs, 1(6):539-47). Bi-specific T-cell engagers (BiTEs) and Dual-Affinity Re-Targeting (DART) are examples of small fragment BsAb, various bigger BsAbs were also developed, such as knob-in-hole IgG, CrossMab, TrioMab, DVD Ig (Kontermann R E et al. (2015) Drug Discov Today, 20(7): 838-47). In BsAbs, one arm could be T or NK cell activation antibody, such as anti-CD3, or anti-CD16 antibody, the other arm could be tumor targeting antibody; or both arm target different tumor markers for synergetic inhibition of tumor growth.

In one embodiment, the present invention provides a composition comprising a chimeric antigen receptor (CAR). For example, in certain embodiments, the composition is a cell genetically modified to express a CAR. For example, in certain embodiments, the invention provides, T or NK cells which are genetically engineered to produce CARs on their surface that allow the T or NK cells to recognize a specific protein (antigen) on tumor cells. scFv is the most often used receptors for such engineering and have been successfully used in clinic for cancer treatment (Grupp S A et al. (2013) N Engl J Med, 368(16):1509-18; Porter D L et al. (2011) N Engl J Med, 365(8):725-33). The scFv is fused via a hinge and a transmembrane domain to a signaling intracellular domain. Such molecules result in activation of the T- or NK-cell in response to recognition by the scFv of its target. When T or NK cells express such a CAR, they recognize and kill target cells that express the target antigen. Several CARs have been developed against tumor associated antigens, and adoptive transfer approaches using such CAR-expressing T cells are currently in clinical trial for the treatment of various cancers.

Antibodies

In one embodiment, the present invention provides a composition comprising an antibody or antibody fragment that specifically binds to the extracellular portion of PSMA. For example, in one embodiment, the extracellular portion of PSMA, to which the antibody or antibody fragment binds, comprises the amino acid sequence of SEQ ID NO: 1.

In some embodiments, the term "epitope" refers to a region of the antigen that binds to the antibody. It is the region of an antigen recognized by a first antibody wherein the binding of the first antibody to the region prevents binding of a second antibody or other bivalent molecule to the region. The region encompasses a particular core sequence or sequences selectively recognized by a class of antibodies. In general, epitopes are comprised by local surface structures that can be formed by contiguous or noncontiguous amino acid sequences.

In another embodiment, the term "selectively recognizes," "selectively bind" or "selectively recognized" means that binding of the antibody or other bivalent molecule to an epitope is at least 2-fold greater, preferably 2-5 fold greater, and most preferably more than 5-fold greater than the binding of the bivalent molecule to an unrelated epitope or than the binding of an unrelated bivalent molecule to the epitope, as determined by techniques known in the art and described herein, such as, for example, ELISA and cold displacement assays.

In some embodiments, the term "antibody" refers to the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, Cγ3 and Cγ4. In each pair, the light and heavy chain variable regions (VL and VH) are together responsible for binding to an antigen, and the constant regions (CL, Cγ1, Cγ2, Cγ3 and Cγ4, particularly Cγ1, Cγ2, and Cγ3) are responsible for antibody effector functions. In some mammals, for example in camels and llamas, full-length antibodies may consist of only two heavy chains, each heavy chain comprising immunoglobulin domains VH, Cγ2, and Cγ3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to VH, Cγ1, Cγ2, Cγ3, Cγ4, VL, and CL.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

In some embodiments, the term "antibody" or "antigen-binding fragment" respectively refer to intact molecules as well as functional fragments thereof, such as Fab, a scFv-Fc bivalent molecule, F(ab')2, and Fv that are capable of specifically interacting with a desired target. In some embodiments, the antigen-binding fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains; and (5) Single chain antibody (SCA or scFv), a genetically engineered molecule containing the variable region of the light chain and the variable region of the heavy chain, linked by a suitable polypeptide linker as a genetically fused single chain molecule.

(6) scFv-Fc, is created by fusing single-chain Fv (scFv) with a hinge region from an immunoglobulin (Ig) such as an IgG, and Fc regions.

In one embodiment, the antibody provided herein is a monoclonal antibody. In another embodiment, the antigen-binding fragment provided herein is a single chain Fv (scFv), a diabody, a tandem scFv, a scFv-Fc bivalent molecule, an Fab, Fab', Fv, or F(ab')2.

In one embodiment, the term "bivalent molecule" or "By" refers to a molecule capable of binding to two separate targets at the same time. The bivalent molecule is not limited to having two and only two binding domains and can be a polyvalent molecule or a molecule comprised of linked monovalent molecules. The binding domains of the bivalent molecule can selectively recognize the same epitope or different epitopes located on the same target or located on a target that originates from different species. The binding domains can be linked in any of a number of ways including, but not limited to, disulfide bonds, peptide bridging, amide bonds, and other natural or synthetic linkages known in the art (Spatola et al., "Chemistry and Biochemistry of Amino Acids, Peptides and Proteins," B. Weinstein, eds., Marcel Dekker, New York, p. 267 (1983) (general review); Morley, J. S., "Trends Pharm Sci" (1980) pp. 463-468 (general review); Hudson et al., Int J Pept Prot Res (1979) 14, 177-185; Spatola et al., Life Sci (1986) 38, 1243-1249; Hann, M. M., J Chem Soc Perkin Trans I (1982) 307-314; Almquist et al., J Med Chem (1980) 23, 1392-1398; Jennings-White et al., Tetrahedron Lett (1982) 23, 2533; Szelke et al., European Application EP 45665; Chemical Abstracts 97, 39405 (1982); Holladay, et al., Tetrahedron Lett (1983) 24, 4401-4404; and Hruby, V. J., Life Sci (1982) 31, 189-199).

The present invention provides an anti-PSMA antibody or antibody fragment isolated from a large yeast display human scFv library. In one embodiment, the antigen-binding fragment thereof is high affinity anti-PSMA scFv gy1, comprises the amino acid sequence of SEQ ID NO: 3.

In one embodiment, the antibody or antibody fragment comprises a light chain comprising an amino acid sequence of SEQ ID NO: 5. In one embodiment, the antibody or antibody fragment comprises VL FR1 comprising the amino acid sequence of SEQ ID NO: 7. In one embodiment, the antibody or antibody fragment comprises a VL CDR1 comprising the amino acid sequence of SEQ ID NO: 9. In one embodiment, the antibody or antibody fragment comprises a VL FR2 comprising the amino acid sequence of SEQ ID NO: 11. In one embodiment, the antibody or antibody fragment comprises a VL CDR2 comprising the amino acid sequence of SEQ ID NO: 13. In one embodiment, the antibody or antibody fragment comprises a VL FR3 comprises an amino acid sequence of SEQ ID NO: 15. In one embodiment, the antibody or antibody fragment comprises a VL CDR3 comprises the amino acid sequence of SEQ ID NO: 17. In one embodiment, the antibody or antibody fragment comprises a VL FR4 comprising the amino acid sequence of SEQ ID NO: 19.

In one embodiment, the antibody or antibody fragment comprises a heavy chain comprising the amino acid sequence of SEQ ID NO: 21. In one embodiment, the antibody or antibody fragment comprises a VH FR1 comprising the amino acid sequence of SEQ ID NO: 23. In one embodiment, the antibody or antibody fragment comprises a VH CDR1 comprising the amino acid sequence of SEQ ID NO: 25. In one embodiment, the antibody or antibody fragment comprises a VH FR2 comprising the amino acid sequence of SEQ ID NO: 27. In one embodiment, the antibody or antibody fragment comprises a VH CDR2 comprising the amino acid sequence of SEQ ID NO: 29. In one embodiment, the antibody or antibody fragment comprises a VH FR3 comprising the amino acid sequence of SEQ ID NO: 31. In one embodiment, the antibody or antibody fragment comprises a VH CDR3 comprising the amino acid sequence of SEQ ID NO: 33. In one embodiment, the antibody or antibody fragment comprises a VH FR4 comprising the amino acid sequence of SEQ ID NO: 35. In one embodiment, the antibody or antibody fragment comprises a scFv linker comprising the amino acid sequence of SEQ ID NO: 37.

For example, in one embodiment, the composition comprises an antibody fragment comprising the scFv denoted herein as gy1. In one embodiment gy1 comprises the amino acid sequence of SEQ ID NO: 3. In one embodiment, gy1 comprises a light chain comprising the amino acid sequence of SEQ ID NO: 5 and a heavy chain comprising the amino acid sequence of SEQ ID NO: 21. In one embodiment, gy1 comprises a VL FR1 comprising the amino acid sequence of SEQ ID NO: 7; a VL CDR1 comprising the amino acid sequence of SEQ ID NO: 9; a VL FR2 comprising the amino acid sequence of SEQ ID NO: 11; a VL CDR2 comprising the amino acid sequence of SEQ ID NO: 13; a VL FR3 comprising the amino acid sequence of SEQ ID NO: 15; a VL CDR3 comprising the amino acid sequence of SEQ ID NO: 17; a VL FR4 comprising the amino acid sequence of SEQ ID NO: 19; a VH FR1 comprising the amino acid sequence of SEQ ID NO: 23; a VH CDR1 comprising the amino acid sequence of SEQ ID NO: 25; a VH FR2 comprising the amino acid sequence of SEQ ID NO: 27; a VH CDR2 comprising the amino acid sequence of SEQ ID NO: 29; a VH FR3 comprising the amino acid sequence of SEQ ID NO: 31; a VH CDR3 comprising the amino acid sequence of SEQ ID NO: 33; a VH FR4 comprising the amino acid sequence of SEQ ID NO: 35; and a scFv linker comprising the amino acid sequence of SEQ ID NO: 37.

In one embodiment, the antibody or antibody fragment comprises one or more mutations. For example, in one embodiment, the antibody or antibody fragment comprises a VL FR2 comprising the amino acid sequence of SEQ ID NO: 39, where SEQ ID NO: 39 comprises a V→A point mutation with respect to SEQ ID NO: 11. In one embodiment, the antibody or antibody fragment comprises a VL CDR2 comprising the amino acid sequence of SEQ ID NO: 41, where SEQ ID NO: 41 comprises a G→E point mutation with respect to SEQ ID NO: 13. In one embodiment, the antibody or antibody fragment comprises a VL FR4 comprising the amino acid sequence of SEQ ID NO: 43, where SEQ ID NO: 43 comprises a V→A point mutation with respect to SEQ ID NO: 19. In one embodiment, the antibody or antibody fragment comprises a VH CDR1 comprising the amino acid sequence of SEQ ID NO: 45, where SEQ ID NO: 45 comprises a S→F point mutation with respect to SEQ ID NO: 25. In one embodiment, the antibody or antibody fragment comprises a VH FR3 comprising the amino acid sequence of SEQ ID NO: 47, where SEQ ID NO: 47 comprises a I→V point mutation with respect to SEQ ID NO: 31. In one embodiment, the antibody or antibody fragment comprises a VH CDR3 comprising the amino acid sequence of SEQ ID NO: 49, where SEQ ID NO: 49 comprises a D→G point mutation with respect to SEQ ID NO: 33. In one embodiment, the antibody or antibody fragment comprises a VH FR4 comprising the amino acid sequence of SEQ ID NO: 51, where SEQ ID NO: 51 comprises a G→E point mutation with respect to SEQ ID NO: 35.

For example, in one embodiment, the composition comprises an antibody fragment comprising a scFv denoted herein as gy1-st. In one embodiment, gy1-st comprises a VL FR2 comprising the amino acid sequence of SEQ ID NO: 39; a VH CDR1 comprising the amino acid sequence of SEQ ID NO: 45, and a VH FR4 comprising the amino acid sequence of SEQ ID NO: 51. In one embodiment, gy1-st comprises a VL FR1 comprising the amino acid sequence of SEQ ID NO: 7; a VL CDR1 comprising the amino acid sequence of SEQ ID NO: 9; a VL FR2 comprising the amino acid sequence of SEQ ID NO: 39; a VL CDR2 comprising the amino acid sequence of SEQ ID NO: 13; a VL FR3 comprising the amino acid sequence of SEQ ID NO: 15; a VL CDR3 comprising the amino acid sequence of SEQ ID NO: 17; a VL FR4 comprising the amino acid sequence of SEQ ID NO: 19; a VH FR1 comprising the amino acid sequence of SEQ ID NO: 23; a VH CDR1 comprising the amino acid sequence of SEQ ID NO: 45; a VH FR2 comprising the amino acid sequence of SEQ ID NO: 27; a VH CDR2 comprising the amino acid sequence of SEQ ID NO: 29; a VH FR3 comprising the amino acid sequence of SEQ ID NO: 31; a VH CDR3 comprising the amino acid sequence of SEQ ID NO: 33; a VH FR4 comprising the amino acid sequence of SEQ ID NO: 51; and a scFv linker comprising the amino acid sequence of SEQ ID NO: 37.

For example, in one embodiment, the composition comprises an antibody fragment comprising a scFv denoted herein as gy1-2. In one embodiment, gy1-2 comprises a VL CDR2 comprising the amino acid sequence of SEQ ID NO: 41; a VL FR4 comprising the amino acid sequence of SEQ ID NO: 43; a VH CDR1 comprising the amino acid sequence of SEQ ID NO: 45, and a VH FR3 comprising the amino acid sequence of SEQ ID NO: 47. In one embodiment, gy1-2 comprises a VL FR1 comprising the amino acid sequence of SEQ ID NO: 7; a VL CDR1 comprising the amino acid sequence of SEQ ID NO: 9; a VL FR2 comprising the amino acid sequence of SEQ ID NO: 11; a VL CDR2 comprising the amino acid sequence of SEQ ID NO: 41; a VL FR3 comprising the amino acid sequence of SEQ ID NO: 15; a VL CDR3 comprising the amino acid sequence of SEQ ID NO: 17; a VL FR4 comprising the amino acid sequence of SEQ ID NO: 43; a VH FR1 comprising the amino acid sequence of SEQ ID NO: 23 a VH CDR1 comprising the amino acid sequence of SEQ ID NO: 45; a VH FR2 comprising the amino acid sequence of SEQ ID NO: 27; a VH CDR2 comprising the amino acid sequence of SEQ ID NO: 29; a VH FR3 comprising the amino acid sequence of SEQ ID NO: 47; a VH CDR3 comprising the amino acid sequence of SEQ ID NO: 33; a VH FR4 comprising the amino acid sequence of SEQ ID NO: 35; and a scFv linker comprising the amino acid sequence of SEQ ID NO: 37.

For example, in one embodiment, the composition comprises an antibody fragment comprising a scFv denoted herein as gy1-3. In one embodiment, gy1-3 comprises a VH CDR1 comprising the amino acid sequence of SEQ ID NO: 45, and a VH CDR3 comprising the amino acid sequence of SEQ ID NO: 49. In one embodiment, gy1 comprises a VL FR1 comprising the amino acid sequence of SEQ ID NO: 7; a VL CDR1 comprising the amino acid sequence of SEQ ID NO: 9; a VL FR2 comprising the amino acid sequence of SEQ ID NO: 11; a VL CDR2 comprising the amino acid sequence of SEQ ID NO: 13; a VL FR3 comprising the amino acid sequence of SEQ ID NO: 15; a VL CDR3 comprising the amino acid sequence of SEQ ID NO: 17; a VL FR4 comprising the amino acid sequence of SEQ ID NO: 19; a VH FR1 comprising the amino acid sequence of SEQ ID NO: 23; a VH CDR1 comprising the amino acid sequence of SEQ ID NO: 45; a VH FR2 comprising the amino acid sequence of SEQ ID NO: 27; a VH CDR2 comprising the amino acid sequence of SEQ ID NO: 29; a VH FR3 comprising the amino acid sequence of SEQ ID NO: 31; a VH CDR3 comprising the amino acid sequence of SEQ ID NO: 49; a VH FR4 comprising the amino acid sequence of SEQ ID NO: 35; and a scFv linker comprising the amino acid sequence of SEQ ID NO: 37.

In one embodiment, an scFv described herein is engineered into another fragment antibody or full-length antibody, wherein fragment antibody refers to a Fab, Fab', (Fab')$_2$, Fv, scFv-Fc, scFv-CH2, scFv-CH3, or a full antibody.

In one embodiment, the composition comprises an antibody comprising an scFv described herein. For example, in one embodiment, the composition comprises an antibody comprising gy1-2 scFv. In one embodiment, the antibody comprising gy1-2 scFv, is denoted herein as PSMAb. In one embodiment, the antibody comprises a heavy chain comprising the amino acid sequence of SEQ ID NO: 68. In one embodiment, the antibody comprises a heavy chain having a signal peptide, wherein the heavy chain having a signal peptide comprises the amino acid sequence of SEQ ID NO: 53. In one embodiment, the heavy chain signal peptide comprises the amino acid sequence of SEQ ID NO: 55. In one embodiment, the antibody comprises a heavy chain variable region comprising the amino acid sequence of SEQ ID NO: 57. In one embodiment, the antibody comprises a heavy chain constant region of SEQ ID NO: 59. In one embodiment, the antibody comprises a light chain comprising the amino acid sequence of SEQ ID NO: 69. In one embodiment, the antibody comprises a light chain having a signal peptide, wherein the light chain having a signal peptide comprises the amino acid sequence of SEQ ID NO: 61. In one embodiment, the light chain signal peptide comprises the amino acid sequence of SEQ ID NO: 63. In one embodiment, the antibody comprises a light chain variable region comprising the amino acid sequence of SEQ ID NO: 65. In one embodiment, the antibody comprises a light chain constant region of SEQ ID NO: 67.

Sequence alignment methods that can be used to achieve the desired sequence alignment include in some embodiments, but are not solely restricted to pair-wise alignment methods or multiple-sequence alignment methods, as will be understood by a skilled artisan. Sequence alignments can be stored in a wide variety of text-based file formats. In one embodiment, this is achieved by converting in certain embodiments, any format, for example a FASTA or GenBank, SwissProt, Entrez and EMBL format, using conversion programs and programming packages such as, READSEQ, EMBOSS and BioPerl, BioRuby. It is to be understood that a skilled artisan can convert, modify, score, update and/or store the sequences as necessary using any program or storage media, as will be appreciated by the skilled artisan.

In some embodiments, the term "sequence alignment" includes use of any program or method, as understood by a skilled artisan, that is used to perform nucleic acid or amino acid sequence alignments to yield results that can be readily probed, assessed and subjected to mathematical and statistical calculations. In one embodiment, methods for sequence or structure alignment are well known in the art, and include alignments based on sequence and structural homology, as will be understood by a skilled artisan.

In one embodiment, the term "homology," "homolog" or "homologous" refer to sequence identity, or to structural identity, or functional identity. By using the term "homology" and the other like forms, it is to be understood that any molecule, whether nucleic acid or peptide, that functions similarly, and/or contains sequence identity, and/or is conserved structurally so that it approximates the reference sequence, is to be considered as part of this invention. In another embodiment, the terms "homology," "homologue" or "homologous", in any instance, indicate that the sequence referred to, whether an amino acid sequence, or a nucleic acid sequence, exhibits at least 86% correspondence with the indicated sequence. In another embodiment, the amino acid sequence or nucleic acid sequence exhibits at least 90% correspondence with the indicated sequence. In another embodiment, the amino acid sequence or nucleic acid sequence exhibits at least 92% correspondence with the indicated sequence. In another embodiment, the amino acid sequence or nucleic acid sequence exhibits at least 95% correspondence with the indicated sequence. In another embodiment, the amino acid sequence or nucleic acid sequence exhibits at least 95% or more correspondence with the indicated sequence. In another embodiment, the amino acid sequence or nucleic acid sequence exhibits at least 97% or more correspondence with the indicated sequence. In another embodiment, the amino acid sequence or nucleic acid sequence exhibits 97%-100% correspondence to the indicated sequence. In another embodiment, the amino acid sequence or nucleic acid sequence exhibits 100% correspondence to the indicated sequence. Similarly, in one embodiment, the reference to a correspondence to a particular sequence includes both direct correspondence, as well as homology to that sequence as herein defined. Accordingly and in one embodiment, the term "non-homologous" refers the amino acid sequence or nucleic acid sequence exhibits no more than 85% correspondence with the indicated sequence. In another embodiment, the amino acid sequence or nucleic acid sequence exhibits no more than 75% correspondence with the indicated sequence. In another embodiment, the amino acid sequence or nucleic acid sequence exhibits no more than 65-74% correspondence with the indicated sequence. In another embodiment, the amino acid sequence or nucleic acid sequence exhibits no more than 55-64% correspondence with the indicated sequence. In another embodiment, the amino acid sequence or nucleic acid sequence exhibits no more than 45-54% correspondence with the indicated sequence. In another embodiment, the amino acid sequence or nucleic acid sequence exhibits no more than 35-44% correspondence with the indicated sequence. In another embodiment, the amino acid sequence or nucleic acid sequence exhibits no more than 35-44% correspondence with the indicated sequence. In another embodiment, the amino acid sequence or nucleic acid sequence exhibits no more than 15-34% correspondence with the indicated sequence. In another embodiment, the amino acid sequence or nucleic acid sequence exhibits no more than 5-14% correspondence with the indicated sequence. In another embodiment, the amino acid sequence or nucleic acid sequence exhibits no more than 0.1-4% correspondence with the indicated sequence. In another embodiment, the term "non-homologous can be used interchangeably with the term "low sequence similarity".

In one embodiment, the light chain contains CDR1, CDR2 and CDR3 sequences that are listed above or have homology more than 70%, for example, more than 75%, 80%, 85%, 90%, 91%, 92%, 93%, 94%, 95%, 96%, 97%, 98%, or 99%; for example with 10, 9, 8, 7, 6, 5, 4, 3, 2, or 1 mutation(s), deletion or insertion of amino acids.

In one embodiment, the light chain contains FR1, FR2 and FR3 sequences that are listed above or have homology more than 70%, for example, more than 75%, 80%, 85%, 90%, 91%, 92%, 93%, 94%, 95%, 96%, 97%, 98%, or 99%; for example with 10, 9, 8, 7, 6, 5, 4, 3, 2, or 1 mutation(s), deletion or insertion of amino acids.

In one embodiment, the heavy chain contains CDR1, CDR2 and CDR3 sequences that are listed above or have homology more than 70%, for example, more than 75%, 80%, 85%, 90%, 91%, 92%, 93%, 94%, 95%, 96%, 97%, 98%, or 99%; for example with 10, 9, 8, 7, 6, 5, 4, 3, 2, or 1 mutation(s), deletion or insertion of amino acids.

In one embodiment, the heavy chain contains FR1, FR2 and FR3 sequences that are listed above or have homology more than 70%, for example, more than 75%, 80%, 85%, 90%, 91%, 92%, 93%, 94%, 95%, 96%, 97%, 98%, or 99%; for example with 10, 9, 8, 7, 6, 5, 4, 3, 2, or 1 mutation(s), deletion or insertion of amino acids.

In one embodiment, full antibody are one of the types of IgG1, IgG2, IgG3 or IgG4. In another embodiment, gy1 scFv was engineered to a IgG1 full antibody.

In one embodiment, full antibody has a constant region of lambda, kappa or a mutated one from them. In another embodiment, gy1 scFv was engineered to a full antibody using a CL2 constant region.

In one embodiment, the heavy chain comprises a constant region of SEQ ID NO: 59, or a sequence having homology of more than 70%, for example, more than 75%, 80%, 85%, 90%, 91%, 92%, 93%, 94%, 95%, 96%, 97%, 98%, or 99%; for example with 10, 9, 8, 7, 6, 5, 4, 3, 2, or 1 mutation(s), deletion or insertion of amino acids.

In one embodiment, the light chain comprises a constant region of SEQ ID NO: 67, or a sequence having homology of more than 70%, for example, more than 75%, 80%, 85%, 90%, 91%, 92%, 93%, 94%, 95%, 96%, 97%, 98%, or 99%; for example with 10, 9, 8, 7, 6, 5, 4, 3, 2, or 1 mutation(s), deletion or insertion of amino acids.

In one embodiment, there may or may not be linker peptide(s) between signal peptide and variable region, between variable region and constant region of heavy and/or light chain; one example of such linker peptides is encoded by restriction enzyme sites.

In one embodiment, the antibody or antibody fragment is displayed on yeast cell surface; in another embodiment, the antibody or antibody fragment is coated on nanoparticle surface; in another embodiment, the antibody or antibody fragment is displayed on mammalian cell surface, such as T cells, NK cells or other human or other mammalian cells; in another embodiment, the antibody or antibody fragment is produced as secretory protein by yeast, E. coli or mammalian cells.

In one embodiment, the term "binds" or "binding" or grammatical equivalents, refers to the compositions having affinity for each other. "Specific binding" is where the binding is selective between two molecules. A particular example of specific binding is that which occurs between an antibody and an antigen. Typically, specific binding can be distinguished from non-specific when the dissociation constant (KD) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding.

In one embodiment, the antibody or antigen binding fragment binds its target with a Kd within the 1 nM range; in another embodiment, the antibody or antigen binding fragment binds its target with a Kd within the 0.1 nM range. In another embodiment, gy1 scFv has an affinity of Kd=1.165 nM and IgG1 full antibody PSMAb has an affinity of Kd=0.1 nM.

In some embodiments, the antibody or antibody fragment has modifications. The modification is one as further defined herein below. In some embodiments, the modification is a N-terminus modification. In another embodiment, the modification is a C-terminal modification. In another embodiment, the modification is in the middle of the protein. In one embodiment, the secretable form of the antibody or antigen-binding fragment comprises an N-terminal modification that allows binding to an Immunoglobulin (Ig) hinge region. In another embodiment, the Ig hinge region is from but is not limited to, an immunoglobulin hinge region. In some embodiments, the modification is direct modification on antibody or antibody fragment. In other embodiments, the modification is indirect modification bridged by one or more other peptides, proteins, chemicals, carbohydrate or even secondary antibodies.

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression.

In one embodiment, the term "polypeptide" generally refers to the antibody, antigen-binding fragments or variants of the present invention.

In one embodiment, the polypeptide of this invention comprises an amino acid substitution. In one embodiment, the amino acid substitution is conservative. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In another embodiment, the amino acid substitution is not a conservative one that results in enhanced activity of the mutated polypeptide compared to the native polypeptide.

The antibodies or antigen-binding fragments of this invention can be produced by any synthetic or recombinant process such as is well known in the art. The antibodies or antigen-binding fragments of the invention can further be modified to alter biophysical or biological properties by means of techniques known in the art. For example, the polypeptide can be modified to increase its stability against proteases, or to modify its lipophilicity, solubility, or binding affinity to its native receptor.

In some embodiments, antibody fragments may be prepared by proteolytic hydrolysis of the antibody or by expression in E. coli or mammalian cells (e.g. Chinese hamster ovary cell culture or other protein expression systems) of DNA encoding the fragment. Antibody fragments can, in some embodiments, be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

A "variant" of a polypeptide, antibody, or protein of the present invention, in one embodiment, refers to an amino acid sequence that is altered with respect to the referenced polypeptide, antibody, or protein by one or more amino acids. In the present invention, a variant of a polypeptide retains the antibody-binding property of the referenced protein. In another embodiment, a "variant" refers to the antigen-binding fragment of the present invention. In yet another embodiment, the variant is a variant of the antigen-binding fragment that retains specificity for a target or marker. The variant may have "conservative" changes, wherein a substituted amino acid has similar structural or chemical properties (e.g., replacement of leucine with isoleucine). In another embodiment, the variants have conservative amino acid substitutions at one or more predicted non-essential amino acid residues. In another embodiment, a "conservative amino acid substitution" is one in which the amino acid residue is replaced with an amino acid residue having a side chain with a similar charge, where, in other embodiments, the opposite is the case for "non-conservative substitutions". Families of amino acid residues having side chains with similar charges have been defined in the art, These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein may routinely be expressed and the functional and/or biological activity of the encoded protein, can be determined using techniques described herein or by routinely modifying techniques known in the art. Analogous minor variations may also include amino acid deletions or insertions, or both. Guidance in determining which amino acid residues may be substituted, inserted, or deleted without abolishing immunological reactivity may be found using computer programs well known in the art, for example, DNASTAR software.

In one embodiment, the term "framework region" or "FR" are those variable domain residues other than the hypervariable region residues. The framework regions have been precisely defined. See, e.g., Kabat, E. A. et al., Sequences of Proteins of Immunological Interest, US Dept. Health and Human Services, National Institutes of Health, USA (5th ed. 1991). Each variable domain typically has four FRs identified as FR1, FR2, FR3 and FR4. In some embodiments, "FR" also refers to an antibody variable region comprising amino acid residues abutting or proximal to, but outside of the CDR regions i.e. regions which directly interact with the antigen, acting as the recognition element of the antibody molecule within the variable region of an antibody. In one embodiment, the term "framework region" is intended to mean each domain of the framework that is separated by the CDRs. In some embodiments, the sequences of the framework regions of different light or heavy chains are relatively conserved within a species. The combined heavy and light chain framework regions of an antibody serve to position and align the CDRs for proper binding to the antigen.

In one embodiment, the term "CDR" or "complementarity determining region" refers to amino acid residues comprising non-contiguous antigen combining sites found within the variable region of both heavy and light chain polypeptides. In other embodiments, the term "CDR" will comprise regions as described by Kabat et al., J. Biol. Chem. 252, 6609-6616 (1977) and Kabat et al., Sequences of protein of immunological interest. (1991), and Chothia and Lesk, J. Mol. Biol. 196:901-917 (1987) and MacCallum et al., J. Mol. Biol. 262:732-745 (1996). The amino acids of the CDRs of the variable domains were initially defined by Kabat, based on sequence variability, to consist of amino acid residues 31-35B (H1), 50-65 (H2), and 95-102 (H3) in the human heavy chain variable domain (VH) and amino acid residues 24-34 (L1), 50-56 (L2), and 89-97 (L3) in the human light chain variable domain (VL), using Kabat's numbering system for amino acid residues of an antibody. See Kabat et al., sequences of proteins of immunological interest, US Dept. Health and Human Services, NIH, USA (5th ed. 1991). Chothia and Lesk, J. Mol. Biol. 196:901-917 (1987) presented another definition of the CDRs based on residues that included in the three-dimensional structural loops of the variable domain regions, which were found to be important in antigen binding activity. Chothia et al. defined the CDRs as consisting of amino acid residues 26-32 (H1), 52-56 (H2), and 95-102 (H3) in the human heavy chain variable domain (VH), and amino acid residues 24-34 (L1), 50-56 (L2), and 89-97 (L3) in the human light chain variable domain (VL). Combining the CDR definitions of Kabat and Chothia, the CDRs consist of amino acid residues 26-35B (H1), 50-65 (H2), and 95-102 (H3) in human VH and amino acid residues 24-34 (L1), 50-56 (L2), and 89-97 (L3) in human VL, based on Kabat's numbering system.

In some embodiments, a "variable region" when used in reference to an antibody or a heavy or light chain thereof is intended to mean the amino terminal portion of an antibody which confers antigen binding onto the molecule and which is not the constant region. The term is intended to include functional fragments thereof which maintain some of all of the binding function of the whole variable region. Therefore, the term "heteromeric variable region binding fragments" is intended to mean at least one heavy chain variable region and at least one light chain variable regions or functional fragments thereof assembled into a heteromeric complex. Heteromeric variable region binding fragments include, for example, functional fragments such as Fab, F(ab)2, Fv, single chain Fv (scfv) and the like. Such functional fragments are well known to those skilled in the art. Accordingly, the use of these terms in describing functional fragments of a heteromeric variable region is intended to correspond to the definitions well known to those skilled in the art. Such terms are described in, for example, Harlow and Lane, Antibodies: A Laboratory Manual, Cold Spring Harbor Laboratory, New York (1989); Molec. Biology and Biotechnology: A Comprehensive Desk Reference (Myers, R. A. (ed.), New York: VCH Publisher, Inc.); Huston et al., Cell Biophysics, 22:189-224 (1993); Plückthun and Skerra, Meth. Enzymol., 178:497-515 (1989) and in Day, E. D., Advanced Immunochemistry, Second Ed., Wiley-Liss, Inc., New York, N.Y. (1990).

In one embodiment the polypeptide of this invention is an isoform of the isolated polypeptide. In one embodiment, "isoform" refers to a version of a molecule, for example, a protein or polypeptide of the present invention, with only slight differences to another isoform of the same protein or polypeptide. In one embodiment, isoforms are produced from different but related genes, or in another embodiment, arise from the same gene by alternative splicing. In another embodiment, isoforms are caused by single nucleic acid polymorphisms.

In one embodiment the isolated polypeptide of this invention is a fragment of the native protein. In one embodiment, "fragment" refers to a protein or polypeptide that is shorter or comprises fewer amino acids than the full length protein or polypeptide. In another embodiment, fragment refers to a nucleic acid that is shorter or comprises fewer nucleic acids than the full length nucleic acid. In another embodiment, the fragment is an N-terminal fragment. In another embodiment, the fragment is a C-terminal fragment. In one embodiment, the fragment of this invention is an intrasequential section of the protein, peptide, or nucleic acid. In another embodiment, the fragment is a functional intrasequential section of the protein, peptide or nucleic acid. In another embodiment, the fragment is a functional intrasequential section within the protein, peptide or nucleic acid. In another embodiment, the fragment is an N-terminal functional fragment. In one embodiment, the fragment is a C-terminal functional fragment.

In one embodiment, the term "functional fragment" refers to a fragment that maintains a certain degree of biological activity as compared to the wild type despite it being a modified version of the native or wild type antibody or polypeptide. This degree of activity could range from moderate to high as compared to the wild type, where the "activity" refers to its natural biophysical or biochemical characteristics, e.g. binding ability, affinity, half-life, etc.

In one embodiment, an isolated polypeptide of this invention comprises a derivate of a polypeptide of this invention. "Derivative" is to be understood as referring, in some embodiments, to less than the full-length portion of the native sequence of the protein in question. In some embodiments, a "derivative" may further comprise (at its termini and/or within said sequence itself) non-native sequences, i.e. sequences which do not form part of the native protein in question. The term "derivative" also includes within its scope molecular species produced by conjugating chemical groups to the amino residue side chains of the native proteins or fragments thereof, wherein said chemical groups do not form part of the naturally-occurring amino acid residues present in said native proteins.

Methods of making antibodies and antibody fragments are known in the art. (See for example, Harlow and Lane, Antibodies: A Laboratory Manual, Cold Spring Harbor Laboratory, New York, 1988, incorporated herein by reference).

Antibodies can be produced by the immunization of various animals, including mice, rats, rabbits, goats, primates, humans and chickens with a target antigen such as PSMA or peptide fragments of PSMA containing the anti-PSMA epitope of the present invention. In one embodiment, the antibody or antigen-binding fragment is purified prior to immunization of the animal. In one embodiment, the antibody or antigen-binding fragment of the present invention can be purified by methods known in the art, for example, gel filtration, ion exchange, affinity chromatography, etc. Affinity chromatography or any of a number of other techniques known in the art can be used to isolate polyclonal or monoclonal antibodies from serum, ascites fluid, or hybridoma supernatants.

"Purified" means that the monoclonal antibody is separated from at least some of the proteins normally associated with the monoclonal antibody and preferably separated from all cellular materials other than proteins.

Also provided by the invention are chemically modified derivatives of antibodies of the invention which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2560, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleic acids 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the antibody with consideration of effects on functional or antigenic domains of the antibody. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins, e.g., antibodies, via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

Nucleic Acids

In one embodiment, the invention provides polynucleic acids comprising, or alternatively consisting of, a nucleic acid sequence encoding an antibody of the invention (including molecules comprising, or alternatively consisting of, antibody fragments or variants thereof). The invention also encompasses polynucleic acids that hybridize under high stringency, or alternatively, under intermediate or lower stringency hybridization conditions, e.g., as defined supra, to polynucleic acids complementary to nucleic acids having a polynucleic acid sequence that encodes an antibody of the invention or a fragment or variant thereof.

In another embodiment, the polynucleic acids are obtained, and the nucleic acid sequence of the polynucleic acids determined, by any method known in the art. Alternatively, a polynucleic acid encoding an antibody (including molecules comprising, or alternatively consisting of, antibody fragments or variants thereof) are generated from nucleic acid from a suitable source. If a clone containing a nucleic acid encoding a particular antibody is not available, but the sequence of the antibody molecule is known, a nucleic acid encoding the immunoglobulin may be chemically synthesized in native or optimized codons for specific species or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleic acid probe specific for the particular gene sequence to identify, e.g. a cDNA clone from a cDNA library that encodes the antibody. Amplified nucleic acids generated by PCR may then be cloned into replicable cloning vectors using any method well known in the art.

In some embodiments, the term "nucleic acid" refers to polynucleic acid or to oligonucleic acids such as deoxyribonucleic acid (DNA), and, where appropriate, ribonucleic acid (RNA) or mimetic thereof. The term should also be understood to include, as equivalents, analogs of either RNA or DNA made from nucleic acid analogs, and, as applicable to the embodiment being described, single (sense or antisense) and double-stranded polynucleic acids. This term includes oligonucleic acids composed of naturally occurring nucleobases, sugars and covalent internucleoside (backbone) linkages as well as oligonucleic acids having non-naturally-occurring portions, which function similarly. Such modified or substituted oligonucleic acids are often preferred over native forms because of desirable properties such as, for example, enhanced cellular uptake, enhanced affinity for nucleic acid target and increased stability in the presence of nucleases.

As will be appreciated by one skilled in the art, a fragment or derivative of a nucleic acid sequence or gene that encodes for a protein or peptide can still function in the same manner as the entire, wild type gene or sequence. Likewise, forms of nucleic acid sequences can have variations as compared to wild type sequences, nevertheless encoding a protein or peptide, or fragments thereof, retaining wild type function exhibiting the same biological effect, despite these variations. Each of these represents a separate embodiment of the present invention.

The nucleic acids of the present invention can be produced by any synthetic or recombinant process such as is well known in the art. Nucleic acids according to the invention can further be modified to alter biophysical or biological properties by means of techniques known in the art. For example, the nucleic acid can be modified to increase its stability against nucleases (e.g., "end-capping"), or to increase expression level by codon-optimization, or to modify its lipophilicity, solubility, or binding affinity to complementary sequences.

Methods for modifying nucleic acids to achieve specific purposes are disclosed in the art, for example, in Sambrook et al. (1989). Moreover, the nucleic acid sequences of the invention can include one or more portions of nucleic acid sequence that are non-coding for the protein of interest. The invention further provides DNA sequences which encode proteins similar to those encoded by sequences as described herein, but which differ in terms of their codon sequence due to the degeneracy of the genetic code or allelic variations (naturally-occurring base changes in the species population which may or may not result in an amino acid change), which may encode the proteins of the invention described herein, as well. Variations in the DNA sequences, which are caused by point mutations or by induced modifications (including insertion, deletion, and substitution) to enhance the activity, half-life or production of the polypeptides encoded thereby, are also encompassed in the invention.

DNA encoding the antibodies or antigen-binding fragments provided herein is readily isolated and sequenced using conventional procedures (e.g., by using oligonucleic acid probes that are capable of binding specifically to genes encoding the heavy and light chains of the antibodies). Once isolated, the DNA may be placed into expression vectors, which are then transfected into host cells such as *E. coli* cells, simian COS cells, Chinese hamster ovary (CHO) cells, yeast cells or myeloma cells that do not otherwise produce immunoglobulin protein, to obtain the synthesis of the antibodies in the recombinant host cells. Recombinant production of antibodies is described in more detail below.

In one embodiment, the composition comprises a nucleic acid molecule encoding an scFv gy1 comprising the amino acid sequence of SEQ ID NO: 3. In one embodiment, the composition comprises a nucleic acid molecule comprising SEQ ID NO: 2.

In one embodiment, the nucleic acid molecule comprises a nucleic acid sequence encoding a light chain comprising an amino acid sequence of SEQ ID NO: 5. For example, in one embodiment, the nucleic acid sequence encoding a light chain comprises the nucleotide sequence of SEQ ID NO: 4. In one embodiment, the nucleic acid molecule comprises a nucleic acid sequence encoding a VL FR1 comprising the amino acid sequence of SEQ ID NO: 7. For example, in one embodiment, the nucleic acid sequence encoding a VL FR1 comprises the nucleotide sequence of SEQ ID NO: 6. In one embodiment, the nucleic acid molecule comprises a nucleic acid sequence encoding a VL CDR1 comprising the amino acid sequence of SEQ ID NO: 9. For example, in one embodiment, the nucleic acid sequence encoding a VL CDR1 comprises the nucleotide sequence of SEQ ID NO: 8. In one embodiment, the nucleic acid molecule comprises a nucleic acid sequence encoding a VL FR2 comprising the amino acid sequence of SEQ ID NO: 11. For example, in one embodiment, the nucleic acid sequence encoding a VL FR2 comprises the nucleotide sequence of SEQ ID NO: 10. In one embodiment, the nucleic acid molecule comprises a nucleic acid sequence encoding a VL CDR2 comprising the amino acid sequence of SEQ ID NO: 13. For example, in one embodiment, the nucleic acid sequence encoding a VL CDR2 comprises the nucleotide sequence of SEQ ID NO: 12. In one embodiment, the nucleic acid molecule comprises a nucleic acid sequence encoding a VL FR3 comprises an amino acid sequence of SEQ ID NO: 15. For example, in one embodiment, the nucleic acid sequence encoding a VL FR3 comprises the nucleotide sequence of SEQ ID NO: 14. In one embodiment, the nucleic acid molecule comprises a nucleic acid sequence encoding a VL CDR3 comprises the amino acid sequence of SEQ ID NO: 17. For example, in one embodiment, the nucleic acid sequence encoding a VL CDR3 comprises the nucleotide sequence of SEQ ID NO: 16. In one embodiment, the nucleic acid molecule comprises a nucleic acid sequence encoding a VL FR4 comprising the amino acid sequence of SEQ ID NO: 19. For example, in one embodiment, the nucleic acid sequence encoding a VL FR4 comprises the nucleotide sequence of SEQ ID NO: 18.

In one embodiment, the nucleic acid molecule comprises a nucleic acid sequence encoding a heavy chain comprising the amino acid sequence of SEQ ID NO: 21. For example, in one embodiment, the nucleic acid sequence encoding a heavy chain comprises the nucleotide sequence of SEQ ID NO: 20. In one embodiment, the nucleic acid molecule comprises a nucleic acid sequence encoding a VH FR1 comprising the amino acid sequence of SEQ ID NO: 23. For example, in one embodiment, the nucleic acid sequence encoding a VH FR1 comprises the nucleotide sequence of SEQ ID NO: 22. In one embodiment, the nucleic acid molecule comprises a nucleic acid sequence encoding a VH CDR1 comprising the amino acid sequence of SEQ ID NO: 25. For example, in one embodiment, the nucleic acid sequence encoding a VH CDR1 comprises the nucleotide sequence of SEQ ID NO: 24. In one embodiment, the nucleic acid molecule comprises a nucleic acid sequence encoding a VH FR2 comprising the amino acid sequence of SEQ ID NO: 27. For example, in one embodiment, the nucleic acid sequence encoding a VH FR2 comprises the nucleotide sequence of SEQ ID NO: 26. In one embodiment, the nucleic acid molecule comprises a nucleic acid sequence encoding a VH CDR2 comprising the amino acid sequence of SEQ ID NO: 29. For example, in one embodiment, the nucleic acid sequence encoding a VH CDR2 comprises the nucleotide sequence of SEQ ID NO: 28. In one embodiment, the nucleic acid molecule comprises a nucleic acid sequence encoding a VH FR3 comprising the amino acid sequence of SEQ ID NO: 31. For example, in one embodiment, the nucleic acid sequence encoding a VH FR3 comprises the nucleotide sequence of SEQ ID NO: 30. In one embodiment, the nucleic acid molecule comprises a nucleic acid sequence encoding a VH CDR3 comprising the amino acid sequence of SEQ ID NO: 33. For example, in one embodiment, the nucleic acid sequence encoding a VH CDR3 comprises the nucleotide sequence of SEQ ID NO: 32. In one embodiment, the nucleic acid molecule comprises a nucleic acid sequence encoding a VH FR4 comprising the amino acid sequence of SEQ ID NO: 35. For example, in one embodiment, the nucleic acid sequence encoding a VH FR4 comprises the nucleotide sequence of SEQ ID NO: 34. In one embodiment, the nucleic acid molecule comprises a nucleic acid sequence encoding a scFv linker comprising the amino acid sequence of SEQ ID NO: 37. For example, in one embodiment, the nucleic acid sequence encoding a scFv linker comprises the nucleotide sequence of SEQ ID NO: 36.

For example, in one embodiment, the nucleic acid molecule encodes gy1. In one embodiment the nucleic acid molecule encodes gy1, comprising the amino acid sequence of SEQ ID NO: 3. For example, in one embodiment, the nucleic acid sequence encoding a gy1 comprises the nucleotide sequence of SEQ ID NO: 2. In one embodiment, the nucleic acid molecule encoding gy1 comprises a nucleotide sequence encoding a light chain comprising the amino acid sequence of SEQ ID NO: 5 and a nucleotide sequence encoding a heavy chain comprising the amino acid sequence of SEQ ID NO: 21. For example, in one embodiment, the nucleotide sequence encoding a light chain comprises the nucleotide sequence of SEQ ID NO: 4, and the nucleotide sequence encoding a heavy chain comprises the nucleotide sequence of SEQ ID NO: 20.

In one embodiment, the nucleic acid molecule encoding gy1 comprises a nucleotide sequence encoding a VL FR1 comprising the amino acid sequence of SEQ ID NO: 7; a nucleotide sequence encoding a VL CDR1 comprising the amino acid sequence of SEQ ID NO: 9; a nucleotide sequence encoding a VL FR2 comprising the amino acid sequence of SEQ ID NO: 11; a nucleotide sequence encoding a VL CDR2 comprising the amino acid sequence of SEQ ID NO: 13; a nucleotide sequence encoding a VL FR3 comprising the amino acid sequence of SEQ ID NO: 15; a nucleotide sequence encoding a VL CDR3 comprising the amino acid sequence of SEQ ID NO: 17; a nucleotide sequence encoding a VL FR4 comprising the amino acid sequence of SEQ ID NO: 19; a nucleotide sequence encoding a VH FR1 comprising the amino acid sequence of SEQ ID NO: 23; a nucleotide sequence encoding a VH CDR1 comprising the amino acid sequence of SEQ ID NO: 25; a nucleotide sequence encoding a VH FR2 comprising the amino acid sequence of SEQ ID NO: 27; a nucleotide sequence encoding a VH CDR2 comprising the amino acid sequence of SEQ ID NO: 29; a nucleotide sequence encoding a VH FR3 comprising the amino acid sequence of SEQ ID NO: 31; a nucleotide sequence encoding a VH CDR3 comprising the amino acid sequence of SEQ ID NO: 33; a nucleotide sequence encoding a VH FR4 comprising the amino acid sequence of SEQ ID NO: 35; and a nucleotide sequence encoding a scFv linker comprising the amino acid sequence of SEQ ID NO: 37.

For example, in one embodiment, the nucleotide sequence encoding a VL FR1 comprises the nucleotide sequence of SEQ ID NO: 6; the nucleotide sequence encoding a VL CDR1 comprises the nucleotide sequence of SEQ ID NO: 8; the nucleotide sequence encoding a VL FR2 comprises the nucleotide sequence of SEQ ID NO: 10; the nucleotide sequence encoding a VL CDR2 comprises the nucleotide sequence of SEQ ID NO: 12; the nucleotide sequence encoding a VL FR3 comprises the nucleotide sequence of SEQ ID NO: 14; the nucleotide sequence encoding a VL CDR3 comprises the nucleotide sequence of SEQ ID NO: 16; the nucleotide sequence encoding a VL FR4 comprises the nucleotide sequence of SEQ ID NO: 18; the nucleotide sequence encoding a VH FR1 comprises the nucleotide sequence of SEQ ID NO: 22; the nucleotide sequence encoding a VH CDR1 comprises the nucleotide sequence of SEQ ID NO: 24; the nucleotide sequence encoding a VH FR2 comprises the nucleotide sequence of SEQ ID NO: 26; the nucleotide sequence encoding a VH CDR2 comprises the nucleotide sequence of SEQ ID NO: 28; the nucleotide sequence encoding a VH FR3 comprises the nucleotide sequence of SEQ ID NO: 30; the nucleotide sequence encoding a VH CDR3 comprises the nucleotide sequence of SEQ ID NO: 32; the nucleotide sequence encoding a VH FR4 comprises the nucleotide sequence of SEQ ID NO: 34; and the nucleotide sequence encoding a scFv linker comprises the nucleotide sequence of SEQ ID NO: 36.

In one embodiment, the nucleic acid molecule encodes an antibody or antibody fragment comprising one or more mutations. For example, in one embodiment, the nucleic acid molecule comprises a nucleotide sequence encoding a VL FR2 comprising the amino acid sequence of SEQ ID NO: 39, where SEQ ID NO: 39 comprises a V→A point mutation with respect to SEQ ID NO: 11. For example, in one embodiment, the nucleotide sequence encoding the mutant VL FR2 comprises the nucleotide sequence of SEQ ID NO: 38. In one embodiment, the nucleic acid molecule comprises a nucleotide sequence encoding a VL CDR2 comprising the amino acid sequence of SEQ ID NO: 41, where SEQ ID NO: 41 comprises a G→E point mutation with respect to SEQ ID NO: 13. For example, in one embodiment, the nucleotide sequence encoding the mutant VL CDR2 comprises the nucleotide sequence of SEQ ID NO: 40. In one embodiment, the nucleic acid molecule comprises a nucleotide sequence encoding a VL FR4 comprising the amino acid sequence of SEQ ID NO: 43, where SEQ ID NO: 43 comprises a V→A point mutation with respect to SEQ ID NO: 19. For example, in one embodiment, the nucleotide sequence encoding the mutant VL FR4 comprises the nucleotide sequence of SEQ ID NO: 42. In one embodiment, the nucleic acid molecule comprises a nucleotide sequence encoding a VH CDR1 comprising the amino acid sequence of SEQ ID NO: 45, where SEQ ID NO: 45 comprises a S→F point mutation with respect to SEQ ID NO: 25. For example, in one embodiment, the nucleotide sequence encoding the mutant VH CDR1 comprises the nucleotide sequence of SEQ ID NO: 44. In one embodiment, the nucleic acid molecule comprises a nucleotide sequence encoding a VH FR3 comprising the amino acid sequence of SEQ ID NO: 47, where SEQ ID NO: 47 comprises a I→V point mutation with respect to SEQ ID NO: 31. For example, in one embodiment, the nucleotide sequence encoding the mutant VH FR3 comprises the nucleotide sequence of SEQ ID NO: 46. In one embodiment, the nucleic acid molecule comprises a nucleotide sequence encoding a VH CDR3 comprising the amino acid sequence of SEQ ID NO: 49, where SEQ ID NO: 49 comprises a D→G point mutation with respect to SEQ ID NO: 33. For example, in one embodiment, the nucleotide sequence encoding the mutant VH CDR3 comprises the nucleotide sequence of SEQ ID NO: 48. In one embodiment, the nucleic acid molecule comprises a nucleotide sequence encoding a VH FR4 comprising the amino acid sequence of SEQ ID NO: 51, where SEQ ID NO: 51 comprises a G→E point mutation with respect to SEQ ID NO: 35. For example, in one embodiment, the nucleotide sequence encoding the mutant VH FR4 comprises the nucleotide sequence of SEQ ID NO: 50.

For example, in one embodiment, the composition comprises a nucleic acid molecule encoding an antibody fragment comprising a scFv denoted herein as gy1-st. In one embodiment, the nucleic acid molecule encoding gy1-st comprises a nucleotide sequence encoding a VL FR2 comprising the amino acid sequence of SEQ ID NO: 39; a nucleotide sequence encoding a VH CDR1 comprising the amino acid sequence of SEQ ID NO: 45, and a nucleotide sequence encoding a VH FR4 comprising the amino acid sequence of SEQ ID NO: 51. In one embodiment, the nucleic acid molecule encoding gy1-st comprises a nucleotide sequence encoding a VL FR1 comprising the amino acid sequence of SEQ ID NO: 7; a nucleotide sequence encoding a VL CDR1 comprising the amino acid sequence of SEQ ID NO: 9; a nucleotide sequence encoding a VL FR2 comprising the amino acid sequence of SEQ ID NO: 39; a nucleotide sequence encoding a VL CDR2 comprising the amino acid sequence of SEQ ID NO: 13; a nucleotide sequence encoding a VL FR3 comprising the amino acid sequence of SEQ ID NO: 15; a nucleotide sequence encoding a VL CDR3 comprising the amino acid sequence of SEQ ID NO: 17; a nucleotide sequence encoding a VL FR4 comprising the amino acid sequence of SEQ ID NO: 19; a nucleotide sequence encoding a VH FR1 comprising the amino acid sequence of SEQ ID NO: 23; a nucleotide sequence encoding a VH CDR1 comprising the amino acid sequence of SEQ ID NO: 45; a nucleotide sequence encoding a VH FR2 comprising the amino acid sequence of SEQ ID NO: 27; a nucleotide sequence encoding a VH CDR2 comprising the amino acid sequence of SEQ ID NO: 29; a nucleotide sequence encoding a VH FR3 comprising the amino acid sequence of SEQ ID NO: 31; a nucleotide sequence encoding a VH CDR3 comprising the amino acid sequence of SEQ ID NO: 33; a nucleotide sequence encoding a VH FR4 comprising the amino acid sequence of SEQ ID NO: 51; and a nucleotide sequence encoding a scFv linker comprising the amino acid sequence of SEQ ID NO: 37. In one embodiment, the nucleotide sequence encoding a VL FR1 comprises the nucleotide sequence of SEQ ID NO: 6; the nucleotide sequence encoding a VL CDR1 comprises the nucleotide sequence of SEQ ID NO: 8; the nucleotide sequence encoding a VL FR2 comprises the nucleotide sequence of SEQ ID NO: 38; the nucleotide sequence encoding a VL CDR2 comprises the nucleotide sequence of SEQ ID NO: 12; the nucleotide sequence encoding a VL FR3 comprises the nucleotide sequence of SEQ ID NO: 14; the nucleotide sequence encoding a VL CDR3 comprises the nucleotide sequence of SEQ ID NO: 16; the nucleotide sequence encoding a VL FR4 comprises the nucleotide sequence of SEQ ID NO: 18; the nucleotide sequence encoding a VH FR1 comprises the nucleotide sequence of SEQ ID NO: 22; the nucleotide sequence encoding a VH CDR1 comprises the nucleotide sequence of SEQ ID NO: 44; the nucleotide sequence encoding a VH FR2 comprises the nucleotide sequence of SEQ ID NO: 26; the nucleotide sequence encoding a VH CDR2 comprises the nucleotide sequence of SEQ ID NO: 28; the nucleotide sequence encoding a VH FR3 comprises the nucleotide sequence of SEQ ID NO: 30; the nucleotide sequence encoding a VH CDR3 comprising comprises the nucleotide sequence of SEQ ID NO: 32; the nucleotide sequence encoding a VH FR4 comprises the nucleotide sequence of SEQ ID NO: 50; and the nucleotide sequence encoding a scFv linker comprises the nucleotide sequence of SEQ ID NO: 36.

For example, in one embodiment, the composition comprises a nucleic acid molecule encoding an antibody fragment comprising a scFv denoted herein as gy1-2. In one embodiment, the nucleic acid molecule encoding gy1-2 comprises a nucleotide sequence encoding VL CDR2 comprising the amino acid sequence of SEQ ID NO: 41; a nucleotide sequence encoding VL FR4 comprising the amino acid sequence of SEQ ID NO: 43; a nucleotide sequence encoding VH CDR1 comprising the amino acid sequence of SEQ ID NO: 45, and a nucleotide sequence encoding VH FR3 comprising the amino acid sequence of SEQ ID NO: 47. In one embodiment, the nucleic acid molecule encoding gy1-2 comprises a nucleotide sequence encoding a VL FR1 comprising the amino acid sequence of SEQ ID NO: 7; a nucleotide sequence encoding a VL CDR1 comprising the amino acid sequence of SEQ ID NO: 9; a nucleotide sequence encoding a VL FR2 comprising the amino acid sequence of SEQ ID NO: 11; a nucleotide sequence encoding a VL CDR2 comprising the amino acid sequence of SEQ ID NO: 41; a nucleotide sequence encoding a VL FR3 comprising the amino acid sequence of SEQ ID NO: 15; a nucleotide sequence encoding a VL CDR3 comprising the amino acid sequence of SEQ ID NO: 17; a nucleotide sequence encoding a VL FR4 comprising the amino acid sequence of SEQ ID NO: 43; a nucleotide sequence encoding a VH FR1 comprising the amino acid sequence of SEQ ID NO: 23; a nucleotide sequence encoding a VH CDR1 comprising the amino acid sequence of SEQ ID NO: 45; a nucleotide sequence encoding a VH FR2 comprising the amino acid sequence of SEQ ID NO: 27; a nucleotide sequence encoding a VH CDR2 comprising the amino acid sequence of SEQ ID NO: 29; a nucleotide sequence encoding a VH FR3 comprising the amino acid sequence of SEQ ID NO: 47; a nucleotide sequence encoding a VH CDR3 comprising the amino acid sequence of SEQ ID NO: 33; a nucleotide sequence encoding a VH FR4 comprising the amino acid sequence of SEQ ID NO: 35; and a nucleotide sequence encoding a scFv linker comprising the amino acid sequence of SEQ ID NO: 37. In one embodiment, the nucleotide sequence encoding a VL FR1 comprises the nucleotide sequence of SEQ ID NO: 6; the nucleotide sequence encoding a VL CDR1 comprises the nucleotide sequence of SEQ ID NO: 8; the nucleotide sequence encoding a VL FR2 comprises the nucleotide sequence of SEQ ID NO: 10; the nucleotide sequence encoding a VL CDR2 comprises the nucleotide sequence of SEQ ID NO: 40; the nucleotide sequence encoding a VL FR3 comprises the nucleotide sequence of SEQ ID NO: 14; the nucleotide sequence encoding a VL CDR3 comprises the nucleotide sequence of SEQ ID NO: 16; the nucleotide sequence encoding a VL FR4 comprises the nucleotide sequence of SEQ ID NO: 42; the nucleotide sequence encoding a VH FR1 comprises the nucleotide sequence of SEQ ID NO: 22; the nucleotide sequence encoding a VH CDR1 comprises the nucleotide sequence of SEQ ID NO: 44; the nucleotide sequence encoding a VH FR2 comprises the nucleotide sequence of SEQ ID NO: 26; the nucleotide sequence encoding a VH CDR2 comprises the nucleotide sequence of SEQ ID NO: 28; the nucleotide sequence encoding a VH FR3 comprises the nucleotide sequence of SEQ ID NO: 46; the nucleotide sequence encoding a VH CDR3 comprises the nucleotide sequence of SEQ ID NO: 32; the nucleotide sequence encoding a VH FR4 comprises the nucleotide sequence of SEQ ID NO: 34; and the nucleotide sequence encoding a scFv linker comprises the nucleotide sequence of SEQ ID NO: 36.

For example, in one embodiment, the composition comprises a nucleic acid molecule encoding an antibody fragment comprising a scFv denoted herein as gy1-3. In one embodiment, the nucleic acid molecule encoding gy1-3 comprises a nucleotide sequence encoding a VH CDR1 comprising the amino acid sequence of SEQ ID NO: 45, and a nucleotide sequence encoding a VH CDR3 comprising the amino acid sequence of SEQ ID NO: 49. In one embodiment, gy1 comprises a nucleotide sequence encoding a VL FR1 comprising the amino acid sequence of SEQ ID NO: 7; a nucleotide sequence encoding a VL CDR1 comprising the amino acid sequence of SEQ ID NO: 9; a nucleotide sequence encoding a VL FR2 comprising the amino acid sequence of SEQ ID NO: 11; a nucleotide sequence encoding a VL CDR2 comprising the amino acid sequence of SEQ ID NO: 13; a nucleotide sequence encoding a VL FR3 comprising the amino acid sequence of SEQ ID NO: 15; a nucleotide sequence encoding a VL CDR3 comprising the amino acid sequence of SEQ ID NO: 17; a nucleotide sequence encoding a VL FR4 comprising the amino acid sequence of SEQ ID NO: 19; a nucleotide sequence encoding a VH FR1 comprising the amino acid sequence of SEQ ID NO: 23; a nucleotide sequence encoding a VH CDR1 comprising the amino acid sequence of SEQ ID NO: 45; a nucleotide sequence encoding a VH FR2 comprising the amino acid sequence of SEQ ID NO: 27; a nucleotide sequence encoding a VH CDR2 comprising the amino acid sequence of SEQ ID NO: 29; a nucleotide sequence encoding a VH FR3 comprising the amino acid sequence of SEQ ID NO: 31; a nucleotide sequence encoding a VH CDR3 comprising the amino acid sequence of SEQ ID NO: 49; a nucleotide sequence encoding a VH FR4 comprising the amino acid sequence of SEQ ID NO: 35; and a nucleotide sequence encoding a scFv linker comprising the amino acid sequence of SEQ ID NO: 37. In one embodiment, the nucleotide sequence encoding a VL FR1 comprises the nucleotide sequence of SEQ ID NO: 6; the nucleotide sequence encoding a VL CDR1 comprises the nucleotide sequence of SEQ ID NO: 8; the nucleotide sequence encoding a VL FR2 comprises the nucleotide sequence of SEQ ID NO: 10; the nucleotide sequence encoding a VL CDR2 comprises the nucleotide sequence of SEQ ID NO: 12; the nucleotide sequence encoding a VL FR3 comprises the nucleotide sequence of SEQ ID NO: 14; the nucleotide sequence encoding a VL CDR3 comprises the nucleotide sequence of SEQ ID NO: 16; the nucleotide sequence encoding a VL FR4 comprises the nucleotide sequence of SEQ ID NO: 18; the nucleotide sequence encoding a VH FR1 comprises the nucleotide sequence of SEQ ID NO: 22; the nucleotide sequence encoding a VH CDR1 comprises the nucleotide sequence of SEQ ID NO: 44; the nucleotide sequence encoding a VH FR2 comprises the nucleotide sequence of SEQ ID NO: 26; the nucleotide sequence encoding a VH CDR2 comprises the nucleotide sequence of SEQ ID NO: 28; the nucleotide sequence encoding a VH FR3 comprises the nucleotide sequence of SEQ ID NO: 30; the nucleotide sequence encoding a VH CDR3 comprises the nucleotide sequence of SEQ ID NO: 48; the nucleotide sequence encoding a VH FR4 comprises the nucleotide sequence of SEQ ID NO: 34; and the nucleotide sequence encoding a scFv linker comprises the nucleotide sequence of SEQ ID NO: 36.

In one embodiment, the composition comprises a nucleic acid molecule encoding PSMAb. In one embodiment, the nucleic acid molecule comprises a nucleotide sequence that encodes a heavy chain comprising the amino acid sequence of SEQ ID NO: 68. In one embodiment, the nucleic acid molecule comprises a nucleotide sequence encoding a heavy chain having a signal peptide, wherein the heavy chain having a signal peptide comprises the amino acid sequence of SEQ ID NO: 53. In one embodiment, the nucleic acid molecule comprises a nucleotide sequence encoding heavy chain signal peptide comprising the amino acid sequence of SEQ ID NO: 55. In one embodiment, the nucleic acid molecule comprises a nucleotide sequence encoding a heavy chain variable region comprising the amino acid sequence of SEQ ID NO: 57. In one embodiment, the nucleic acid molecule comprises a nucleotide sequence encoding a heavy chain constant region of SEQ ID NO: 59. In one embodiment, the nucleic acid molecule comprises a nucleotide sequence encoding a light chain comprising the amino acid sequence of SEQ ID NO: 69. In one embodiment, the nucleic acid molecule comprises a nucleotide sequence encoding a light chain having a signal peptide, wherein the light chain having a signal peptide comprises the amino acid sequence of SEQ ID NO: 61. In one embodiment, the nucleic acid molecule comprises a nucleotide sequence encoding the light chain signal peptide comprising the amino acid sequence of SEQ ID NO: 63. In one embodiment, the nucleic acid molecule comprises a nucleotide sequence encoding a light chain variable region comprising the amino acid sequence of SEQ ID NO: 65. In one embodiment, the nucleic acid molecule comprises a nucleotide sequence encoding a light chain constant region of SEQ ID NO: 67. In one embodiment, the nucleotide sequence encoding a heavy chain having a signal peptide comprises the nucleotide sequence of SEQ ID NO: 52. In one embodiment, the nucleotide sequence encoding heavy chain signal peptide comprises the nucleotide sequence of SEQ ID NO: 54. In one embodiment, the nucleotide sequence encoding a heavy chain variable region comprises the nucleotide sequence of SEQ ID NO: 56. In one embodiment, the nucleotide sequence encoding a heavy chain constant region comprises the nucleotide sequence of SEQ ID NO: 58. In one embodiment, the nucleotide sequence encoding a light chain having a signal peptide comprises the nucleotide sequence of SEQ ID NO: 60. In one embodiment, the nucleotide sequence encoding the light chain signal peptide comprises the nucleotide sequence of SEQ ID NO: 62. In one embodiment, the nucleotide sequence encoding a light chain variable region comprises the nucleotide sequence of SEQ ID NO: 64. In one embodiment, the nucleotide sequence encoding a light chain constant region comprises the nucleotide sequence of SEQ ID NO: 66.

The present invention encompasses a nucleic acid molecule comprising a nucleotide sequence having homology to one or more nucleotide sequences described herein. For example, in certain embodiments, the nucleic acid molecule comprises a nucleotide sequence having 70% or more, 75% or more, 80% or more, 82% or more, 85% or more, 87% or more, 90% or more, 91% or more, 92% or more, 93% or more, 94% or more, 95% or more, 96% or more, 97% or more, 98% or more, 99% or more, or 99.5% or more homology to a nucleotide sequence described herein.

The invention further provides the methods to express or produce the recombinant protein of the anti-PSMA antibody or antibody fragment using various protein expression system.

In one embodiment, the invention also provides transformed cells and progeny thereof into which a nucleic acid molecule encoding an antibody or antigen-binding fragment, has been introduced by means of recombinant DNA techniques in vitro, ex vivo or in vivo. The transformed cells, eukaryotic or prokaryotic, may be used to produce recombinant antibody or antibody fragment for purification, or for in situ or secretory expression for various purposes, such as diagnosis or therapy for tumor. The transformed cells can be propagated and the introduced nucleic acid transcribed, or encoded protein expressed. It is understood that a progeny cell may not be identical to the parental cell, since there may be mutations that occur during replication. Transformed cells include but are not limited to prokaryotic and eukaryotic cells such as bacteria, fungi, plant, insect, and animal (e.g., mammalian, including human) cells. The cells may be present in culture, in a cell, tissue or organ ex vivo or present in a subject.

Typically cell transformation employs a vector. The term "vector," refers to, e.g., a plasmid, virus, such as a viral vector, or other vehicle known in the art that can be manipulated by insertion or incorporation of a nucleic acid, for genetic manipulation (i.e., "cloning vectors"), or can be used to transcribe or translate the inserted polynucleic acid (i.e., "expression vectors"). Such vectors are useful for introducing nucleic acids, including a nucleic acid that encodes an antibody operably linked with an expression control element, and expressing the encoded protein in vitro (e.g., in solution or in solid phase), in cells or in vivo.

In one embodiment, the expression vector(s) is(are) transferred to a host cell by conventional techniques and the transfected cells are then cultured by conventional techniques to produce an antibody or antigen-binding fragment of the invention. Thus, the invention includes host cells containing polynucleic acid(s) encoding an antibody of the invention (e.g., whole antibody, a heavy or light chain thereof, or portion thereof, or a single chain antibody, or a fragment or variant thereof), operably linked to a heterologous promoter. In other embodiments, for the expression of entire antibody molecules, vectors encoding both the heavy and light chains are co-expressed in the host cell for expression of the entire immunoglobulin molecule.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleic acid coding sequences, express an antibody molecule of the invention in situ. These include, but are not limited to, bacteriophage particles engineered to express antibody fragments or variants thereof (single chain antibodies), microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter; CMV promoter or EF1α promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (11990); B ebbington et al., Bio/Techniques 10:169 (1992); Keen and Hale, Cytotechnology 18:207 (1996)). These references are incorporated in their entireties by reference herein.

A vector used to transform a cell or a host-expression vector generally contains at least an origin of replication for propagation in the cell. Control elements, including expression control elements as set forth herein, present within a vector, are included to facilitate transcription and translation. The term "expression control element" is intended to include, at a minimum, one or more components whose presence can influence expression, and can include components other than or in addition to promoters or enhancers, for example, leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of a gene of interest, stop codons, etc.

Vectors can include a selection marker. As is known in the art, "selection marker" means a gene that allows for the selection of cells containing the gene. "Positive selection" refers to a process whereby only cells that contain the selection marker will survive upon exposure to the positive selection. Drug resistance is one example of a positive selection marker; cells containing the marker will survive in culture medium containing the selection drug, and cells which do not contain the marker will die. Such markers include drug resistance genes such as neo, which confers resistance to G418, hygr, which confers resistance to hygromycin, or puro which confers resistance to puromycin, among others. Other positive selection marker genes include genes that allow identification or screening of cells containing the marker. These genes include genes for fluorescent proteins (GFP), the lacZ gene, the alkaline phosphatase gene, and surface markers such as CD8, among others.

Vectors can contain negative selection markers. "Negative selection" refers to a process whereby cells containing a negative selection marker are killed upon exposure to an appropriate negative selection agent. For example, cells which contain the herpes simplex virus-thymidine kinase (HSV-tk) gene (Wigler et al., Cell 11:223 (1977)) are sensitive to the drug gancyclovir (GANC). Similarly, the gpt gene renders cells sensitive to 6-thioxanthine.

Mammalian expression systems further include vectors specifically designed for in vivo and ex vivo expression. Such systems include adeno-associated virus (AAV) vectors (U.S. Pat. No. 5,604,090). AAV vectors have previously been shown to provide expression of Factor IX in humans and in mice at levels sufficient for therapeutic benefit (Kay et al., Nat. Genet. 24:257 (2000); Nakai et al., Blood 91:4600 (1998)). Adenoviral vectors (U.S. Pat. Nos. 5,700,470, 5,731,172 and 5,928,944), herpes simplex virus vectors (U.S. Pat. No. 5,501,979) and retroviral (e.g., lentivirus vectors are useful for infecting dividing as well as non-dividing cells and foamy virues) vectors (U.S. Pat. Nos. 5,624,820, 5,693,508, 5,665,577, 6,013,516 and 5,674,703 and WIPO publications WO92/05266 and WO92/14829) and papilloma virus vectors (e.g., human and bovine papilloma virus) have all been employed in gene therapy (U.S. Pat. No. 5,719,054). Vectors also include cytomegalovirus (CMV) based vectors (U.S. Pat. No. 5,561,063). Vectors that efficiently deliver genes to cells of the intestinal tract have been developed and also may be used (see, e.g., U.S. Pat. Nos. 5,821,235, 5,786,340 and 6,110,456). In yeast, vectors that facilitate integration of foreign nucleic acid sequences into a chromosome, via homologous recombination, for example, are known in the art and can be used. Yeast artificial chromosomes (YAC) are typically used when the inserted nucleic acids are too large for more conventional vectors (e.g., greater than about 12 kb).

In one embodiment, phagemid vectors for use in the invention include any available in the art suitable for the production of the antibodies/antibody templates/FR libraries of the present invention and include phagemid vectors pCB04, pIT1, pIT2, CANTAB 6, pComb 3 HS. Filamentous vectors and methods of phagemid construction are described in, for example, U.S. Pat. Nos. 6,054,312 and 6,803,230, each incorporated herein by reference. Bacteriophage display systems involving non-filamentous bacteriophage vectors known as cytoplasmic bacteriophage or lytic phage can also be utilized as described in for example, U.S. Pat. No. 5,766,905, incorporated herein by reference.

Suitable bacterial expression constructs for use with the present invention include, but are not limited to the pCAL, pUC, pET, pETBlue™ (Novagen), pBAD, pLEX, pTrcHis2, pSE280, pSE380, pSE420 (Invitrogen), pKK223-2 (Clontech), pTrc99A, pKK223-3, pRIT2T, pMC1871, pEZZ 18 (Pharmacia), pBluescript II SK (Stratagene), pALTER-Ex1, pALTER-Ex2, pGEMEX (Promega), pFivE (MBI), pQE (Qiagen) commercially available expression constructs, and their derivatives, and others known in the art. In some embodiments of the present invention the construct may also include, a virus, a plasmid, a bacmid, a phagemid, a cosmid, or a bacteriophage.

The use of liposomes for introducing various compositions into cells, including nucleic acids, is known to those skilled in the art (see, e.g., U.S. Pat. Nos. 4,844,904, 5,000,959, 4,863,740, and 4,975,282). A carrier comprising a natural polymer, or a derivative or a hydrolysate of a natural polymer, described in WO 94/20078 and U.S. Pat. No. 6,096,291, is suitable for mucosal delivery of molecules, such as polypeptides and polynucleic acids. piperazine based amphilic cationic lipids useful for gene therapy also are known (see, e.g., U.S. Pat. No. 5,861,397). Cationic lipid systems also are known (see, e.g., U.S. Pat. No. 5,459,127). Accordingly, viral and non-viral vector means of delivery into cells or tissue, in vitro, in vivo and ex vivo are included.

In one embodiment, nucleic acid sequences can be "operably linked", i.e., positioned, to ensure the functioning of an expression control sequence. These expression constructs are typically replicable in the cells either as episomes or as integral parts of the cell's chromosomal DNA, and may contain appropriate origins of replication for the respective prokaryotic strain employed for expression. Commonly, expression constructs contain selection markers, such as for example, tetracycline resistance, ampicillin resistance, kanamycin resistance or chlormaphenicol resistance, facilitating detection and/or selection of those bacterial cells transformed with the desired nucleic acid sequences (see, e.g., U.S. Pat. No. 4,704,362). These markers, however, are not exclusionary, and numerous others may be employed, as known to those skilled in the art. In another embodiment of the present invention expression constructs contain both positive and negative selection markers.

Similarly, reporter genes may be incorporated within expression constructs to facilitate identification of transcribed products. Accordingly, in one embodiment of the present invention, reporter genes utilized are selected from the group consisting of β-galactosidase, chloramphenicol acetyl transferase, luciferase and a fluorescent protein.

Prokaryotic promoter sequences regulate expression of the encoded polynucleic acid sequences, and in some embodiments of the present invention, are operably linked to polynucleic acids encoding the polypeptides of this invention. In additional embodiments of the present invention, these promoters are either constitutive or inducible, and provide a means of high and low levels of expression of the polypeptides of this invention, and in some embodiments, for regulated expression of multiple polypeptides of the invention, which in some embodiments are expressed as a fusion protein.

Many well-known bacterial promoters, including the T7 promoter system, the lactose promoter system, typtophan (Trp) promoter system, Trc/Tac Promoter Systems, beta-lactamase promoter system, tetA Promoter systems, arabinose regulated promoter system, Phage T5 Promoter, or a promoter system from phage lambda, may be employed, and others, as well, and comprise embodiments of the present invention. The promoters will typically control expression, optionally with an operator sequence and may include ribosome binding site sequences for example, for initiating and completing transcription and translation. According to additional embodiments, the vector may also contain expression control sequences, enhancers that may regulate the transcriptional activity of the promoter, appropriate restriction sites to facilitate cloning of inserts adjacent to the promoter and other necessary information processing sites, such as RNA splice sites, polyadenylation sites and transcription termination sequences as well as any other sequence which may facilitate the expression of the inserted nucleic acid.

In another embodiment, the present invention comprises methods of use of a polynucleic acid, vector, antibodies and/or fragment thereof as herein described and/or compositions comprising the same in treating, inhibiting or preventing.

Detection of PSMA

It is to be understood by a skilled artisan that the antibody, antigen-binding fragments, or compositions provided herein can be used in diagnostic or therapeutic procedures.

In one embodiment, provided herein is a method of diagnosing the presence of a tumor or a cancer growth in a subject. In another embodiment, the method comprises sampling a tissue sample isolated from the subject with a composition comprising the antibody or antigen-binding fragment provided herein, whereby specific binding of said antibody or antigen-binding fragment to the tissue sample is indicative of the presence of a tumor or cancer growth in the subject. In another embodiment, the method further comprises detecting a secondary reagent that specifically binds to the antibody or antigen-binding fragment but does not antagonize binding of the antibody or antigen-binding fragment to its target. In another embodiment, the "secondary reagent" is a photoactivatable agent, a fluorophore, a radioisotope, a bioluminescent protein, a bioluminescent peptide, a fluorescent tag, a fluorescent protein, or a fluorescent peptide.

In one embodiment, the term "cancer" and "cancerous" refer to or describe, in one embodiment, the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

In one embodiment, the term "cancer" includes but is not limited to, ovarian cancers, breast cancers, glioblastoma, gastrointestinal cancers. In another embodiment, the cancer is prostate cancer.

In another embodiment, "sampling" comprises the step of testing or analyzing the sample using a detection assay that enables the detection of a secondary reagent that is complexed with or conjugated to the antibody or antigen-binding fragment and emits a detectable "signal" when the antibody or antigen-binding fragment is specifically bound to the target. In another embodiment, the detection is achieved using assays routinely used in the art such as, but not limited to immunological assays (for e g, immunohistochemistry, ELISA, etc.) or microscopic imaging.

In one embodiment, the term "labeled" refers to antibodies of the invention having one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and calorimetric dyes, or molecules such as biotin that enable other labeling methods. In one embodiment, antibodies of the invention are labeled with biotin. In other related embodiments, biotinylated antibodies of the invention may be used, for example, as an imaging agent or as a means of identifying one or more ligand molecules. In another embodiment, the label can be a nanoparticle that can be detected or visualized once bound to the antibody or antigen-binding fragment. Labels may be incorporated into the compound at any position and may be incorporated in vitro or in vivo during protein expression.

In one embodiment, the conjugate formed by the antibody or antigen-binding fragment and the secondary reagent provided herein are used for various applications such as, but not limited to, flow cytometry, ELISA, Western blotting, immunohistochemistry, membrane assays, and diagnostic and therapeutic methods as further described herein or as routinely applied in the art.

Imaging of Tumors with Abnormal PSMA Expression

In one embodiment, the composition of the present invention is administered to a subject having a disease involving inappropriate expression of a target antigen, a protein or other molecule. For example, in one embodiment, the composition comprising an antibody or antibody fragment that binds to PSMA is administered to detect the presence, abundance, location, or combination thereof of PSMA in the subject. Within the scope of the present invention this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the antibodies of the present invention.

In one embodiment, antibody or antibody fragment of the present invention binds the antigen expressed on tumor cells, such as prostate cancer cells when administrated in a subject; in another embodiment, antibody or antibody fragment of the present invention administrated in a subject binds the antigen expressed on neovasculature of solid tumors, such as the tumors with PSMA positive neovasculature, including but not limited to lung cancer, liver cancer, pancreas cancer, colon cancer, gastric cancer, breast cancer, ovarian cancer, kidney cancer, prostate cancer, bladder cancer, melanoma, glioma etc.

In one embodiment, provided herein is a method of imaging a PSMA-containing tumor. In another embodiment, the method comprises the step of applying the antibody or antigen-binding fragment provided herein that is operably linked to a secondary reagent. In another embodiment, the prostate or other types solid tumor could be visualized once the antibody or antigen-binding fragment has bound its target. In yet another embodiment, the secondary reagent is a photoactivatable agent, a fluorophore, a radioisotope, a bioluminescent protein, a bioluminescent peptide, a fluorescent tag, a fluorescent protein, or a fluorescent peptide. Non-limiting examples of secondary reagents are provided below.

In one embodiment, the detectable label or secondary reagent attached thereto, include labels such as, but not limited to a fluorescent label (e.g., fluorescein, isothiocyanate (FITC), a cyanine dye, etc.), an affinity label (e.g., biotin, avidin, protein A, etc.), an enzymatic label (e.g., horseradish peroxidase or alkaline phosphatase), or an isotopic label (e.g., 124I) or any other such detectable moiety to allow for detection and isolation of the antibody.

Detection methods for identification of binding species within the population of altered variable regions can be direct or indirect and can include, for example, the measurement of light emission, radioisotopes, calorimetric dyes and fluorochromes. Direct detection includes methods that operate without intermediates or secondary measuring procedures to assess the amount of bound antigen or ligand. Such methods generally employ ligands that are themselves labeled by, for example, radioactive, light emitting or fluorescent moieties. In contrast, indirect detection includes methods that operate through an intermediate or secondary measuring procedure. These methods generally employ molecules that specifically react with the antigen or ligand and can themselves be directly labeled or detected by a secondary reagent. For example, an antibody specific for a ligand can be detected using a secondary antibody capable of interacting with the first antibody specific for the ligand, again using the detection methods described above for direct detection. Indirect methods can additionally employ detection by enzymatic labels. Moreover, for the specific example of screening for catalytic antibodies, the disappearance of a substrate or the appearance of a product can be used as an indirect measure of binding affinity or catalytic activity.

In specific embodiments, antibodies of the invention are labeled with near infrared dye. For example, antibodies of the invention may be labeled with IRDye800CW or Indocyanine Green (ICG).

In specific embodiments, antibodies of the invention are attached to macrocyclic chelators useful for conjugating radiometal ions, including but not limited to, 111In, 177Lu, 90Y, 166Ho, 153Sm, 215Bi and 225Ac to polypeptides. In a preferred embodiment, the radiometal ion associated with the macrocyclic chelators attached to antibodies of the invention is 111In. In another preferred embodiment, the radiometal ion associated with the macrocyclic chelator attached to antibodies polypeptides of the invention is 90Y. In specific embodiments, the macrocyclic chelator is 1,4,7,10-tetraazacyclododecane-N,N',N'',N'''-tetraacetic acid (DOTA). In specific embodiments, the macrocyclic chelator is .quadrature.-(5-isothiocyanato-2-methoxyphenyl)-1,4,7,10-tetraaza-cyclodo-decane-1,4,7,10-tetraacetic acid. In other specific embodiments, the DOTA is attached to the antibody of the invention via a linker molecule. Examples of linker molecules useful for conjugating a macrocyclic chelator such as DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

Methods of Treatment

The present invention also provides a method of treating a PSMA-expression cancer in a subject comprising the step of targeting said tumor cell with said antibody or antigen binding fragment.

In certain embodiments, the method comprises administering to the subject a composition comprising an antibody or antibody fragment. In one embodiment, the antibody or antibody fragment is operably linked to a biologically active agent or a combination of such agents, wherein said agent is a toxin, a radioisotope, a nanoparticle or a bio-active peptide.

In one embodiment, the invention provides a method of treating a solid tumor with abnormal PSMA expression, such as prostate cancer or solid tumors with high PSMA expression in neovasculature, in a subject comprising the step of targeting PSMA high expression cells with said antibody or antigen binding fragment. In certain embodiments, the method comprises administering to a subject having a tumor associated with high PSMA expression, a composition comprising an antibody or antibody fragment. In one embodiment, the antibody or antibody fragment is operably linked to a biologically active agent or a combination of such agents, wherein said agent is a toxin, a radioisotope, a nanoparticle or a bio-active peptide. These tumors include but not limited to prostate cancer, lung cancer, liver cancer, pancreas cancer, colon cancer, gastric cancer, breast cancer, ovarian cancer, kidney cancer, prostate cancer, bladder cancer, melanoma, glioma etc.

In one embodiment, provided herein is a method of inhibiting or suppressing a tumor in a subject. In another embodiment, the method comprises the step of administering an effective amount of the antibody or antigen-binding fragment of the present invention.

In another embodiment, provided herein is a method of delaying progression of a solid tumor in a subject. In yet another embodiment, the method comprises administering to the subject an effective amount of the antibody or antigen-binding fragment thereof provided herein. In another embodiment, the subject mounts an immune response against a vasculature of the solid tumor, thereby delaying progression of the solid tumor in the subject.

In one embodiment, the term "operably linked" refers to the positioning/linking of the two or more molecules or sequences in such a manner as to ensure the proper function or expression of the molecule and sequence.

In one embodiment, the term "therapeutically effective amount" refers to an amount that provides a therapeutic effect for a given condition and administration regimen. In the present invention, the therapeutic effect is the prevention or inhibition of tumor growth, infiltration, spread, metastasis or relapse, or preferably reduction of tumor burden, or the improvement of patient outcome.

In one embodiment, the term "preventing, or treating" refers to any one or more of the following: delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics. In one embodiment, "treating" refers to both therapeutic treatment and prophylactic or preventive measures, wherein the object is to prevent or lessen the targeted pathologic condition or disorder as described hereinabove.

In another embodiment, "symptoms" are manifestation of a disease or pathological condition as described hereinabove.

In another embodiment, the methods provided herein further comprise proteolytic inhibitors, pharmaceutical carriers, diluents, and adjuvants.

In one embodiment the compositions of this invention comprise a polypeptide, antibody, or antigen-binding fragment of this invention, alone or in some embodiments, in combination with a second pharmaceutically active agent. In one embodiment, the term "pharmaceutically active agent" refers to any medicament which satisfies the indicated purpose. In some embodiments, the pharmaceutically active agent of this invention includes, but is not limited to a chemotherapeutic drug, radio therapy drug, angiogenesis inhibitor, tumor imaging probe, immune modulator or any other tumor therapy and/or imaging drug/agent, and the like.

In another embodiment, provided herein is a method of delivering a biologically active agent and the antibody or antigen-binding fragment of the present invention for the treatment of a tumor in a subject. In another embodiment, the method comprises the step of concomitantly but individually administering the biologically active agent and the antibody or antigen-binding fragment. In another embodiment, the method comprises the step of separately administering the biologically active agent and the antibody or antigen-binding fragment.

In one embodiment, the antibody or antigen-binding fragment provided herein are themselves "biologically active," meaning they are able to exert the biological action or an enhanced action of their corresponding parental antibodies even after modification, in particular in binding to the target antigen, inhibiting binding of ligands to receptors, further in terms of modulation, in particular inhibition of antigen-mediated signal transduction and prophylaxis or therapy of antigen-mediated diseases. The term "biologically active", when used in reference to any of the biologically active agents described herein also refers to the agent's ability to modulate the immune response in a manner that can lead to a preventive, diagnostic, or therapeutic effect as will be understood by a skilled artisan. In some embodiments, agents that are used to achieve this biological activity include but are not limited to a cytokine, an enzyme, a chemokine, a radioisotope, an enzymatically active toxin, a therapeutic nano particle or a chemotherapeutic agent, as will be understood by a skilled artisan.

In an alternate embodiment, the polypeptides of antibodies are conjugated or operably linked so as to function in their intended purpose to an enzyme in order to employ Antibody Dependent Enzyme Mediated Prodrug Therapy (ADEPT). ADEPT may be used by conjugating or operably linking the antibody or Fc fusion to a prodrug-activating enzyme that converts a prodrug (e.g. a peptidyl chemotherapeutic agent) to an active anti-cancer drug. The enzyme component of the immunoconjugate useful for ADEPT includes any enzyme capable of acting on a prodrug in such a way so as to convert it into its more active, cytotoxic form. Other additional modifications of the modified molecules provided herein are contemplated herein. For example, the polypeptide/antibody may be linked to one of a variety of nonproteinaceous polymers, e.g., polyethylene glycol (PEG), polypropylene glycol, polyoxyalkylenes, or copolymers of polyethylene glycol and polypropylene glycol.

In another embodiment, the antibody/polypeptide provided herein is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but are not limited to: non-steroidal anti-inflammatory drugs (NSAIDs) such as aspirin, ibuprofen, celecoxib, diclofenac, etodolac, fenoprofen, indomethacin, ketorolac, oxaprozin, nabumentone, sulindac, tolmentin, rofecoxib, naproxen, ketoprofen, and nabumetone; steroids (e.g. glucocorticoids, dexamethasone, cortisone, hydroxycortisone, methylprednisolone, prednisone, prednisolone, trimcinolone, azulfidineicosanoids such as prostaglandins, thromboxanes, and leukotrienes; as well as topical steroids such as anthralin, calcipotriene, clobetasol, and tazarotene); cytokines such as TGFb, IFNa, IFNb, IFNg, IL-2, IL-4, IL-10; cytokine, chemokine, or receptor antagonists including antibodies, soluble receptors, and receptor-Fc fusions against BATF, B7, CCR2, CCR5, CD2, CD3, CD4, CD6, CD7, CD8, CD11, CD14, CD15, CD17, CD18, CD2O, CD23, CD28, CD40, CD40L, CD44, CD45, CD52, CD64, CD80, CD86, CD147, CD152, complement factors (C5, D) CTLA4, eotaxin, Fas, ICAM, ICOS, IFN-α IFN-β, IFN-γ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGF-β, TNF-α, TNF-β, TNF-R1, T-cell receptor, including Enbrel®. (etanercept), Humira®. (adalimumab), Remicade® (infliximab), PD1 antibodies (OPDIVO® (nivolumab), KEYTRUDA® (pembrolizumab)) or PD-L1 antibodies (durvalumab, MPDL3280A); heterologous anti-lymphocyte globulin; other immunomodulatory molecules such as 2-amino-6-aryl-5 substituted pyrimidines, anti-idiotypic antibodies for MHC binding peptides and MHC fragments, azathioprine, brequinar, bromocryptine, cyclophosphamide, cyclosporine A, D-penicillamine, deoxyspergualin, FK506, glutaraldehyde, gold, hydroxychloroquine, leflunomide, malononitriloamides (e.g. leflunomide), methotrexate, minocycline, mizoribine, mycophenolate mofetil, rapamycin, and sulfasasazine.

In an alternate embodiment, antibodies of the present invention are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO);

osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

A chemotherapeutic or other cytotoxic agent may be administered as a prodrug. The term "prodrug" refers to a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; and Stella et al., "Prodrugs: A Chemical Approach to Targeted Drug Delivery," Directed Drug Delivery, Borchardt et al., (ed.): 247-267, Humana Press, 1985. The prodrugs that may find use with the compositions and methods as provided herein include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies/polypeptides of the compositions and methods provided herein include but are not limited to any of the aforementioned chemotherapeutic agents.

In some embodiments, any combination of the antibody/polypeptide with the biological active agents specified above, i.e., a cytokine, an enzyme, a chemokine, a radioisotope, an enzymatically active toxin, or a chemotherapeutic agent can be applied. In another embodiment, the antibody/polypeptide can be operably-linked with the biologically active agent and used in the methods described herein or antibody/polypeptide provided herein can merely be used in combination with the biologically active agents, in a manner in which both are administered separately (i.e.—not conjugated) to achieve the desired preventive, diagnostic, or therapeutic effect.

PSMA-Targeted Antibody Drug Conjugate

In one embodiment, the invention provides antibody-drug conjugates (ADCs), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In one specific embodiment, the drugs include but not limited to tubulin inhibitor and DNA cleavage reagent, such as Maytansinoids, Auristatins, Dolastatins and Calicheamicin. In another embodiment, the invention further provides methods of using the ADCs. In one aspect, an ADC comprises any of the above PSMA antibodies or antibody fragments covalently attached to a cytotoxic agent or a detectable agent.

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical applications, A. Pinchera et al. (ed.$), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may affect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Examples of antibody drug conjugates are, ZEVALIN® (ibritumomab tiuxetan, Biogen/Idec) which is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69).

Additionally, MYLOTARG™ (gemtuzumab ozogamicin, Wyeth Pharmaceuticals), an antibody drug conjugate composed of a human CD33 antibody linked to calicheamicin, was approved in 2000 for the treatment of acute myeloid leukemia by injection (Drugs of the Future (2000) 25(7): 686; U.S. Pat. Nos. 4,970,198; 5,079,233; 5,585,089; 5,606,040; 5,693,762; 5,739,116; 5,767,285; 5,773,001).

Finally, the auristatin peptides, such as monomethyl auristatin E (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784). The cAC10 is under therapeutic development.

Further, chemotherapeutic agents useful in the generation of ADCs are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include 212Bi, 131I, 131In, 90Y, and 186Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987) Science, 238:1098. Carbon-14-labeled 1-isothiocyanatobenzyl-3-methyldiethylene triaminepentaacetic acid (MX-DTPA) is an exemplary chelating agent for conjugation of radionucleic acid to the antibody (WO94/11026).

Conjugates of an antibody and one or more small molecule toxins, such as a calicheamicin, maytansinoids, dolastatins, auristatins, a trichothecene, and CC1065, and the derivatives of these toxins that have toxin activity, are also contemplated herein.

Maytansinoids:

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/-C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions Exemplary maytansinoid drug moieties also include those having modifications such as: C-9-SH (U.S. Pat. No. 4,424,219) (prepared by the reaction of maytansinol with H2S or P2S5); C-14-alkoxymethyl (demethoxy/CH2OR)(U.S. Pat. No. 4,331,598); C-14-hydroxymethyl or acyloxymethyl (CH2OH or CH2OAc) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol). ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×10$^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

An exemplary maytansinoids embodiment is DM1 (wherein the wavy line indicates the covalent attachment to a linker (L) of an antibody drug conjugate).

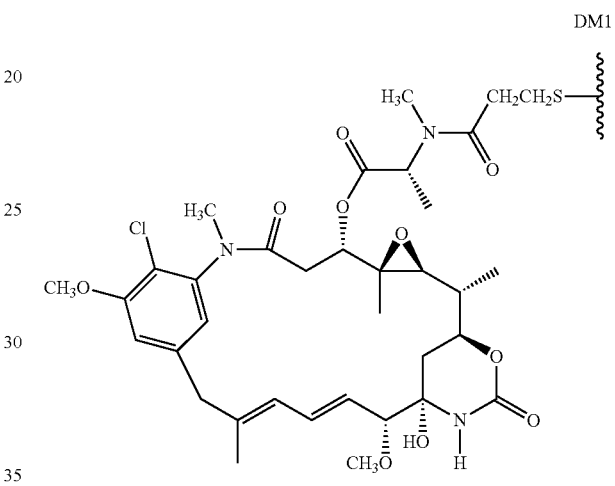

DM1

Auristatins and Dolastatins:

In some embodiments, the ADC comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238649, the disclosure of which is expressly incorporated by reference in its entirety.

ADC using MMAE and MMAF with various linker components have been disclosed (US 2005/0238649, U.S. Ser. No. 08/968,742).

An exemplary auristatin embodiment is MMAE (wherein the wavy line indicates the covalent attachment to a linker (L) of an antibody drug conjugate).

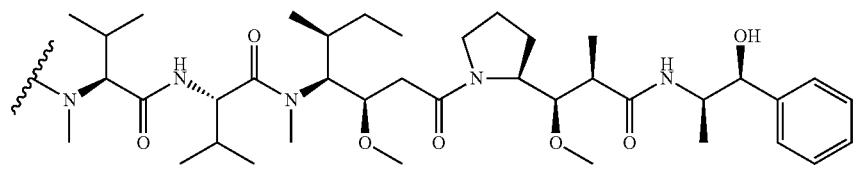 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

Another exemplary auristatin embodiment is MMAF, wherein the wavy line indicates the covalent attachment to a linker (L) of an antibody drug conjugate (US 2005/0238649):

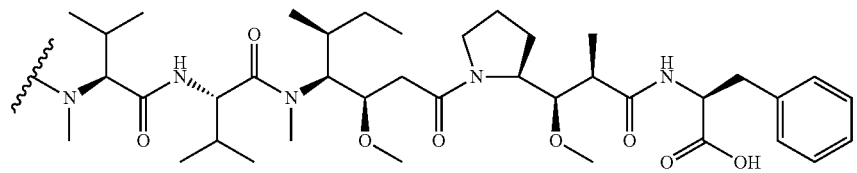 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lake, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

Calicheamicin:

In other embodiments, the ADC comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, γ1 I, α2 I, α3 I, N-acetyl-γ1 I, PSAG and θ1 I (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents:

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

PSMA-Targeted Antibody Drug Conjugate Compounds:

The present invention provides, inter alia, antibody-drug conjugate compounds for targeted delivery of drugs. The inventors have made the discovery that the antibody-drug conjugate compounds have potent cytotoxic and/or cyto-static activity against cells expressing PSMA. The antibody-drug conjugate compounds comprise an Antibody unit covalently linked to at least one Drug unit. The Drug units can be covalently linked directly or via a Linker unit (-LU-).

In some embodiments, the antibody drug conjugate compound has the following formula:

Ab-(LU-D)p or a pharmaceutically acceptable salt or solvate thereof; wherein:
Ab is the Antibody unit, e.g., gy1 or its mutated variants derived full antibody or antibody fragment of the present invention—such as PSMAb, and
(LU-D) is a Linker unit-Drug unit moiety, wherein:
LU- is a Linker unit, and
D is a drug unit having cytostatic or cytotoxic activity against a target cell; and
p is an integer from 1 to 20.

In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 10, 2 to 9, 2 to 8, 2 to 7, 2 to 6, 2 to 5, 2 to 4 or 2 to 3. In other embodiments, p is 1, 2, 3, 4, 5 or 6. In some embodiments, p is 2 or 4.

In some embodiments, the antibody drug conjugate compound has the following formula:

Ab-($A_a$-$W_w$—$Y_y$-D)$_p$ or a pharmaceutically acceptable salt or solvate thereof, wherein:
Ab is the Antibody unit, e.g., gy1 or its mutated variants derived full antibody or antibody fragment of the present invention, such as PSMAb; and
$A_a$-$W_w$—$Y_y$— is a Linker unit (LU), wherein:
A- is a Stretcher unit,
a is 0 or 1,
each —W— is independently an Amino Acid unit,
w is an integer ranging from 0 to 12,
—Y— is a self-immolative spacer unit,
y is 0, 1 or 2;
-D is a drug units having cytostatic or cytotoxic activity against the target cell; and
p is an integer from 1 to 20.

In some embodiments, a is 0 or 1, w is 0 or 1, and y is 0, 1 or 2. In some embodiments, a is 0 or 1, w is 0 or 1, and y is 0 or 1. In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 8, 2 to 7, 2 to 6, 2 to 5, 2 to 4 or 2 to 3. In other embodiments, p is 1, 2, 3, 4, 5 or 6. In some embodiments, p is 2 or 4. In some embodiments, when w is not zero, y is 1 or 2. In some embodiments, when w is 1 to 12, y is 1 or 2. In some embodiments, w is 2 to 12 and y is 1 or 2. In some embodiments, a is 1 and w and y are 0.

For compositions comprising a plurality antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined. In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is from 2 to 8.

The generation of Antibody-drug conjugate compounds can be accomplished by any technique known to the skilled artisan. Briefly, the Antibody-drug conjugate compounds comprise gy1 or its mutated variants derived full antibody or antibody fragment of the present invention as the Antibody unit, a drug, and optionally a linker that joins the drug and the binding agent. In a preferred embodiment, the Antibody is antibody or antibody fragments derived from gy1 or its variants with point mutations, as described elsewhere herein. A number of different reactions are available for covalent attachment of drugs and/or linkers to binding agents. This is often accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the gy1 or its variants derived full antibody or antibody fragment under appropriate conditions.

PSMA-Targeted CAR-T or CAR-NK

Recent developments using chimeric antigen receptor (CAR) modified autologous T cell (CART) therapy, which relies on redirecting T cells to a suitable cell-surface molecule on cancer cells such as B cell malignancies, show promising results in harnessing the power of the immune system to treat B cell malignancies and other cancers (see, e.g., Sadelain et al., Cancer Discovery 3:388-398 (2013)). The clinical results of the murine derived CART19 (i.e., "CTL019") have shown promise in establishing complete remissions in patients suffering with CLL as well as in childhood ALL (see, e.g., Kalos et al., Sci Transl Med 3:95ra73 (2011), Porter et al., NEJM 365:725-733 (2011), Grupp et al., NEJM 368:1509-1518 (2013)). Besides the ability for the chimeric antigen receptor on the genetically modified T cells to recognize and destroy the targeted cells, a successful therapeutic T cell therapy needs to have the ability to proliferate and persist over time, and to further monitor for leukemic cell escapees. The variable quality of T cells whether it's a result of energy, suppression or exhaustion will have effects on CAR-transformed T cells' performance but for which skilled practitioners have limited control over at this time. To be effective, CAR transformed patient T cells need to persist and maintain the ability to proliferate in response to the CAR's antigen. It has been shown that ALL patient T cells perform can do this with CART19 comprising a murine scFv (see, e.g., Grupp et al., NEJM 368:1509-1518 (2013)).

The invention addresses controlling an immune response in patients by providing fully human antibody fragments (e.g., scFv) that bind PMSA integrated into a Chimeric Antigen Receptor (CAR) construct that will redirect the engineered T cell to recognize and kill PSMA positive tumor cells.

Accordingly, in one aspect, the invention pertains to an isolated nucleic acid molecule encoding a chimeric antigen receptor (CAR), wherein the CAR comprises an antibody or antibody fragment which includes a PSMA binding domain, a transmembrane domain, and an intracellular signaling domain (e.g., an intracellular signaling domain comprising a costimulatory domain and/or a primary signaling domain). In one embodiment, the CAR comprises an antibody or antibody fragment which includes a fully human anti-PSMA binding domain described herein, a transmembrane domain described herein, and an intracellular signaling domain described herein (e.g., an intracellular signaling domain comprising a costimulatory domain and/or a primary signaling domain).

In one embodiment, the encoded human anti-PSMA binding domain comprises one or more (e.g., all three) light chain complementary determining region 1 (LC CDR1), light chain complementary determining region 2 (LC CDR2), and light chain complementary determining region 3 (LC CDR3) of a fully human anti-PSMA binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a fully human anti-PSMA binding domain described herein, e.g., a fully human anti-PSMA binding domain comprising one or more, e.g., all three, LC CDRs and/or one or more, e.g., all three, HC CDRs. In one embodiment, the encoded light chain variable region comprises one, two, three or all four framework regions described herein. In one embodiment, the encoded heavy chain variable region comprises one, two, three or all four framework regions described below. In one embodiment, the encoded fully human anti-PSMA binding domain comprises a human light chain variable region described below and/or a human heavy chain variable region described below. In one embodiment, the encoded anti-PSMA binding domain is a scFv comprising a light chain and a heavy chain of an amino acid sequence described below. In an embodiment, the anti-PSMA binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided below, or a sequence with 95-99% identity with an amino acid sequence described below; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided below, or a sequence with 95-99% identity to an amino acid sequence described below. In one embodiment, the encoded human anti-PSMA binding domain comprises a sequence described below, or a sequence with 95-99% identify thereof. In one embodiment, the nucleic acid sequence encoding the human anti-PSMA binding domain comprises a sequence described below, or a sequence with 95-99% identify thereof. In one embodiment, the encoded human anti-PSMA binding domain is a scFv, and a light chain variable region is attached to a heavy chain variable region via a linker, e.g., a linker described herein. In one embodiment, the encoded human anti-PSMA binding domain includes a (Gly4-Ser)n linker, wherein n is 1, 2, 3, 4, 5, or 6, preferably 3 or 4. In another embodiment, the encoded human anti-PSMA binding domain contains a linker sequence as described in SEQ ID NO: 37. The light chain variable region and heavy chain variable region of a scFv can be, e.g., in any of the following orientations: light chain variable region-linker-heavy chain variable region or heavy chain variable region-linker-light chain variable region.

In certain embodiments, the anti-PSMA binding domain comprises an antibody or antibody fragment described elsewhere herein. For example, in certain embodiments, the anti-PSMA binding domain comprises gy1, gy1-st, gy1-2, gy1-3 or PSMAb, as described elsewhere herein.

For example, in certain embodiments, the anti-PSMA binding domain comprises one or more of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO:67, SEQ ID NO: 68, and SEQ ID NO: 69.

For example, in certain embodiments, the anti-PSMA binding domain is encoded by one or more nucleotide sequences of SEQ ID NO: 2, SEQ ID NO: 4, SEQ ID NO: 6, SEQ ID NO: 8, SEQ ID NO: 10 SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, and SEQ ID NO:66.

In one embodiment, the encoded transmembrane domain is a transmembrane domain of a protein selected from the group consisting of the alpha, beta or zeta chain of the T-cell receptor, CD27, CD28, CD3 epsilon, CD45, CD4, CD5, CD8, CD9, CD16, CD22, CD33, CD37, CD64, CD80, CD86, CD134, CD137 and CD154. In one embodiment, the encoded transmembrane domain comprises the amino acid sequence of SEQ ID NO: 75. In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO:75, or a sequence with 95-99% identity to an amino acid sequence of SEQ ID NO:75. In one embodiment, the nucleic acid sequence encoding the transmembrane domain comprises a sequence of SEQ ID NO:74, or a sequence with 95-99% identify thereof.

In one embodiment, the encoded anti-PSMA binding domain is connected to the transmembrane domain by a hinge region, e.g., a hinge region described herein. In one embodiment, the encoded hinge region comprises the amino acid sequence of SEQ ID NO:73, or a sequence with 95-99% identity thereof. In one embodiment, the nucleic acid sequence encoding the hinge region comprises a sequence of SEQ ID NO:72, or a sequence with 95-99% identify thereof.

In one embodiment, the nucleic acid molecule further comprises a sequence encoding a costimulatory domain. In one embodiment, the costimulatory domain is a functional signaling domain obtained from a protein selected from the group consisting of OX40, CD2, CD27, CD28, CDS, ICAM-1, LFA-1 (CD11a/CD18), ICOS (CD278), and 4-1BB (CD137). In one embodiment, the encoded costimulatory domain comprises a sequence of SEQ ID NO:77. In one embodiment, the encoded costimulatory domain comprises an amino acid sequence having at least one, two or three modifications (e.g., substitutions) but not more than 20, 10 or 5 modifications (e.g., substitutions) of an amino acid sequence of SEQ ID NO:77, or a sequence with 95-99% identity to an amino acid sequence of SEQ ID NO:77. In one embodiment, the nucleic acid sequence encoding the costimulatory domain comprises a sequence of SEQ ID NO:76, or a sequence with 95-99% identify thereof. In one embodiment, the isolated nucleic acid molecule further comprises a sequence encoding an intracellular signaling domain, e.g., an intracellular signaling domain described herein. In one embodiment, the encoded intracellular signaling domain comprises a functional signaling domain of 4-1BB and/or a functional signaling domain of CD3 zeta. In one embodiment, the encoded functional CD3 zeta intracellular signal domain comprises a sequence of SEQ ID NO: 79. In one embodiment, the encoded costimulatory domain comprises an amino acid sequence having at least one, two or three modifications (e.g., substitutions) but not more than 20, 10 or 5 modifications (e.g., substitutions) of an amino acid sequence of SEQ ID NO:79, or a sequence with 95-99% identity to an amino acid sequence of SEQ ID NO:79. In one embodiment, the nucleic acid sequence encoding the costimulatory domain comprises a sequence of SEQ ID NO:78, or a sequence with 95-99% identify thereof. In another embodiment, the CAR constructure may contain two or more costimulation signal domains that selected from the group consisting of OX40, CD2, CD27, CD28, CDS, ICAM-1, LFA-1 (CD11a/CD18), ICOS (CD278), and 4-1BB (CD137).

In another aspect, the invention pertains to an nucleic acid molecule encoding a CAR construct comprising a leader sequence, e.g., a leader sequence described herein, e.g., of SEQ ID NO:71; a human anti-PSMA binding domain described herein, e.g., a human anti-PSMA binding domain comprising a LC CDR1, a LC CDR2, a LC CDR3, a HC CDR1, a HC CDR2 and a HC CDR3 described herein, e.g., a human anti-PSMA binding domain with the sequences listed from SEQ ID NO: 1 through SEQ ID NO: 69, or a sequence with 95-99% identify thereof; a hinge region described herein, e.g., of SEQ ID NO:73; a transmembrane domain described herein, e.g., a transmembrane domain comprising SEQ ID NO:75; and an intracellular signaling domain, e.g., an intracellular signaling domain described herein. In one embodiment, the encoded intracellular signaling domain comprises a costimulatory domain, e.g., a costimulatory domain described herein, e.g., a 4-1BB costimulatory domain having a sequence of SEQ ID NO:77, and/or a primary signaling domain, e.g., a primary signaling domain described herein, e.g., a CD3 zeta stimulatory domain having a sequence of SEQ ID NO:79. In one embodiment, the isolated nucleic acid molecule encoding the CAR construct includes a leader sequence encoded by the nucleic acid sequence of SEQ ID NO:71, or a sequence with 95-99% identity thereto.

In another embodiment, the CAR comprises the amino acid sequence of SEQ ID NO: 81, or a sequence with 95-99% identity thereto. In one embodiment, the CAR is encoded by a nucleotide sequence comprising SEQ ID NO:80 or a sequence with 95-99% identity thereto.

The invention provides an isolated host cell which expresses the inventive nucleic acid sequence encoding the CAR described herein. In one embodiment, the host cell is a T-cell. The T-cell of the invention can be any T-cell, such as a cultured T-cell, e.g., a primary T-cell, or a T-cell from a cultured T-cell line, or a T-cell obtained from a mammal. If obtained from a mammal, the T-cell can be obtained from numerous sources, including but not limited to blood, bone marrow, lymph node, the thymus, or other tissues or fluids. T-cells can also be enriched for or purified. The T-cell preferably is a human T-cell (e.g., isolated from a human). The T-cell can be of any developmental stage, including but not limited to, a CD4+/CD8+ double positive T-cell, a CD4+ helper T-cell, e.g., Th, and Th2 cells, a CD8+ T– cell (e.g., a cytotoxic T-cell), a tumor infiltrating cell, a memory T-cell, a naive T-cell, and the like. In one embodiment, the T-cell is a CD8+ T-cell or a CD4+ T-cell. T-cell lines are available from, e.g., the American Type Culture Collection (ATCC, Manassas, Va.), and the German Collection of Microorganisms and Cell Cultures (DSMZ) and include, for example, Jurkat cells (ATCC™-152), Sup-T1 cells (ATCC CRL-1942), RPMI 8402 cells (DSMZ ACC-290), Karpas 45 cells (DSMZ ACC-545), and derivatives thereof.

In another embodiment, the host cell is a natural killer (NK) cell. NK cells are a type of cytotoxic lymphocyte that plays a role in the innate immune system. NK cells are defined as large granular lymphocytes and constitute the third kind of cells differentiated from the common lymphoid progenitor which also gives rise to B and T lymphocytes (see, e.g., Immunobiology, 5th ed., Janeway et al., eds., Garland Publishing, New York, N.Y. (2001)). NK cells differentiate and mature in the bone marrow, lymph node, spleen, tonsils, and thymus. Following maturation, NK cells enter into the circulation as large lymphocytes with distinctive cytotoxic granules. NK cells are able to recognize and kill some abnormal cells, such as, for example, some tumor cells and virus-infected cells, and are thought to be important in the innate immune defense against intracellular pathogens. As described above with respect to T-cells, the NK cell can be any NK cell, such as a cultured NK cell, e.g., a primary NK cell, or an NK cell from a cultured NK cell line, or an NK cell obtained from a mammal. If obtained from a mammal, the NK cell can be obtained from numerous sources, including but not limited to blood, bone marrow, lymph node, the thymus, or other tissues or fluids. NK cells can also be enriched for or purified. The NK cell preferably is a human NK cell (e.g., isolated from a human). NK cell lines are available from, e.g., the American Type Culture Collection (ATCC, Manassas, Va.) and include, for example, NK-92 cells (ATCC CRL-2407), NK92MI cells (ATCC CRL-2408), and derivatives thereof.

In another aspect, the present invention provides a population of CAR-expressing cells, e.g., CART cells. In some embodiments, the population of CAR-expressing cells comprises a mixture of cells expressing different CARs. For example, in one embodiment, the population of CART cells can include a first cell expressing a CAR having an anti-PSMA binding domain described herein, and a second cell expressing a CAR having a different anti-PSMA binding domain, e.g., an anti-PSMA binding domain described herein that differs from the anti-PSMA binding domain in the CAR expressed by the first cell. As another example, the population of CAR-expressing cells can include a first cell expressing a CAR that includes an anti-PSMA binding domain, e.g., as described herein, and a second cell expressing a CAR that includes an antigen binding domain to a target other than PSMA (e.g., PSCA). In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an anti-PSMA domain described herein, and a second cell expressing another agent, e.g., an agent which enhances the activity of a CAR-expressing cell. For example, in one embodiment, the agent can be an agent which inhibits an inhibitory molecule. Inhibitory molecules, e.g., can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, CTLA4, TIM3, LAG3, VISTA, BTLA, TIGIT, LAIR1, CD160, 2B4 and TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

The present invention also provides nucleic acid molecules encoding one or more CAR constructs described herein. In one aspect, the nucleic acid molecule is provided as a messenger RNA transcript. In one aspect, the nucleic acid molecule is provided as a DNA construct.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, crisper, CAS9, and zinc finger nucleases. See below June et al. 2009 Nature Reviews Immunology 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a CAR transgene in a mammalian T cell is the EF1α promoter. The native EF1α promoter drives expression of the alpha subunit of the elongation factor-1 complex, which is responsible for the enzymatic delivery of aminoacyl tRNAs to the ribosome. The EF1α promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009). In one aspect, the EF1α promoter comprises the sequence provided as SEQ ID NO:100.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or proteins thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5'flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell or NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells. In one aspect, the mammalian T cell is a human T cell.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention, any number of T cell lines available in the art, may be used. In certain aspects of the present invention, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines.

Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is 5×10e6/ml. In other aspects, the concentration used can be from about $1 \times 10^5$/ml to $1 \times 10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol. Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then crosslinked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, 104 to 109 T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one aspect of the present invention, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2).

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a PSMA CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a PSMA CAR are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of CD4+ and CD8+ T cells) expressing the CARs are expanded in vitro for more than 10 days followed by lysis and SDS-PAGE under reducing conditions. CARs containing the full length TCR-t cytoplasmic domain and the endogenous TCR-t chain are detected by western blotting using an antibody to the TCR-chain. The same T cell subsets are used for SDS-PAGE analysis under non-reducing conditions to permit evaluation of covalent dimer formation.

In vitro expansion of CAR+ T cells following antigen stimulation can be measured by flow cytometry. For example, a mixture of CD4+ and CD8+ T cells are stimulated with aCD3/aCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters.

Sustained CAR+ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter following stimulation with aCD3/aCD28 coated magnetic beads on day 0, and transduction with the indicated CAR on day 1.

PSMA Targeted Bispecific Antibodies

Different from natural antibodies, bispecific antibodies (BsAbs) are artificial antibodies that bear double specificities, targeting two different tumor antigens, or one on tumor cells and the other on effector cells that can recruit the immunological effector cells to tumor sites efficiently and activate them to kill tumor cells specifically. Examples for the former, i.e., BsAbs targeting two different tumor associated antigens are bH1, which binds Her2 and VEGF simultaneously (Bostrom J1 et al. 2009, Science 323: 1610-4), or ErBb2/ErBb3 dual targeting bispecific scFv (Robinson M K et al. 2008, Br J Cancer 99:1415-25). The two tumor associated antigens could both be expressed on tumor cells, or one expressed on tumor cells and the other on tumor cell associated cells, such as tumor microenvironment cells, e.g., fibroblast, vasular cells, endothelium, pericytes or immuno cells in tumor microenvironent (macrophage, B cells, T cells etc.). Examples for the latter, i.e., BsAbs targeting one tumor associated antigen and an immunoactiavable antigen are BsAbs with one arm targeting a tumor antigen, such as Her2, CD19, or CD123 and the other arm targeting immunoactivatable antigen, such as CD3 or CD16 (Kontermann R E, et al. 2015, Drug Discovery Today 20: 838-847) that could engage tumor cells and immuno cells such as T cells, NK cells or macrophage etc.

A BsAb containing an anti-CD3 antibody will engage T cells and tumor cells together, leading to killing of the tumor cells (Muller and Kontermann, BioDrugs 2010; 24: 89-98, Baeuerle and Reinhardt 2009, Cancer Research 96: 4941) activated T cells. Blinatumomab (Bargou et al, Science 2008, 321: 974-976) is a single chain antibody construct named BiTE which induces cytotoxicity by targeting CD19 and CD3. Other antibody fragment based T-cell engaging bispecifics have been described (Moore et al. 2011, Blood 117:4542-4551, Baeuerle et el. Current opinion in Molecular Therapeutics 2009, 11: 22-30). The BiTE™ format is a bi-specific single chain antibody construct that links variable domains derived from two different antibodies. Blinatumomab, however, possesses poor half-life in vivo, and is difficult to manufacture in terms of production and stability. Thus, there is a need for improved bi-specific antibodies, capable of targeting T-cells to tumor cells and having improved manufacturability.

BsAbs are hybrid proteins that can be generated by chemical cross-link, hybridoma technology or genetic methods. In the chemical cross-link method, two kinds of monoclonal antibodies and fragments thereof were dissociated by reductants to generate monovalent antibodies and fragments thereof. The resulting BsAb is constructed via chemical cross-linking of two monovalent antibodies and fragments thereof from different parental antibodies. This strategy can be used for rapid production of BsAb in large scale but BsAb can be inactivated sometimes during cross-link and it is difficult to guarantee the homogeneity of products. Another strategy for production of BsAb is hybridoma technology by which an established hybridoma cell line secreting one monoclonal antibody was fused to spleen cells immunized with the other antigen or two established hybridoma cell lines secreting two different monoclonal antibodies were fused each other to create hybrid hybridomas. The former resulting hybridoma is called dimeric hybridoma and tetrameric hybridoma. Generally, BsAb produced by hybridoma technology keeps high bioactivities. However, the procedures are tedious and time-consuming and it is not easy to isolate BsAb from other non-active and unwanted antibodies generated simultaneously. These BsAb formats encountered another predictable problems: too large size and murine components contained in BsAb are immunogenic in patients and will induce the production of human anti-mouse antibodies (HAMA), which may prevent reuse of these BsAbs in clinic. Furthermore, production and purification of these formats of BsAb are expensive, which limits the application of BsAbs in clinic. Replacement of these traditional methods with gene recombination approaches has accelerated progress in this area. Based on the technology of small molecular antibodies, production of BsAb by gene engineering has advantages over those described above, such as the stability of process, large scale production, low cost and easy-to-use. Gene engineering has led to the development of various small molecular BsAb formats by connecting two different kinds of scFvs. There are three kinds of BsAb formats classified by different links. (1) mini-antibodies are heterodimers assembled by connecting two scFv fragments together with an oligomerized domain (e.g. leucine zipper motifs derived from Fos or Jun transcription factors). (2) Diabodies are non-covalently associated dimmers which are assembled by two single chains VH1-VL2 and VH2-VL1, both connected by a short linker that is too short to allow pairing between V-domains from the same chain. Thus, each chain alone is not capable of binding antigen, but co-expression of two chains (VH1-VL2 and VH2-VL1) leads to assembly of heterodimeric diabodies which can bind to two kinds of antigens. (3) ScBsAb: a interlinker was used for connecting two different scFvs with different specificities and ScBsAb was expressed in the host cells as a single polypeptide. The intralinker between two domains within scFv is often $(Gly4Ser)_3$. As for the interlinker between two scFvs, there are two strategies for designing it. For the purpose of avoiding false paring between heterogenous variable regions, the interlinker is often a short peptide linker less than ten amino acid residues such as Gly4Ser. Another strategy is to select a longer linker for the interlinker. In a word, the most important for designing interlinkers is to ensure the proper pairing between variable domains and folding of proteins, resulting in the formation of BsAb which maintains biological activities and stability. Some novel properties for facilitating purification and extending the plasma half-life time should be introduced.

BsAb-mediated immunotherapy plays a promising role in the clinical biotherapy for tumors. Tumor-killing effects mediated by BsAb is based on stimulating the immune system, highly specific with tumors and free of MEW restriction. Therefore, BsAb-mediated therapy is the complementarity of traditional methods such as surgery, radiotherapy and chemotherapy. BsAb can not only cure tumors but also stimulate the immune system to provide and keep the immune protection for a long time. Based on results of experiments in mouse and clinic, optimal BsAb prepared for trial use should have at least five characteristics as follows: 1): It targets to the relevant tumor antigens with high specificity and affinity; 2): It can bind to trigger factors on effector cells-cytotoxic cells and result in cross link only when BsAb binds to tumor antigens; 3): BsAb is able to promote the effective cytotoxicity and inflammation selectively produced by the corresponding group of leukocytes at tumor sites; 4): BsAb must be humanized to minimize induction of human anti-mouse response following repeated uses; Finally, 5): BsAb should be not only small enough to penetrate into tumors but also large enough to keep in the circulation for a sufficient time.

Based on these points described above, numerous BsAbs triggering many kinds of immune effector cells and targeting different tumor cells have been developed in the past few years, wherein the effector cells include T lymphocytes, NK cells, monocytes, macropghages, neutrophils, LAK cells (lymphokine-activated cytotoxic cells) and TIL cells (tumor infiltrating lymphocytes) etc. T cells are commonly recognized as the major specific cells for immune responses. CD3 expressed on the surface of all mature T cells is the common surface marker for T cells. CD3 binds to TCR non-covalently, forming the whole TCR-CD3 complex, and involves in immune responses against antigen stimulus. Now CD3 is surface trigger molecule on immune effector cells used most widely and successfully. Following anti-CD3 antibody within BsAb binds to CD3 molecule on the surface of T cells, numerous effects as follows will be produced to kill tumor cells. These effects include: (1) proliferation and differentiation of T cells. Firstly, BsAb can activate the rest T cells, resulting in Th cell and Tc cell derived from the premature effector T cells with CD4+ or CD8+. Secondly, BsAb can activate numerous memory cells to proliferate and differentiate into effector T cells which will attack and kill tumor cells. The number of effector cells is directly related to the rate of tumor elimination. (2) release of cytokines: CD4+ Th cells activated by BsAb can secrete a great deal of IL-2. IL-2 not only stimulates the proliferation of Th cells in autocrine, but also activates naive CD8+ T cells in paracrine to become Tc cells, resulting in enlargement of cytotoxicity of Tc cells. In addition, IL-2 is a costimulating signal for activating T cells. Therefore, IL-2 plays a vital role in BsAb-mediated immune effects. Some other cytokines, such as TNF-α and IFN-γ are produced in the process of T-cell activation and can produce 'stander-by' effect by inhibiting the growth of 'stander-by' tumor cells through the medium among cells. (3) cytotoxicity: In vitro experiments indicate that mediated by BsAb, CD8+ Tc interacts with tumor cells directly, releases cytotoxic materials through granule exocytosis and lyses target cells, which takes place rapidly usually within 4-6 hours following targeting tumor cells. The major components in the cytotoxic materials are perforin and serine easterases or granzymes. Perforins can attack the plasma membrane and form ion channels, thus causing entry of plenty of ions and water, resulting in the lysis and necrosis of cells while granzymes are similar to lymphotoxin, capable of activating DNases in the cell, thus causing lysis of nucleic DNA, resulting in the apoptosis of target cells.

Currently, Fv fragment is widely used for construction of BsAb, since it is the minimal unit with the complete antigen-binding site, small (about ⅙ of the whole antibody), absence of Fc domain, lower immunogenicity, easily penetration into the wall of blood vessels and solid tumors. However, Fv is unstable and easy to dissociate in vivo because the covalent bond between VH and VL domains is unable to generate. In order to improve the stability of Fv fragment, a polypeptide intralinker between VH and VL domains is used to form so called ScFv. The intralinker is commonly a short flexible peptide with 15 amino acid residues in length such as (Gly4Ser)$_3$. In one embodiment of the present invention, the said intralinker was used in anti-CD3 ScFv and a different intralinker is used for anti-PSMA scFv.

Bispecific antibodies having a standard IgG format can be challenging to produce because they include four different polypeptide chains. The efficacy of a smaller, more easily-produced bispecific molecule has been clinically demonstrated in non-Hodgkin's lymphoma. See, e.g., Bargou et al. (2008), Science 321(5891): 974-977.

Prolonged administration by continuous intravenous infusion was used to achieve these results because of the short in vivo half life of this small, single chain molecule. Hence, there is a need in the art for bispecific therapeutics that retain similar therapeutic efficacy, that have a format that is straightforward to produce, and that have favorable pharmacokinetic properties, including a longer half-life.

A Bispecific-Fc (Bs-Fc) as described herein can bind to two different proteins and contains an Fc region of an antibody or a portion thereof. A Bs-Fc can have favorable pharmacokinetic properties relative to a bispecific single chain molecule lacking an Fc region. One protein bound by a Bs-Fc can be expressed on an immune effector cell such as a T cell, an NK cell, a neutrophil, or a macrophage, and the other protein can be expressed on a target cell, for example, a cancer cell, a cell infected by a pathogen, or a cell mediating a disease, such as a fibroblast causing fibrosis. The Bs-Fc molecules described herein can elicit activation of an immune effector cell in the presence of a target cell and/or killing of a target cell in the presence of an immune effector cell.

Figure 25A:
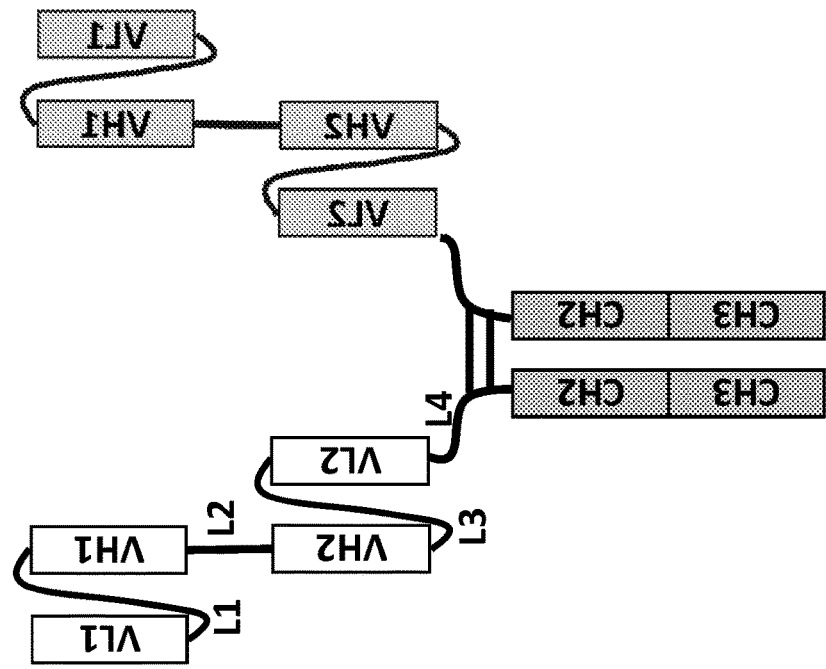
FIG. 25A through FIG. 25D, depicts various configurations of a bispecific antibody.
Figure 25B:
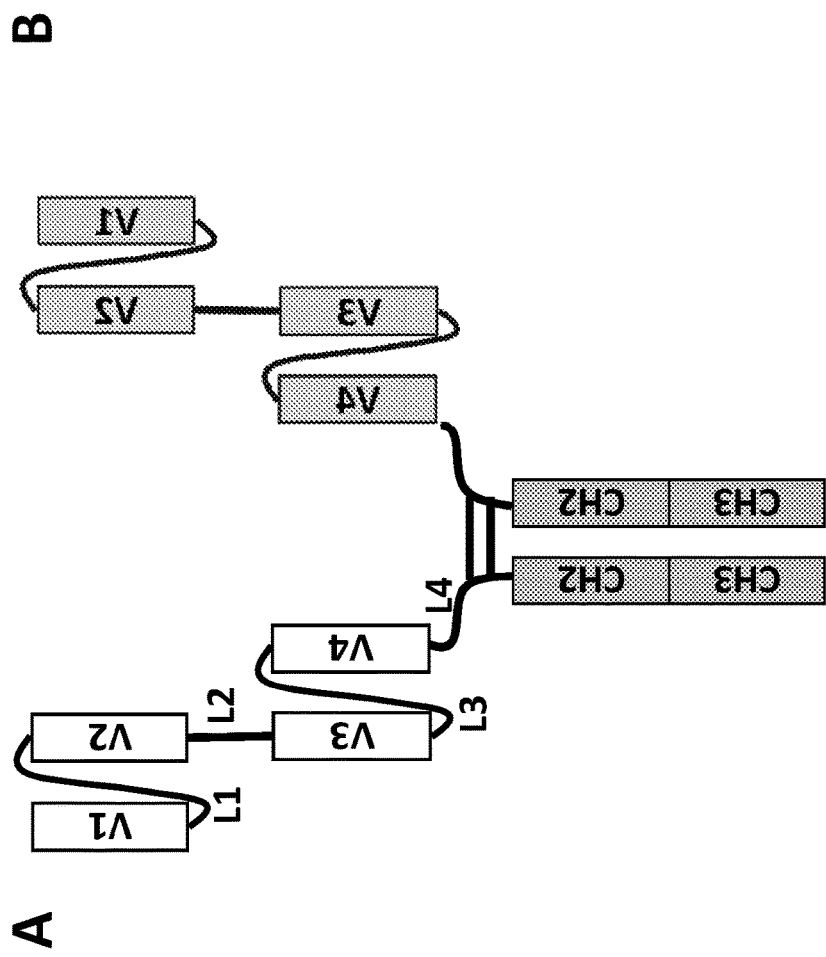
Figure 25C:
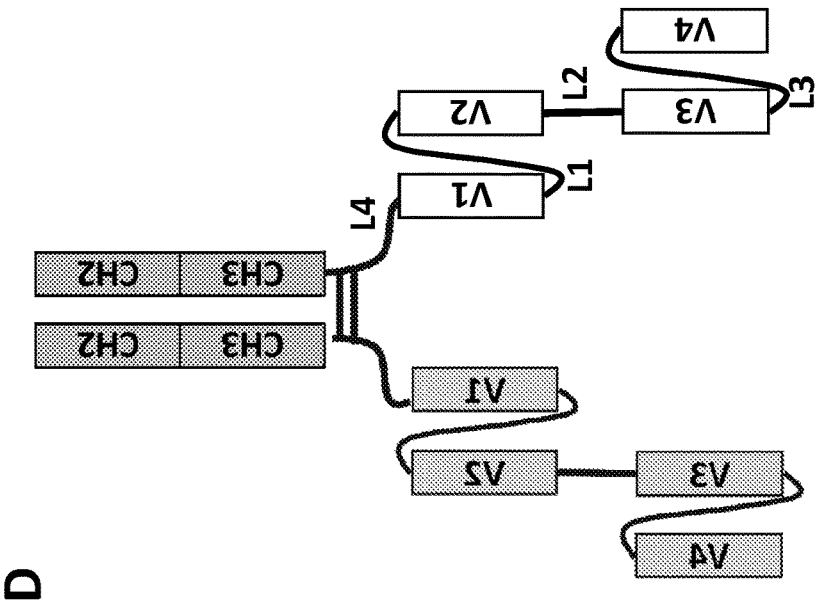
Figure 25D:
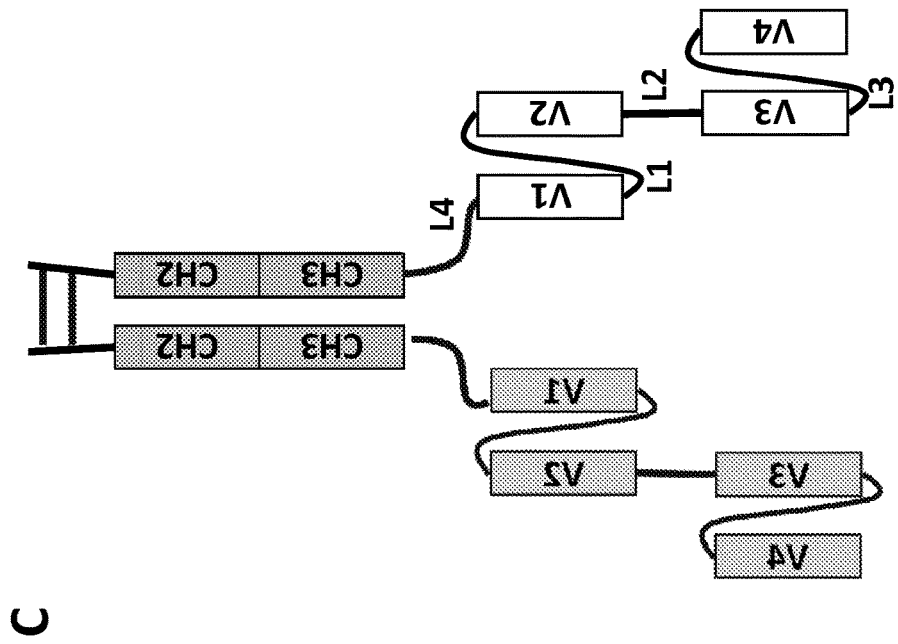

In one aspect, provided herein is a Bs-Fc (FIG. 25A-FIG. 25D), which can comprise: (a) a polypeptide chain having the formula V1-L1-V2-L2-V3-L3-V4-L4-Fc, wherein Fc is an Fc polypeptide chain, wherein V1, V2, V3, and V4 are each immunoglobulin variable regions that have different amino acid sequences, wherein L1, L2, L3, and L4 are linkers, and wherein L2 and/or L4 can be present or absent (FIG. 25A); or (b) a polypeptide chain having the formula Fc-L4-V1-L1-V2-L2-V3-L3-V4, wherein Fc is an Fc polypeptide chain, wherein V1, V2, V3, and V4 are each immunoglobulin variable regions that have different amino acid sequences, wherein L1, L2, L3, and L4 are linkers, and wherein L2 and/or L4 can be present or absent wherein the disulfide bonds of Fc can be at the N terminus (FIG. 25C) or C terminus (FIG. 25D); wherein the Bs-Fc mediates cytolysis of a target cell displaying a target cell protein by an immune is effector cell, and does not mediate cytolysis of a cell not displaying the target cell protein by the immune effector cell and/or wherein the Bs-Fc can bind to a target cell and to an immune effector cell. The Fc polypeptide chains in the first and second polypeptide chains can be human IgG Fc polypeptide chains. V1 can be a heavy chain variable (VH) region, and V2 can be a light chain variable (VL) region. In an alternate embodiment, V1 can be a VL region and V2 can be a VH region. V3 and V4 can be a VH and a VL region, respectively, or V3 and V4 can be a VL and a VH region, respectively, wherein FIG. 25B shows an example. L1 and L3 can be at least 15 amino acids long, and L2, when present, can be less than 12 amino acids long. V1 and V2 can bind to a target cell or an immune effector cell when they are part of an IgG and/or an scFv antibody, and V3 and V4 can bind to a target cell or an immune effector cell when they are part of an IgG and/or an scFv antibody.

In the present invention, the single-chain bispecific antibody (ScBsAb) connected by an Gly$_4$Ser interlinker and fused to an engineered IgG4 Fc was constructed to prolong the circulating life.

In one embodiment of the present invention, one of the two scFvs of ScBsAb was anti-CD3 scFv. In one embodiment of the present invention, the anti-CD3 scFv was derived from OKT3 antibody with a nucleic acid sequence shown in SEQ ID NO. 82 and amino acid sequence shown in SEQ ID NO. 83. In one embodiment of the present invention, the anti-CD3 scFv was derived from humanized OKT3 antibody with a nucleic acid sequence shown in SEQ ID NO. 88 and amino acid sequence shown in SEQ ID NO. 89.

In one embodiment, the other scFv of the ScBsAb targets PSMA. In one embodiment, the anti-PSMA scFv is gy1, gy1-st, gy1-2, or gy1-3, as described elsewhere herein. For example, in one embodiment, the PSMA-binding portion of the BsAb comprises one or more of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, and SEQ ID NO: 51. In certain embodiments, the PSMA– binding portion of the BsAb is encoded by one or more nucleotide sequences of SEQ ID NO: 2, SEQ ID NO: 4, SEQ ID NO: 6, SEQ ID NO: 8, SEQ ID NO: 10 SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, and SEQ ID NO: 50.

In one embodiment of the present invention, the anti-PSMA scFv in the ScBsAb has an amino acid sequence with a homology of more than 90%, 91%, 92%, 93%, 94% or 95% with gy1 or gy1 variants described herein.

To prolong the circulation life of ScBsAb, the size has to be increased above the molecular weight cutoff for glomerular filtration, i.e., around 60 kDa (Pisal D S et al. 2010, J Pharm Sci. 99: 2557-2575). Among the tags or fusion proteins, Fc is perfect because it prolong circulation time not only by enlarging the size of the protein of interest, but also by its interaction with the neonatal Fc receptor (FcRn). Therefore, in one embodiment of the present invention, a Fc domain was fused to the ScBsAb. In another embodiment of the invention, IgG4 Fc was fused to ScBsAb.

ADCC and CDC function is unwanted in BsAb since the binding of BsAb on CD3 will trigger the depletion of T cells through these functions. IgG4 does not bind C1q so there is no CDC. Furthermore, IgG4 has low affinity to activating FcγR while retaining relatively high affinity to the inhibiting FcγRIIb, IgG4 therefore has very weak ADCC. To completely abrogate ADCC, we have mutated the N297 to A297 to inhibit IgG4 binding to Fc receptors. But IgG binding to FcRn dose not depend on Fc glycosylation, so N297A mutation will not affect the half life of the IgG4 Fc fused protein. In one embodiment of the present invention, a N297A mutated IgG4 Fc is fused to the ScBsAb to prolong the circulation life. The nucleic acid and amino acid sequences were shown in SEQ ID NO. 96 and 97.

Both the S228 at the hinge region and R409 at CH3 of IgG4 are required for Fab Arm Exchange (FAE) for IgG4, which happens in physiological conditions, such as that observed in therapeutic IgG4 antibody natalizumab. So we used IgG1 hinge between the ScBsAb and Fc to avoid FAE. The other advantage of the use of IgG1 hinge is that IgG1 hinge is longer (15 aa) than that of IgG4 (12 aa) so is more flexible. To avoid disulfide bond mismatch, the C220 responsible for Fab formation with CL is mutated to A (C220A). Therefore, in one embodiment of the present invention, the linker between ScBsAb and Fc is IgG1 hinge; in another specific embodiment, the linker between ScBsAb and Fc is a C220A mutated IgG1 hinge, whose nucleic acid and amino acid sequences were shown in SEQ ID NO. 94 and 95.

In one embodiment of the invention, an expression vector for ScBsAb expression has the expression cassette selected from the following 5 options:

Cassette 1: (Kozak)-SP-MCS-G4S-scFv2-mIgG1 hinge-mIgG4 Fc

Cassette 2: SP-MCS-G4S-scFv2-mIgG1 hinge-mIgG4 Fc

Cassette 3: (Kozak)-SP-scFv1-G4S-scFv2-mIgG1 hinge-mIgG4 Fc

Cassette 4: SP-scFv1-G4S-scFv2-mIgG1 hinge-mIgG4 Fc

Cassette 5: scFv1-G4S-scFv2-mIgG1 hinge-mIgG4 Fc (abbreviation: SP: signal peptide; MCS: multiple clone site; mIgG1 hinge: mutated IgG1 hinge; mIgG4 Fc: mutated IgG4 Fc)

In embodiment, the bispecific antibody comprises the amino acid sequence of SEQ ID NO: 99. In one embodiment, the composition comprises a nucleotide sequence encoding SEQ ID NO. 99. In one specific embodiment of the invention, the composition comprises a nucleotide sequence of SEQ ID NO. 98.

In one embodiment, the bispecific antibody comprises the amino acid sequence of SEQ ID NO: 101. In one embodiment, the composition comprises a nucleotide sequence encoding SEQ ID NO. 101. In one specific embodiment of the invention, the composition comprises a nucleotide sequence of SEQ ID NO. 100.

In one embodiment, the bispecific antibody comprises the amino acid sequence of SEQ ID NO: 103. In one embodiment, the composition comprises a nucleotide sequence encoding SEQ ID NO. 103. In one specific embodiment of the invention, the composition comprises a nucleotide sequence of SEQ ID NO. 102.

In one embodiment, an anti-PSMA & anti-CD3 ScBsAb comprises the amino acid of SEQ ID NO. 105 or an amino acid sequence with homology more than 90%, 91%, 92%, 93%, 94% or 95% thereof.

In one embodiment, an anti-PSMA & anti-CD3 ScBsAb comprises the amino acid of SEQ ID NO. 106 or an amino acid sequence with homology more than 90%, 91%, 92%, 93%, 94% or 95% thereof.

In one embodiment, an anti-PSMA & anti-CD3 ScBsAb comprises the amino acid of SEQ ID NO. 108 or a amino acid sequence with homology more than 90%, 91%, 92%, 93%, 94% or 95% thereof.

In one embodiment, an anti-PSMA & anti-CD3 ScBsAb comprises the amino acid of SEQ ID NO. 109 or an amino acid sequence with homology more than 90%, 91%, 92%, 93%, 94% or 95% thereof.

In one embodiment, a BsAb expression vector comprises a nucleic acid sequence of SEQ ID NO. 104 or nucleic acid sequence encoding the amino acid sequence of SEQ ID NO. 105 or an amino acid sequence with homology more than 90%, 91%, 92%, 93%, 94% or 95% thereof.

In one embodiment, a BsAb expression vector comprises a nucleic acid sequence of SEQ ID NO. 107 or nucleic acid sequence encoding the amino acid sequence of SEQ ID NO. 108 or an amino acid sequence with homology more than 90%, 91%, 92%, 93%, 94% or 95% thereof.

For most murine antibody or BsAb derived from murine antibodies, human anti-mouse antibody (HAMA) problem induced by murine antibodies in clinic strongly limits repeated use and dose. Murine antibodies must be humanized to minimize their heterology, which is the urgent affairs for preparation of antibodies used in clinic. The scFv against CD3 molecule in anti-PSMA ScBsAb used in the present invention is a humanized scFv and the PSMA scFv is a fully human antibody, which will significantly minimize the immunogenicity of the BsAb and improve the overall outcome of cancer treatment.

Combination Therapies

A composition comprising an antibody, antibody fragment, ADC, CAR-expressing cell, or bispecific antibody described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A composition comprising an antibody, antibody fragment, ADC, CAR-expressing cell, or bispecific antibody described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

In further aspects, a composition comprising an antibody, antibody fragment, ADC, CAR-expressing cell, or bispecific antibody described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, a composition comprising an antibody, antibody fragment, ADC, CAR-expressing cell, or bispecific antibody described herein can be used in combination with a chemotherapeutic agent. Exemplary chemotherapeutic agents include an antiandrogen (androgen antagonists), anthracycline (e.g., doxorubicin (e.g., liposomal doxorubicin)). a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplating), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary Antiandrogen (androgen antagonists) agents include Bicalutamide, Goserelin Acetate SR Depo.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil Nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexylen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexylen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexylen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®). Exemplary mTOR inhibitors include, e.g., temsirolimus; ridaforolimus (formally known as deferolimus, (1R,2R,4S)-4-[(2R)-2[(1R,9S,12S,15R,16E, 18R,19R,21R, 23 S,24E,26E,28Z,30S,32S,35R)-1,18-dihydroxy-19,30-dimethoxy-15,17,21,23,29,35-hexamethyl-2,3, 10,14,20-pentaoxo-11,36-dioxa-4-azatricyclo[30.3.1.04,9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS164301-51-3); emsirolimus, (5-{2,4-Bis[(3 S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl] methoxy]butyl]-L-arginylglycyl-L-α-aspartylL-serine-, inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®);

daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyl oxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the subject can be administered an agent which reduces or ameliorates a side effect associated with the administration of a naked antibody or antibody fragment, ADC, CAR-expressing cell, or Bispecific antibody.

In one embodiment, the subject can be administered an agent which enhances the activity of a naked antibody or antibody fragment, ADC, CAR-expressing cell, or Bispecific antibody. For example, in one embodiment, the agent can be an agent which inhibits an inhibitory molecule. Inhibitory molecules, e.g., Programmed Death 1 (PD1), can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. Inhibition of an inhibitory molecule, e.g., by inhibition at the DNA, RNA or protein level, can optimize a naked antibody or antibody fragment, ADC, CAR-expressing cell, or Bispecific antibody performance. In embodiments, an inhibitory nucleic acid, e.g., an inhibitory nucleic acid, e.g., a dsRNA, e.g., an siRNA or shRNA, can be used to inhibit expression of an inhibitory molecule in the CAR-expressing cell or bispecific Ab reacting cells. In an embodiment the inhibitor is an shRNA. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3.

PD1 is an inhibitory member of the CD28 family of receptors that also includes CD28, CTLA-4, ICOS, and BTLA. PD1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD 1 (Freeman et al. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1. Antibodies, antibody fragments, and other inhibitors of PD1, PD-L1 and PD-L2 are available in the art and may be used combination with a PSMA targeted naked antibody or antibody fragment, ADC, CAR-expressing cell, or Bispecific antibody described herein. For example, nivolumab (also referred to as BMS-936558 or MDX1106; Bristol-Myers Squibb) is a fully human IgG4 monoclonal antibody which specifically blocks PD 1. Nivolumab (clone 5C4) and other human monoclonal antibodies that specifically bind to PD1 are disclosed in U.S. Pat. No. 8,008,449 and WO2006/121168. Pidilizumab (CT-011; Cure Tech) is a humanized IgG1k monoclonal antibody that binds to PD1Pidilizumab and other humanized anti-PD1 monoclonal antibodies are disclosed in WO2009/101611. Lambrolizumab (also referred to as MK03475; Merck) is a humanized IgG4 monoclonal antibody that binds to PD1. Lambrolizumab and other humanized anti-PD1 antibodies are disclosed in U.S. Pat. No. 8,354,509 and WO2009/114335. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.S70 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD1 and B7-H1. Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an antracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein.

In one embodiment, the fusion protein is expressed by the same cell that expressed the CAR. In another embodiment, the fusion protein is expressed by a cell, e.g., a T cell that does not express an anti-PSMA CAR.

Formulations and Route of Administration

The antibodies, ADC, CAR-expressing cell, or Bispecific antibody of the present invention may find use in a wide range of products. In one embodiment the antibody, ADC, CAR-expressing cell, or Bispecific antibody of the invention is a therapeutic, a diagnostic, or a research reagent. In one embodiment, an antibody ADC, CAR-expressing cell, or Bispecific antibody of the invention is a therapeutic. In some embodiments, antibody or antibody fragment, ADC, CAR-expressing cell, or Bispecific antibody of the present invention is used for industrial uses. An antibody of the present invention may find use in an antibody composition that is monoclonal or polyclonal. The antibodies of the present invention may be agonists, antagonists, neutralizing, inhibitory, or stimulatory. In one embodiment, the antibodies or antibody fragments, ADC, CAR-expressing cell, or Bispecific antibody of the present invention are used to kill target cells that bear the target antigen, for example cancer cells. In an alternate embodiment, the antibodies of the present invention are used to block, antagonize, or agonize the target antigen. In an alternate embodiment, the antibodies of the present invention are used to block, antagonize, or agonize the target antigen and kill the target cells that bear the target antigen. In another embodiment, the target cell is a tumor cell or it's neovasculature. In one embodiment, neovasculature plays an important role in angiogenesis and are also considered to be a target of the antibodies or antibody fragments, ADC, CAR-expressing cell, or Bispecific antibody provided herein.

The invention further provides kits comprising one or more compositions of the invention, including pharmaceutical formulations, packaged into suitable packaging material. In another embodiment, a kit includes a nucleic acid encoding the antibody or antigen-binding fragments, Car T or Car NK cells, or bispecific antibody, thereof of the invention. In additional embodiments, a kit includes nucleic acids that further include an expression control element; an expression vector; a viral expression vector; an adeno-associated virus expression vector; an adenoviral expression vector; and a retroviral expression vector. In yet an additional embodiment, a kit includes a cell that express the antibody or antigen-binding fragments thereof of the invention, such as the Car T or Car NK cells.

In additional embodiments, a kit includes a label or packaging insert including instructions for expressing an antibody or bispecific antibody or a nucleic acid encoding the antibody, antigen-binding fragments or bispecific antibody thereof in cells in vitro, in vivo, or ex vivo. In yet additional embodiments, a kit includes a label or packaging insert including instructions for treating a subject (e.g., a subject having or at risk of having asthma) with the antibody or antibody fragment, ADC, CAR-expressing cell, or Bispecific antibody thereof of the invention in vivo, or ex vivo.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., treating the common cold. Kits of the invention therefore can additionally include instructions for using the kit components in a method of the invention.

Instructions can include instructions for practicing any of the methods of the invention described herein. Thus, invention pharmaceutical compositions can be included in a container, pack, or dispenser together with instructions for administration to a subject. Instructions may additionally include indications of a satisfactory clinical endpoint or any adverse symptoms that may occur, or additional information required by the Food and Drug Administration for use on a human subject.

In one embodiment, polypeptides of the present invention are administered as part of a vaccine. In some embodiments, the term vaccine is to be understood to encompass any immunomodulating composition, and such vaccines may comprise an adjuvant, an antigen, an immuno-modulatory compound, or a combination thereof, in addition to the polypeptides of this invention.

In some embodiments, an adjuvant may include, but is not limited to: (A) aluminium compounds (e.g. aluminium hydroxide, aluminium phosphate, aluminium hydroxyphosphate, oxyhydroxide, orthophosphate, sulphate, etc. [e.g. see chapters 8 & 9 of ref. 96]), or mixtures of different aluminium compounds, with the compounds taking any suitable form (e.g. gel, crystalline, amorphous, etc.), and with adsorption being preferred; (B) MF59 (5% Squalene, 0.5% Tween 80, and 0.5% Span 85, formulated into submicron particles using a microfluidizer); (C) liposomes; (D) ISCOMs, which may be devoid of additional detergent; (E) SAF, containing 10% Squalane, 0.4% Tween 80, 5% pluronic-block polymer L121, and thr-MDP, either micro fluidized into a submicron emulsion or vortexed to generate a larger particle size emulsion; (F) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21, also known as Stimulon™; (H) chitosan; (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-y), macrophage colony stimulating factor, tumor necrosis factor, etc.; (K) monophosphoryl lipid A (MPL) or 3-O-deacylated MPL (3dMPL)]; (L) combinations of 3dMPL with, for example, QS21 and/or oil-in-water emulsions; (M) oligonucleic acids comprising CpG motifs] i.e. containing at least one CG dinucleic acid, with 5-methylcytosine optionally being used in place of cytosine; (N) a polyoxyethylene ether or a polyoxyethylene ester; (O) a polyoxyethylene sorbitan ester surfactant in combination with an octoxynol or a polyoxyethylene alkyl ether or ester surfactant in combination with at least one additional non-ionic surfactant such as an octoxynol; (P) an immunostimulatory oligonucleic acid (e.g. a CpG oligonucleic acid) and a saponin; (0) an immuno-stimulant and a particle of metal salt; (R) a saponin and an oil-in-water emulsion; (S) a saponin (e.g. QS21)+3dMPL+IL12 (optionally+a sterol); (T) E. coli heat-labile enterotoxin ("LT"), or detoxified mutants thereof, such as the K63 or R72 mutants; (U) cholera toxin ("CT"), or diphtheria toxin ("DT") or detoxified mutants of either; (V) double-stranded RNA; (W) monophosphoryl lipid A mimics, such as aminoalkyl glucosaminide phosphate derivatives e.g. RC-529]; (X) polyphosphazene (PCPP); or (Y) a bioadhesive such as esterified hyaluronic acid microspheres or a mucoadhesive such as crosslinked derivatives of poly(acrylic acid), polyvinyl alcohol, polyvinyl pyrollidone, polysaccharides and carboxymethylcellulose.

In some embodiments, administration of the compounds of this invention is intended to reduce the severity of the pathologic condition. By the term "reduce the severity of the pathologic condition", it is to be understood that any reduction via the methods, compounds and compositions disclosed herein, is to be considered encompassed by the invention. Reduction in severity may, in one embodiment comprise enhancement of survival, or in another embodiment, halting disease progression, or in another embodiment, delay in disease progression.

In one embodiment, dosing is dependent on the cellular responsiveness to the administered molecules/compounds or compositions comprising same. In general, the doses utilized for the above described purposes will vary, but will be in an effective amount to exert the desired effect, as determined by a clinician of skill in the art. As used herein, the term "pharmaceutically effective amount" refers to an amount of a compound as described herein, which will produce the desired alleviation in symptoms or other desired phenotype in a patient.

In one embodiment of the invention, the concentrations of the compounds will depend on various factors, including the nature of the condition to be treated, the condition of the patient, the route of administration and the individual tolerability of the compositions.

In some embodiments, any of the compositions of this invention will comprise a compound, in any form or embodiment as described herein. In some embodiments, any of the compositions of this invention will consist essentially of a compound, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry.

In some embodiments, the compositions of this invention will consist essentially of a polypeptide/polynucleic acid/vector as herein described. In some embodiments, the term "consisting essentially of" refers to a composition whose only active ingredient of a particular class of agents, is the indicated active ingredient, however, other compounds may be included which are involved directly in the therapeutic effect of the indicated active ingredient. In some embodiments, the term "consisting essentially of" refers to a composition whose only active ingredient of targeting a particular mechanism, or acting via a particular pathway, is the indicated active ingredient, however, other compounds may be included which are involved directly in the therapeutic effect of the indicated active ingredient, which for example have a mechanism of action related to but not directly to that of the indicated agent. In some embodiments, the term "consisting essentially of" refers to a composition whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

It will be appreciated that the actual amounts of active compound in a specific case will vary according to the specific compound being utilized, the particular compositions formulated, the mode of application, and the particular conditions and organism being treated. Dosages for a given host can be determined using conventional considerations, e.g., by customary comparison of the differential activities of the subject compounds and of a known agent, e.g., by means of an appropriate, conventional pharmacological protocol.

In one embodiment, the compounds of the invention are administered acutely for acute treatment of temporary conditions, or may be administered chronically, especially in the case of progressive, recurrent, or degenerative disease. In one embodiment, one or more compounds of the invention may be administered simultaneously, or in another embodiment, they may be administered in a staggered fashion. In one embodiment, the staggered fashion may be dictated by the stage or phase of the disease.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In one embodiment, the route of administration may be parenteral, or a combination thereof. In another embodiment, the route may be intra-ocular, conjunctival, topical, transdermal, intradermal, subcutaneous, intraperitoneal, intravenous, intra-arterial, vaginal, rectal, intratumoral, parcanceral, transmucosal, intramuscular, intravascular, intraventricular, intracranial, inhalation (aerosol), nasal aspiration (spray), intranasal (drops), sublingual, oral, aerosol or suppository or a combination thereof. In one embodiment, the dosage regimen will be determined by skilled clinicians, based on factors such as exact nature of the condition being treated, the severity of the condition, the age and general physical condition of the patient, body weight, and response of the individual patient.

For intranasal administration or application by inhalation, solutions or suspensions of the compounds mixed and aerosolized or nebulized in the presence of the appropriate carrier suitable. Such an aerosol may comprise any agent described herein.

For parenteral application, particularly suitable are injectable, sterile solutions, preferably oily or aqueous solutions, as well as suspensions, emulsions, or implants, including suppositories and enemas. Ampoules are convenient unit dosages. Such a suppository may comprise any agent described herein.

Sustained or directed release compositions can be formulated, e.g., liposomes or those wherein the active compound is protected with differentially degradable coatings, e.g., by microencapsulation, multiple coatings, etc. Such compositions may be formulated for immediate or slow release. It is also possible to freeze-dry the new compounds and use the lyophilisates obtained, for example, for the preparation of products for injection.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate.

Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

In one embodiment, a composition of or used in the methods of this invention may be administered alone or within a composition. In another embodiment, compositions of this invention admixture with conventional excipients, i.e., pharmaceutically acceptable organic or inorganic carrier substances suitable for parenteral, enteral (e.g., oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g., vitamins.

Pharmaceutical compositions include "pharmaceutically acceptable" and "physiologically acceptable" carriers, diluents or excipients. In one embodiment, the terms "pharmaceutically acceptable" and "physiologically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration. The terms include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary active compounds (e.g., preservatives, antibacterial, antiviral and antifungal agents) can also be incorporated into the compositions.

Pharmaceutical compositions of the present invention can include one or more further chemotherapeutic agents selected from the group consisting of nitrogen mustards (e.g., cyclophosphamide and ifosfamide), aziridines (e.g., thiotepa), alkyl sulfonates (e.g., busulfan), nitrosoureas (e.g., carmustine and streptozocin), platinum complexes (e.g., carboplatin and cisplatin), non-classical alkylating agents (e.g., dacarbazine and temozolamide), folate analogs (e.g., methotrexate), purine analogs (e.g., fludarabine and mercaptopurine), adenosine analogs (e.g., cladribine and pentostatin), pyrimidine analogs (e.g., fluorouracil (alone or in combination with leucovorin) and gemcitabine), substituted ureas (e.g., hydroxyurea), antitumor antibiotics (e.g., bleomycin and doxorubicin), epipodophyllotoxins (e.g., etoposide and teniposide), microtubule agents (e.g., docetaxel and paclitaxel), camptothecin analogs (e.g., irinotecan and topotecan), enzymes (e.g., asparaginase), cytokines (e.g., interleukin-2 and interferon-a), monoclonal antibodies (e.g., trastuzumab and bevacizumab), recombinant toxins and immunotoxins (e.g., recombinant cholera toxin-B and TP-38), cancer gene therapies, physical therapies (e.g., hyperthermia, radiation therapy, and surgery) and cancer vaccines (e.g., vaccine against telomerase).

The compositions (e.g., antibodies, and bispecific molecules) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Pharmaceutical compositions can be formulated to be compatible with a particular local or systemic route of administration. Thus, pharmaceutical compositions include carriers, diluents, or excipients suitable for administration by particular routes. Specific non-limiting examples of routes of administration for compositions of the invention are inhalation or intranasal delivery. Additional routes include parenteral, e.g., intravenous, intradermal, subcutaneous, oral, transdermal (topical), transmucosal, and rectal administration.

Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminenetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, sodium chloride can be included in the composition. Including an agent which delays absorption, for example, aluminum monostearate and gelatin can prolong absorption of injectable compositions.

Sterile injectable solutions can be prepared by incorporating the active compound in the required amount in an appropriate solvent with one or a combination of above ingredients followed by filtered sterilization. Generally, dispersions are prepared by incorporating the active compound into a sterile vehicle containing a basic dispersion medium and other ingredients as above. In the case of sterile powders for the preparation of sterile injectable solutions, methods of preparation include, for example, vacuum drying and freeze-drying which yields a powder of the active ingredient plus any additional desired ingredient from a previously sterile-filtered solution thereof.

For transmucosal or transdermal administration, penetrants appropriate to the barrier be permeated are used in the formulation. Such penetrants are generally known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdermal administration, the active compounds are formulated into ointments, salves, gels, or creams as generally known in the art.

The present invention's antibodies, including subsequences and modified forms and nucleic acids encoding them, can be prepared with carriers that protect against rapid elimination from the body, such as a controlled release formulation or a time delay material such as glyceryl monostearate or glyceryl stearate. The compositions can also be delivered using implants and microencapsulated delivery systems to achieve local or systemic sustained delivery or controlled release.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known to those skilled in the art, for example, as described in U.S. Pat. No. 4,522,811.

Additional pharmaceutical formulations appropriate for the compositions for administration in the methods of the invention are known in the art (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; and Pharmaceutical Principles of Solid Dosage Forms, Technonic Publishing Co., Inc., Lancaster, Pa., (1993)). The pharmaceutical formulations can be packaged in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the pharmaceutical carrier or excipient.

Although the pharmaceutical compositions provided herein are principally directed to pharmaceutical compositions which are suitable for administration to humans, it will be understood by the skilled artisan that such compositions are generally suitable for administration to animals of all sorts. Modification of pharmaceutical composition suitable for administration to humans in order to render the compositions suitable for administration to various animals is well understood, and the ordinarily skilled veterinary pharmacologist can design and perform such modification with little, if any, experimentation. Subjects to which administration of the pharmaceutical compositions of the invention is contemplated include, but are not limited to, humans and other primates, and other mammals.

It is to be understood that any amino acid sequence, whether obtained naturally or synthetically by any means, exhibiting sequence, structural or functional homology to the polypeptides described herein, are considered part of this invention.

In one embodiment, the term "about" means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

It is to be understood that reference to any publication, patent application or issued patent is to be considered as fully incorporated herein by reference in its entirety.

It is to be understood that any assay for measuring a particular activity which is modulated by the therapeutic compound may be employed, as a means of determining the efficacy of the compound, in one embodiment, optimal loading of the compound, in another embodiment, timing and dosage, in another embodiment, or a combination thereof.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Panning of Yeast Display Human scFv Library

The $1\times10^{"}$ yeast display naive human scFv library was constructed and the extracellular domain of human PSMA was purchased from R&D systems. The method of library panning was previously described (Zhao et al., J Immunol Methods. 2011; 363(2):221-32.). Briefly, the recombinant PSMA protein was biotinylated and incubated with induced yeast display scFv library; the PSMA binding yeast cells were isolated using streptavidin (SA) conjugated microbeads and then flowcytometry activated cell sorting (FACS); scFv gene was amplified from the isolated yeast cells and cloned into a secretory expression yeast strain YVH10; individual secretory scFv expression was induced in 96 well plates and PSMA binding clones were identified by high throughput ELISA.

Biotinylation of PSMA Recombinant Protein

PSMA recombinant protein buffer was changed into PBS via dialysis against PBS at 4° C. and the concentration was adjusted to 0.5 mg/ml. EZ-Link Sulfo-NHS-Biotin Reagent (10 mM; dissolved in cold water) (life technologies) was mixed with PSMA recombinant protein to a final molar ratio of 1:20 (protein:biotin). The PSMA recombinant protein mixture was incubated at 4° C. for 2 hours. Unreacted free biotin reagents was removed by dialysis and the biotinylated protein was aliquoted and stored at −80° C.

Yeast Display scFv Library Panning Using Magnetic Beads

The yeast display scFv library was thawed from −80° C. and centrifugated at 3000 rpm for 5 minutes. The supernatant was discarded, and the yeast cells were resuspended with 12 L SD-CAA medium (one liter SD-CAA medium contains 5 g casamino acids, 1.7 g Yeast Nitrogen Base without ammonium $SO_4$ & amino acids, 5.3 g ammonium sulfade, 10.2 g $Na_2HPO_4.7H_2O$, 8.6 g $NaH_2PO_4.H_2O$ and 20 g dextrose). The cells were cultured at 30° C. overnight with rocking at 200 rpm. The next day, yeast cells were harvested by centrifuging at 3000 rpm for 5 minutes and an appropriate amount was resuspended into 12 L S-CAA-GRD induction medium (one liter S-CAA-GRD medium contains 5 g casamino acids, 1.7 g Yeast Nitrogen Base without ammonium $SO_4$ & amino acids, 5.3 g ammonium sulfade, 10.2 g $Na_2HPO_4.7H_2O$, 8.6 g $NaH_2PO_4.H_2O$, 1 g dextrose, 20 g galactose and 20 g raffinose) so that the final concentration was OD600=0.5 and induced at 20° C. overnight. Induced yeast cells were harvested by centrifugation at 3000 rpm for 5 minutes and washed twice by 2 L PBE buffer (PBE buffer is PBS buffer containing 2 mM EDTA and 0.5% BSA) and finally resuspended in 200 ml PBE. Cells were incubated with 40 μg biotinylated PSMA protein at room temperature (RT) for 1.5 hours and then 4° C. for 0.5 hour. The following steps were done at 4° C. or on ice. Cells were harvested by centrifuging at 3000 rpm for 5 minutes and washed twice with 2 L PBE and resuspended in 200 ml PBE. Then, 2 ml streptavidin microbeads (Miltenyi Biotec) was added to the cells and incubated with slow rocking for 1 hour. One liter PBE was added to cells, the solution was vortexed to make sure the cells were separated in single cells, and filtered using 70 μm strainer. Sixteen Miltenyi LS columns were used for PSMA binding yeast cell isolation. Briefly, 7 mL of the strained cell suspension was added to the column. After each 7 mL of cells entered the column and the flow has stopped, the column was removed from magnet and immediately put back into magnet. This rearranges the iron beads in the column and allows the cells that are physically trapped between the beads to pass through. With the column back in the magnet, 1 ml of wash buffer was added, and after the wash flowed through, another 7 mL of cells was added onto column. The column removal procedure was repeated between each loading of cells. Once all of the cells were loaded on the column, the column was washed with 3 mL of wash buffer. This wash removes the cells in the void volume of the column. The column was removed from magnet and immediately replaced as before. Wash was repeated twice. Once the column has stopped dripping, the column was removed from magnet and 7 mL of wash buffer was then added. The plunger was used to push all remaining cells out into a 15-mL conical tube.

The harvested cells were loaded once more to two new columns to further remove the nonspecific cells. The final eluted cells were harvested by centrifuging at 3000 rpm for 5 minutes. The cells were spread on SD-CAA plates and cultured for 2 days at 30° C. A total of $2.5 \times 10^7$ clones were obtained from the first round of magnetic sorting. Cells were scraped and induced for the second round of magnetic sorting. An aliquot was also stored in SD-CAA containing 10% glycerol at −80° C. $5 \times 10^9$ first round magnetic sorted yeast cells were inoculated into 200 ml S-CAA-GRD medium for induction at 20° C. overnight. The next day, $2.5 \times 10^9$ induced cells were harvested by centrifuging at 3000 rpm for 5 minutes and washed twice with 15 ml PBE. Cells were resuspended in 3 ml PBE and incubated with 3 μg biotinylated PSMA protein at RT for 1.5 hours and then at 4° C. for half hour. All the following steps were performed at 4° C. or on ice. After incubation, cells were pelleted by centrifuging at 3000 rpm for 5 minutes and then washed three times with 15 ml PBE. Cells were pelleted again and resuspended in 3 ml PBE and incubated with 50 μl anti-biotin antibody conjugated microbads at 4° C. for 1 hour. Cells were washed once with PBE, resuspended in 15 ml PBE and filtered through a 70 μm strainer, and the PSMA binding yeast cells were isolated using one Miltenyi Macs LS column as described above. The second round magnetic sorting gave rise to $5.1 \times 10^6$ clones.

A third round of magnetic sorting was performed to further enrich PSMA specific yeast population. Briefly, $1 \times 10^9$ cells were induced in 50 ml S-CAA-GRD at 20° C. overnight and $5 \times 10^8$ cells were taken for further panning. Cells were washed twice with 15 ml PBE and resuspended in 3 ml PBE, followed by incubation with 1 μg biotinylated PSMA protein at RT for 1.5 hour and then at 4° C. for half hour. All the following steps were performed at 4° C. or on ice. After incubation, cells were pelleted by centrifuging at 3000 rpm for 5 minutes and then washed three times with 15 ml PBE. Cells were pelleted again and resuspended in 3 ml PBE and incubated with 50 μl streptavidin conjugated microbads at 4° C. for 1 hour. Cells were washed once with PBE, resuspended in 15 ml PBE and filtered through a 70 μm strainer, and the PSMA binding yeast cells were isolated using one Miltenyi Macs LS column as described above. The third round magnetic sorting gave rise to $1 \times 10^7$ clones.

Yeast Display scFv Library Panning Using Flow Sorting

Yeast cells obtained from the third magnetic sorting were further subjected to three rounds of flow sorting. All the centrifuging were 3000 rpm for 5 minutes and all the steps were at 4° C. or on ice if not indicated otherwise. $2 \times 10^9$ cells isolated from the third magnetic sorting were induced in 100 ml S-CAA-GRD medium at 20° C. overnight, from which, $1 \times 10^8$ cells were taken for the first round flow sorting. Cells were pelleted and washed twice with 15 ml PBE and then resuspended in 1 ml PBE and incubated with 0.2 μg biotinylated PSMA protein at RT for 1.5 hours and then at 4° C. for half hour. Cells were washed three times with PBE and then incubated with 50 μl anti-VS-Alexa647 (AbD Stereo) and 50 μl Streptavidin-PE (SA-PE) (BD biosciences) in 1 ml PBE at 4° C. for 1 hour in darkness. After staining, cells were washed three time with 15 ml PBE and resuspended in 1 ml PBE for flow sorting by flowcytometry, in which Alexa647 and PE double positive cells were sorted as PSMA binding population. Staining controls that were also set up in parallel included: (1) unstaining control; (2) anti-V5-Alexa647 staining only; and (3) SA-PE staining only. $1.2 \times 10^6$ double positive cells were sorted and cultured on SD-CAA plates at 30° C. for 2 days.

Cells isolated from the first flow sorting were further subjected to the second and third flow sorting. Sample preparation was similar to the first flow sorting except that in the second flow sorting, 50 ng biotinylated PSMA protein and anti-biotin-FITC (Abcam) were used instead for staining; and in the third round flow sorting, biotinylated PSMA protein further decreased to 2 ng and SA-PE was used for detection of PSMA binding. Finally, $1\times10^6$ and $2\times10^4$ cells (top 0.1% population) were sorted in the second and third flow sorting.

Example 2: Identification of Individual Anti-PSMA Clones

Conversion of enriched display scFv library to secretory scFv library Plasmid harboring the scFv gene in the display EBY100 cells were extracted and scFv gene fragments were amplified and cloned into the secretory vector pYS1 and transformed into yeast strain YVH10 for secretory scFv expression.

Yeast plasmid was extracted after expansion of the top 0.1% population sorted during the third flow sorting following the protocol of a yeast plasmid extraction kit (Zymo Research) and the scFv gene fragments were amplified by PCR using the following primers, Forward: 5'-GACTA-CAAGGACGACGATGAC-3' (SEQ ID NO: 111), and Reverse: 5'-AGTAGAATCAAGACCTAGTAGAGGG-3' (SEQ ID NO: 112). The amplified scFv gene fragments were then purified and co-transformed into yeast strain YVH10 along with Sfi I/Not I linearized secretory scFv expression vector pYS1. The molar ratio of the scFv gene/vector was 3:1 and 1 µg vector was used for transformation. YVH10 competent cell preparation and transformation was described previously (Zhao et al., J Immunol Methods. 2011; 363(2):221-32.). Transformed cells were cultured on SD-CCA-Trp (SD-CAA plus 0.008% tryptophan) at 30° C. for 2 days.

Identification of PSMA Binding scFv Clones

Three hundred and eighty four secretory scFv clones were picked, cultured in SD-CAA-Trp and soluble scFv expression was induced in 96 deep well plates for 2 days at 20° C. in S-CAA-GRD-Trp. PSMA binding scFv was identified using ELISA. Briefly, ELISA plates were coated with 50 µl/well 1 µg/ml anti-Flag antibody (Sigma) at 4° C. overnight, washed twice with PBST (PBS containing 0.05% Tween 20) and blocked with PBST™ (PBST containing 5% non-fat dry milk (Biorad)) for 2 hours at RT. The plates were then incubated with 100 µl scFv containing supernatant that was 1:1 diluted with PBST™ at RT for 1 hour, washed six times with PBST and then incubated with 0.4 µg/ml, 50 ml/well biotinylated PSMA protein in PBST™ at RT for 1 hour. After 6 washes as above, the plates were incubated with 100 µl 1:1000 diluted Streptavidin-HRP)(BD Biosciences) in PBST™ at RT for 1 hour, washed again for six times and TMB (KPL) and stop buffer was incubated sequentially with the plate to develop colorimetric assay. Light absorbance was measured at OD450. Among the 384 clones analyzed, 260 showed positive signals (OD450 values are greater than two folds of the background value). Ninety-six randomly picked clones were further analyzed for PSMA binding. Results showed that all of bound specifically to PSMA but not to control protein Fc (human IgG1 Fc recombinant protein), among which, 30 clones were picked for plasmid extraction, and scFv fragments were PCR amplified and sequenced after purification using a Qiagen PCR purification kit. The PCR primers are: forward: CTAT-TGCCAGCATTGCTGC (SEQ ID NO: 113), reverse: ATAGGGACCTAGACTTCAGG (SEQ ID NO: 114); the sequencing primers are: forward: CCTTCTACTCCTCCTA-CACC (SEQ ID NO: 115), reverse: GGAGGGCGT-GAATGTAAGC (SEQ ID NO: 116). Sequencing showed all the clones have almost the same scFv sequence, i.e., gy1 as shown in SEQ ID NOs 2, 4 and 20, with some point mutations shown in SEQ ID NOs: 38, 40, 42, 44, 46, 48, and 50.

Example 3: Characterization of Anti-PSMA scFv

Yeast display library panning used recombinant extracellular domain of PSMA, which may have a different conformation from the one expressed on living cell surface. Therefore, it is necessary to evaluate the binding capability of gy1 scFv to natively conformational PSMA expressed on cell surface, and the internalization upon antigen binding.

Binding of Gy1 scFv to PSMA Expressed on Cells Surface scFv gy1 binding on PSMA was studied on LNCap FGC cells using flowcytometry. Briefly, LNCap FGC cells were cultured in RPMI 1640 medium containing 10% FBS at 37° C. with 5% CO2. Cells were washed with PBS and detached by incubation with 0.02% Versene buffer (1.37 M NaCl, 26.8 mM KCl, 80.7 mM $Na_2HPO_4$, 14.7 mM $KH_2PO_4$, 5.4 mM disodium EDTA, 0.2% D-glucose). Cells were washed once with PBS and incubated on ice for 1 hour with gy1-containing yeast supernatant that was diluted 3-fold with FACS (PBS containing 0.2% FBS) buffer. Cells were washed three time with cold PBS and then incubated with 1:200 diluted anti-V5-Alexa647 in FACS buffer on ice for 1 hour in darkness. Non-bound anti-V5-Alexa647 was removed by three time washes with cold PBS and then cells were resuspended in 300 µl FACS containing 8 µl via-probe (BD biosciences). Gy1 binding on LNCap FGC cells were detected using flow cytometry where only living cells were gated and analyzed. Flow cytometry controls include: (1) dead cells resuspended in via-probe containing FACS buffer. Dead cells were prepared by freeze-thawing cells at −80° C. and 37° C. for two cycles; (2) dead cells resuspended in FACS buffer without via-probe; (3) unstaining cells with via-probe; and (4) anti-V5-Alexa647 staining only with via-probe. Results showed that gy1 scFv could significantly bind on Ln-Cap FGC cells (FIG. 1).

Internalization

Internalization is the prerequisite for an antibody if used to deliver drugs selectively into tumor cells. To evaluate the potential of gy1 for development of ADC, immunotoxin and nanomedicine, gy1 internalization was examined using flow cytometry. Flow cytometry is a simple alternative to confocal for internalization assay. The rationale is that internalization is an active process that is very efficient at 37° C. but will not happen at 4° C. If dye-labeled antibody are incubated with cells at 37° C. and 4° C. respectively, antibody molecules will bind on cell surface and some of them will be internalized at 37° C.; while antibody will bind on cell surface only at 4° C. because internalization will not happen. Trypsin is then used to remove all the cell surface proteins, including the dye labeled antibody. Positive dye signal in cells indicates internalization occurred while negative dye signal means internalization did not occur.

Briefly, LnCap FGC cells were seeded in two 48 well plates. The next day, 100 µl gy1 scFv containing yeast supernatant was preincubated with 4 µl anti-V5-Alexa467 in 200 µl volume (100 µl supernatant plus 100 µl cell medium) at RT for 1 hour. Then, cells were washed once with medium and incubated with the 200 µl gy1 containing medium (100 µl fresh medium plus 100 µl preincubated gy1-dye medium) at 37° C. and 4° C. respectively for 1 hour in darkness. As controls, cells were also incubated with same concentrated anti-V5-Alexa467 for the both temperatures. After two washes with cold PBS, 200 µl trypsin was added into wells to digest cell surface proteins for 30 min at RT. Then 500 µl medium was added to each well to stop trypsinization and cells were washed twice and then suspended in via-probe containing FACS buffer for flowcytometry analysis. Dead cell controls were also set up as above.

Figure 2:
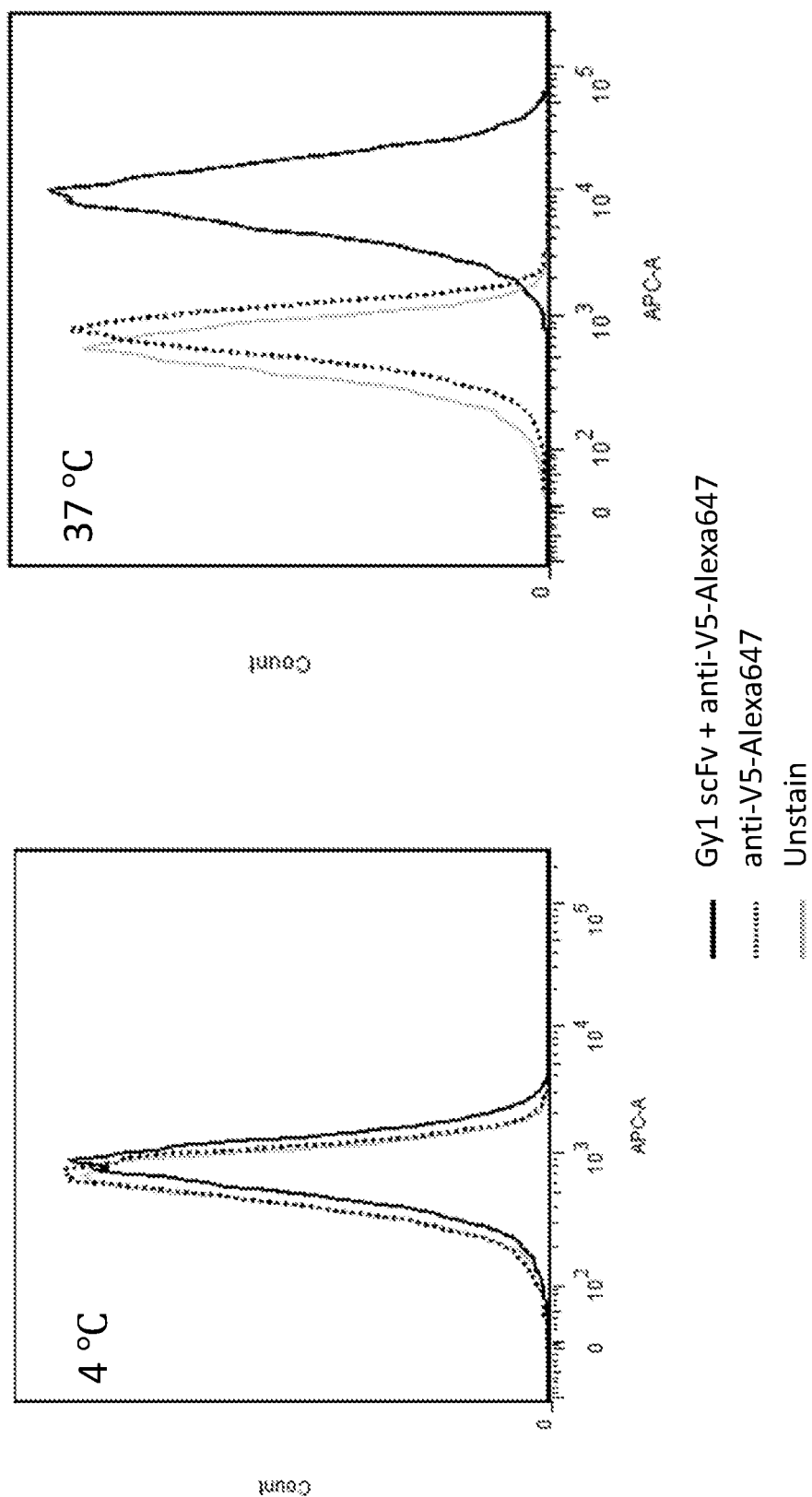
FIG. 2 depicts the results of experiments demonstrating that gy1 scFv was significant internalized upon antigen binding on LnCap cells. LnCap FGC cells were seeded in two 48 well plates. The next day, 100 µl gy1 scFv containing yeast supernatant was pre-incubated with 4 µl anti-V5-Alexa467 in 200 µl volume (100 µl supernatant plus 100 µl cell medium) at room temperature for 1 hour. Then cells were washed once with medium and incubated with the 200 µl gy1 containing medium (100 µl fresh medium plus 100 µl preincubated gy1-dye medium) at 37° C. and 4° C. respectively for 1 hour in darkness. As controls, cells were also incubated with same concentrated anti-V5-Alexa467 for the both temperatures. After two washes with cold PBS, 200 µl trypsin was added into wells to digest cell surface proteins for 30 min at RT. Then 500 µl medium was added to each well to stop trypsinization and cells were washed twice and then suspended in via-probe containing FACS buffer for flow cytometry analysis. Left panel represent 4° C. incubated cells and the right panel represent the 37° C. incubated cells. Solid gray line represents cells incubated with only plain medium; dotted black line represents cells incubated with anti-V5-Alexa647; while solid black line represents cells incubated with pre-formed gy1-anti-V5-Alexa647 complex.

Flow cytometry results showed that when gy1 scFv was incubated with Ln-Cap FGC cells at 4° C., antibody could only bind on cell surface; while when the incubation was at 37° C., gy1 scFv could not only bind to cells, but also significantly internalized (FIG. 2), which laid the foundation of PSMA targeted drug delivery using gy1 antibody or antibody fragments.

Affinity Measurement

Soluble gy1 expression YVH10 clone cultured in SD-CAA-Trp medium was scaled up to 500 ml and then cells were pelleted and resuspended in the same volume YEPD-GRD-Trp induction medium (YEPD medium contains Peptone 20 g/L, yeast extract 10 g/L, Dextrose20 g/L. YEPD-GRD-Trp is YEPD medium containing 1 g/L dextrose, 20 g/L galactose and 20 g/L raffinose and 0.008% tryptophan) to induce scFv expression at 20° C. for 4 days. scFv was purified using Nickel column because scFv has a 6×His tag at C terminus. The supernatant were filtered through a 0.45 µm filter and pH was adjusted to 8.0 by mixing with same volume EQ buffer (0.3 M NaCl, 0.05 M phosphate buffer, pH8.0) and loaded on a HisTrp HP column (GE healthcare) that equilibrated with 5 column volume EQ buffer. Column was washed with more than 10 column volume wash buffer (EQ buffer containing 10 mM imidazole) and scFv was eluted with elution buffer (EQ buffer containing 250 mM imidazole). scFv was then concentrated with centrifugal filter units (Amico) and imidazole was removed by dialysis against PBS. Aliquoted scFv was stored at −80° C.

Figure 3:
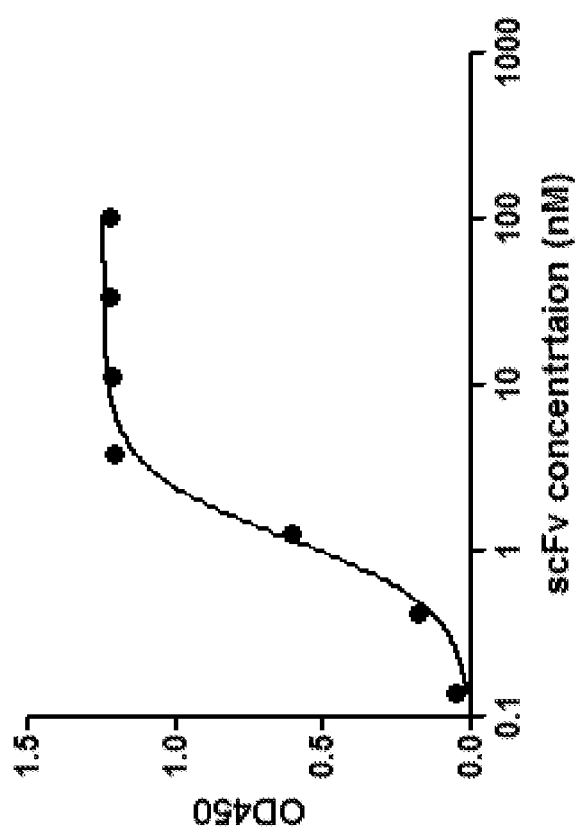
FIG. 3 depicts the results of experiments measuring affinity for gy1 scFv. Gy1 scFv affinity was measured using capture ELISA. Briefly, anti-Flag antibody (Sigma) was coated on ELISA plate at 4° C. overnight in PBS. Plates were washed and blocked with PBSTM and incubated with triplicate 3-fold serially diluted gy1 scFv. Plate was then washed and incubated with biotinylated PSMA and the binding was detected with streptavidin-HRP, and analyzed by colorimetric development using TMB and then stop buffer. Absorbance at OD450 was measured and the affinity was calculated using GraphPad Prism software.

Capture ELISA was used to measure the affinity of gy1 scFv. There is a Flag tag and a V5 tag at the N and C terminus of scFv, and thus antibodies to these tags were used to capture the scFv for ELISA assay. Briefly, anti-Flag antibody (Sigma) was coated on ELISA plate at 1 µg/ml, 50 µl/well at 4° C. overnight in PBS. Plates were washed twice with PBST, blocked with PBS™ 2 hours at RT and incubated with triplicate 3-fold serially diluted gy1 scFv, starting from 100 nM down to 0.137 nM in PBS™ at RT for 1 hour. Plate was washed 6 times with PBST and then incubated with 0.5 µg/ml biotinylated PSMA in PBS™ for 1 more hour at RT. After 6 washes, plate was incubated with 1:1000 diluted streptavidin-HRP (BD Bioscience) in PBS™ at RT for 30 min. Plate was washed again for 6 times and incubated with TMB for 20 min at RT, colorimertric reaction was stopped with stop buffer and the absorbance was read at OD450. Affinity was calculated using GraphPad Prism software, which was Kd=1.165 nM (FIG. 3).

Example 4: Gy1 Expression and Purification in *E. coli*

Figures 4A, 4B, 4C:
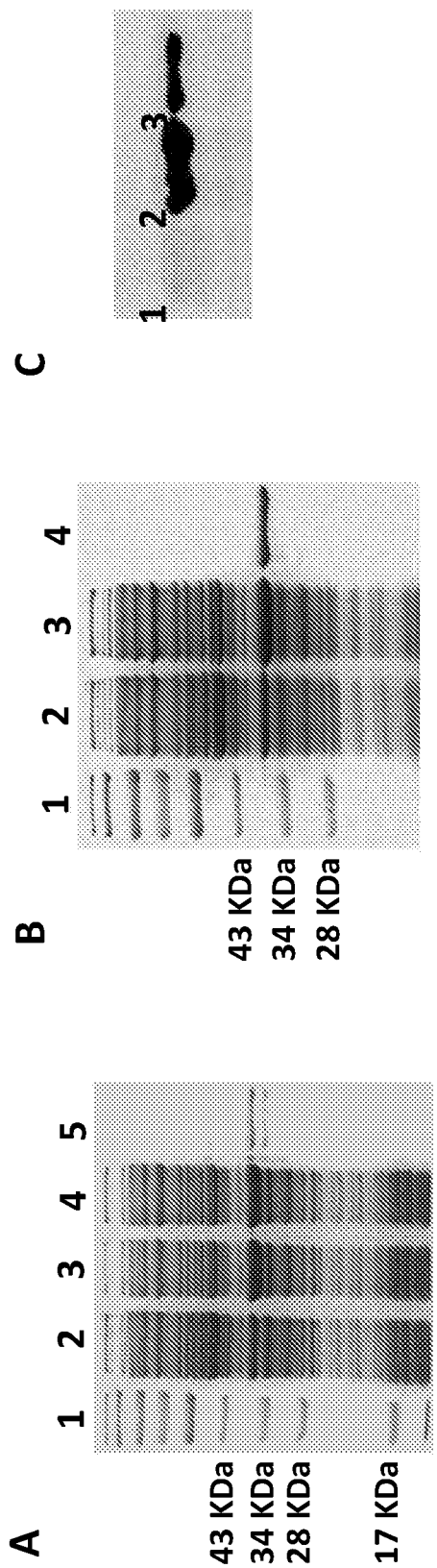
FIG. 4A through FIG. 4C, depicts the results of experiments of gy1 scFv expression in *E. coli*. The gy1 scFv was expressed in *E. coli* BL21 using vector pET302 induced with 0.05 mM IPTG for 4 h at 30° C. *E. coli* cells were lysed using sonicator and gy1 protein was purified using HisTrp HP column.

Over glycosylation of recombinant proteins expressed in yeast usually arises immunogenicity issues which may restrain their clinical application. To overcome this potential problem, prokaryotic expression of gy1 scFv in *E. coli* was pursued. The gy1 gene was amplified and cloned into the prokaryotic expression vector pET302 (named pET302-gy1), and then transformed into *E. coli* BL21 and induced to expression by 0.05 mM isopropyl-1-thio-b-galactopyranoside (IPTG) for 4 hours at 30° C. *E. coli* cells were lysed using sonicator and gy1 protein was then purified using HisTrp HP column as described above (FIG. 4). An anti-HER2 scFv (named NCP1) was expressed and purified in the same way and was used as a negative control.

Figure 5:
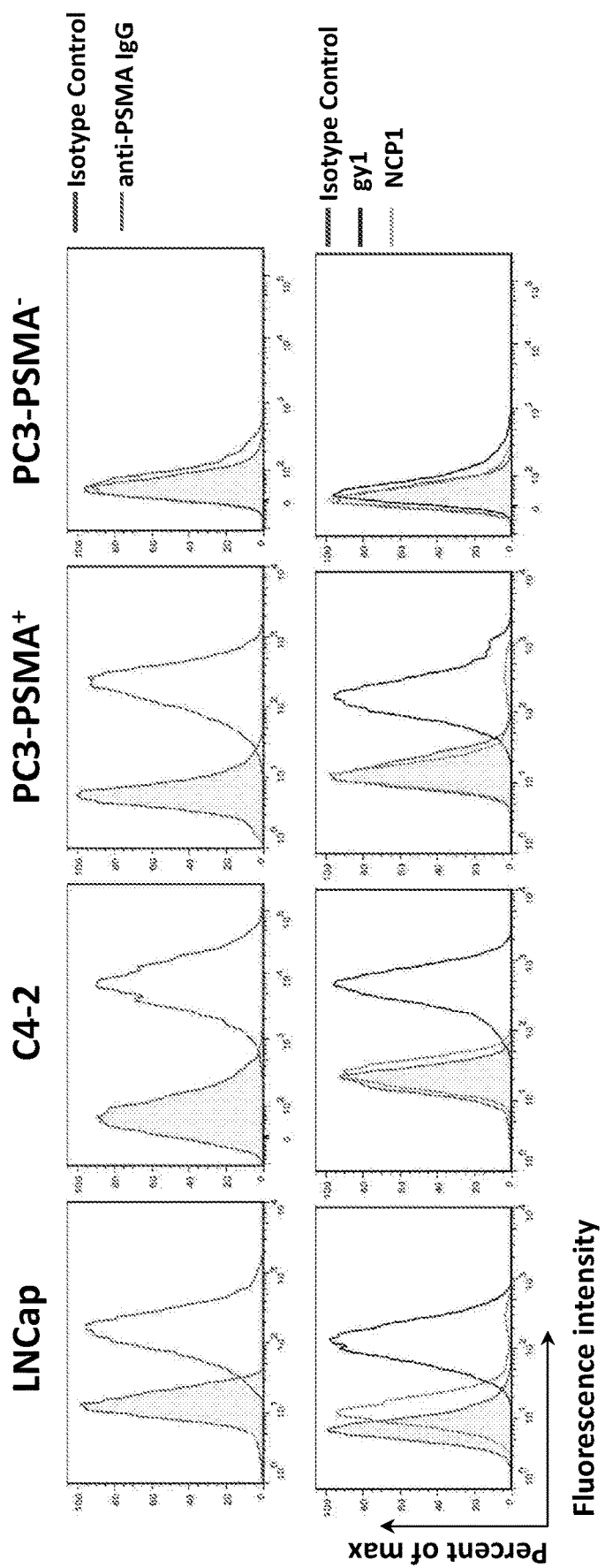
FIG. 5 depicts the results of experiments demonstrating that *E. coli* expressed gy1 scFv binds specifically on PSMA+ cells. Binding of *E. coli* expressed gy1 scFv to PMSA positive and negative cells were studied using flow cytometry. Prostate cancer cells, LNCaP, C4-2, PC3-PSMA+ and PC3-PSMA– cells were detached with Versene solution and incubated with 100 nM gy1 or control scFv NCP1 at 4° C. for 30 min, followed by washing and incubation with FITC-conjugated mouse anti-6His IgG (AbD Serotec; Bio-Rad) for 30 min at 4° C. in darkness. Cells were then washed and analyzed by flow cytometry. In parallel, PSMA protein expression was detected by a PE conjugated commercial anti-PSMA monoclonal antibody.

Binding of *E. coli* expressed gy1 scFv to PMSA positive and negative cells was studied using flow cytometry. Briefly, Prostate cancer cells, LNCaP, C4-2, PC3-PSMA+ and PC3-PSMA− cells were detached with Versene solution (1.37 M NaCl, 26.8 mM KCl, 80.7 mM Na$_2$HPO$_4$, 14.7 mM KH$_2$PO$_4$, 5.4 mM disodium EDTA, 0.2% D-glucose) and suspended in PBS at a density of 1×10$^6$ cells/mL, cells were washed with PBS and incubated with 100 nM gy1 or control scFv NCP1 at 4° C. for 30 min, followed by washing and incubation with FITC-conjugated mouse anti-6His IgG (AbD Serotec; Bio-Rad) for 30 minutes at 4° C. in darkness. Cells were then washed and analyzed by flow cytometry. In parallel, PSMA protein expression was detected by a PE conjugated commercial anti-PSMA monoclonal antibody (Biolegend, CA, USA). Results showed that *E. coli* expressed gy1 can bind only PSMA positive cells, but not negative cells (FIG. 5).

Example 5: Gy1 Affinity Measurement by Cell ELISA

Figure 6:
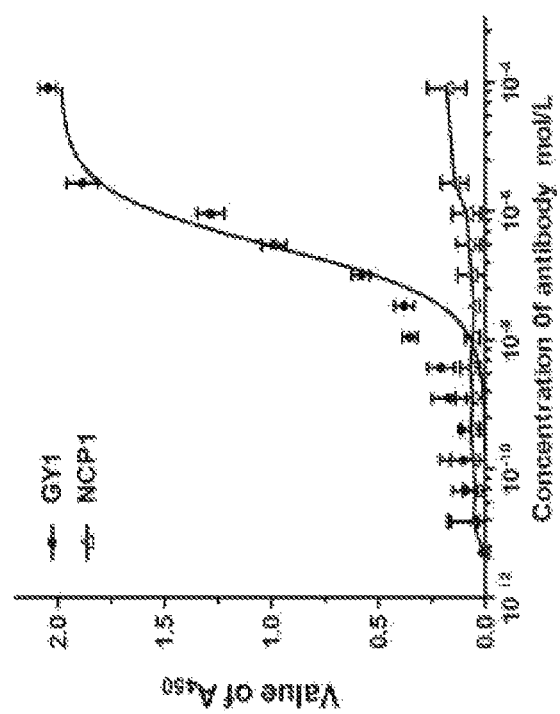
FIG. 6 depicts the results of experiments reassuring the affinity of *E. coli* expressed gy1 scFv by cell ELISA. Affinity of *E. coli* expressed gy1 scFv was measured on PSMA positive cell line C4-2. Briefly, C4-2 cultured in 96-well plate were fixed with 4% paraformaldehyde, blocked with 3% $H_2O_2$ and 6% bovine serum albumin sequentially. Cells were then incubated with three-fold serially diluted gy1 and the control scFv NCP1, from 8100 nM down to 0.005 nM, for 1h at 37° C. Cell binding was detected with HRP-conjugated mouse anti-6His and colorimetric signals were developed by TMB and stopped by STOP buffer. The absorbance at 450 nm was used to calculate gy1 affinity using GraphPad Prism 5.0 software.

To evaluate the binding affinity of *E. coli* expressed gy1 scFv to cell surface PSMA, PSMA-positive C4-2 cells were seeded at 5×10$^4$ per well in 96-well plate and cultured overnight. The next day, cells were fixed with 4% paraformaldehyde for 20 min before being treated with 3% H$_2$O$_2$ for 20 minutes to block endogenous peroxidase followed by blocking with 6% bovine serum albumin for 30 min at room temperature. Three-fold serially diluted gy1 and the control scFv NCP1, from 8100 nM down to 0.005 nM, were added and incubated for 1 hour at 37° C. Cells were then washed with PBST and incubated with HRP-conjugated mouse anti-6His antibody (AbD Serotec, Bio-Rad, Oxford, UK) for 1h at room temperature. Colorimetric signals were developed by addition of 3, 3', 5, 5'-tetramethylbenzidine (TMB, eBioscience, CA, USA) and stopped by incubation with 1 M H2SO4 for 15 minutes. The absorbance was measured at 450 nm using a Sunrise microplate reader (Tecan, Groedig, Austria) and the binding curves were analyzed using Graph-Pad Prism 5.0 software. The gy1 affinity was calculated using non-linear regression analysis of a one-site binding hyperbola equation. The affinity of *E. coli* expressed scFv gy1 was calculated as Kd=4.134 nM (FIG. 6)

Example 6: Gy1 Internalization Assay Using Confocal Imaging

Figure 7:
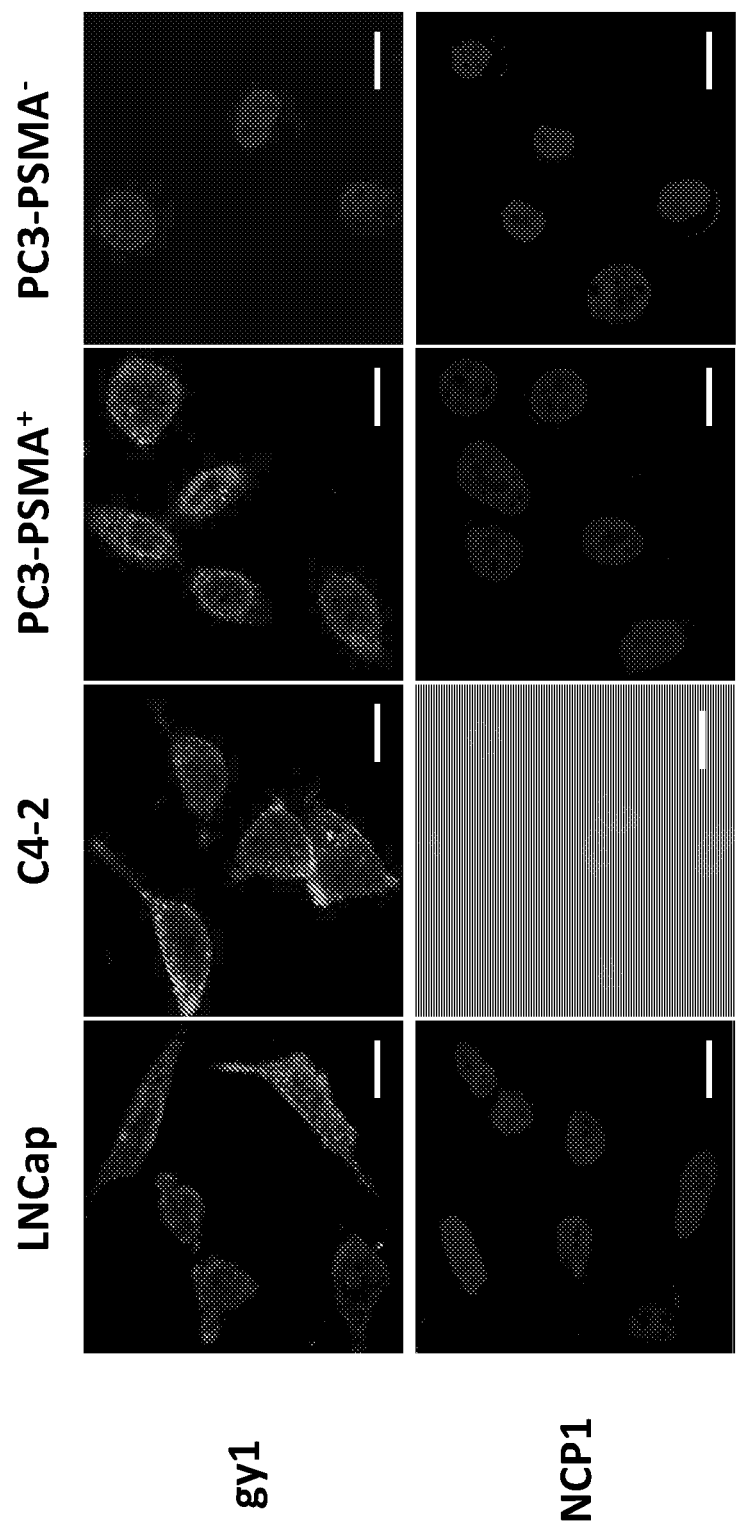
FIG. 7 depicts the results of experiments demonstrating that gy1 scFv is capable of being internalized upon antigen binding. Gy1 internalization upon antigen binding was studied on prostate cancer cells, i.e., LnCap, C4-2, PC3-PSMA+, and PC3-PSMA–. Cells grown on coverslips at 50% confluence were incubated with 200 nM gy1 or NCP1 for 2 hours at 37° C. Cells were washed, fixed with 4% paraformaldehyde and internalized gy1 was detected by FITC-conjugated mouse anti-6His IgG. Nuclei was stained with DAPI. Internalization was observed under confocal imaging system.

*E. coli* expressed gy1 scFv was used to study internalization using confocal imaging. Prostate cancer cells, i.e., LnCap, C4-2, PC3-PSMA$^+$, and PC3-PSMA$^-$, grown on coverslips at 50% confluence were incubated with 200 nM gy1 or NCP1 for 2 h at 37° C. Cells were washed, fixed with 4% paraformaldehyde for 20 minutes. Internalized gy1 was detected by FITC-conjugated mouse anti-6His IgG (AbD Serotec; Bio-Rad). Cell were then stained with 4',6-diamidino-2-phenylindole (DAPI) to visualize the nuclei. Finally, cells were washed with PBS and mounted on slides and observed under laser scanning confocal microscopy (FluoView FV1000, Olympus). Results showed that intense fluorescence signal can be observed in the cytoplasm of PSMA positive cell lines LNCaP, C4-2 and PC3-PSMA+. While in PSMA negative PC3-PSMA-cells, no fluorescence signal can be detected (FIG. 7). These results further demonstrated that gy1 can be effectively internalized into PSMA positive cells.

Figure 8A:
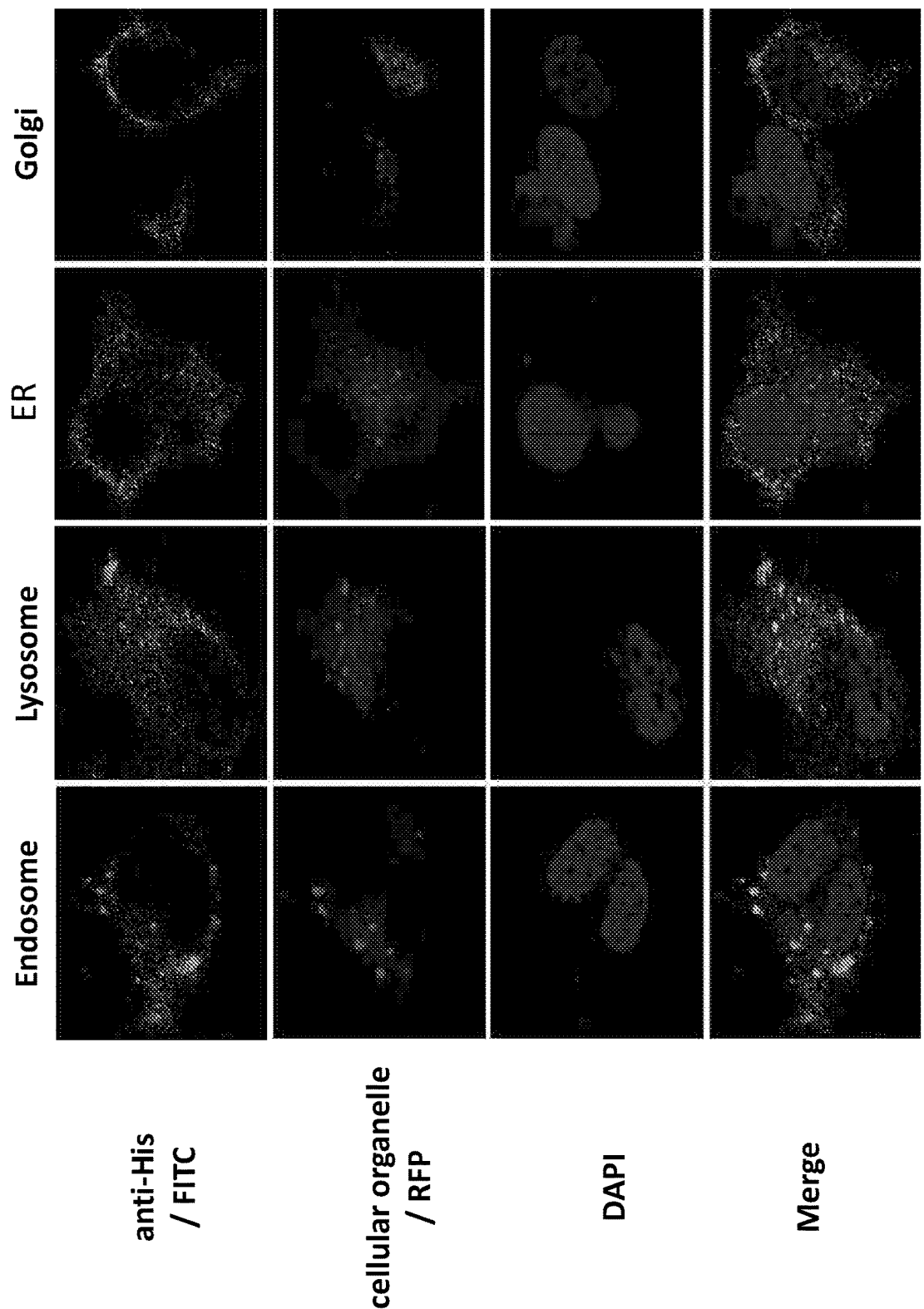
FIG. 8A and FIG. 8B, depicts the results of experiments visualizing intracellular trafficking of gy1.
Figure 8B:
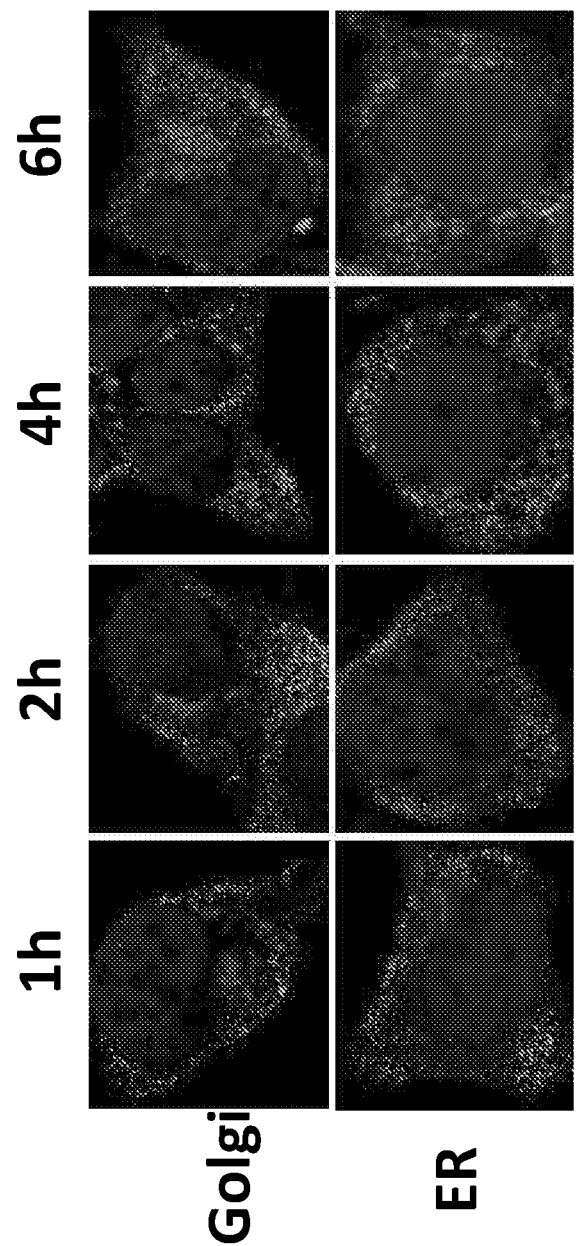

To investigate the subcellular transportation of gy1 after internalization, immunofluorescent staining was performed to examine the co-localization of gy1 (green fluorescence) with certain cellular organelles, including endosome, lysosome, Golgi and ER (red fluorescence) in C4-2 cells. Staining of the cellular organelles were performed using CellLight® Reagents (Invitrogen Life technologies, CA, USA) including CellLight® Lysosomes-RFP, CellLight® Endosomes-RFP, CellLight® Golgi-RFP and CellLight® ER-RFP according to the manufacturer's protocol. Cell images were captured by laser scanning confocal microscopy (FluoView FV1000, Olympus). Results showed that after a 4 hour incubation, gy1 was predominantly accumulated in endosomes and lysosomes (yellow fluorescence, FIG. 8A), suggesting that gy1 internalizes into target cells through the endosome-lysosome pathway. There was no overlap between the signals of gy1 and Golgi or ER for different periods of incubation times (FIG. 8B).

Internalized protein mainly have two trafficking pathways. One is directly through endosome to lysosome and the other is from Golgi apparatus to ER, which is called retrograde trafficking and is commonly used for recycling transportation. It was further investigated whether gy1 may also use the second pathway by co-staining gy1 with Golgi apparatus or ER. Results showed that even being incubated for different time points, no co-localization could be observed between gy1 and Golgi or ER (FIG. 8B), which abrogates the possibility of the second trafficking pathway after gy1 internalization.

Example 7: In Vivo Tumor Targeting by Gy1

Figure 9:
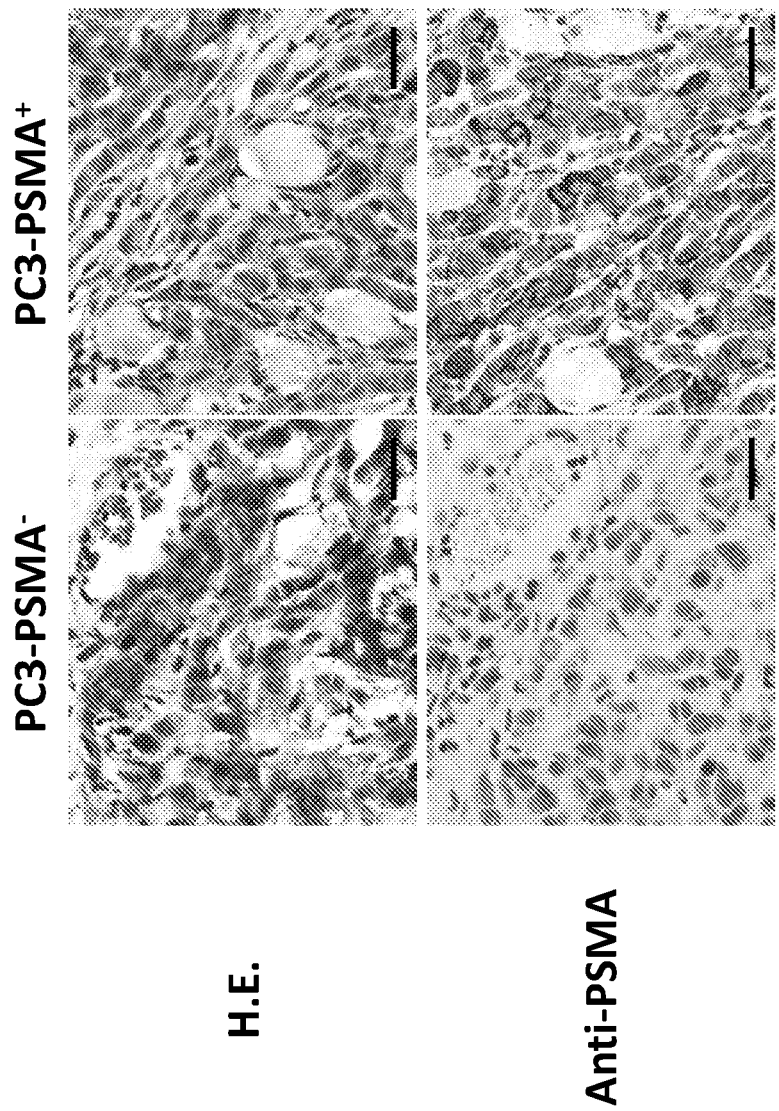
FIG. 9 depicts results of validation experiments using PC3-PSMA+/PC3-PSMA-mouse model. PSMA positive and negative xenograft nude mouse models were established using luciferase-expressing PC3-PSMA+ and PC3-PSMA– cells. The xenograft tumor models were developed by injecting $5 \times 10^6$ firefly luciferase-expressing PC3-PSMA+ or PC3-PSMA– cells in 0.1 mL PBS subcutaneously in the right hip of each mouse. Two weeks after inoculation, tumor tissue was isolated and H&E and immunohistochemistry staining were performed to check the tissue morphology and PSMA expression level.
Figure 11:
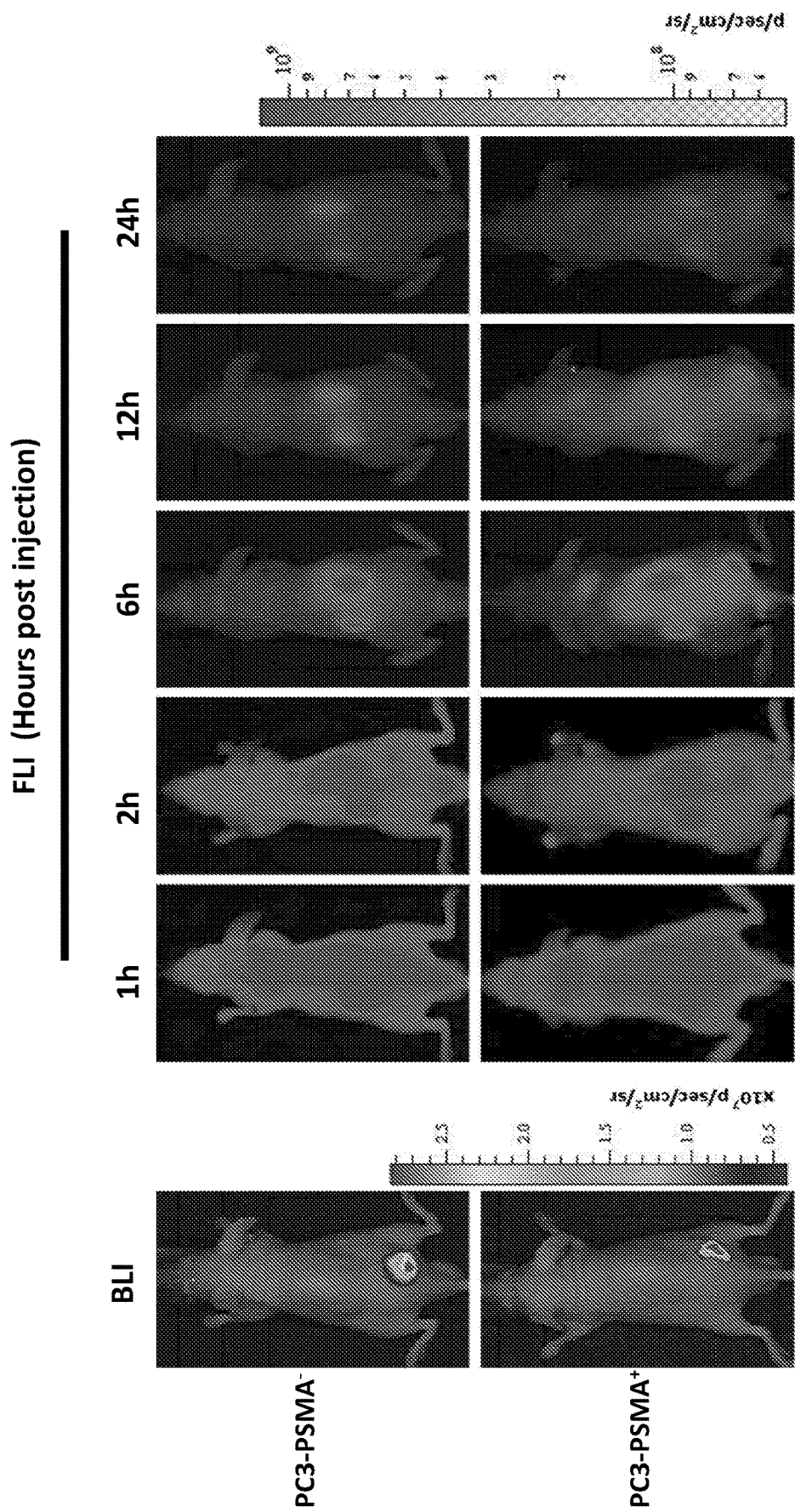
FIG. 11 depicts the results of experiments evaluating the dynamic biodistribution of gy1 scFv in prostate tumor models. Dynamic distribution of gy1 scFv in PC3-PSMA$^+$/PC3-PSMA" xenograft nude mice was studied using Xenogen IVIS Kinetic imaging system at an excitation wavelength of 745 nm post tail-vein injection of 0.2 μmol/kg IRDye800cw-labeled gy1 scFv. Bioluminescence imaging (BLI) was acquired to identify the prostate tumor tissues (Left). The distribution of IRDye800cw-labeled gy1 was monitored at indicated time points in the same mouse of each group. Representative result was shown.

To evaluate the capability and efficiency of gy1 for in vivo PSMA targeting, as well as to evaluate the feasibility of gy1 based intraoperative optical imaging for PCa, PSMA positive and negative xenograft nude mouse models were established using luciferase-expressing PC3-PSMA+ and PC3-PSMA− cells. The xenograft tumor models were developed by injecting $5 \times 10^6$ firefly luciferase-expressing PC3-PSMA+ or PC3-PSMA− cells in 0.1 mL PBS subcutaneously in the right hip of each mouse. Two weeks after inoculation, tumor tissue was isolated and H&E and immunohistochemistry staining were performed to check the tissue morphology and PSMA expression level. Results showed PSMA can be detected in the PC3-PSMA+ prostate cancer tissue, but not the PC3-PSMA− prostate cancer tissue (FIG. 9). Luciferase expression was also confirmed in both xenograft models by Xenogen IVIS Kinetic imaging system (FIG. 11, left panel). This pair of PSMA positive and negative prostate cancer xenograft mouse model was used for gy1 targeting evaluation.

Figure 10:
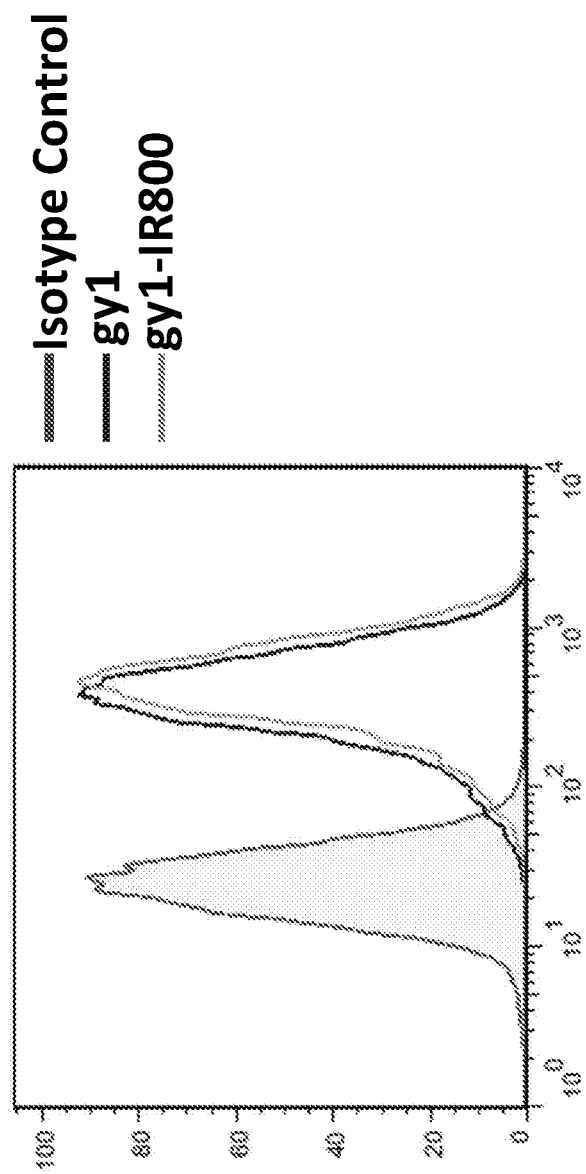
FIG. 10 depicts the results of experiments demonstrating that IRDye800cw labeling does not compromise PSMA binding of gy1. The binding affinity of infrared dye IRDye800cw labeled gy1 scFv was evaluated on PC3-PSMA$^+$ cells using unlabeled gy1 as a positive control. The result indicated that dye labeling did not compromise PSMA binding of gy1.

For in vivo optical imaging study, the gy1 and NCP1 proteins were labeled with IRDye800 using IRDye800cw labeling kit (Li-Cor Biosciences, Nebraska, USA) with a protein/dye ratio of 1:20 at concentration of 1 mg/ml following the manufacture's protocol. Extra dye was removed through dialysis. Dye labeling did not compromise the PSMA binding affinity of gy1 as confirmed on PC3-PSMA+ cells by flow cytometry analysis (FIG. 10). For each mouse, 0.2 µmol/kg of the IRDye800-labeled gy1 or NCP1 was injected intravenously, and the mouse was anesthetized at indicated time points and the IRDye800 fluorescence was monitored in a real-time manner under the Xenogen IVIS Kinetic imaging system at an excitation wavelength of 745 nm. Identical illumination settings (1 second exposure, f/stop=2) were used for all images. In parallel with the in vivo whole-body near-infrared fluorescence imaging (FLI), five mice in each group treated for 12 hours were sacrificed and different tissues were isolated and their fluorescence intensities were analyzed. Fluorescence intensities were calculated using Living Image software and presented as photon flux ($p/s/cm^2/sr$).

Figure 12:
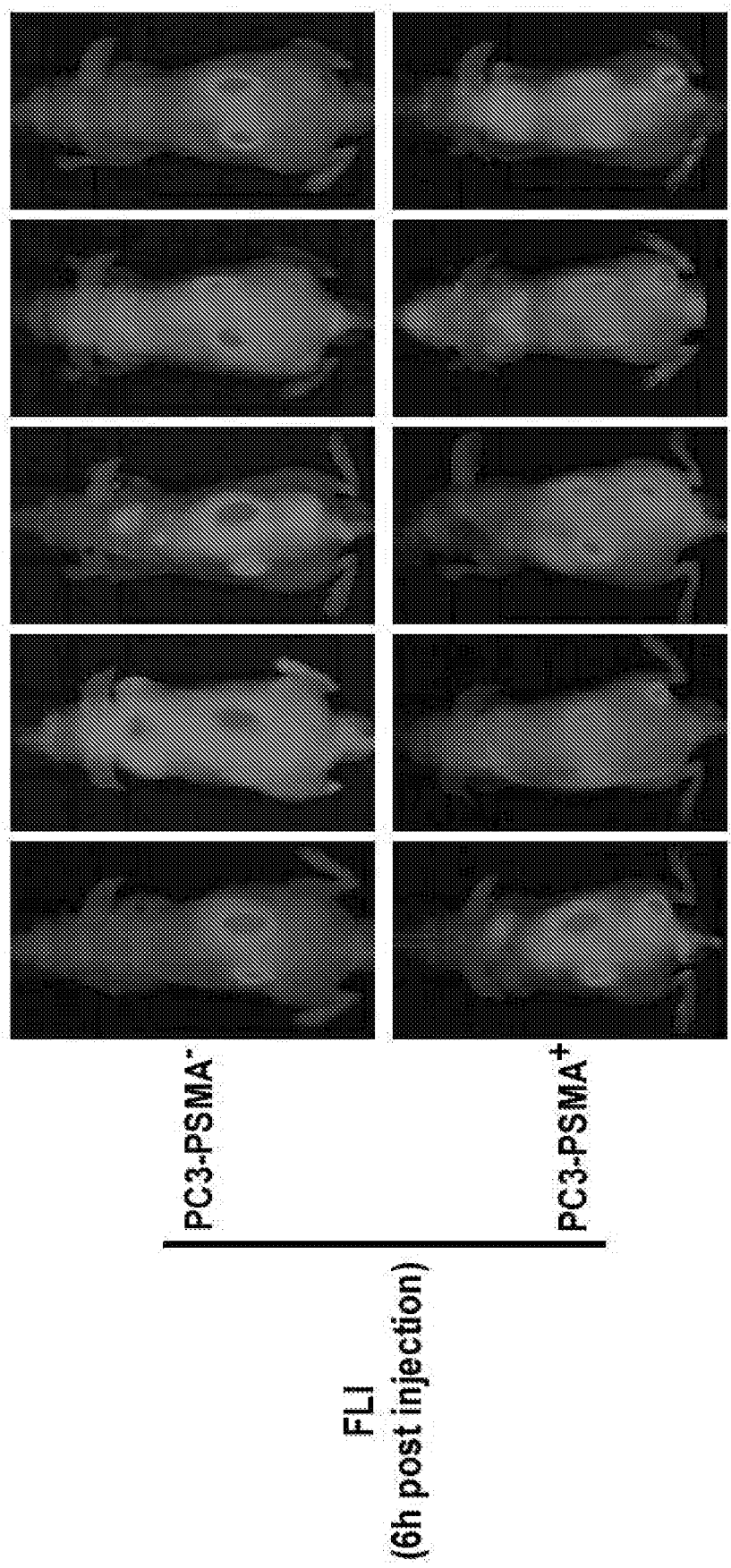
FIG. 12 depicts the in vivo PSMA targeting of gy1 scFv. At 6 hours post injection, gy1 scFv shows the best tumor localization signals. Shown here are two groups of mice with PSMA positive or negative tumors.
Figure 13A:
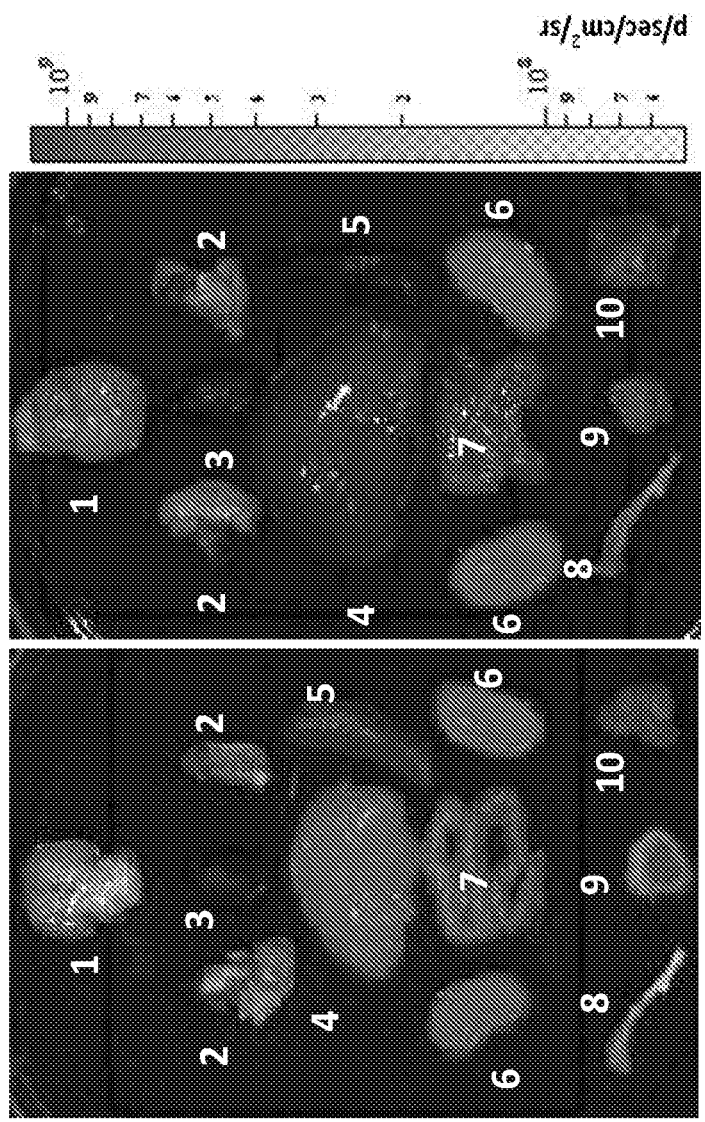
FIG. 13A and FIG. 13B, depicts the results of experiments evaluating gy1 scFv biodistribution in mouse organs 12 hours post intravenous injection.
Figure 13B:
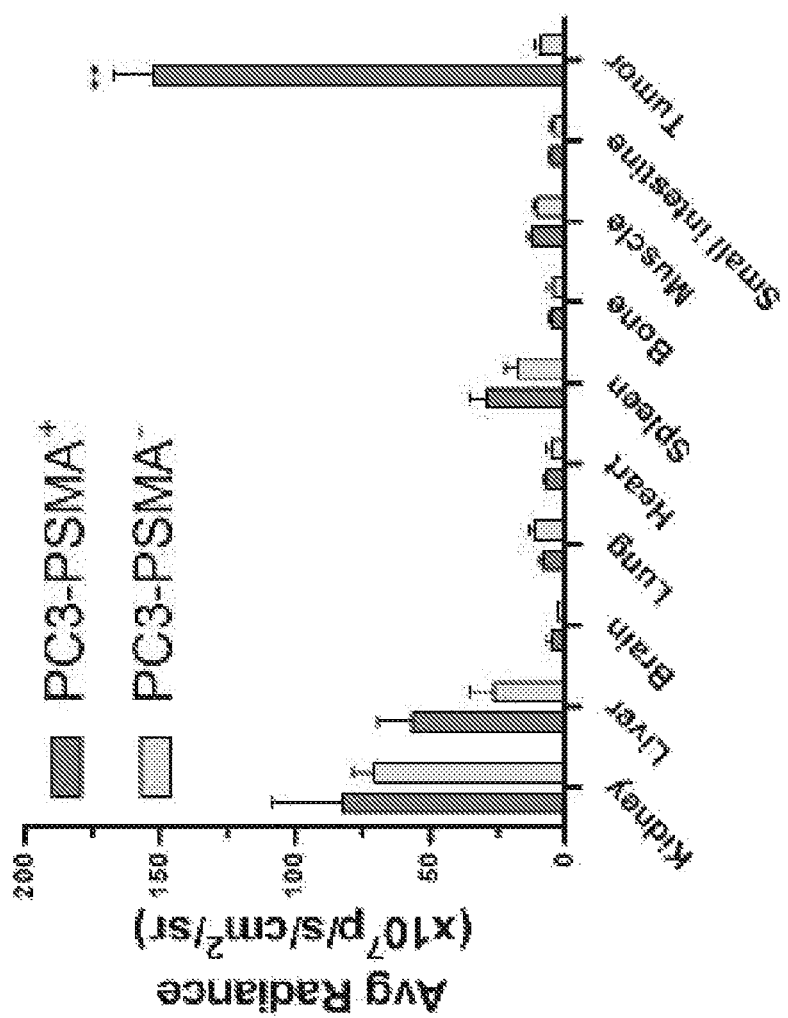

Results showed that the IRDye800 labeled gy1 diffused rapidly throughout the whole body after 1 hour and can be detected in tumor tissues from 2 hours. The IRDye800 labeled gy1 was then gradually cleared from the body, but was still specifically retained in PSMA positive tumor tissues, but not in PSMA negative tumor tissues (FIG. 11, right panel, FIG. 12). Highest signal/background ratio in tumor was obtained at 6 hour post-injection, and the signal in tumor was nearly undetectable after 24 hours. Five mice in each group were sacrificed at 12 hours after gy1 injection and different tissues were collected for further bio-distribution evaluation. Consistent with the FLI data, strongest fluorescent signal can be detected in tumor tissues in the PC3-PSMA+ group, relatively weak signals can be detected in kidney, liver and spleen, while only negligible signals can be detected in other tissues. While in the PC3-PSMA− group, no obvious fluorescent signal can be detected in tumor tissues (FIG. 13A and FIG. 13B). These data suggested that gy1 can specifically target and distribute in PSMA positive tumor tissues in vivo, which encourages the development of PSMA targeted imaging and therapy strategy using gy1, such as intraoperative optical imaging, PET imaging, nanomedicine and antibody drug conjugate.

Example 8: Engineering of Gy1 scFv into Full Antibody

Figures 14A, 14B:
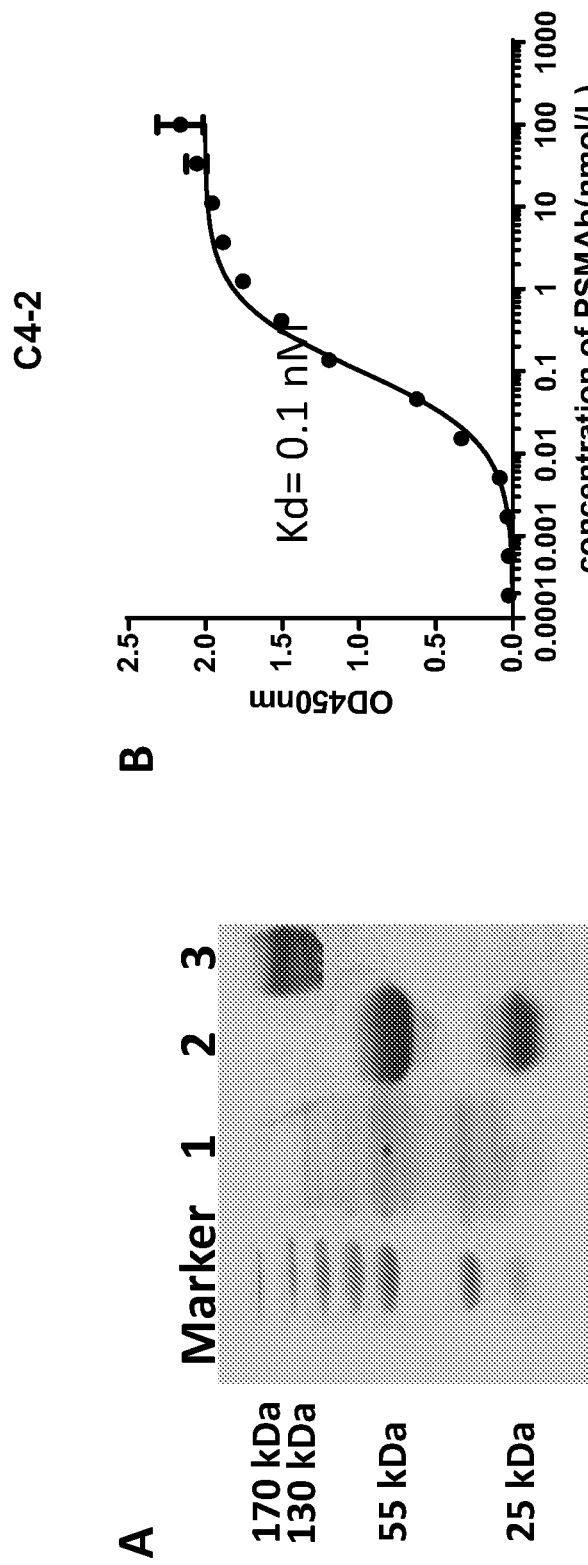
FIG. 14A and FIG. 14B, depicts the results of experiments measuring PSMAb expression and affinity.

Gy1 scFv with mutations of SEQ ID NOS: 40/41, 42/43, 44/45, 46/47 (gy1-2) were engineered into full antibody by grafting signal peptides and constant regions for both heavy and light chains respectively. By sequence analysis of antibody germline data base, IGHV3-30-3*02 and IGLV1-50*01 signal peptide, and IgG1 and CL1 constant regions were chosen for heavy and light chain respectively. The nucleic acid and amino acid sequence of heavy and light chain is shown in SEQ ID NOs. 52/53 and 60/61 and matured heavy and light chain (after signal peptide cleavage) sequences are shown in SEQ ID NOs. 68 and 69. The engineered full antibody was named PSMAb. The nucleic acid sequences of heavy and light chain were codon optimized for CHO cell expression, synthesized, and cloned into vector pcDNA3 respectively. Recombinant PSMAb was expressed by transient co-transfection of heavy and light chain expression vector at the ratio of 1:4 into suspension CHO cells (CHO—S) following the manufacture's protocol (FreeStyle™ CHO Expression system of life technologies). After 7 days expression, the supernatant was collected and PSMAb was purified using HiTrap rProtein A FF column (GE healthcare life sciences). Briefly, supernatant was mixed with same volume buffer A (20 mM sodium pho'sphate buffer, pH 7.0), filtered through a 0.45 µm membrane and applied onto a HiTrap rProtein A FF column that was equilibrated with 5 column volume buffer A. Column was washed with 10 column volume buffer A and antibody was eluted with buffer B (0.1 M citric acid, pH 3.5) and neutralized with buffer C (1.0 M Tris-Hcl pH 9.0). Antibody was buffer changed into PBS by dialysis, aliquoted and stored at −80° C. (FIG. 14A).

Example 9: Characterization of PSMAb Full Antibody

Affinity Measurement

ELISA was used to measure the affinity of PSMAb as described in Example 5, except that a control human IgG1 (Sigma) was used instead of PSMAb for negative controls, and a HRP-conjugated anti-human IgG Fc Ab (1:20000, Abcam) was used as the secondary antibody. PSMAb 3-fold serially dilution started from 100 nM down to 0.19 pM. The calculated affinity of PSMAb is 0.1 nM (FIG. 14B)

Cell Binding and Blocking Assay

Figure 15:
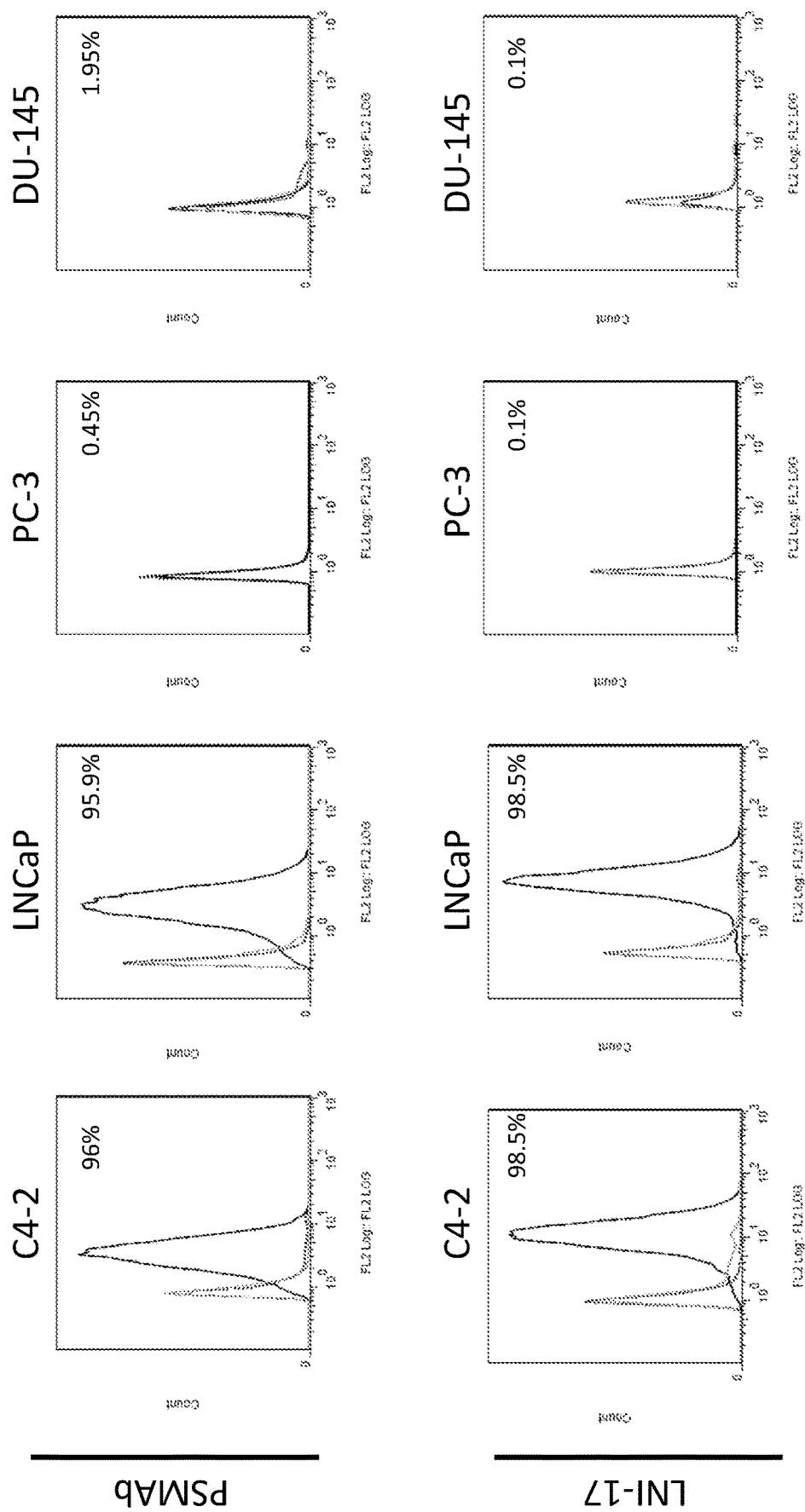
FIG. 15 depicts the results of experiments demonstrating that PSMAb binds specifically on PSMA+ cell lines. Binding of PSMAb on PSMA positive and negative cells were studied using flow cytometry. upper row: negative control IgG (gray); PSMAb (black); lower row: negative control IgG (gray); positive control antibody LNI-17 (black).

PSMAb binding to PSMA expressed on cell surface have been studied by flow cytometry on several prostate cell lines, i.e., PSMA+ cells C4-2, LNCaP, PC-3-PSMA+, and PSMA− cells PC-3 and DU-145. Briefly, detached cells were incubated with PSMAb, negative control human IgG (Sigma) or positive control antibody LNI-17 (Biolegend) first, after 3 washed and then incubated with 1:20 diluted PE conjugated secondary antibody (Biolegend). Cell binding signal was detected by flowcytometry. Results showed that PSMAb can bind only on PSMA-positive cells, but not negative cells (FIG. 15), consistent with the PSMA expression levels confirmed by LNI-17 staining.

Figure 16:
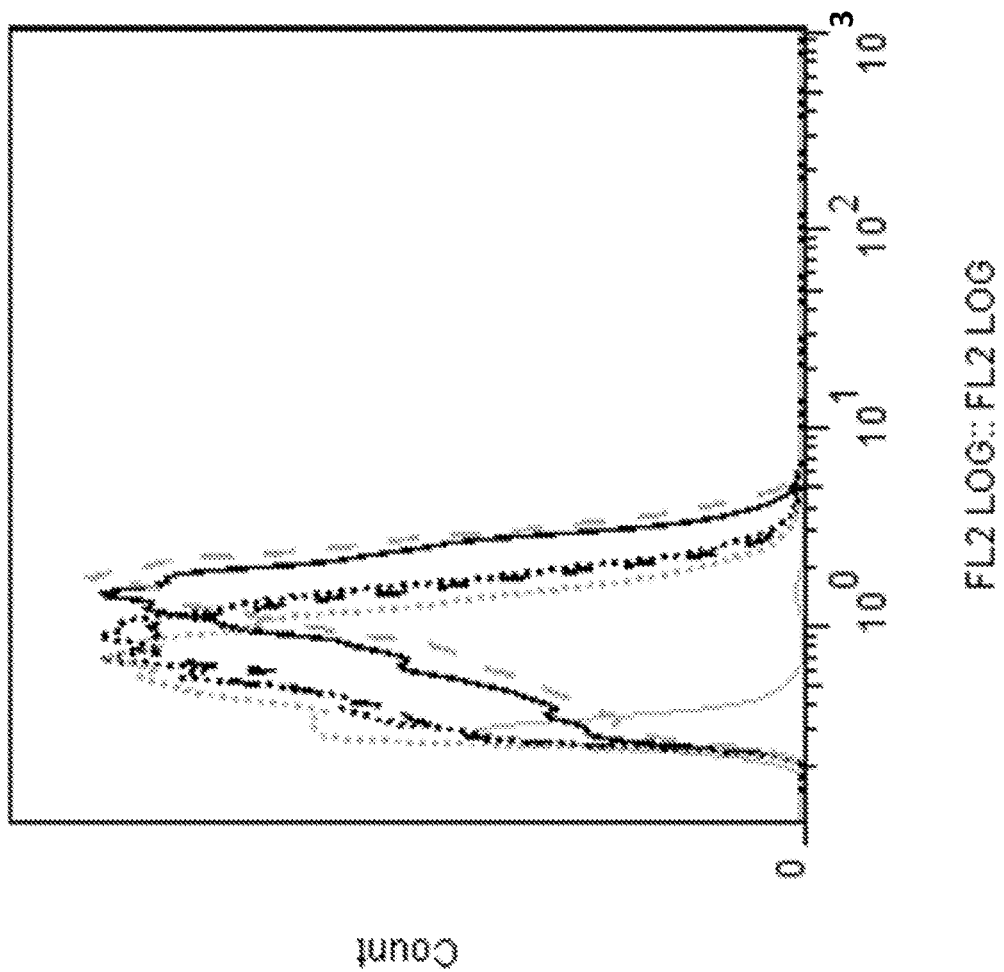
FIG. 16 depicts the results of experiments demonstrating that PSMAb binding on PC3-PSMA+ cells is blocked by recombinant PSMA protein. PSMAb at concentration of 2 nM was preincubated respectively with 0, 2, 6 and 10 nM recombinant PSMA, or 10 nM control protein BSA at RT for 2 hours and the then incubated with PC3-PSMA+ cells. Blocking effect on PSMAb binding on PC3-PSMA+ cells were studied by flow cytometry. Negative control: gray solid line; PSMAb 2 nM: black solid line; PSMAb 2 nM blocked by 10 nM BSA: gray broken line; PSMAb 2 nM blocked by 2 nM PSMA: black dot line; PSMAb 2 nM blocked by 6 nM PSMA: black broken line; PSMAb 2 nM blocked by 10 nM PSMA: gray dot line.
Figure 17A:
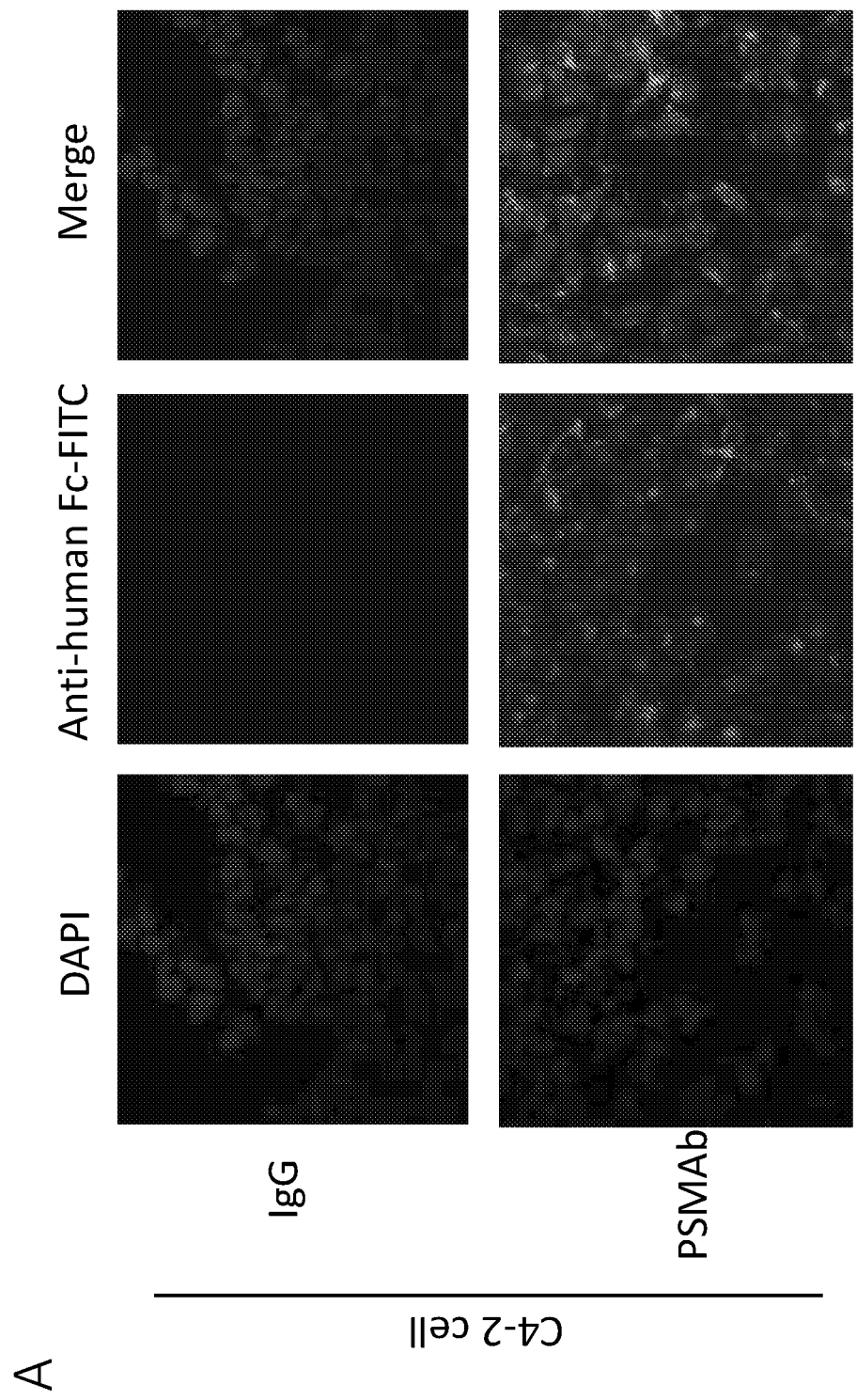
FIG. 17A through FIG. 17D, depicts the results of experiments examining PSMA specific internalization of PSMAb. PSMAb internalization was studied on prostate cancer cells, i.e., C4-2 (FIG. 17A), PC-3 (FIG. 17B), LnCap (FIG. 17C), and DU-145 (FIG. 17D) cells. Cells grown on coverslips at 50% confluence were incubated with 200 nM PSMAb or a control human IgG1 for 2 hours at 37° C. Cells were washed, fixed with 4% paraformaldehyde and internalized PSMAb was detected by FITC conjugated anti-human IgG Fc antibody. Nuclei were stained with DAPI. Internalization was observed under confocal imaging system.
Figure 17B:
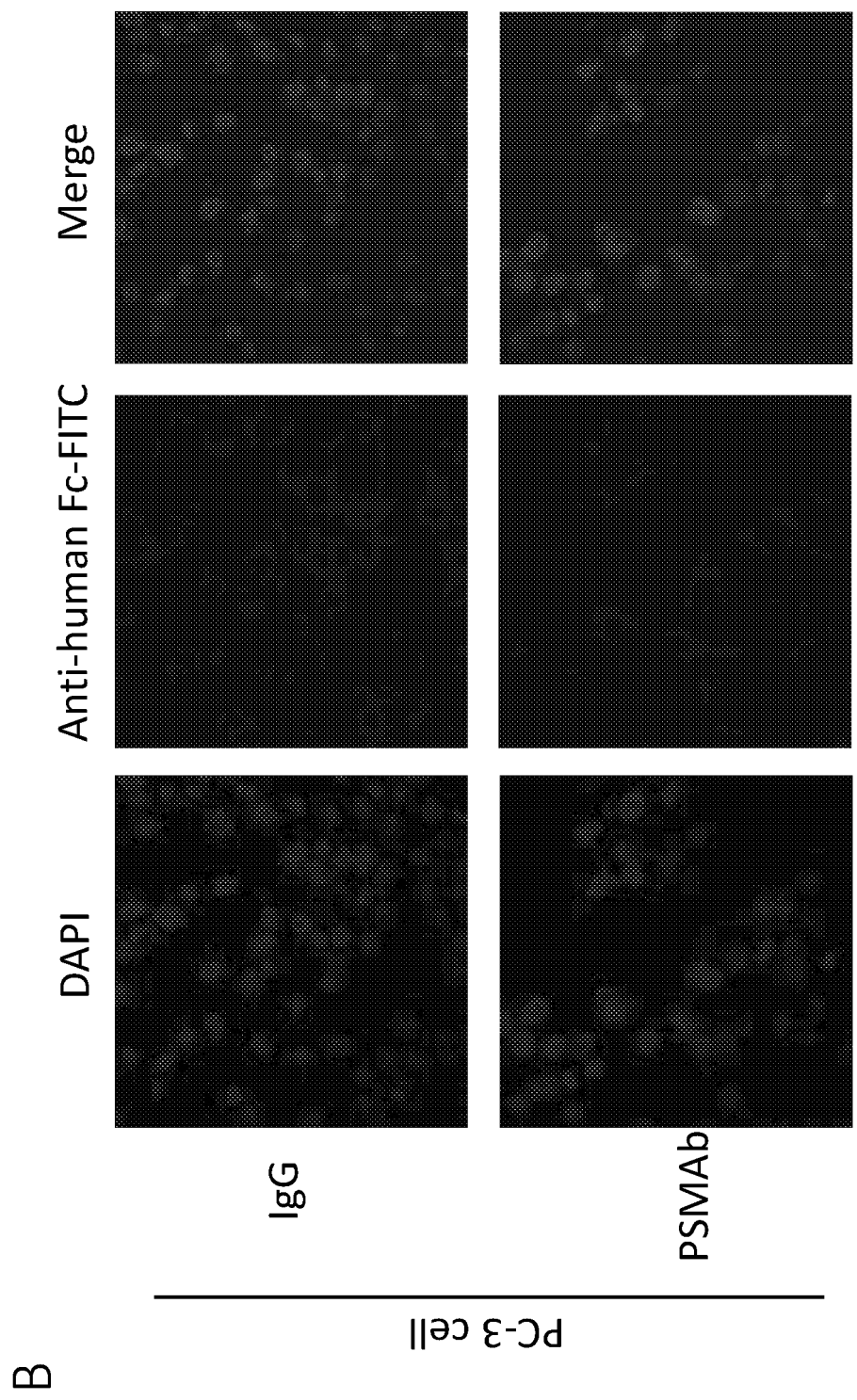
Figure 17C:
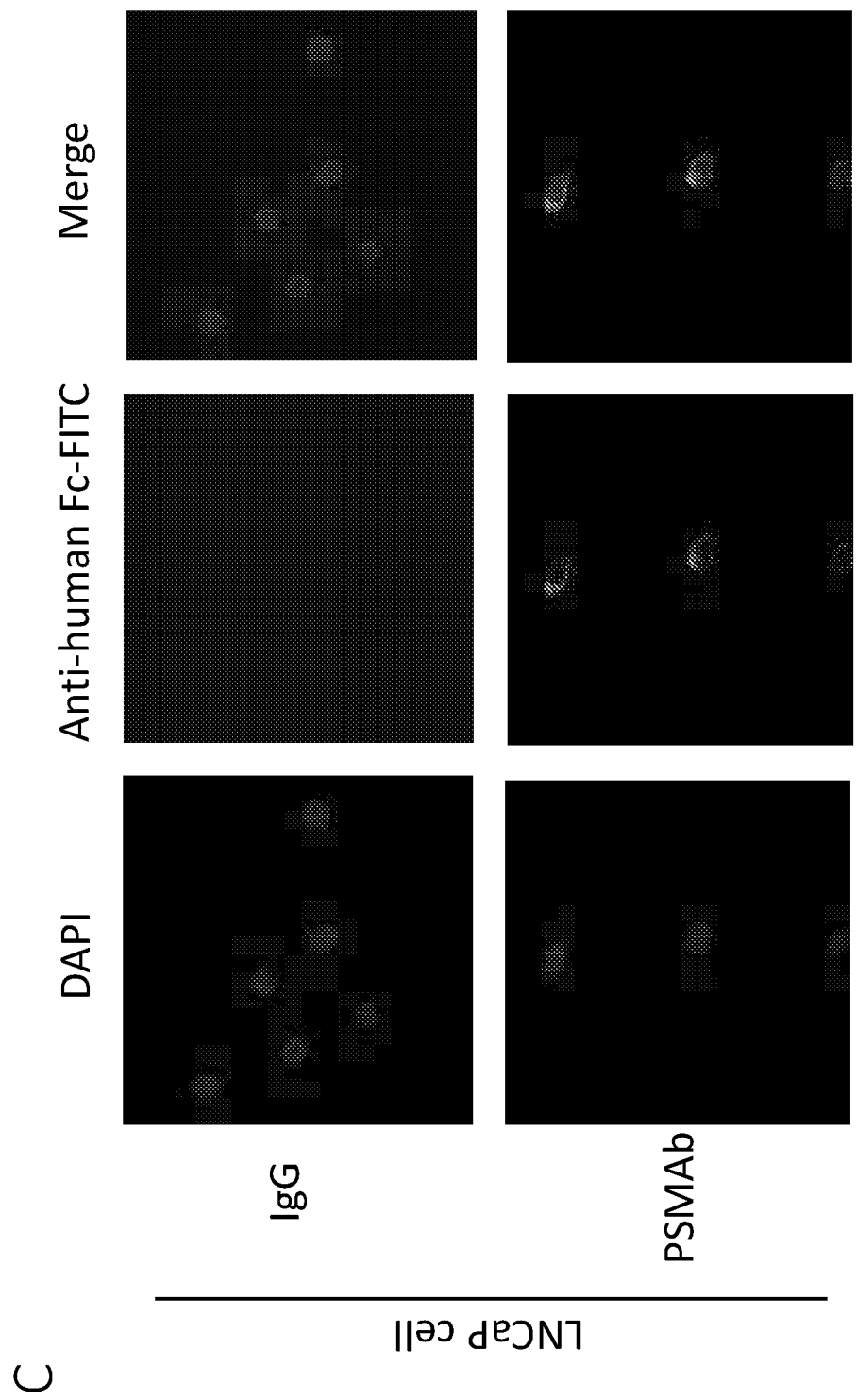
Figure 17D:
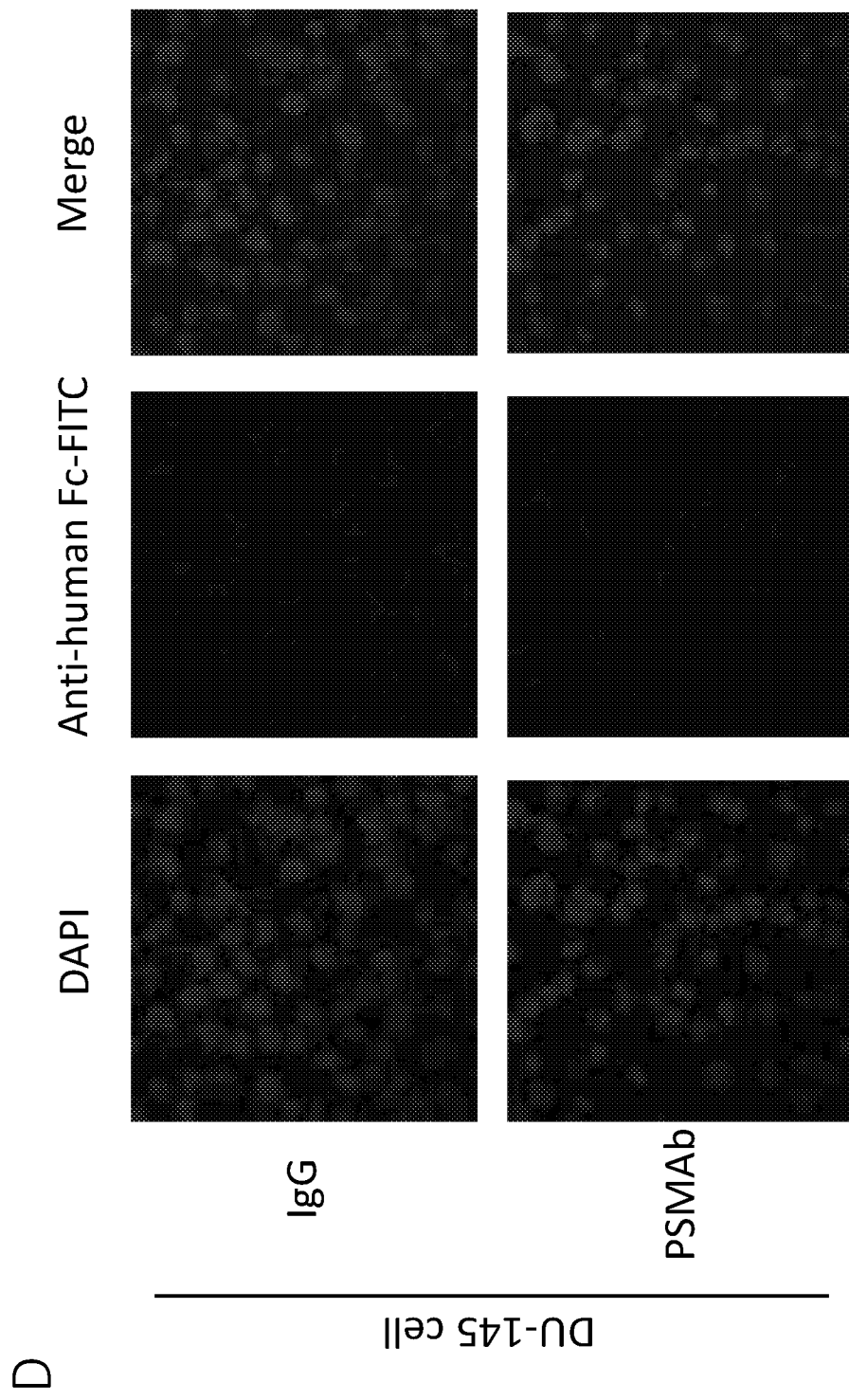

To further confirm the binding of PSMAb to PSMA+ cells was PSMA specific, a blocking assay was performed using recombinant PSMA protein or control protein BSA. The blocking assay was studied on PC3-PSMA+ cells using flow cytometry as described above, except that before incubation with cells, PSMAb at concentration of 2 nM was pre-incubated with 2, 6 and 10 nM recombinant PSMA, or 10 nM BSA as a control at RT for 2 hours. Results showed that PSMA recombinant protein can completely block the binding of PSMAb to PC3-PSMA+ cells even at the same concentration of the antibody, i.e., 2 nM (FIG. 16).

Internalization of PSMAb

Internalization of PSMAb was studied on prostate cancer cells C4-2, LNCaP, PC-3 and DU-145 as described in Example 6 except that a control human IgG1 was used as negative control and the secondary antibody was FITC conjugated anti-human IgG Fc antibody (1:50; Santa Cruz biotechnology, USA). Results demonstrated that PSMAb can be selectively and effectively internalized into PSMA positive cells (FIG. 17).

Example 10: In Vivo Tumor Targeting of PSMAb

Figure 18A:
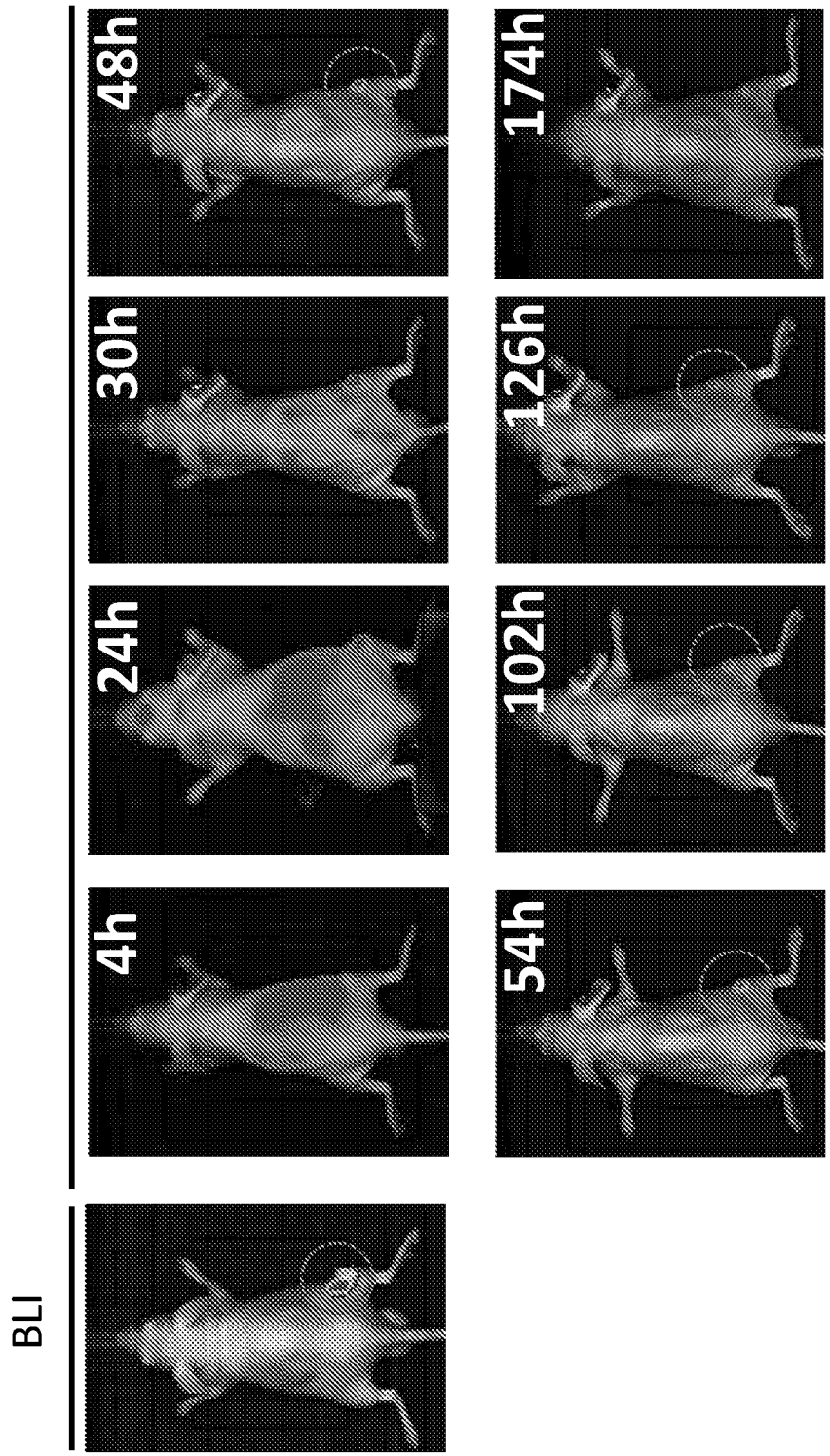
FIG. 18A through FIG. 18C, depicts the results of experiments investigating in vivo PSMA targeting by PSMAb. The efficiency of tumor targeting and the potential for intraoperative optical imaging of PSMAb was studied using IRDye800CW labeled PSMAb. 50 µg labeled PSMAb/mouse was tail-vein injected into PC3-PSMA+(FIG. 18A) or PC3-PSMA− (FIG. 18B) xenograft model and the biodistribution of PSMAb at 4 hours, 24 hours, 30 hours, 48 hours, 54 hours, 102 hours, 126 hours and 174 hours was monitored using Xenogen IVIS Kinetic imaging system. Images of 4 mice in each group 48 hours post-injection were shown in FIG. 18C. In vivo optical imaging showed that PSMAb diffused rapidly throughout the whole body and can be detected in tumor tissues from 24 hours post-injection, and was then gradually cleared from body while specifically retained at PSMA+ tumor, but not PSMA− tumor
Figure 18B:
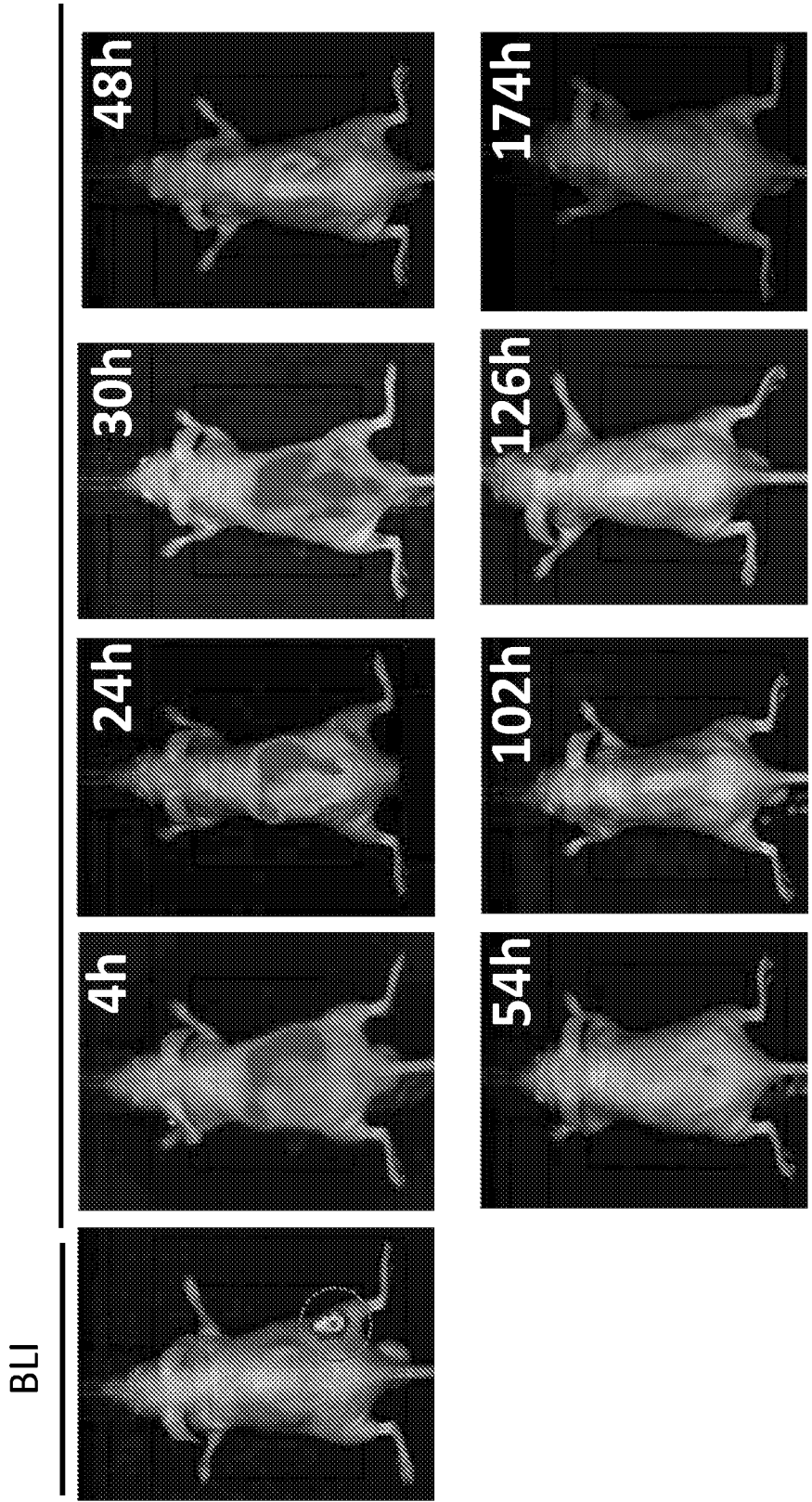
Figure 18C:
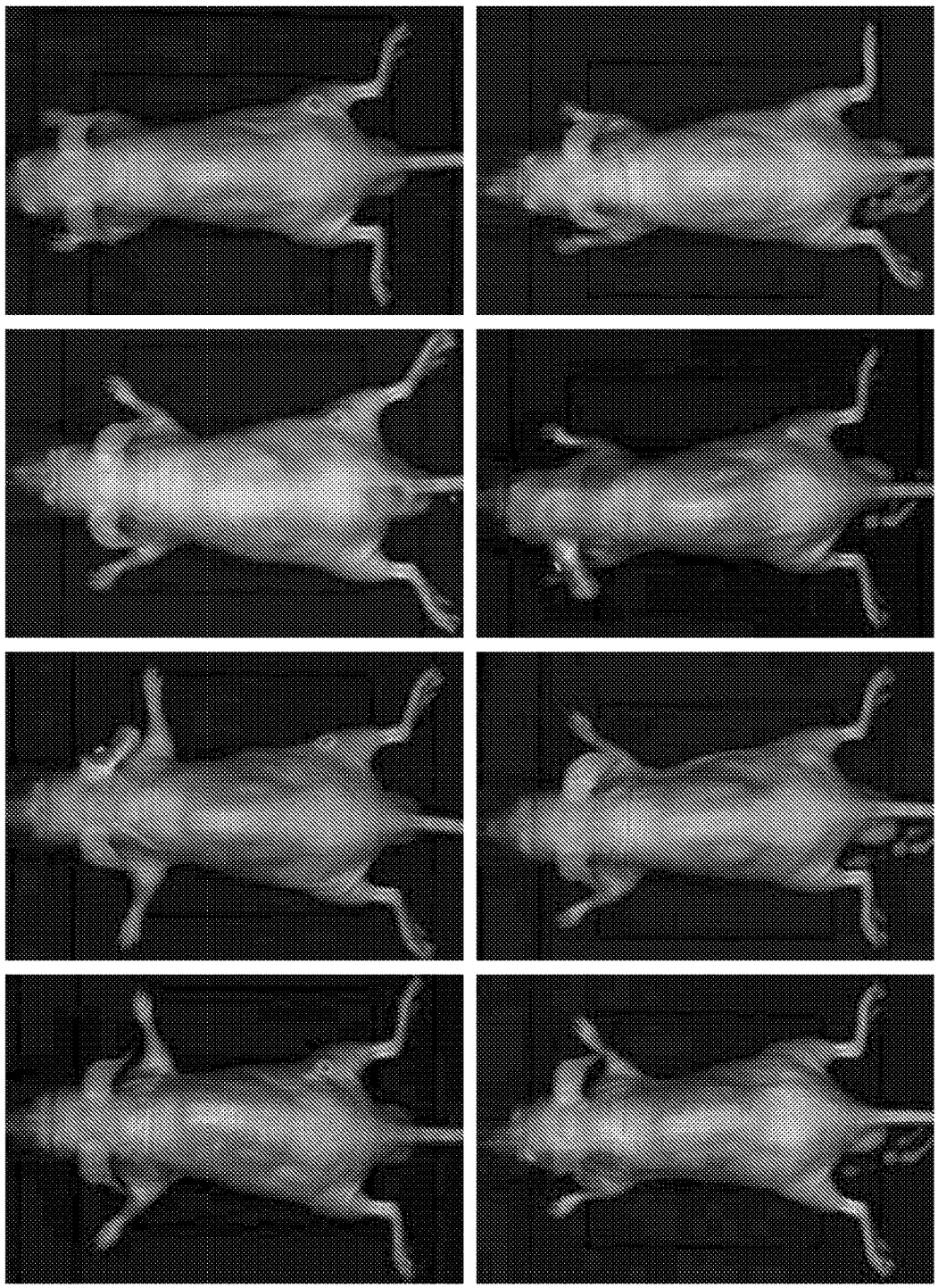

To evaluate the efficiency of tumor targeting and the potential for intraoperative optical imaging of PSMAb, PSMAb was labeled with a near infrared dye IRDye800CW, and 50 labeled PSMAb/mouse was tail-vein injected to the PC3-PSMA+ or PC3-PSMA− xenograft model and the real time biodistribution of PSMAb was monitored using Xenogen IVIS Kinetic imaging system as described in Example 7. In vivo optical imaging showed that PSMAb diffused rapidly throughout the whole body and can be detected in tumor tissues from 24 hours post-injection, and was then gradually cleared from body while specifically retained at PSMA+ tumor, but not PSMA− tumor (FIG. 18A-FIG. 18C). Good signal/background ratio was observed 48 hours post-injection (FIG. 18A-FIG. 18C). Compared to scFv, full antibody has a longer circulation time and therefore a better signal/background ratio for optical imaging.

Example 11: DM1 Antibody Drug Conjugation

Figure 19:
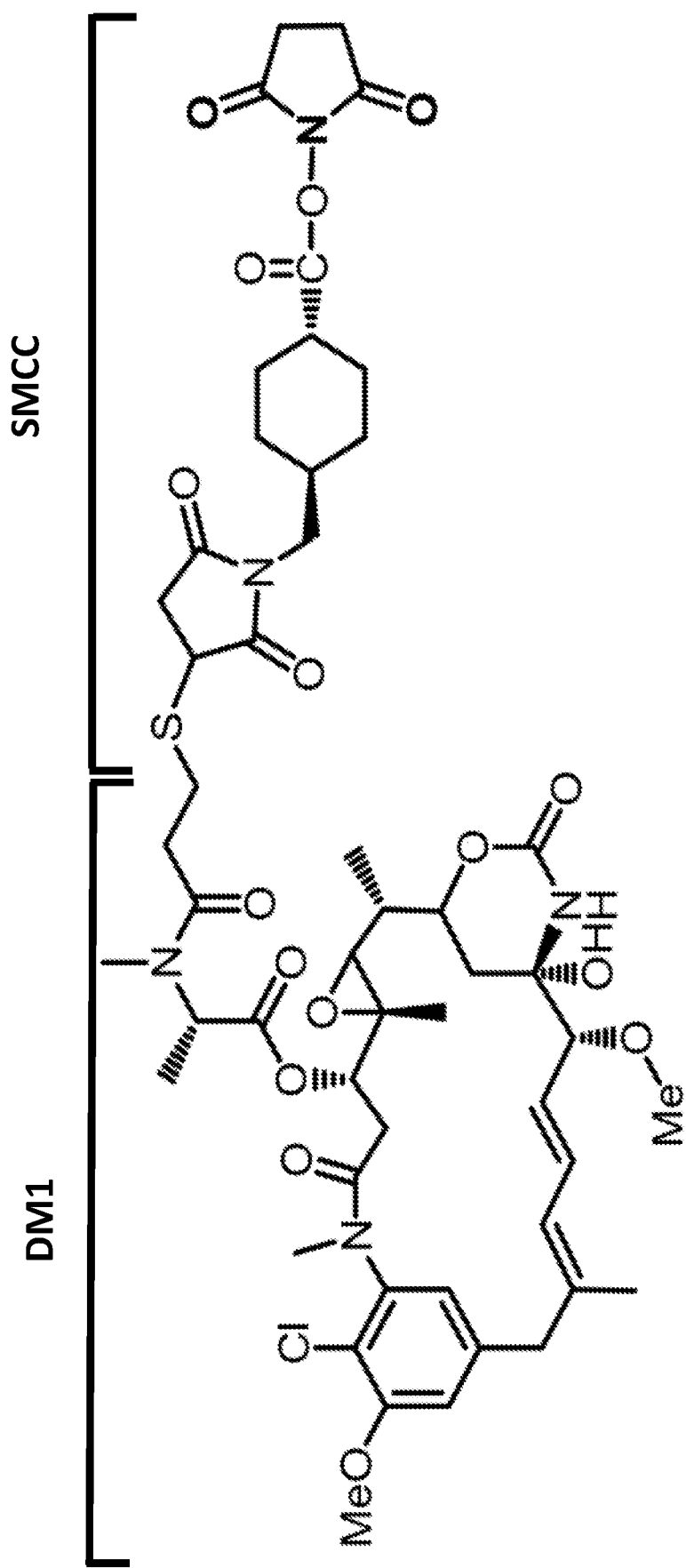
FIG. 19 is a schematic depicting SMCC-DM1.

To develop PSMA targeted ADC, PSMAb was conjugated with DM1 via a stable linker SMCC (FIG. 19). Briefly, PSMAb was buffer exchanged to 50 mM Potassium Phosphate, 50 mM NaCl, 2 mM EDTA, pH7.2, and concentration was adjusted to 4 mg/ml. SMCC-DM1 (Concortis Biosystems) was dissolved in DMA to get a final concentration of 10 mM. Into each volume of antibody solution, add 0.43% volume DMA, mix, then add 2.67% volume 10 mM SMCC-DM1. The final concentration of DMA is 3% (v/v) and drug/Ab ratio is 10:1. The solution is allowed to proceed for three hours at room temperature with mixing and then buffer was exchanged to PBS by dialysis. The drug/Ab conjugation ratio was measured at 3.3 as described previously (US 20060088539 A1) based on the absorbance at 252 and 280 nm of the conjugate.

Example 12: MMAF and MMAF Antibody Drug Conjugation

Figure 20:
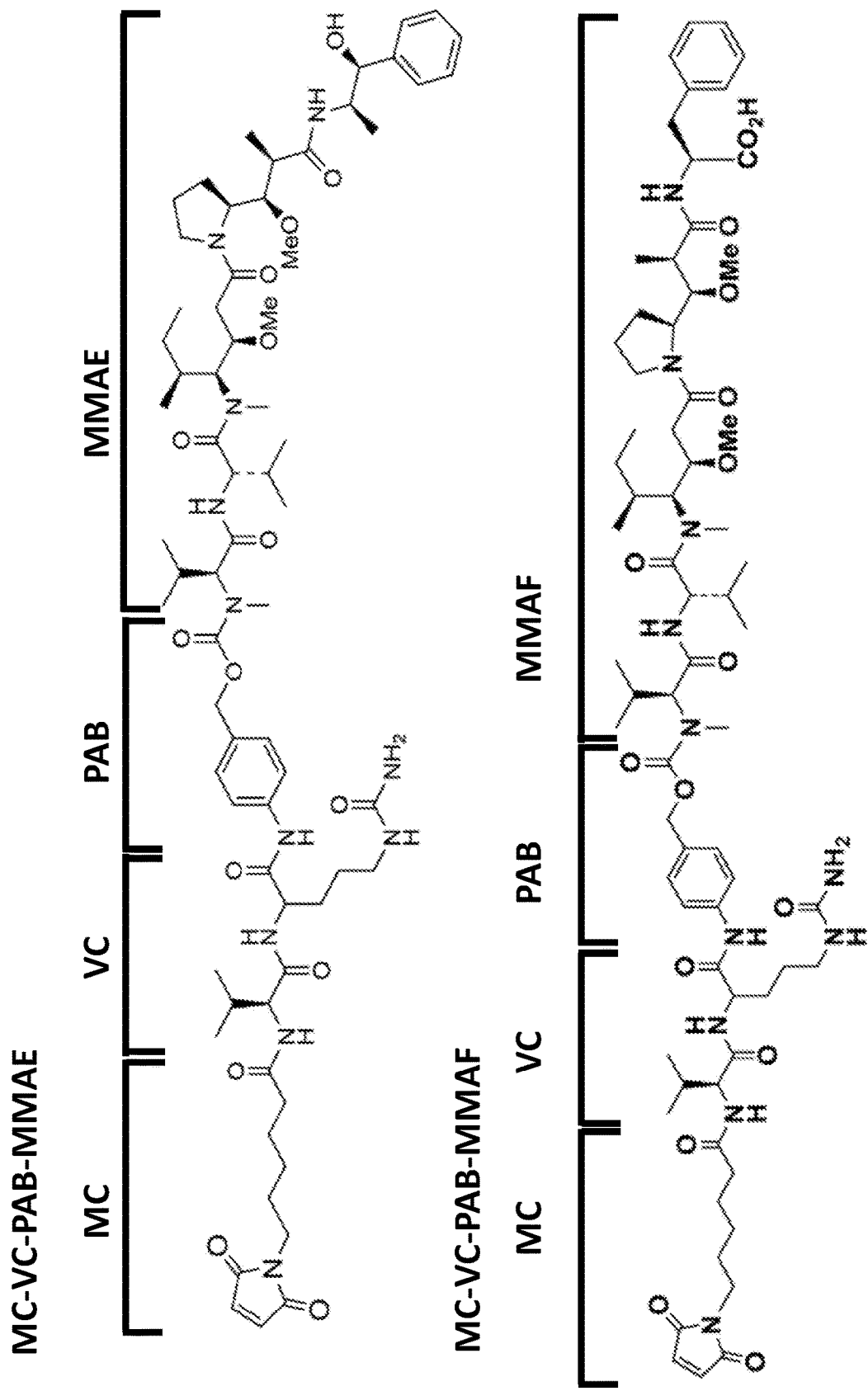
FIG. 20 is a set of schematic drawings depicting MC-VC-PAB-MMAE and MC-VC-PAB-MMAE.

To develop PSMA targeted ADC, PSMAb was conjugated with MMAF and MMAF respectively via a cleavable linker Mc-vc-PAB (FIG. 20). Antibody concentration was adjusted to 8 mg/ml in 0.025 M sodium borate pH8, 0.025 M NaCl, 1 mM DTPA and was partially reduced by 2.75 molar equivalents of TCEP for 2 hours at 37° C. The mixture was then cooled to 0° C. and the antibody concentration was adjusted to 5.625 mg/ml and was mixed with 0.25 volume 700 mM MC-vc-PAB-MMAE and MC-vc-PAB-MMAF dissolved in cold acetonitrile and the reaction was allowed to continue for 30 minutes on ice. The excess MC-vc-PAB-MMAE or MC-vc-PAB-MMAF was quenched with cysteine (1 mM final concentration). The antibody drug conjugate was purified using PD-10 column as described (Kevin J. Hamblett et al., 2004, Clin Cancer Res, 10; 7063). Drug loading is determined for MMAE and MMAF at 3.5 and 3.03 per antibody by measuring the ratio of the absorbance at 250 and 280 nM as described (Kevin J. Hamblett et al., 2004, Clin Cancer Res, 10; 7063).

Figure 21:
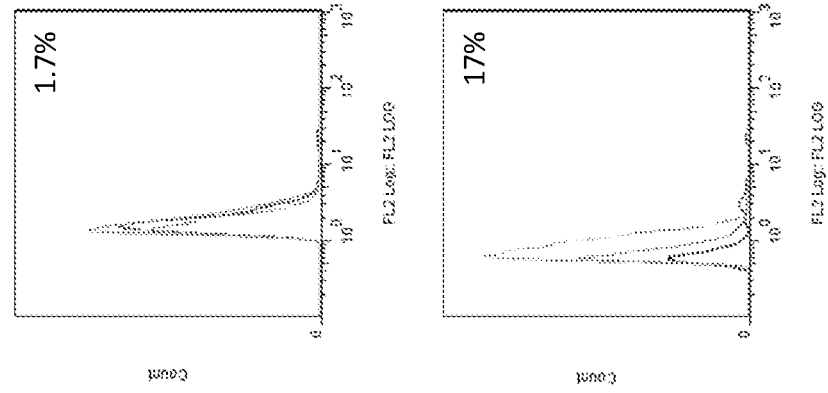
FIG. 21 depicts the results of experiments demonstrating that PSMAb-ADC remains efficient binding on PSMA+ cells. PSMA specific binding of PSMAb conjugate with DM1, MMAE or MMAF was studied on PC-3 (upper) and C4-2 cells (lower) using flow cytometry.
Figure 21:
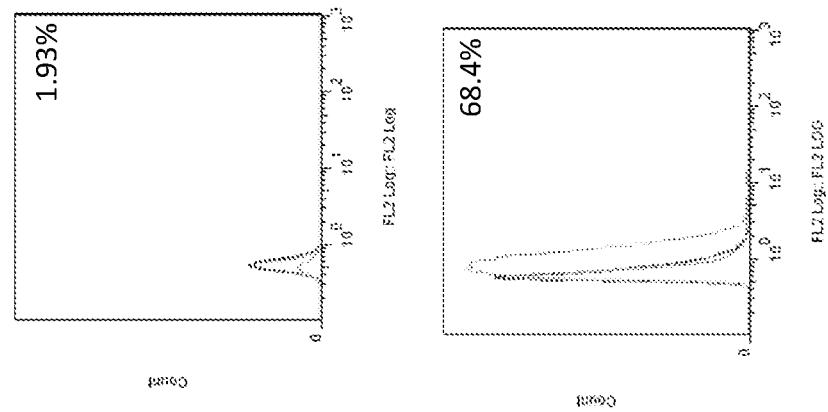
Figure 21:
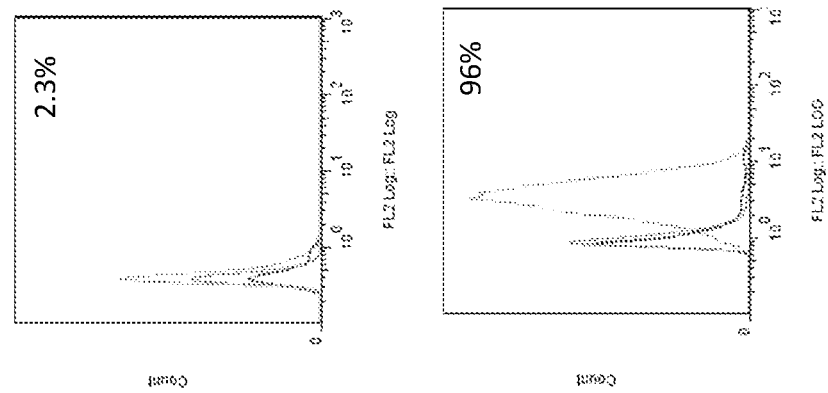
Figure 22A:
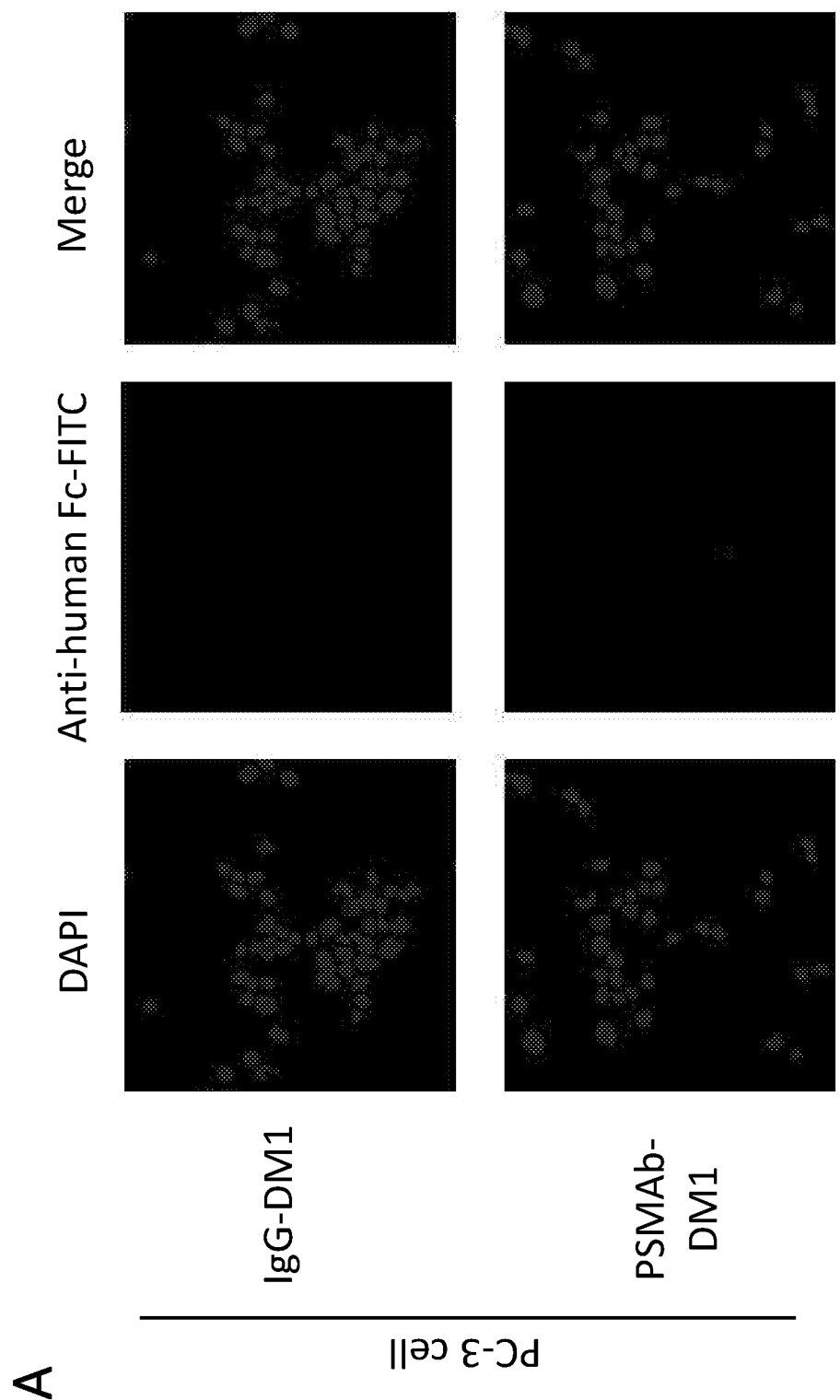
FIG. 22A and FIG. 22B, depicts the results of experiments demonstrating that PSMAb-ADC is efficiently taken up by PSMA+ cells. PSMA specific internalization of PSMAb conjugate with DM1 was studied on PC-3 (FIG. 22A) and C4-2 cells (FIG. 22B). Cells grown on coverslips at 50% confluence were incubated with 200 nM PSMAb-ADC or a control human IgG1-ADC for 2 h at 37° C. Cells were washed, fixed with 4% paraformaldehyde and internalized PSMAb was detected by FITC conjugated anti-human IgG Fc antibody. Nuclei were stained with DAPI. Internalization was observed under confocal imaging system.
Figure 22B:
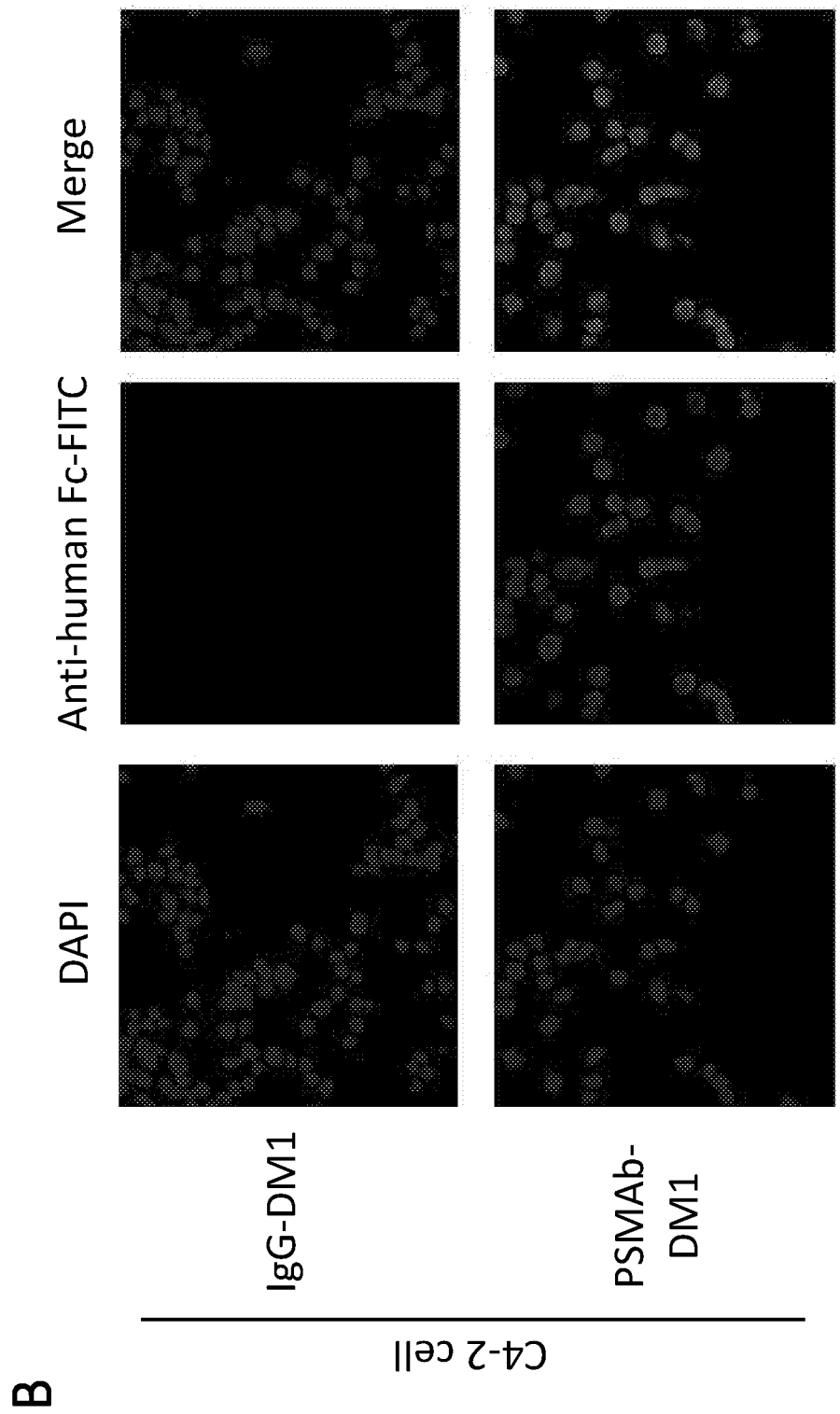

Example 13: PSMAb Retains PSMA Binding and Internalizaton Capability after Drug Conjugation After conjugation with DM1, MMAE or MMAF, PSMA binding and internalization of PSMAb drug conjugate were evaluated by flow cytometry and confocal imaging respectively as described above. The results showed that antigen binding and internalization of PSMAb drug conjugate were well retained (FIG. 21 and FIG. 22).

Example 14: PSMA Specific Cytotoxicity of PSMAb Antibody Drug Conjugates

Figures 23A, 23B, 23C:
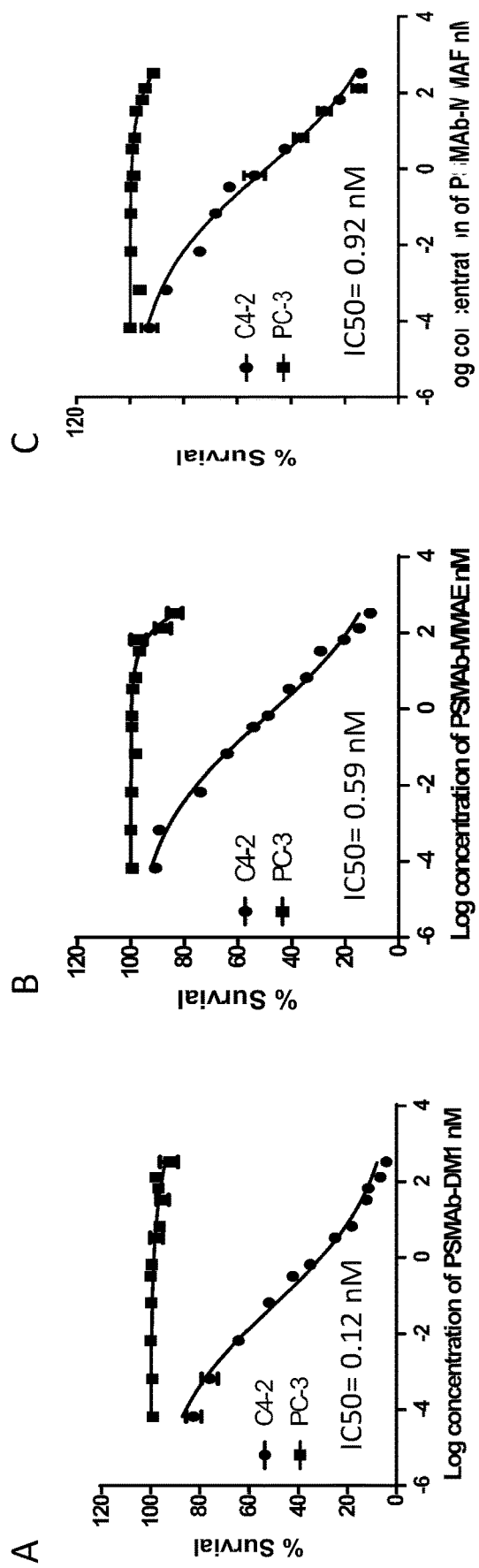
FIG. 23A through FIG. 23C, depicts the results of experiments evaluating PSMA specific cytotoxicity of PSMAb ADC. Cytotoxicity of PSMAb based ADCs were evaluated on PSMA− cell line PC-3 and PSMA+ cell line C4-2. Briefly, C4-2 and PC-3 cells were seeded in 96 well plates in DMEM medium with 10% FBS, 2000 cells/200 mL/well. The next day, cell density was around 20-30% and medium was changed to fresh medium containing PSMAb-DM1, PSMAb-MMAE or PSMAb-MMAF at the concentrations of 333.33 nM, 133.33 nM, 66.67 nM, 33.33 nM, 6.67 nM, 3.33 nM, 0.67 nM, 0.33 nM, 0.067 nM, 0.0067 nM, 0.00067 nM and 0.000067 nM with triplications of each concentration. Medium was changed daily with the same drug concentrations for each well. After 4 day incubation, cell viability was evaluated using alamarBlue kit following manufacture's protocol. IC50 calculated for PSMAb-DM1 (FIG. 23A), PSMAb-MMAE (FIG. 23B) and PSMAb-MMAF (FIG. 23C) on C4-2 cells was 0.12 nM, 0.59 nM and 0.92 nM respectively.
Figures 24A, 24B, 24C:
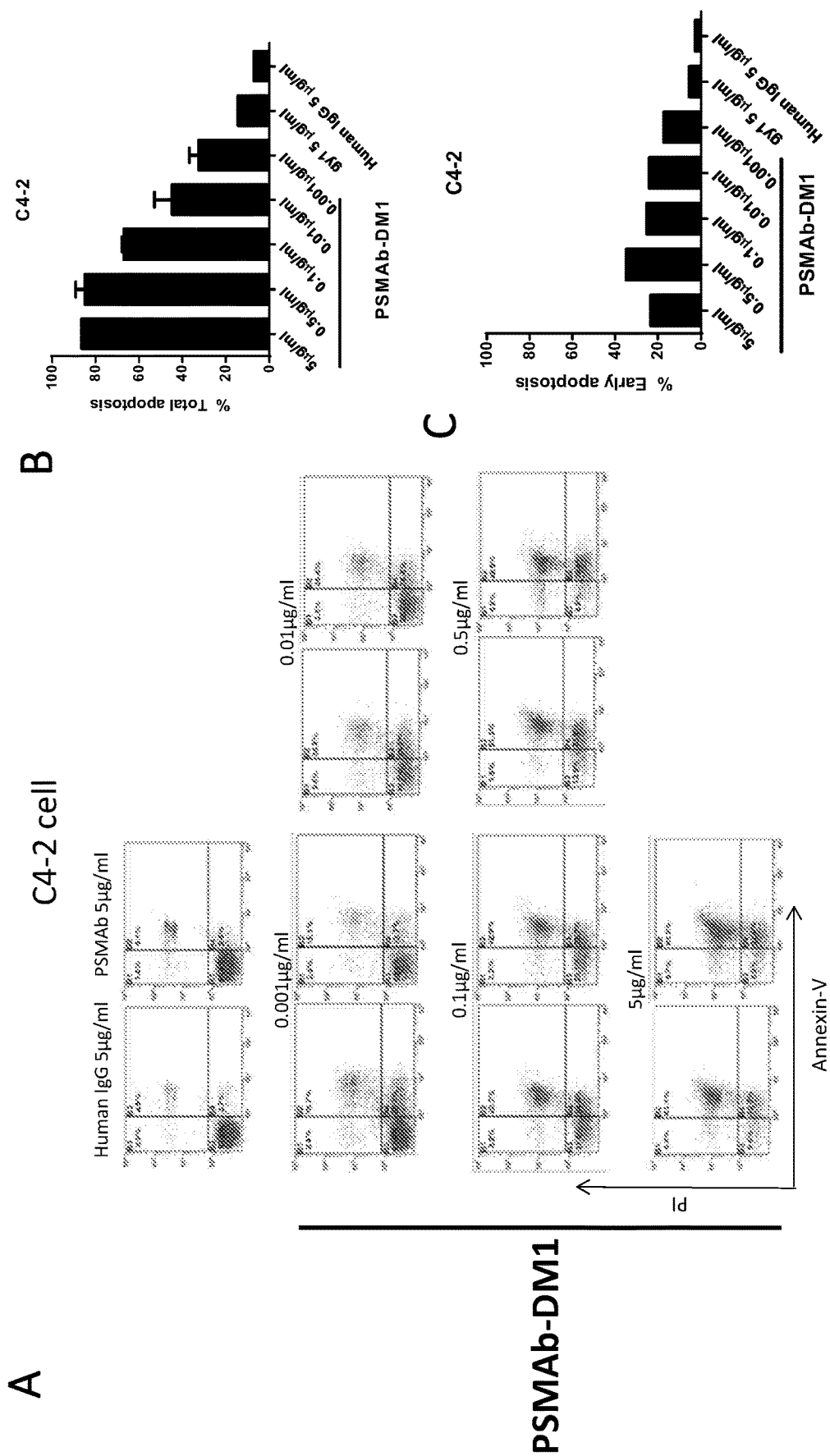
FIG. 24A through FIG. 24R, depicts the results of experiments demonstrating that PSMAb ADC induces apoptosis specifically on PSMA positive cells. PC-3 and C4-2 cells were seeded in 6 well plates at the density of $2\times10^5$/2 ml medium/well and cultured overnight. The next day, medium was changed and cells were incubated with PSMAb-ADC at the concentrations of 50 µg/ml, 20 µg/ml, 10 µg/ml, 5 µg/ml, 1 µg/ml, 0.5 µg/ml, 0.01 µg/ml, and 0.001 µg/ml in 2 ml medium. Human IgG and PSMAb at the concentration of 50 mg/ml were used as controls. After 48 hour incubation, cells were trypsinized and washed twice with PBS, and stained with Annexin-V/PI and apoptosis was detected using flow cytometry. Signals with Annexin-V(+)/PI (−) indicates early apoptosis and double positive staining, i.e., Annexin-V(+)/PI (+), indicates late apoptosis. Total apoptosis is the sum of early and late apoptosis. Results of PSMAb-DM1 (FIG. 24A-FIG. 24F), PSMAb-MMAE (FIG. 24G FIG. 24L), and PSMAb-MMAF (FIG. 24M-FIG. 24R) on C4-2 (FIG. 24A-FIG. 24C, FIG. 24G-FIG. 24I, FIG. 24M-FIG. 24O) and PC-3 (FIG. 24D-FIG. 24F, FIG. 24J-FIG. 24L, FIG. 24P-FIG. 24R) cells were shown in flow cytometry data (FIG. 24A, FIG. 24D, FIG. 24G, FIG. 24J, FIG. 24M, and FIG. 24P) and calculated percentages of total (FIG. 24B, FIG. 24E, FIG. 24H, FIG. 24K, FIG. 24N, and FIG. 24Q) and early apoptosis (FIG. 24C, FIG. 24F, FIG. 24I, FIG. 24L, FIG. 24O and FIG. 24R).
Figures 24D, 24E, 24F:
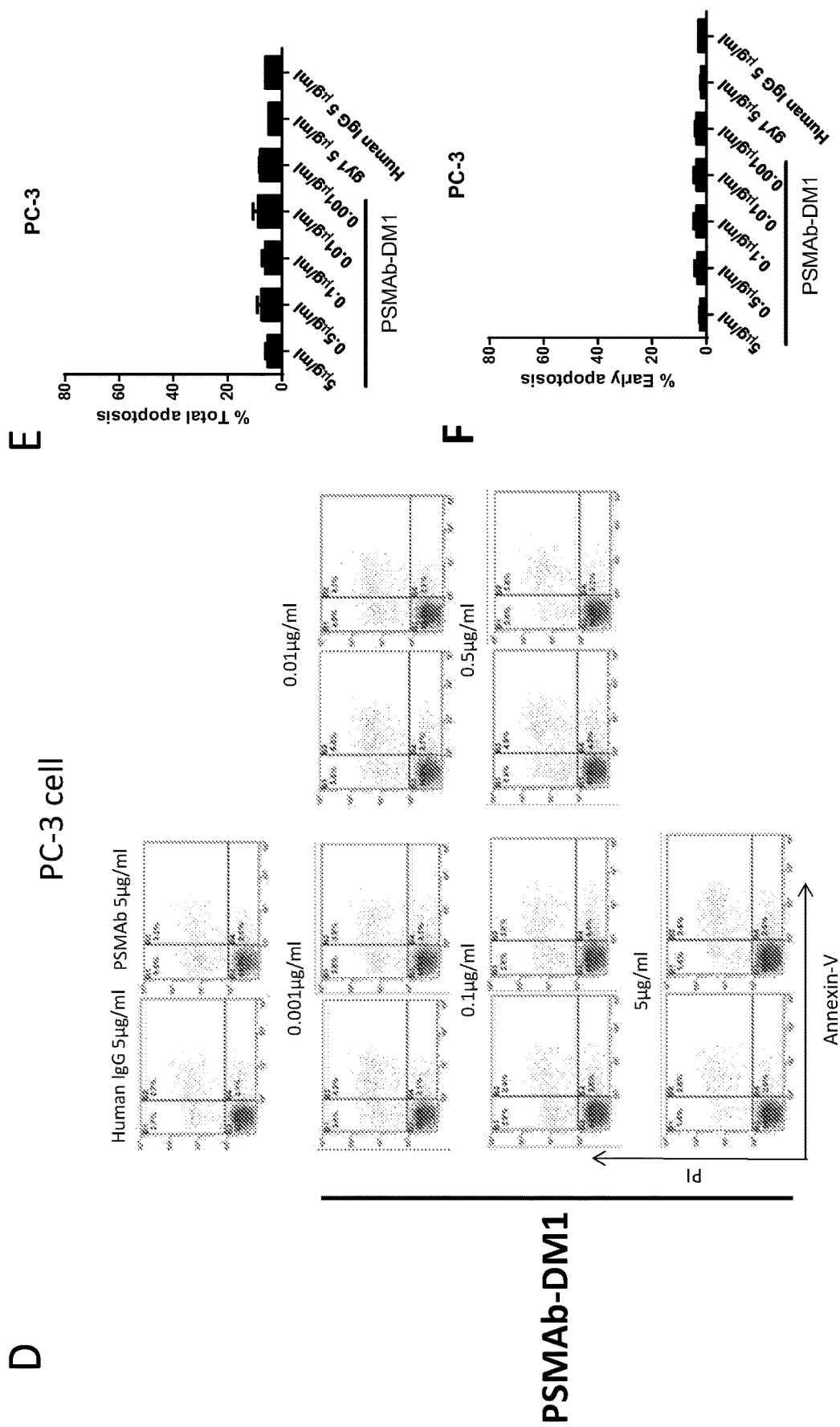
FIG. 24, comprising
Figures 24J, 24K, 24L:
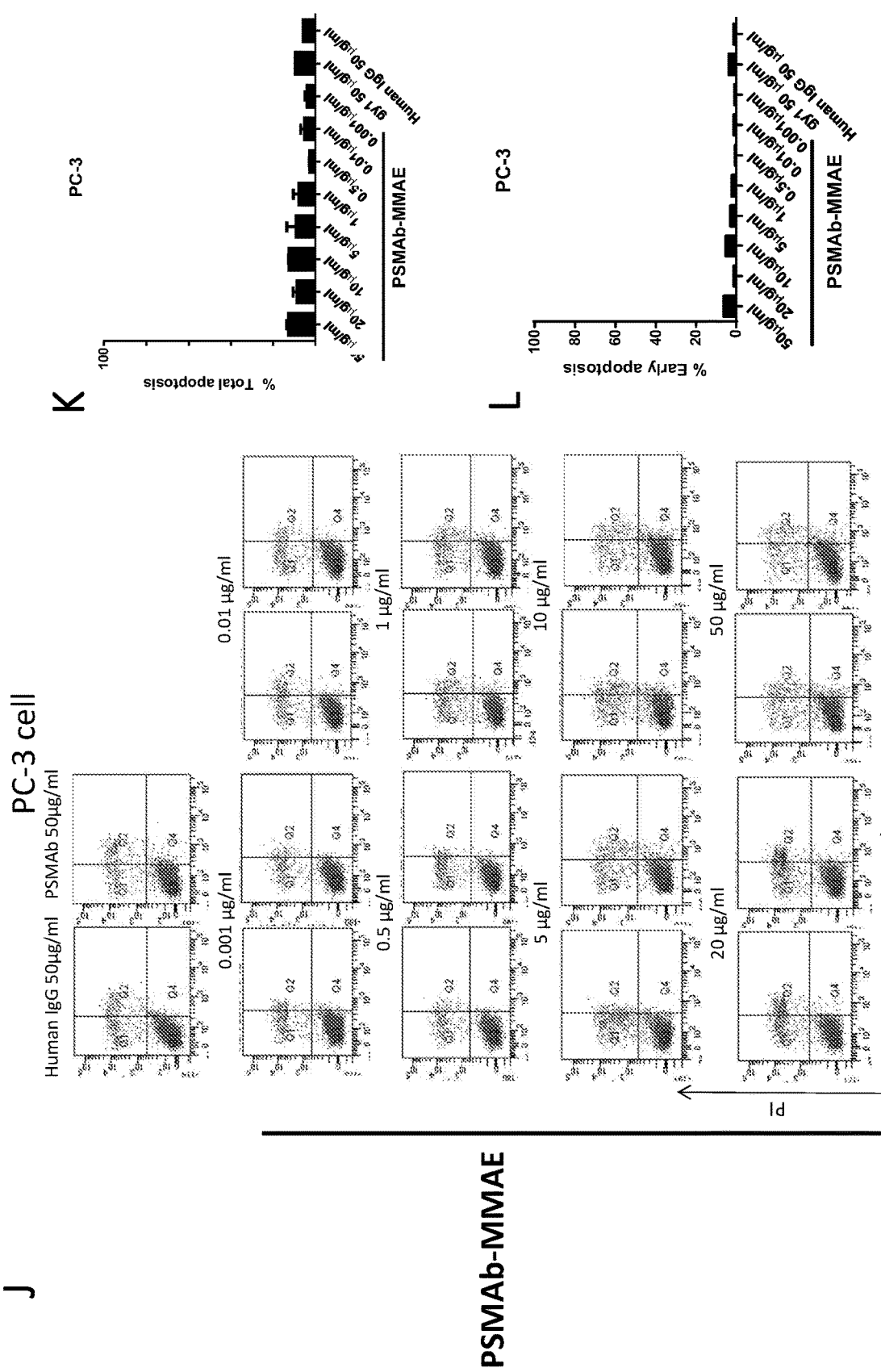
Figure 24M:
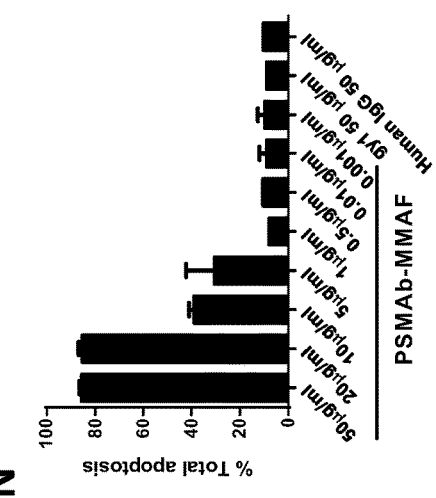
Figure 24N:
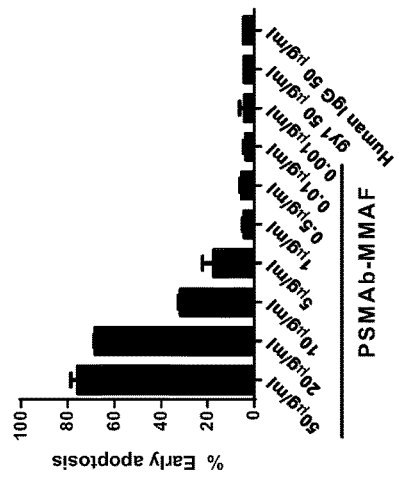
Figure 24O:
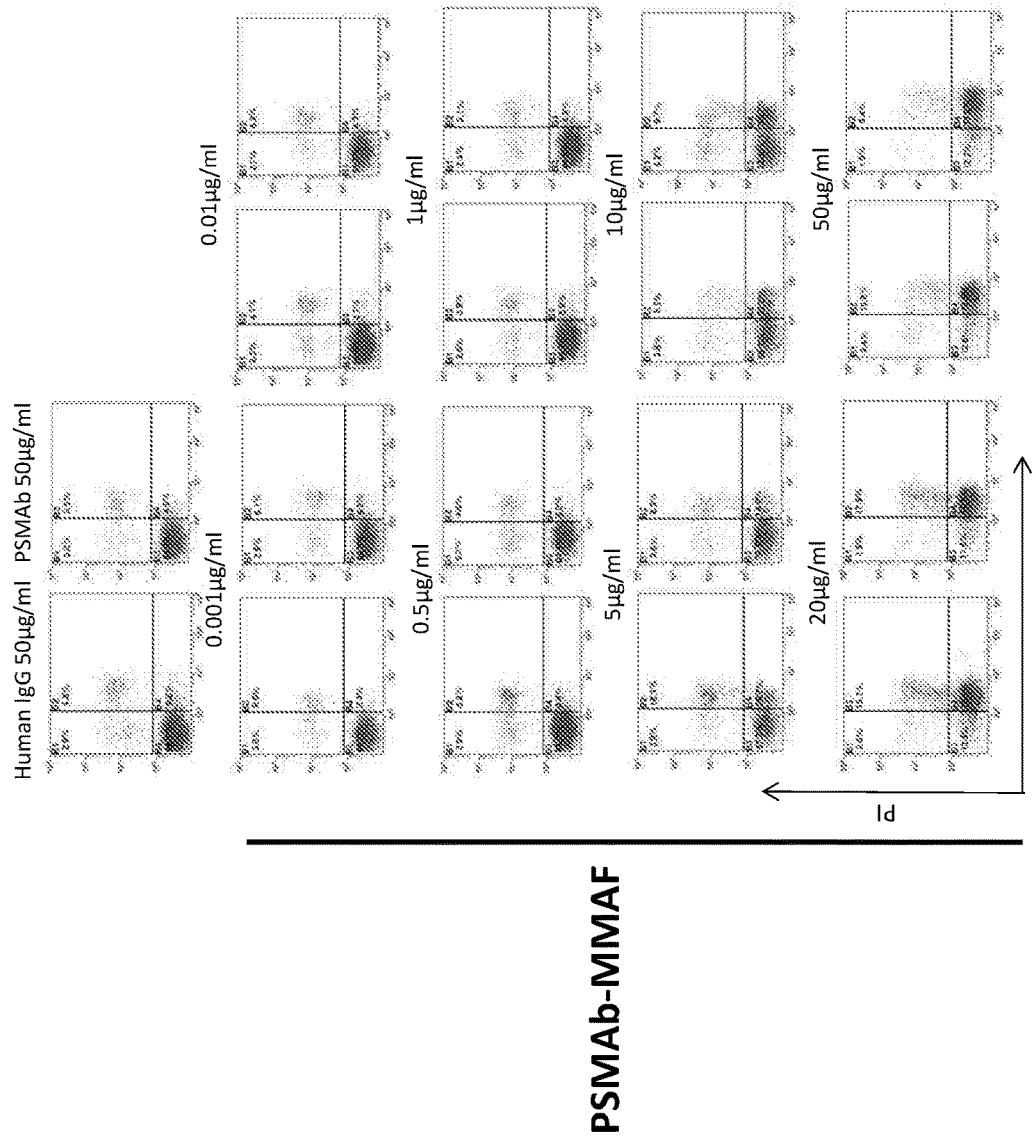
Figures 24P, 24Q, 24R:
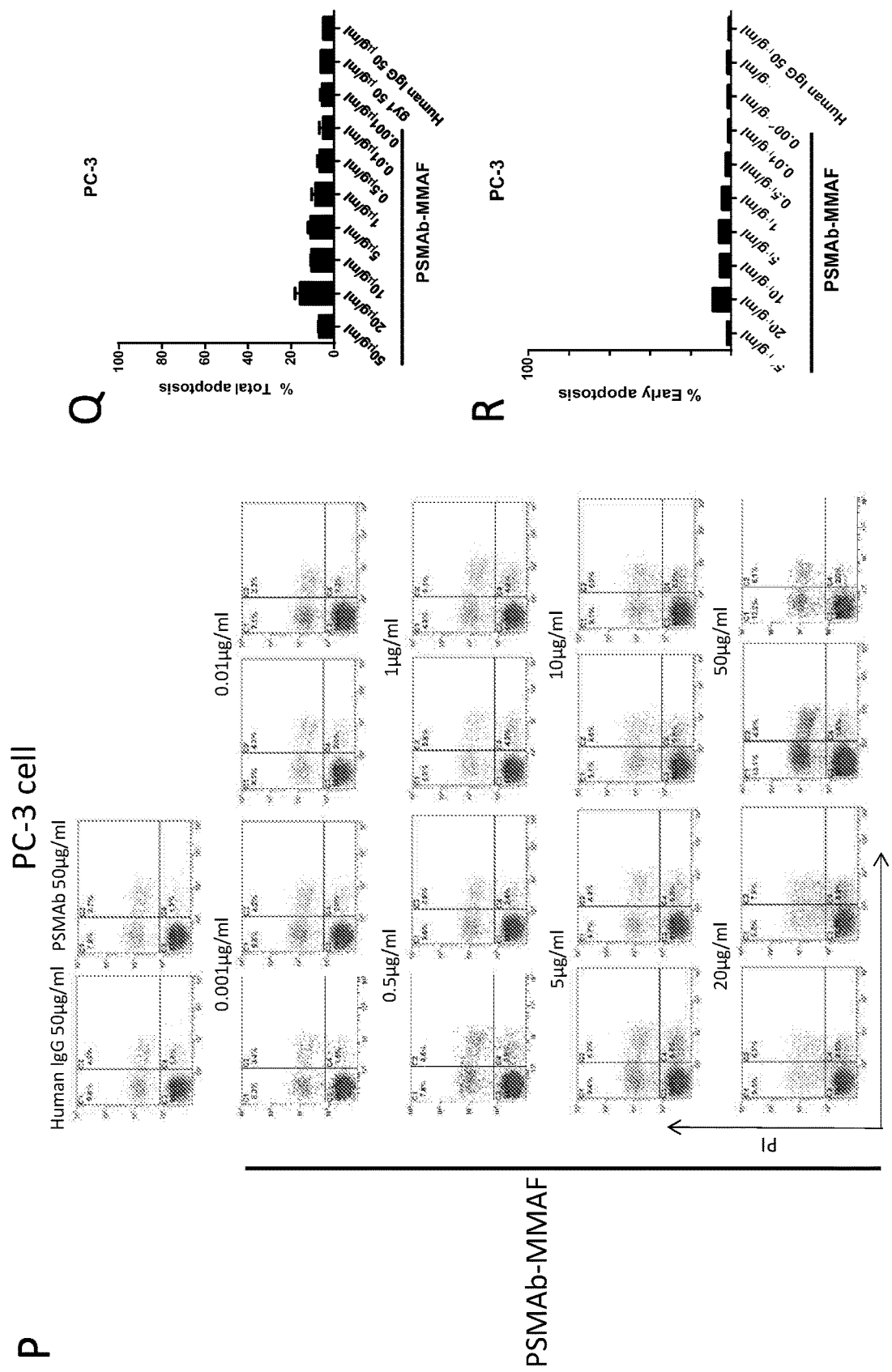

Cytotoxicity of PSMAb based ADCs were evaluated on PSMA− cell line PC-3 and PSMA+ cell line C4-2. Briefly, C4-2 and PC-3 cells were seeded in 96 well plates in DMEM medium with 10% FBS, 2000 cells/200 mL/well. The next day, cell density was around 20-30% and medium was changed to fresh medium containing PSMAb-DM1, PSMAb-MMAE or PSMAb-MMAF at the concentrations of 333.33 nM, 133.33 nM, 66.67 nM, 33.33 nM, 6.67 nM, 3.33 nM, 0.67 nM, 0.33 nM, 0.067 nM, 0.0067 nM, 0.00067 nM and 0.000067 nM with triplications of each concentration. Medium was changed daily with the same drug concentrations for each well. After 4 day incubation, cell viability was evaluated using alamarBlue kit (Invitrogen) following manufacture's protocol. Results showed that PSMAb-DM1, PSMAb-MMAE and PSMAb-MMAF have no toxicity on PC-3 cells but a dose dependent toxicity on C4-2 cells, with IC50 at 0.12 nM, 0.59 nM and 0.92 nM respectively for PSMAb-DM1, PSMAb-MMAE and PSMAb-MMAF (FIG. 23).

Example 15: PSMA-ADC Specifically Induce Apoptosis of in PSMA+ Cells

To further investigate the mechanism of PSMAb ADC in PSMA specific cell killing, PSMAb ADC induced apoptosis was studied in PC-3 and C4-2 cells. Briefly, PC-3 and C4-2 cells were seeded in 6 well plates at the density of 2×10$^5$/2 ml medium/well and cultured overnight. The next day, medium was changed and cells were incubated with PSMAb-ADC at the concentrations of 50 µg/ml, 20 µg/ml, 10 µg/ml, 5 µg/ml, 1 µg/ml, 0.5 µg/ml, 0.01 µg/ml, and 0.001 µg/ml in 2 ml medium. Human IgG and PSMAb at the concentration of 50 mg/ml were used as controls. After 48 hour incubation, cells were trypsinized and washed twice with PBS, and stained with Annexin-V/PI (Roche) following the manufacture's instruction. Apoptosis was detected using flow cytometry, signals with Annexin-V(+)/PI (−) indicating early apoptosis and double positive staining, i.e., Annexin-V(+)/PI (+), indicating late apoptosis. Total apoptosis is the sum of early and late apoptosis. Results showed that all the three PSMAb based ADCS, i.e., PSMAb-DM1, PSMAb-MMAE, and PSMAb-MMAF, were capable of efficient induction of both early and late apoptosis, while PSMAb-DM1 mainly induced late apoptosis and PSMAb-MMAE and PSMAb-MMAF mainly induced early apoptosis (FIG. 24).

Example 16: Sequences

```
SEQ ID NO: 1 Extracellular domain of PSMA:
KSSNEATNITPKHNMKAFLDELKAENIKKFLYNFTQIPHLAGTEQNFQLAKQIQSQWKEF

GLDSVELAHYDVLLSYPNKTHPNYISIINEDGNEIFNTSLFEPPPPGYENVSDIVPPFSA

FSPQGMPEGDLVYVNYARTEDFFKLERDMKINCSGKIVIARYGKVFRGNKVKNAQLAGAK

GVILYSDPADYFAPGVKSYPDGWNLPGGGVQRGNILNLNGAGDPLTPGYPANEYAYRRGI

AEAVGLPSIPVHPIGYYDAQKLLEKMGGSAPPDSSWRGSLKVPYNVGPGFTGNFSTQKVK

MHIHSTNEVTRIYNVIGTLRGAVEPDRYVILGGHRDSWVFGGIDPQSGAAVVHEIVRSFG

TLKKEGWRPRRTILFASWDAEEFGLLGSTEWAEENSRLLQERGVAYINADSSIEGNYTLR

VDCTPLMYSLVHNLTKELKSPDEGFEGKSLYESWTKKSPSPEFSGMPRISKLGSGNDFEV

FFQRLGIASGRARYTKNWETNKFSGYPLYHSVYETYELVEKFYDPMFKYHLTVAQVRGGM

VFELANSIVLPFDCRDYAVVLRKYADKIYSISMKHPQEMKTYSVSFDSLFSAVKNFTEIA

SKFSERLQDFDKSNPIVLRMMNDQLMFLERAFIDPLGLPDRPFYRHVIYAPSSHNKYAGE

SFPGIYDALFDIESKVDPSKAWGEVKRQIYVAAFTVQAAAETLSEVA

SEQ ID NO: 2 gy1 scFv nucleic acid sequence:
CAGTCTGTGCTGACTCAGCCGCCCTCAGTGTCTGGGGCCCCAGGGCAGAGTGTCATTATC

TCCTGCACTGGGAGCAGCTCCAACATCGGGGCAGGTTCTCATGTACACTGGTACCAGCAG

GTTCCAGGAACAGCCCCCAAACTCCTCATCTATGGAAACACCAATCGGCCCTCAGGGGTC

CCTGACCGATTCTCTGGCTCCAAGTCTGGCACCTCAGGTTCCCTGGCCATCACTGGACTC

CAGCCTGAGGATGAGGCTGATTATTATTGTGCAACATGGGATGACAGTCTGAATGGTGTA

ATATTCGGCGGAGGGACCAAGGTCACCGTCCTAGGCGGATCCTCTAGGTCAAGTTCCAGC

GGCGGCGGTGGCAGCGGAGGCGGCGGTGAGGTGCAGCTGGTGGAGTCTGGGGGAGCCCTG

GCCAAGCCTGGGGGGTCCCTGAGACTCTCCTGTGCAGCCTCTGGATCCACCCTCAGTGGC

TATGCTATGCACTGGGTCCGCCAGGCTCCAGGCAAGGGGCTGGAGTGGGTGGCAGTTATA

TCATATGATGGAAGCAATAAATACTACGCAGACTCCGTGAAGGGCCGATTCACCATCTCC

AGAGACAATTCCAAGAACACGCTGTTTCTGCAAATGAACAGCCTGAGACCTGAGGACACG

GCTGTGTACTATTGTGCTAAAGGCCTTACTTGGGGACTCGGTGACAATGATGCTCTCGAT

ATCTGGGGCCCCGGGACCACGGTCACCGTCTCCTCA

SEQ ID NO: 3 gy1 scFv amino acid sequence:
QSVLTQPPSVSGAPGQSVIISCTGSSSNIGAGSHVHWYQQVPGTAPKLLIYGNTNRPSGV

PDRFSGSKSGTSGSLAITGLQPEDEADYYCATWDDSLNGVIFGGGTKVTVLGGSSRSSSS

GGGGSGGGGEVQLVESGGALAKPGGSLRLSCAASGSTLSGYAMHWVRQAPGKGLEWVAVI
```

-continued

SYDGSNKYYADSVKGRFTISRDNSKNTLFLQMNSLRPEDTAVYYCAKGLTWGLGDNDALD

IWGPGTTVTVSS

SEQ ID NO: 4 gy1 VL nucleic acid sequence:
CAGTCTGTGCTGACTCAGCCGCCCTCAGTGTCTGGGGCCCCAGGGCAGAGTGTCATTATC

TCCTGCACTGGGAGCAGCTCCAACATCGGGGCAGGTTCTCATGTACACTGGTACCAGCAG

GTTCCAGGAACAGCCCCCAAACTCCTCATCTATGGAAACACCAATCGGCCCTCAGGGGTC

CCTGACCGATTCTCTGGCTCCAAGTCTGGCACCTCAGGTTCCCTGGCCATCACTGGACTC

CAGCCTGAGGATGAGGCTGATTATTATTGTGCAACATGGGATGACAGTCTGAATGGTGTA

ATATTCGGCGGAGGGACCAAGGTCACCGTCCTA

SEQ ID NO: 5 gy1 VL amino acid sequence:
QSVLTQPPSVSGAPGQSVIISCTGSSSNIGAGSHVHWYQQVPGTAPKLLIYGNTNRPSGV

PDRFSGSKSGTSGSLAITGLQPEDEADYYCATWDDSLNGVIFGGGTKVTVL

SEQ ID NO: 6 gy1 VL frame region 1 (FR1) nucleic acid sequence:
CAGTCTGTGCTGACTCAGCCGCCCTCAGTGTCTGGGGCCCCAGGGCAGAGTGTCATTATC

TCCTGCACTGGGAGC

SEQ ID NO: 7 gy1 VL frame region 1 (FR1) amino acid sequence:
QSVLTQPPSVSGAPGQSVIISCTGS SEQ ID NO: 8 gy1 VL CDR1 nucleic acid sequence:
AGCTCCAACATCGGGGCAGGTTCTCAT SEQ ID NO: 9 gy1 VL CDR1 amino acid sequence:
SSNIGAGSH SEQ ID NO: 10 gy1 VL frame region 2 (FR2) nucleic acid sequence:
GTACACTGGTACCAGCAGGTTCCAGGAACAGCCCCCAAACTCCTCATCTAT SEQ ID NO: 11 gy1 VL frame region 2 (FR2) amino acid sequence:
VHWYQQVPGTAPKLLIY SEQ ID NO: 12 gy1 VL CDR2 nucleic acid sequence:
GGAAACACC SEQ ID NO: 13 gy1 VL CDR2 amino acid sequence:
GNT SEQ ID NO: 14 gy1 VL frame region 3 (FR3) nucleic acid sequence:
AATCGGCCCTCAGGGGTCCCTGACCGATTCTCTGGCTCCAAGTCTGGCACCTCAGGTTCC

CTGGCCATCACTGGACTCCAGCCTGAGGATGAGGCTGATTATTATTGT

SEQ ID NO: 15 gy1 VL frame region 3 (FR3) amino acid sequence:
NRPSGVPDRFSGSKSGTSGSLAITGLQPEDEADYYC SEQ ID NO: 16 gy1 VL CDR3 region nucleic acid sequence:
GCAACATGGGATGACAGTCTGAATGGTGTAATA

SEQ ID NO: 17:
ATWDDSLNGVI

SEQ ID NO: 18:
TTCGGCGGAGGGACCAAGGTCACCGTCCTA

SEQ ID NO: 19 gy1 VL frame region 4 (FR4) amino acid sequence:
FGGGTKVTVL

SEQ ID NO: 20 gy1 VH nucleic acid sequence:
GAGGTGCAGCTGGTGGAGTCTGGGGGAGCCCTGGCCAAGCCTGGGGGGTCCCTGAGACTC

TCCTGTGCAGCCTCTGGATCCACCCTCAGTGGCTATGCTATGCACTGGGTCCGCCAGGCT

CCAGGCAAGGGGCTGGAGTGGGTGGCAGTTATATCATATGATGGAAGCAATAAATACTAC

GCAGACTCCGTGAAGGGCCGATTCACCATCTCCAGAGACAATTCCAAGAACACGCTGTTT

CTGCAAATGAACAGCCTGAGACCTGAGGACACGGCTGTGTACTATTGTGCTAAAGGCCTT

ACTTGGGGACTCGGTGACAATGATGCTCTCGATATCTGGGGCCCCGGGACCACGGTCACC

GTCTCCTCA

SEQ ID NO: 21 gy1 VH amino acid sequence:
EVQLVESGGALAKPGGSLRLSCAASGSTLSGYAMHWVRQAPGKGLEWVAVISYDGSNKYY

ADSVKGRFTISRDNSKNTLFLQMNSLRPEDTAVYYCAKGLTWGLGDNDALDIWGPGTTVT

VSS

SEQ ID NO: 22 gy1 VH frame region 1 (FR1) nucleic acid sequence:
GAGGTGCAGCTGGTGGAGTCTGGGGGAGCCCTGGCCAAGCCTGGGGGGTCCCTGAGACTC

TCCTGTGCAGCCTCT

SEQ ID NO: 23 gy1 VH frame region 1 (FR1) amino acid sequence:
EVQLVESGGALAKPGGSLRLSCAAS SEQ ID NO: 24 gy1 VH CDR1 nucleic acid sequence:
GGATCCACCCTCAGTGGCTATGCT SEQ ID NO: 25 gy1 VH CDR1 amino acid sequence:
GSTLSGYA SEQ ID NO: 26 gy1 VH frame region 2 (FR2) nucleic acid sequence:
ATGCACTGGGTCCGCCAGGCTCCAGGCAAGGGGCTGGAGTGGGTGGCAGTT SEQ ID NO: 27 gy1 VH frame region 2 (FR2) amino acid sequence:
MHWVRQAPGKGLEWVAV SEQ ID NO: 28 gy1 VH CDR2 region nucleic acid sequence:
ATATCATATGATGGAAGCAATAAA SEQ ID NO: 29 gy1 VH CDR2 region amino acid sequence:
ISYDGSNK SEQ ID NO: 30 gy1 VH frame region 3 (FR3) nucleic acid sequence:
TACTACGCAGACTCCGTGAAGGGCCGATTCACCATCTCCAGAGACAATTCCAAGAACACG

CTGTTTCTGCAAATGAACAGCCTGAGACCTGAGGACACGGCTGTGTACTATTGT

SEQ ID NO: 31 gy1 VH frame region 3 (FR3) amino acid sequence:
YYADSVKGRFTISRDNSKNTLFLQMNSLRPEDTAVYYC SEQ ID NO 32 gy1 VH CDR3 region nucleic acid sequence:
GCTAAAGGCCTTACTTGGGGACTCGGTGACAATGATGCTCTCGATATC SEQ ID NO: 33 gy1 VH CDR3 region amino acid sequence:
AKGLTWGLGDNDALDI SEQ ID NO: 34 gy1 VH frame region 4 (FR4) nucleic acid sequence:
TGGGGCCCCGGGACCACGGTCACCGTCTCCTCA SEQ ID NO: 35 gy1 VH frame region 4 (FR4) amino acid sequence:
WGPGTTVTVSS SEQ ID NO: 36 gy1 scFv Linker nucleic acid sequence:
GGCGGATCCTCTAGGTCAAGTTCCAGCGGCGGCGGTGGCAGCGGAGGCGGCGGT SEQ ID NO: 37 gy1 scFv Linker amino acid sequence:
GGSSRSSSGGGGSGGGG SEQ ID NO: 38 gy1 VL frame region 2 (FR2) nucleic acid sequence with point mutation:
GTACACTGGTACCAGCAGGCTCCAGGAACAGCCCCCAAACTCCTCATCTAT SEQ ID NO: 39 gy1 VL frame region 2 (FR2) amino acid sequence with point mutation:
VHWYQQAPGTAPKLLIY (V⇒A)

SEQ ID NO: 40 gy1 VL CDR2 nucleic acid sequence with point mutation:
GAAAACACC

SEQ ID NO: 41 gy1 VL CDR2 amino acid sequence with point mutation:
E N T (G⇒E)

SEQ ID NO: 42 gy1 VL frame region 4 (FR4) nucleic acid sequence with point mutation:
TTCGGCGGAGGGACCAGGCCACCGTCCTA SEQ ID NO: 43 gy1 VL frame region 4 (FR4) amino acid sequence with point mutation:
F G G G T K A T V L (V⇒A)

SEQ ID NO: 44
GGATTCACCCTCAGTGGCTATGCT

SEQ ID NO: 45 gy1 VH CDR1 amino sequence with point mutation:
G F T L S G Y A (S⇒F)

SEQ ID NO: 46:
TACTACGCAGACTCCGTGAAGGGCCGATTCACCGTCTCCAGAGACAATTCCAAGAACACG

CTGTTTCTGCAAATGAACAGCCTGAGACCTGAGGACACGGCTGTGTACTATTGT

SEQ ID NO: 47 gy1 VH frame region 3 (FR3) amino acid sequence with point mutation
Y Y A D S V K G R F T V S R D N S K N T L F L Q M N S L R P
E D T A V Y Y C (I⇒V)

SEQ ID NO: 48 gy1 VH CDR3 region nucleic acid sequence with point mutation:
GCTAAAGGCCTTACTTGGGGACTCGGTGACAATGATGCTCTCGGTATC SEQ ID NO: 49 gy1 VH CDR3 region amino acid sequence with point mutation:
A K G L T W G L G D N D A L G I (D⇒G)

SEQ ID NO: 50:
TGGGGCCCCGAGACCACGGTCACCGTCTCCTCA

SEQ ID NO: 51 gy1 VH frame region 4 (FR4) amino acid sequence with point mutation:
W G P E T T V T V S S (G⇒E)

SEQ ID NO: 52 PSMAb heavy chain nucleic acid sequence:
ATGGAGTTTGGGCTGAGCTGGGTTTTCCTCGTTGCTCTTTTAAGAGGTGTCCAGTGTGAG

GTGCAGCTGGTGGAGTCTGGGGGAGCCCTGGCCAAGCCTGGGGGGTCCCTGAGACTCTCC

TGTGCAGCCTCTGGATTCACCCTCAGTGGCTATGCTATGCACTGGGTCCGCCAGGCTCCA

GGCAAGGGGCTGGAGTGGGTGGCAGTTATATCATATGATGGAAGCAATAAATACTACGCA

GACTCCGTGAAGGGCCGATTCACCGTCTCCAGAGACAATTCCAAGAACACGCTGTTTCTG

CAAATGAACAGCCTGAGACCTGAGGACACGGCTGTGTACTATTGTGCTAAAGGCCTTACC

TGGGGACTCGGTGACAATGATGCTCTCGATATCTGGGGCCCCGGGACCACGGTCACCGTC

TCCTCAGCCTCCACCAAGGGCCCATCGGTCTTCCCCCTGGCACCCTCCTCCAAGAGCACC

TCTGGGGGCACAGCGGCCCTGGGCTGCCTGGTCAAGGACTACTTCCCCGAACCGGTGACG

GTGTCGTGGAACTCAGGCGCCCTGACCAGCGGCGTGCACACCTTCCCGGCTGTCCTACAG

TCCTCAGGACTCTACTCCCTCAGCAGCGTGGTGACCGTGCCCTCCAGCAGCTTGGGCACC

CAGACCTACATCTGCAACGTGAATCACAAGCCCAGCAACACCAAGGTGGACAAGAAAGTT

GAGCCCAAATCTTGTGACAAAACTCACACATGCCCACCGTGCCCAGCACCTGAACTCCTG

GGGGGACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAG

TACAACAGCACGTACCGGGTGGTCAGCGTCCTCACCGTCCTGCACCAGGACTGGCTGAAT

GGCAAGGAGTACAAGTGCAAGGTCTCCAACAAAGCCCTCCCAGCCCCCATCGAGAAAACC

ATCTCCAAAGCCAAAGGGCAGCCCCGAGAACCACAGGTGTACACCCTGCCCCCATCCCGG

GATGAGCTGACCAAGAACCAGGTCAGCCTGACCTGCCTGGTCAAAGGCTTCTATCCCAGC

GACATCGCCGTGGAGTGGGAGAGCAATGGGCAGCCGGAGAACAACTACAAGACCACGCCT

CCCGTGCTGGACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCTGCACAACCAC

TACACGCAGAAGAGCCTCTCCCTGTCTCCGGGTAAATGA

SEQ ID NO: 53 PSMAb heavy chain amino acid sequence:
M E F G L S W V F L V A L L R G V Q C E V Q L V E S G G A L

A K P G G S L R L S C A A S G F T L S G Y A M H W V R Q A P

G K G L E W V A V I S Y D G S N K Y Y A D S V K G R F T V S

R D N S K N T L F L Q M N S L R P E D T A V Y Y C A K G L T

W G L G D N D A L D I W G P G T T V T V S S A S T K G P S V

F P L A P S S K S T S G G T A A L G C L V K D Y F P E P V T

V S W N S G A L T S G V H T F P A V L Q S S G L Y S L S S V

V T V P S S S L G T Q T Y I C N V N H K P S N T K V D K K V

E P K S C D K T H T C P P C P A P E L L G G P S V F L F P P

K P K D T L M I S R T P E V T C V V V D V S H E D P E V K F

N W Y V D G V E V H N A K T K P R E E Q Y N S T Y R V V S V

L T V L H Q D W L N G K E Y K C K V S N K A L P A P I E K T

I S K A K G Q P R E P Q V Y T L P P S R D E L T K N Q V S L

T C L V K G F Y P S D I A V E W E S N G Q P E N N Y K T T P

P V L D S D G S F F L Y S K L T V D K S R W Q Q G N V F S C

S V M H E A L H N H Y T Q K S L S L S P G K

SEQ ID NO: 54 PSMAb heavy chain signal peptide nucleic acid sequence:
ATGGAGTTTGGGCTGAGCTGGGTTTTCCTCGTTGCTCTTTTAAGAGGTGTCCAGTGT SEQ ID NO: 55 PSMAb heavy chain signal peptide amino acid sequence:
M E F G L S W V F L V A L L R G V Q C SEQ ID NO: 56 PSMAb heavy chain variable region nucleic acid sequence:
GAGGTGCAGCTGGTGGAGTCTGGGGGAGCCCTGGCCAAGCCTGGGGGGTCCCTGAGACTC

TCCTGTGCAGCCTCTGGATTCACCCTCAGTGGCTATGCTATGCACTGGGTCCGCCAGGCT

CCAGGCAAGGGGCTGGAGTGGGTGGCAGTTATATCATATGATGGAAGCAATAAATACTAC

GCAGACTCCGTGAAGGGCCGATTCACCGTCTCCAGAGACAATTCCAAGAACACGCTGTTT

CTGCAAATGAACAGCCTGAGACCTGAGGACACGGCTGTGTACTATTGTGCTAAAGGCCTT

ACCTGGGGACTCGGTGACAATGATGCTCTCGATATCTGGGGCCCCGGGACCACGGTCACC

GTCTCCTCA

SEQ ID NO: 57 PSMAb heavy chain variable region amino acid sequence:
E V Q L V E S G G A L A K P G G S L R L S C A A S G F T L S

G Y A M H W V R Q A P G K G L E W V A V I S Y D G S N K Y Y

A D S V K G R F T V S R D N S K N T L F L Q M N S L R P E D

T A V Y Y C A K G L T W G L G D N D A L D I W G P G T T V T

V S S

SEQ ID NO: 58 PSMAb heavy chain constant region nucleic acid sequence:
GCCTCCACCAAGGGCCCATCGGTCTTCCCCCTGGCACCCTCCTCCAAGAGCACCTCTGGG

GGCACAGCGGCCCTGGGCTGCCTGGTCAAGGACTACTTCCCCGAACCGGTGACGGTGTCG

TGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACC

TACATCTGCAACGTGAATCACAAGCCCAGCAACACCAAGGTGGACAAGAAAGTTGAGCCC

-continued

AAATCTTGTGACAAAACTCACACATGCCCACCGTGCCCAGCACCTGAACTCCTGGGGGGA

CCGTCAGTCTTCCTCTTCCCCCCAAAACCCAAGGACACCCTCATGATCTCCCGGACCCCT

GAGGTCACATGCGTGGTGGTGGACGTGAGCCACGAAGACCCTGAGGTCAAGTTCAACTGG

TACGTGGACGGCGTGGAGGTGCATAATGCCAAGACAAAGCCGCGGGAGGAGCAGTACAAC

AGCACGTACCGGGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAAACCATCTCC

AAAGCCAAAGGGCAGCCCCGAGAACCACAGGTGTACACCCTGCCCCCATCCCGGGATGAG

CTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTG

CTGGACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTACACG

CAGAAGAGCCTCTCCCTGTCTCCGGGTAAA

SEQ ID NO: 59 PSMAb heavy chain constant region amino acid sequence:
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO: 60 PSMAb light chain nucleic acid sequence:
ATGGCCTGGTCTCCTCTCCTCCTCACTCTCCTCGCTCACTGCACAGGGTCCTGGGCCCAG

TCTGTGCTGACTCAGCCGCCCTCAGTGTCTGGGGCCCCAGGGCAGAGTGTCATTATCTCC

TGCACTGGGAGCAGCTCCAACATCGGGGCAGGTTCTCATGTACACTGGTACCAGCAGGTT

CCAGGAACAGCCCCCAAACTCCTCATCTATGAAAACACCAATCGGCCCTCAGGGGTCCCT

GACCGATTCTCTGGCTCCAAGTCTGGCACCTCAGGTTCCCTGGCCATCACTGGACTCCAG

CCTGAGGATGAGGCTGATTATTATTGTGCAACATGGGATGACAGTCTGAATGGTGTAATA

TTCGGCGGAGGGACCAAGGCCACCGTCCTAGGTCAGCCCAAGGCTGCCCCCTCGGTCACT

CTGTTCCCGCCCTCCTCTGAGGAGCTTCAAGCCAACAAGGCCACACTGGTGTGTCTCATA

AGTGACTTCTACCCGGGAGCCGTGACAGTGGCCTGGAAGGCAGATAGCAGCCCCGTCAG

GCGGGAGTGGAGACCACCACACCCTCCAAACAAAGCAACAACAAGTACGCGGCCAGCAGC

TATCTGAGCCTGACGCCTGAGCAGTGGAAGTCCCACAGAAGCTACAGCTGCCAGGTCACG

CATGAAGGGAGCACCGTGGAGAAGACAGTGGCCCCTACAGAATGTTCATGA

SEQ ID NO: 61 PSMAb light chain amino acid sequence:
M A W S P L L L I L L A H C T G S W A Q S V L T Q P P S V S

G A P G Q S V I I S C T G S S S N I G A G S H V H W Y Q Q V

P G T A P K L L I Y E N T N R P S G V P D R F S G S K S G T

S G S L A I T G L Q P E D E A D Y Y C A T W D D S L N G V I

F G G G T K A T V L G Q P K A A P S V T L F P P S S E E L Q

A N K A T L V C L I S D F Y P G A V T V A W K A D S S P V K

A G V E T T T P S K Q S N N K Y A A S S Y L S L T P E Q W K

S H R S Y S C Q V T H E G S T V E K T V A P T E C S

SEQ ID NO: 62 PSMAb light chain signal peptide nucleic acid sequence:
ATGGCCTGGTCTCCTCTCCTCCTCACTCTCCTCGCTCACTGCACAGGGTCCTGGGCC SEQ ID NO: 63 PSMAb light chain signal peptide amino acid sequence:
M A W S P L L L I L L A H C T G S W A SEQ ID NO: 64 PSMAb light chain variable region nucleic acid sequence:
CAGTCTGTGCTGACTCAGCCGCCCTCAGTGTCTGGGGCCCCAGGGCAGAGTGTCATTATC

TCCTGCACTGGGAGCAGCTCCAACATCGGGGCAGGTTCTCATGTACACTGGTACCAGCAG

GTTCCAGGAACAGCCCCCAAACTCCTCATCTATGAAAACACCAATCGGCCCTCAGGGGTC

CCTGACCGATTCTCTGGCTCCAAGTCTGGCACCTCAGGTTCCCTGGCCATCACTGGACTC

CAGCCTGAGGATGAGGCTGATTATTATTGTGCAACATGGGATGACAGTCTGAATGGTGTA

ATATTCGGCGGAGGGACCAAGGCCACCGTCCTA

SEQ ID NO: 65 PSMAb light chain variable region amino acid sequence:
Q S V L T Q P P S V S G A P G Q S V I I S C T G S S S N I G

A G S H V H W Y Q Q V P G T A P K L L I Y E N T N R P S G V

P D R F S G S K S G I S G S L A I T G L Q P E D E A D Y Y C

A T W D D S L N G V I F G G G T K A T V L

SEQ ID NO: 66 PSMAb light chain constant region nucleic acid sequence:
GGTCAGCCCAAGGCTGCCCCCTCGGTCACTCTGTTCCCGCCCTCCTCTGAGGAGCTTCAA

GCCAACAAGGCCACACTGGTGTGTCTCATAAGTGACTTCTACCCGGGAGCCGTGACAGTG

GCCTGGAAGGCAGATAGCAGCCCCGTCAAGGCGGGAGTGGAGACCACCACACCCTCCAAA

CAAAGCAACAACAAGTACGCGGCCAGCAGCTATCTGAGCCTGACGCCTGAGCAGTGGAAG

TCCCACAGAAGCTACAGCTGCCAGGTCACGCATGAAGGGAGCACCGTGGAGAAGACAGTG

GCCCCTACAGAATGTTCA

SEQ ID NO: 67 PSMAb light chain constant region amino acid sequence:
G Q P K A A P S V T L F P P S S E E L Q A N K A T L V C L I

S D F Y P G A V T V A W K A D S S P V K A G V E T T T P S K

Q S N N K Y A A S S Y L S L T P E Q W K S H R S Y S C Q V T

H E G S T V E K T V A P T E C S

SEQ ID NO: 68 PSMAb heavy chain amino acid sequence without signal peptide:
E V Q L V E S G G A L A K P G G S L R L S C A A S G F T L S

G Y A M H W V R Q A P G K G L E W V A V I S Y D G S N K Y Y

A D S V K G R F T V S R D N S K N T L F L Q M N S L R P E D

T A V Y Y C A K G L T W G L G D N D A L D I W G P G T T V T

V S S A S T K G P S V F P L A P S S K S T S G G T A A L G C

L V K D Y F P E P V T V S W N S G A L T S G V H T F P A V L

Q S S G L Y S L S S V V T V P S S S L G T Q T Y I C N V N H

K P S N T K V D K K V E P K S C D K T H T C P P C P A P E L

L G G P S V F L F P P K P K D T L M I S R T P E V T C V V V

D V S H E D P E V K F N W Y V D G V E V H N A K T K P R E E

Q Y N S T Y R V V S V L T V L H Q D W L N G K E Y K C K V S

N K A L P A P I E K T I S K A K G Q P R E P Q V Y T L P P S

R D E L T K N Q V S L T C L V K G F Y P S D I A V E W E S N

-continued

GQPENNYKTTPPVLDSDGSFFLYSKLTVDK

SRWQQGNVFSCSVMHEALHNHYTQKSLSLS

PGK

SEQ ID NO: 69 PSMAb light chain amino acid sequence without signal peptide:
QSVLTQPPSVSGAPGQSVIISCTGSSSNIG

AGSHVHWYQQVPGTAPKLLIYENTNRPSGV

PDRFSGSKSGTSGSLAITGLQPEDEADYYC

ATWDDSLNGVIFGGGTKATVLGQPKAAPSV

TLFPPSSEELQANKATLVCLISDFYPGAVT

VAWKADSSPVKAGVETTTPSKQSNNKYAAS

SYLSLTPEQWKSHRSYSCQVTHEGSTVEKT

VAPTECS

SEQ ID NO: 70 CD8a leader nucleic acid sequence:
ATGGCCTTACCAGTGACCGCCTTGCTCCTGCCGCTGGCCTTGCTGCTCCACGCCGCCAGG

CCG

SEQ ID NO: 71 CD8a leader amino acid sequence:
MALPVTALLLPLALLLHAARP

SEQ ID NO: 72 CD8a hinge nucleic acid sequence:
ACCACGACGCCAGCGCCGCGACCACCAACACCGGCGCCCACCATCGCGTCGCAGCCCCTG

TCCCTGCGCCCAGAGGCGTGCCGGCCAGCGGCGGGGGGCGCAGTGCACACGAGGGGGCTG

GACTTCGCCTGTGAT

SEQ ID NO: 73 CD8a hinge amino acid sequence:
TTTPAPRPPTPAPTIASQPLSLRPEACRPAAGGAVHTRGLDFACD SEQ ID NO: 74 CD8a transmembrane domain nucleic acid sequence
ATCTACATCTGGGCGCCCTTGGCCGGGACTTGTGGGGTCCTTCTCCTGTCACTGGTTATC

ACCCTTTACTGC

SEQ ID NO: 75 CD8a transmembrane domain amino acid sequence:
IYIWAPLAGTCGVLLLSLVITLYC SEQ ID NO: 76 4-1 BB intracellular domain (ICD) nucleic acid sequence:
AAACGGGGCAGAAAGAAACTCCTGTATATATTCAAACAACCATTTATGAGACCAGTACAA

ACTACTCAAGAGGAAGATGGCTGTAGCTGCCGATTTCCAGAAGAAGAAGAAGGAGGATGT

GAACTG

SEQ ID NO: 77 4-1 BB intracellular domain (ICD) amino sequence:
KRGRKKLLYIFKQPFMRPVQTTQEEDGCSCRFPEEEEGGCEL SEQ ID NO: 78 CD3 zeta nucleic acid sequence
AGAGTGAAGTTCAGCAGGAGCGCAGACGCCCCCGCGTACAAGCAGGGCCAGAACCAGCTC

TATAACGAGCTCAATCTAGGACGAAGAGAGGAGTACGATGTTTTGGACAAGAGACGTGGC

CGGGACCCTGAGATGGGGGGAAAGCCGAGAAGGAAGAACCCTCAGGAAGGCCTGTACAAT

GAACTGCAGAAAGATAAGATGGCGGAGGCCTACAGTGAGATTGGGATGAAAGGCGAGCGC

CGGAGGGGCAAGGGGCACGATGGCCTTTACCAGGGTCTCAGTACAGCCACCAAGGACACC

TACGACGCCCTTCACATGCAGGCCCTGCCCCCTCGC

SEQ ID NO: 79 CD3 zeta amino acid sequence:
RVKFSRSADAPAYKQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR

SEQ ID NO: 80 gy1-2 CAR construct nucleic acid sequence:
ATGGCCTTACCAGTGACCGCCTTGCTCCTGCCGCTGGCCTTGCTGCTCCACGCCGCCAGG

CCGTCTAGACAGTCTGTGCTGACTCAGCCGCCCTCAGTGTCTGGGGCCCCAGGGCAGAGT

GTCATTATCTCCTGCACTGGGAGCAGCTCCAACATCGGGGCAGGTTCTCATGTACACTGG

TACCAGCAGGTTCCAGGAACAGCCCCCAAACTCCTCATCTATGAAAACACCAATCGGCCC

TCAGGGGTCCCTGACCGATTCTCTGGCTCCAAGTCTGGCACCTCAGGTTCCCTGGCCATC

ACTGGACTCCAGCCTGAGGATGAGGCTGATTATTATTGTGCAACATGGGATGACAGTCTG

AATGGTGTAATATTCGGCGGAGGGACCAAGGCCACCGTCCTAGGCGGATCCTCTAGGTCA

AGTTCCAGCGGCGGCGGTGGCAGCGGAGGCGGCGGTGAGGTGCAGCTGGTGGAGTCTGGG

GGAGCCCTGGCCAAGCCTGGGGGGTCCCTGAGACTCTCCTGTGCAGCCTCTGGATTCACC

CTCAGTGGCTATGCTATGCACTGGGTCCGCCAGGCTCCAGGCAAGGGGCTGGAGTGGGTG

GCAGTTATATCATATGATGGAAGCAATAAATACTACGCAGACTCCGTGAAGGGCCGATTC

ACCGTCTCCAGAGACAATTCCAAGAACACGCTGTTTCTGCAAATGAACAGCCTGAGACCT

GAGGACACGGCTGTGTACTATTGTGCTAAAGGCCTTACCTGGGGACTCGGTGACAATGAT

GCTCTCGATATCTGGGGCCCCGGGACCACGGTCACCGTCTCCTCAAGATCCACCACGACG

CCAGCGCCGCGACCACCAACACCGGCGCCCACCATCGCGTCGCAGCCCCTGTCCCTGCGC

CCAGAGGCGTGCCGGCCAGCGGCGGGGGGCGCAGTGCACACGAGGGGGCTGGACTTCGCC

TGTGATATCTACATCTGGGCGCCCTTGGCCGGGACTTGTGGGGTCCTTCTCCTGTCACTG

GTTATCACCCTTTACTGCAAACGGGGCAGAAAGAAACTCCTGTATATATTCAAACAACCA

TTTATGAGACCAGTACAAACTACTCAAGAGGAAGATGGCTGTAGCTGCCGATTTCCAGAA

GAAGAAGAAGGAGGATGTGAACTGAGAGTGAAGTTCAGCAGGAGCGCAGACGCCCCCGCG

TACCAGCAGGGCCAGAACCAGCTCTATAACGAGCTCAATCTAGGACGAAGAGAGGAGTAC

GATGTTTTGGACAAGAGACGTGGCCGGGACCCTGAGATGGGGGGAAAGCCGAGAAGGAAG

AACCCTCAGGAAGGCCTGTACAATGAACTGCAGAAAGATAAGATGGCGGAGGCCTACAGT

GAGATTGGGATGAAAGGCGAGCGCGGAGGGGCAAGGGGCACGATGGCCTTTACCAGGGT

CTCAGTACAGCCACCAAGGACACCTACGACGCCCTTCACATGCAGGCCCTGCCCCCTCGC

TAA

SEQ ID NO: 81 gy1-2 CAR construct amino acid sequence
MALPVTALLLPLALLLHAARPSRQSVLTQPPSVSGAPGQSVIISCTGSSSNIGAGSHVHW

YQQVPGTAPKLLIYENTNRPSGVPDRFSGSKSGTSGSLAITGLQPEDEADYYCATWDDSL

NGVIFGGGTKATVLGGSSRSSSSGGGGSGGGGEVQLVESGGALAKPGGSLRLSCAASGFT

LSGYAMHWVRQAPGKGLEWVAVISYDGSNKYYADSVKGRFTVSRDNSKNTLFLQMNSLRP

EDTAVYYCAKGLTWGLGDNDALDIWGPGTTVTVSSRSTTTPAPRPPTPAPTIASQPLSLR

PEACRPAAGGAVHTRGLDFACDIYIWAPLAGTCGVLLLSLVITLYCKRGRKKLLYIFKQP

FMRPVQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGHDGLYQG

LSTATKDTYDALHMQALPPR

SEQ ID NO: 82 mOKT3 Murine scFv nucleic acid sequence:
CAGGTGCAGCTGCAGCAGAGCGGCGCGGAACTGGCGCGCCCGGGCGCGAGCGTGAAAATG

AGCTGCAAAGCGAGCGGCTATACCTTTACCCGCTATACCATGCATTGGGTGAAACAGCGC

CCGGGCCAGGGCCTGGAATGGATTGGCTATATTAACCCGAGCCGCGGCTATACCAACTAT

AACCAGAAATTTAAAGATAAAGCGACCCTGACCACCGATAAAAGCAGCAGCACCGCGTAT

ATGCAGCTGAGCAGCCTGACCAGCGAAGATAGCGCGGTGTATTATTGCGCGCGCTATTAT

GATGATCATTATTGCCTGGATTATTGGGGCCAGGGCACCACCCTGACCGTGAGCAGCGGC

GGCGGCGGCAGCGGCGGCGGCGGCAGCGGCGGCGGCGGCAGCCAGATTGTGCTGACCCAG

AGCCCGGCGATTATGAGCGCGAGCCCGGGCGAAAAAGTGACCATGACCTGCAGCGCGAGC

AGCAGCGTGAGCTATATGAACTGGTATCAGCAGAAAAGCGGCACCAGCCCGAAACGCTGG

ATTTATGATACCAGCAAACTGGCGAGCGGCGTGCCGGCGCATTTTCGCGGCAGCGGCAGC

GGCACCAGCTATAGCCTGACCATTAGCGGCATGGAAGCGGAAGATGCGGCGACCTATTAT

TGCCAGCAGTGGAGCAGCAACCCGTTTACCTTTGGCAGCGGCACCAAACTGGAAATTAAC

CGC

SEQ ID NO: 83 mOKT3 Murine scFv amino acid sequence:
QVQLQQSGAELARPGASVKMSCKASGYTFTRYTMHWVKQRPGQGLEWIGYINPSRGYTNY

NQKFKDKATLTTDKSSSTAYMQLSSLTSEDSAVYYCARYYDDHYCLDYWGQGTTLTVSSG

GGGSGGGGSGGGGSQIVLTQSPAIMSASPGEKVTMTCSASSSVSYMNWYQQKSGTSPKRW

IYDTSKLASGVPAHFRGSGSGTSYSLTISGMEAEDAATYYCQQWSSNPFTFGSGTKLEIN

R

SEQ ID NO: 84 mOKT3 VH nucleic acid sequence:
CAGGTGCAGCTGCAGCAGAGCGGCGCGGAACTGGCGCGCCCGGGCGCGAGCGTGAAAATG

AGCTGCAAAGCGAGCGGCTATACCTTTACCCGCTATACCATGCATTGGGTGAAACAGCGC

CCGGGCCAGGGCCTGGAATGGATTGGCTATATTAACCCGAGCCGCGGCTATACCAACTAT

AACCAGAAATTTAAAGATAAAGCGACCCTGACCACCGATAAAAGCAGCAGCACCGCGTAT

ATGCAGCTGAGCAGCCTGACCAGCGAAGATAGCGCGGTGTATTATTGCGCGCGCTATTAT

GATGATCATTATTGCCTGGATTATTGGGGCCAGGGCACCACCCTGACCGTGAGCAGC

SEQ ID NO: 85 mOKT3 VH amino acid sequence:
QVQLQQSGAELARPGASVKMSCKASGYTFTRYTMHWVKQRPGQGLEWIGYINPSRGYTNY

NQKFKDKATLTTDKSSSTAYMQLSSLTSEDSAVYYCARYYDDHYCLDYWGQGTTLTVSS

SEQ ID NO: 86 mOKT3 VL nucleic acid sequence:
CAGATTGTGCTGACCCAGAGCCCGGCGATTATGAGCGCGAGCCCGGGCGAAAAAGTGACC

ATGACCTGCAGCGCGAGCAGCAGCGTGAGCTATATGAACTGGTATCAGCAGAAAAGCGGC

ACCAGCCCGAAACGCTGGATTTATGATACCAGCAAACTGGCGAGCGGCGTGCCGGCGCAT

TTTCGCGGCAGCGGCAGCGGCACCAGCTATAGCCTGACCATTAGCGGCATGGAAGCGGAA

GATGCGGCGACCTATTATTGCCAGCAGTGGAGCAGCAACCCGTTTACCTTTGGCAGCGGC

ACCAAACTGGAAATTAACCGC

SEQ ID NO: 87 mOKT3 VL amino acid sequence:
QIVLTQSPAIMSASPGEKVTMTCSASSSVSYMNWYQQKSGTSPKRWIYDTSKLASGVPAH

FRGSGSGTSYSLTISGMEAEDAATYYCQQWSSNPFTFGSGTKLEINR

SEQ ID NO: 88 hOKT3 humanized scFv nucleic acid sequence:
CAGGTGCAGCTGGTGCAGAGCGGCGGCGGCGTGGTGCAGCCGGGCCGCAGCCTGCGCCTG

AGCTGCAAAGCGAGCGGCTATACCTTTACCCGCTATACCATGCATTGGGTGCGCCAGGCG

CCCGGGCAAAGGCCTGGAATGGATTGGCTATATTAACCCGAGCCGCGGCTATACCAACTAT

-continued

AACCAGAAAGTGAAAGATCGCTTTACCATTAGCACCGATAAAAGCAAAAGCACCGCGTTT

CTGCAGATGGATAGCCTGCGCCCGGAAGATACCGGCGTGTATTTTTGCGCGCGCTATTAT

GATGATCATTATTGCCTGGATTATTGGGGCCAGGGCACCACCCTGACCGTGAGCAGCGGC

GGCGGCGGCAGCGGCGGCGGCAGCGGCGGCGGCGGCAGCGATATTCAGATGACCCAG

AGCCCGAGCAGCCTGAGCGCGAGCGTGGGCGATCGCGTGACCATTACCTGCAGCGCGAGC

AGCAGCGTGAGCTATATGAACTGGTATCAGCAGACCCCGGGCAAAGCGCCGAAACGCTGG

ATTTATGATACCAGCAAACTGGCGAGCGGCGTGCCGAGCCGCTTTAGCGGCAGCGGCAGC

GGCACCGATTATACCTTTACCATTAGCAGCCTGCAGCCGGAAGATATTGCGACCTATTAT

TGCCAGCAGTGGAGCAGCAACCCGTTTACCTTTGGCCAGGGCACCAAACTGCAGATTACC

CGC

SEQ ID NO: 89 hOKT3 humanized scFv amino acid sequence:
QVQLVQSGGGVVQPGRSLRLSCKASGYTFTRYTMHWVRQAPGKGLEWIGYINPSRGYTNY

NQKVKDRFTISTDKSKSTAFLQMDSLRPEDTGVYFCARYYDDHYCLDYWGQGTTLTVSSG

GGGSGGGGSGGGGSDIQMTQSPSSLSASVGDRVTITCSASSSVSYMNWYQQTPGKAPKRW

IYDTSKLASGVPSRFSGSGSGTDYTFTISSLQPEDIATYYCQQWSSNPFTFGQGTKLQIT

R

SEQ ID NO: 90 hOKT3 VH nucleic acid sequence:
CAGGTGCAGCTGGTGCAGAGCGGCGGCGGCGTGGTGCAGCCGGGCCGCAGCCTGCGCCTG

AGCTGCAAAGCGAGCGGCTATACCTTTACCCGCTATACCATGCATTGGGTGCGCCAGGCG

CCGGGCAAAGGCCTGGAATGGATTGGCTATATTAACCCGAGCCGCGGCTATACCAACTAT

AACCAGAAAGTGAAAGATCGCTTTACCATTAGCACCGATAAAAGCAAAAGCACCGCGTTT

CTGCAGATGGATAGCCTGCGCCCGGAAGATACCGGCGTGTATTTTTGCGCGCGCTATTAT

GATGATCATTATTGCCTGGATTATTGGGGCCAGGGCACCACCCTGACCGTGAGCAGC

SEQ ID NO: 91 hOKT3 VH amino acid sequence:
QVQLVQSGGGVVQPGRSLRLSCKASGYTFTRYTMHWVRQAPGKGLEWIGYINPSRGYTNY

NQKVKDRFTISTDKSKSTAFLQMDSLRPEDTGVYFCARYYDDHYCLDYWGQGTTLTVSS

SEQ ID NO: 92 hOKT3 VL nucleic acid sequence:
GATATTCAGATGACCCAGAGCCCGAGCAGCCTGAGCGCGAGCGTGGGCGATCGCGTGACC

ATTACCTGCAGCGCGAGCAGCAGCGTGAGCTATATGAACTGGTATCAGCAGACCCCGGGC

AAAGCGCCGAAACGCTGGATTTATGATACCAGCAAACTGGCGAGCGGCGTGCCGAGCCGC

TTTAGCGGCAGCGGCAGCGGCACCGATTATACCTTTACCATTAGCAGCCTGCAGCCGGAA

GATATTGCGACCTATTATTGCCAGCAGTGGAGCAGCAACCCGTTTACCTTTGGCCAGGGC

ACCAAACTGCAGATTACCCGC

SEQ ID NO: 93 hOKT3 VL amino acid sequence:
DIQMTQSPSSLSASVGDRVTITCSASSSVSYMNWYQQTPGKAPKRWIYDTSKLASGVPSR

FSGSGSGTDYTFTISSLQPEDIATYYCQQWSSNPFTFGQGTKLQITR

SEQ ID NO: 94 MUTATED IGG1 HINGE NUCLEIC ACID SEQUENCE:
GAGCCCAAATCTGCTGACAAAACTCACACATGCCCACCGTGCCCA

SEQ ID NO: 95 mutated IgG1 hinge amino acid sequence:
EPKSADKTHICPPCP

SEQ ID NO: 96 mutated IgG4 Fc (N297A) nucleic acid sequence:
GCACCTGAGTTCCTGGGGGGACCATCAGTCTTCCTGTTCCCCCCAAAACCCAAGGACACT

CTCATGATCTCCCGGACCCCTGAGGTCACGTGCGTGGTGGTGGACGTGAGCCAGGAAGAC

CCCGAGGTCCAGTTCAACTGGTACGTGGATGGCGTGGAGGTGCATAATGCCAAGACAAAG

```
CCGCGGGAGGAGCAGTTCGCTAGCACGTACCGTGTGGTCAGCGTCCTCACCGTCCTGCAC

CAGGACTGGCTGAACGGCAAGGAGTACAAGTGCAAGGTCTCCAACAAAGGCCTCCCGTCC

TCCATCGAGAAAACCATCTCCAAAGCCAAAGGGCAGCCCCGAGAGCCACAGGTGTACACC

CTGCCCCCATCCCAGGAGGAGATGACCAAGAACCAGGTCAGCCTGACCTGCCTGGTCAAA

GGCTTCTACCCCAGCGACATCGCCGTGGAGTGGGAGAGCAATGGGCAGCCGGAGAACAAC

TACAAGACCACGCCTCCCGTGCTGGACTCCGACGGCTCCTTCTTCCTCTACAGCAGGCTA

ACCGTGGACAAGAGCAGGTGGCAGGAGGGGAATGTCTTCTCATGCTCCGTGATGCATGAG

GCTCTGCACAACCACTACACACAGAAGAGCCTCTCCCTGTCTCTGGGTAA

SEQ ID NO: 97 mutated IgG4 Fc (N297A) amino acid sequence:
APEFLGGPSVFLFPPKPKDTLMISRTPEVTCVVVDVSQEDPEVQFNWYVDGVEVHNAKTK

PREEQFASTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRL

TVDKSRWQEGNVFSCSVMHEALHNHYTQKSLSLSLGK

SEQ ID NO: 98 mutated IgG1 Hinge-IgG4 Fc nucleic acid sequence:
GAGCCCAAATCTGCTGACAAAACTCACACATGCCCACCGTGCCCAGCACCTGAGTTCCTG

GGGGGACCATCAGTCTTCCTGTTCCCCCCAAAACCCAAGGACACTCTCATGATCTCCCGG

ACCCCTGAGGTCACGTGCGTGGTGGTGGACGTGAGCCAGGAAGACCCCGAGGTCCAGTTC

AACTGGTACGTGGATGGCGTGGAGGTGCATAATGCCAAGACAAAGCCGCGGGAGGAGCAG

TTCGCTAGCACGTACCGTGTGGTCAGCGTCCTCACCGTCCTGCACCAGGACTGGCTGAAC

GGCAAGGAGTACAAGTGCAAGGTCTCCAACAAAGGCCTCCCGTCCTCCATCGAGAAAACC

ATCTCCAAAGCCAAAGGGCAGCCCCGAGAGCCACAGGTGTACACCCTGCCCCCATCCCAG

GAGGAGATGACCAAGAACCAGGTCAGCCTGACCTGCCTGGTCAAAGGCTTCTACCCCAGC

GACATCGCCGTGGAGTGGGAGAGCAATGGGCAGCCGGAGAACAACTACAAGACCACGCCT

CCCGTGCTGGACTCCGACGGCTCCTTCTTCCTCTACAGCAGGCTAACCGTGGACAAGAGC

AGGTGGCAGGAGGGGAATGTCTTCTCATGCTCCGTGATGCATGAGGCTCTGCACAACCAC

TACACACAGAAGAGCCTCTCCCTGTCTCTGGGTAAA

SEQ ID NO: 99 mutated IgG1 Hinge-IgG4 Fc amino acid sequence:
EPKSADKTHTCPPCPAPEFLGGPSVFLFPPKPKDTLMISRTPEVTCVVVDVSQEDPEVQF

NWYVDGVEVHNAKTKPREEQFASTYRVVSVLTVLHQDWLNGKEYKCKVSNKGLPSSIEKT

ISKAKGQPREPQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSLGK

SEQ ID NO: 100 scFv1 MCS-G4S-hOKT3 scFv-IgG1 hinge-IgG4 Fc expression
cassette nucleic acid sequence:
ACTAGTGCCACCATGGAGTTTGGGCTGAGCTGGGTCTTCCTGGTGGCTATCTTGAAGGGT

GTCCAGTGTGAATTCAAGCTTTCTAGAAGCGCTGCTAGCGGTGGAGGTGGATCCCAGGTC

CAGCTGGTGCAGTCAGGGGGGGAGTCGTGCAGCCCGGTCGGTCTCTGCGTCTGTCTTGT

AAGGCATCCGGTTATACTTTTACCAGGTACACAATGCACTGGGTGCGGCAGGCTCCTGGC

AAGGGCCTGGAGTGGATCGGCTATATCAACCCATCCAGGGGCTACACCAACTATAATCAG

AAGGTGAAGGACCGGTTCACCATCTCTACAGATAAGAGCAAGTCTACAGCCTTTCTGCAG

ATGGACTCCCTGAGACCTGAGGATACCGGCGTGTACTTCTGCGCTCGCTACTATGACGAT

CATTACTGTCTGGACTATTGGGGCCAGGGCACCACACTGACAGTGTCCAGCGGAGGAGGA

GGCTCCGGAGGAGGAGGCAGCGGCGGCGGCGGCTCTGACATCCAGATGACCCAGAGCCCA

TCTTCCCTGTCCGCCAGCGTGGGCGATAGAGTGACCATCACATGCTCCGCCTCCTCCTCC
```

-continued

```
GTGTCCTACATGAACTGGTATCAGCAGACACCCGGCAAGGCCCCTAAGAGATGGATCTAC

GATACCTCCAAGCTGGCCTCCGGAGTGCCCTCTCGCTTCTCTGGCTCCGGCAGCGGCACA

GACTATACCTTTACAATCAGCTCTCTGCAGCCTGAGGATATCGCTACCTACTATTGTCAG

CAGTGGTCCAGCAATCCATTCACCTTTGGCCAGGGCACAAAGCTGCAGATCACCAGGCTC

GAGCCAAAGAGCGCCGACAAGACCCACACATGCCCCCCTTGTCCAGCTCCCGAGTTTCTG

GGCGGCCCATCCGTGTTCCTGTTTCCACCCAAGCCCAAGGATACACTGATGATCAGCCGG

ACCCCAGAGGTGACATGCGTGGTGGTGGACGTGTCTCAGGAGGACCCCGAGGTGCAGTTC

AACTGGTACGTGGACGGCGTGGAGGTGCACAATGCCAAGACCAAGCCCAGGGAGGAGCAG

TTTGCTTCTACATACCGGGTGGTGTCCGTGCTGACCGTGCTGCATCAGGATTGGCTGAAC

GGCAAGGAGTATAAGTGCAAGGTGTCCAATAAGGGCCTGCCTTCTTCCATCGAGAAGACA

ATCAGCAAGGCTAAGGGACAGCCTCGCGAGCCACAGGTGTACACCCTGCCTCCATCTCAG

GAGGAGATGACAAAGAACCAGGTGTCCCTGACCTGTCTGGTGAAGGGCTTCTATCCCTCC

GACATCGCTGTGGAGTGGGAGAGCAATGGCCAGCCTGAGAACAATTACAAGACCACACCC

CCTGTGCTGGACAGCGATGGCTCTTTCTTTCTGTATAGCAGACTGACCGTGGATAAGTCT

CGCTGGCAGGAGGGCAACGTGTTCTCCTGTTCCGTGATGCACGAGGCACTGCACAACCAC

TACACTCAGAAATCACTGTCACTGTCCCTGGGCAAGTAGGCGGCCGC

SEQ ID NO: 101 scFv1 MCS-G45-hOKT3 scFv-IgG1 hinge-IgG4 Fc expression
cassette amino acid sequence:
MEFGLSWVFLVAILKGVQC-MCS-
QVQLVQSGGGVVQPGRSLRLSCKASGYTFTRYTMHWVRQAPGKGLEWIGYINPSRGYTNY

NQKVKDRFTISTDKSKSTAFLQMDSLRPEDTGVYFCARYYDDHYCLDYWGQGTTLTVSSG

GGGSGGGGSGGGGSDIQMTQSPSSLSASVGDRVTITCSASSSVSYMNWYQQTPGKAPKRW

IYDTSKLASGVPSRFSGSGSGTDYTFTISSLQPEDIATYYCQQWSSNPFTFGQGTKLQIT

RLEPKSADKTHTCPPCPAPEFLGGPSVFLFPPKPKDTLMISRTPEVTCVVVDVSQEDPEV

QFNWYVDGVEVHNAKTKPREEQFASTYRVVSVLTVLHQDWLNGKEYKCKVSNKGLPSSIE

KTISKAKGQPREPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSLSLGK

SEQ ID NO: 102 scFv1 MCS-G4S-mOKT3 scFv-IgG1 hinge-IgG4 Fc expression
cassette nucleic acid sequence:
ACTAGTGCCACCATGGAGTTTGGGCTGAGCTGGGTCTTCCTGGTGGCTATCTTGAAGGGT

GTCCAGTGTGAATTCAAGCTTTCTAGAAGCGCTGCTAGCGGTGGAGGTGGATCCCAGGTC

CAGCTGCAGCAGAGCGGTGCCGAACTGGCCCGTCCCGGAGCAAGCGTGAAAATGTCCTGT

AAAGCAAGTGGCTATACCTTCACCAGGTACACAATGCACTGGGTGAAGCAGAGGCCAGGA

CAGGGCCTGGAGTGGATCGGCTATATCAACCCCTCTAGGGGCTACACAAACTATAATCAG

AAGTTCAAGGACAAGGCCACCCTGACCACCGATAAGTCCAGCTCTACAGCTTACATGCAG

CTGTCCAGCCTGACCAGCGAGGACTCTGCCGTGTACTATTGCGCTAGATACTATGACGAT

CATTACTGTCTGGATTATTGGGGCCAGGGCACCACACTGACAGTGTCTTCCGGAGGAGGA

GGCAGCGGAGGAGGAGGCTCTGGCGGCGGCGGCTCCCAGATCGTGCTGACCCAGTCCCCA

GCTATCATGTCCGCCTCCCTGGAGAGAAGGTGACCATGACATGCAGCGCCAGCTCTTCC

GTGTCTTACATGAATTGGTATCAGCAGAAGTCCGGCACAAGCCCTAAGAGATGGATCTAC

GACACCTCTAAGCTGGCCTCCGGAGTGCCAGCTCACTTTCGCGGCTCCGGCAGCGGCACC

TCTTATTCCCTGACAATCAGCGGCATGGAGGCTGAGGATGCCGCTACCTACTATTGTCAG

CAGTGGTCATCARATCCTTTCACCTTCGGTTCAGGGACAAAACTGGAGATCAATAGGCTC
```

-continued

```
GAGCCAAAGAGCGCCGACAAGACCCACACATGCCCCCCTTGTCCAGCTCCCGAGTTTCTG

GGCGGCCCATCCGTGTTCCTGTTTCCACCCAAGCCCAAGGATACACTGATGATCAGCCGG

ACCCCAGAGGTGACATGCGTGGTGGTGGACGTGTCTCAGGAGGACCCCGAGGTGCAGTTC

AACTGGTACGTGGACGGCGTGGAGGTGCACAATGCCAAGACCAAGCCCAGGGAGGAGCAG

TTTGCTTCTACATACCGGGTGGTGTCCGTGCTGACCGTGCTGCATCAGGATTGGCTGAAC

GGCAAGGAGTATAAGTGCAAGGTGTCCAATAAGGGCCTGCCTTCTTCCATCGAGAAGACA

ATCAGCAAGGCTAAGGGACAGCCTCGCGAGCCACAGGTGTACACCCTGCCTCCATCTCAG

GAGGAGATGACAAAGAACCAGGTGTCCCTGACCTGTCTGGTGAAGGGCTTCTATCCCTCC

GACATCGCTGTGGAGTGGGAGAGCAATGGCCAGCCTGAGAACAATTACAAGACCACACCC

CCTGTGCTGGACAGCGATGGCTCTTTCTTTCTGTATAGCAGACTGACCGTGGATAAGTCT

CGCTGGCAGGAGGGCAACGTGTTCTCCTGTTCCGTGATGCACGAGGCACTGCACAACCAC

TACACTCAGAAATCACTGTCACTGTCCCTGGGCAAGTAGGCGGCCGC
```

SEQ ID NO: 103 scFy1 MCS-G4S-mOKT3 scFy-IgG1 hinge-IgG4 Fc expression cassette amino acid sequence:
```
MEFGLSWVFLVAILKGVQC-MCS-
QVQLQQSGAELARPGASVKMSCKASGYTFTRYTMHWVKQRPGQGLEWIGYINPSRGYTNY

NQKFKDKATLTTDKSSSTAYMQLSSLTSEDSAVYYCARYYDDHYCLDYWGQGTTLTVSSG

GGGSGGGGSGGGGSQIVLTQSPAIMSASPGEKVTMTCSASSSVSYMNWYQQKSGTSPKRW

IYDTSKLASGVPAHFRGSGSGTSYSLTISGMEAEDAATYYCQQWSSNPFTFGSGTKLEIN

RLEPKSADKTHTCPPCPAPEFLGGPSVFLFPPKPKDTLMISRTPEVTCVVVDVSQEDPEV

QFNWYVDGVEVHNAKTKPREEQFASTYRVVSVLTVLHQDWLNGKEYKCKVSNKGLPSSIE

KTISKAKGQPREPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSLSLGK
```

SEQ ID NO: 104 anti-PSMA & hOKT3 bispecific Ab nucleic acid sequence (gy1-2):
```
ATGGAGTTTGGGCTGAGCTGGGTCTTCCTGGTGGCTATCTTGAAGGGTGTCCAGTGTGAA

TTCCAGTCTGTGCTGACTCAGCCGCCCTCAGTGTCTGGGGCCCCAGGGCAGAGTGTCATT

ATCTCCTGCACTGGGAGCAGCTCCAACATCGGGGCAGGTTCTCATGTACACTGGTACCAG

CAGGTTCCAGGAACAGCCCCCAAACTCCTCATCTATGAAAACACCAATCGGCCCTCAGGG

GTCCCTGACCGATTCTCTGGCTCCAAGTCTGGCACCTCAGGTTCCCTGGCCATCACTGGA

CTCCAGCCTGAGGATGAGGCTGATTATTATTGTGCAACATGGGATGACAGTCTGAATGGT

GTAATATTCGGCGGAGGGACCAAGGCCACCGTCCTAGGCGGATCCTCTAGGTCAAGTTCC

AGCGGCGGCGGTGGCAGCGGAGGCGGCGGTGAGGTGCAGCTGGTGGAGTCTGGGGGAGCC

CTGGCCAAGCCTGGGGGGTCCCTGAGACTCTCCTGTGCAGCCTCTGGATTCACCCTCAGT

GGCTATGCTATGCACTGGGTCCGCCAGGCTCCAGGCAAGGGGCTGGAGTGGGTGGCAGTT

ATATCATATGATGGAAGCAATAAATACTACGCAGACTCCGTGAAGGGCCGATTCACCGTC

TCCAGAGACAATTCCAAGAACACGCTGTTTCTGCAAATGAACAGCCTGAGACCTGAGGAC

ACGGCTGTGTACTATTGTGCTAAAGGCCTTACCTGGGACTCGGTGACAATGATGCTCTC

GATATCTGGGGCCCCGGGACCACGGTCACCGTCTCCTCAGCTAGCGGTGGAGGTGGATCC

CAGGTCCAGCTGGTGCAGTCAGGGGGGGGAGTCGTGCAGCCCGGTCGGTCTCTGCGTCTG

TCTTGTAAGGCATCCGGTTATACTTTTACCAGGTACACAATGCACTGGGTGCGGCAGGCT

CCTGGCAAGGGCCTGGAGTGGATCGGCTATATCAACCCATCCAGGGGCTACACCAACTAT

AATCAGAAGGTGAAGGACCGGTTCACCATCTCTACAGATAAGAGCAAGTCTACAGCCTTT
```

-continued

```
CTGCAGATGGACTCCCTGAGACCTGAGGATACCGGCGTGTACTTCTGCGCTCGCTACTAT

GACGATCATTACTGTCTGGACTATTGGGGCCAGGGCACCACACTGACAGTGTCCAGCGGA

GGAGGAGGCTCCGGAGGAGGAGGCAGCGGCGGCGGCGGCTCTGACATCCAGATGACCCAG

AGCCCATCTTCCCTGTCCGCCAGCGTGGGCGATAGAGTGACCATCACATGCTCCGCCTCC

TCCTCCGTGTCCTACATGAACTGGTATCAGCAGACACCCGGCAAGGCCCCTAAGAGATGG

ATCTACGATACCTCCAAGCTGGCCTCCGGAGTGCCCTCTCGCTTCTCTGGCTCCGGCAGC

GGCACAGACTATACCTTTACAATCAGCTCTCTGCAGCCTGAGGATATCGCTACCTACTAT

TGTCAGCAGTGGTCCAGCAATCCATTCACCTTTGGCCAGGGCACAAAGCTGCAGATCACC

AGGCTCGAGCCAAAGAGCGCCGACAAGACCCACACATGCCCCCCTTGTCCAGCTCCCGAG

TTTCTGGGCGGCCCATCCGTGTTCCTGTTTCCACCCAAGCCCAAGGATACACTGATGATC

AGCCGGACCCCAGAGGTGACATGCGTGGTGGTGGACGTGTCTCAGGAGGACCCCGAGGTG

CAGTTCAACTGGTACGTGGACGGCGTGGAGGTGCACAATGCCAAGACCAAGCCCAGGGAG

GAGCAGTTTGCTTCTACATACCGGGTGGTGTCCGTGCTGACCGTGCTGCATCAGGATTGG

CTGAACGGCAAGGAGTATAAGTGCAAGGTGTCCAATAAGGGCCTGCCTTCTTCCATCGAG

AAGACAATCAGCAAGGCTAAGGGACAGCCTCGCGAGCCACAGGTGTACACCCTGCCTCCA

TCTCAGGAGGAGATGACAAAGAACCAGGTGTCCCTGACCTGTCTGGTGAAGGGCTTCTAT

CCCTCCGACATCGCTGTGGAGTGGGAGAGCAATGGCCAGCCTGAGAACAATTACAAGACC

ACACCCCCTGTGCTGGACAGCGATGGCTCTTTCTTTCTGTATAGCAGACTGACCGTGGAT

AAGTCTCGCTGGCAGGAGGGCAACGTGTTCTCCTGTTCCGTGATGCACGAGGCACTGCAC

ACCACTACACTCAGAAATCACTGTCACTGTCCCTGGGCAAGTAG
```

SEQ ID NO: 105 anti-PSMA & hOKT3 bispecific Ab amino acid sequence (gy1-2):
MEFGLSWVFLVAILKGVQCEFQSVLTQPPSVSGAPGQSVIISCTGSSSNIGAGSHVHWYQ

QVPGTAPKLLIYENTNRPSGVPDRFSGSKSGTSGSLAITGLQPEDEADYYCATWDDSLNG

VIFGGGTKATVLGGSSRSSSSGGGGSGGGGEVQLVESGGALAKPGGSLRLSCAASGFTLS

GYAMHWVRQAPGKGLEWVAVISYDGSNKYYADSVKGRFTVSRDNSKNTLFLQMNSLRPED

TAVYYCAKGLTWGLGDNDALDIWGPGTTVTVSSASGGGGSQVQLVQSGGGVVQPGRSLRL

SCKASGYTFTRYTMHWVRQAPGKGLEWIGYINPSRGYTNYNQKVKDRFTISTDKSKSTAF

LQMDSLRPEDTGVYFCARYYDDHYCLDYWGQGTTLTVSSGGGGSGGGGSGGGGSDIQMTQ

SPSSLSASVGDRVTITCSASSSVSYMNWYQQTPGKAPKRWIYDTSKLASGVPSRFSGSGS

GTDYTFTISSLQPEDIATYYCQQWSSNPFTFGQGTKLQITRLEPKSADKTHTCPPCPAPE

FLGGPSVFLFPPKPKDTLMISRTPEVTCVVVDVSQEDPEVQFNWYVDGVEVHNAKTKPRE

EQFASTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVD

KSRWQEGNVFSCSVMHEALHNHYTQKSLSLSLGK

SEQ ID NO: 106 anti-PSMA & hOKT3 bispecific Ab amino acid sequence (gy1-2)
without signal peptide:
EFQSVLTQPPSVSGAPGQSVIISCTGSSSNIGAGSHVHWYQQVPGTAPKLLIYENTNRPS

GVPDRFSGSKSGTSGSLAITGLQPEDEADYYCATWDDSLNGVIFGGGTKATVLGGSSRSS

SSGGGGSGGGGEVQLVESGGALAKPGGSLRLSCAASGFTLSGYAMHWVRQAPGKGLEWVA

VISYDGSNKYYADSVKGRFTVSRDNSKNTLFLQMNSLRPEDTAVYYCAKGLTWGLGDNDA

LDIWGPGTTVTVSSASGGGGSQVQLVQSGGGVVQPGRSLRLSCKASGYTFTRYTMHWVRQ

APGKGLEWIGYINPSRGYTNYNQKVKDRFTISTDKSKSTAFLQMDSLRPEDTGVYFCARY

-continued

YDDHYCLDYWGQGTTLTVSSGGGGSGGGGSGGGGSDIQMTQSPSSLSASVGDRVTITCSA

SSSVSYMNWYQQTPGKAPKRWIYDTSKLASGVPSRFSGSGSGTDYTFTISSLQPEDIATY

YCQQWSSNPFTFGQGTKLQITRLEPKSADKTHTCPPCPAPEFLGGPSVFLFPPKPKDTLM

ISRTPEVTCVVVDVSQEDPEVQFNWYVDGVEVHNAKTKPREEQFASTYRVVSVLTVLHQD

WLNGKEYKCKVSNKGLPSSIEKTISKAKGQPREPQVYTLPPSQEEMTKNQVSLTCLVKGF

YPSDIAVEWESNGQPENNYKTTPPVLDSDGSFFLYSRLTVDKSRWQEGNVFSCSVMHEAL

HNHYTQKSLSLSLGK

SEQ ID NO: 107 anti-PSMA & mOKT3 bispecific Ab nucleic acid sequence (gy1-2):
ATGGAGTTTGGGCTGAGCTGGGTCTTCCTGGTGGCTATCTTGAAGGGTGTCCAGTGTGAA

TTCCAGTCTGTGCTGACTCAGCCGCCCTCAGTGTCTGGGGCCCCAGGGCAGAGTGTCATT

ATCTCCTGCACTGGGAGCAGCTCCAACATCGGGGCAGGTTCTCATGTACACTGGTACCAG

CAGGTTCCAGGAACAGCCCCCAAACTCCTCATCTATGAAAACACCAATCGGCCCTCAGGG

GTCCCTGACCGATTCTCTGGCTCCAAGTCTGGCACCTCAGGTTCCCTGGCCATCACTGGA

CTCCAGCCTGAGGATGAGGCTGATTATTATTGTGCAACATGGGATGACAGTCTGAATGGT

GTAATATTCGGCGGAGGGACCAAGGCCACCGTCCTAGGCGGATCCTCTAGGTCAAGTTCC

AGCGGCGGCGGTGGCAGCGGAGGCGGCGGTGAGGTGCAGCTGGTGGAGTCTGGGGGAGCC

CTGGCCAAGCCTGGGGGGTCCCTGAGACTCTCCTGTGCAGCCTCTGGATTCACCCTCAGT

GGCTATGCTATGCACTGGGTCCGCCAGGCTCCAGGCAAGGGGCTGGAGTGGGTGGCAGTT

ATATCATATGATGGAAGCAATAAATACTACGCAGACTCCGTGAAGGGCCGATTCACCGTC

TCCAGAGACAATTCCAAGAACACGCTGTTTCTGCAAATGAACAGCCTGAGACCTGAGGAC

ACGGCTGTGTACTATTGTGCTAAAGGCCTTACCTGGGGACTCGGTGACAATGATGCTCTC

GATATCTGGGGCCCCGGGACCACGGTCACCGTCTCCTCAGCTAGCGGTGGAGGTGGATCC

CAGGTCCAGCTGCAGCAGAGCGGTGCCGAACTGGCCCGTCCCGGAGCAAGCGTGAAAATG

TCCTGTAAAGCAAGTGGCTATACCTTCACCAGGTACACAATGCACTGGGTGAAGCAGAGG

CCAGGACAGGGCCTGGAGTGGATCGGCTATATCAACCCCTCTAGGGGCTACACAAACTAT

AATCAGAAGTTCAAGGACAAGGCCACCCTGACCACCGATAAGTCCAGCTCTACAGCTTAC

ATGCAGCTGTCCAGCCTGACCAGCGAGGACTCTGCCGTGTACTATTGCGCTAGATACTAT

GACGATCATTACTGTCTGGATTATTGGGGCCAGGGCACCACACTGACAGTGTCTTCCGGA

GGAGGAGGCAGCGGAGGAGGAGGCTCTGGCGGCGGCGGCTCCCAGATCGTGCTGACCCAG

TCCCCAGCTATCATGTCCGCCTCCCCTGGAGAGAAGGTGACCATGACATGCAGCGCCAGC

TCTTCCGTGTCTTACATGATTGGTATCAGCAGAAGTCCGGCACAAGCCCTAAGAGATGG

ATCTACGACACCTCTAAGCTGGCCTCCGGAGTGCCAGCTCACTTTCGCGGCTCCGGCAGC

GGCACCTCTTATTCCCTGACAATCAGCGGCATGGAGGCTGAGGATGCCGCTACCTACTAT

TGTCAGCAGTGGTCATCAAATCCTTTCACCTTCGGTTCAGGGACAAAACTGGAGATCAAT

AGGCTCGAGCCAAAGAGCGCCGACAAGACCCACACATGCCCCCCTTGTCCAGCTCCCGAG

TTTCTGGGCGGCCCATCCGTGTTCCTGTTTCCACCCAAGCCCAAGGATACACTGATGATC

AGCCGGACCCCAGAGGTGACATGCGTGGTGGTGGACGTGTCTCAGGAGGACCCCGAGGTG

CAGTTCAACTGGTACGTGGACGGCGTGGAGGTGCACAATGCCAAGACCAAGCCCAGGGAG

GAGCAGTTTGCTTCTACATACCGGGTGGTGTCCGTGCTGACCGTGCTGCATCAGGATTGG

CTGACGGCAAGGAGTATAAGTGCAAGGTGTCCAATAAGGGCCTGCCTTCTTCCATCGAG

AAGACAATCAGCAAGGCTAAGGGACAGCCTCGCGAGCCACAGGTGTACACCCTGCCTCCA

```
TCTCAGGAGGAGATGACAAAGAACCAGGTGTCCCTGACCTGTCTGGTGAAGGGCTTCTAT

CCCTCCGACATCGCTGTGGAGTGGGAGAGCAATGGCCAGCCTGAGAACAATTACAAGACC

ACACCCCCTGTGCTGGACAGCGATGGCTCTTTCTTTCTGTATAGCAGACTGACCGTGGAT

AAGTCTCGCTGGCAGGAGGGCAACGTGTTCTCCTGTTCCGTGATGCACGAGGCACTGCAC

ACCACTACACTCAGAAATCACTGTCACTGTCCCTGGGCAAGTAG
```

SEQ ID NO: 108 anti-PSMA & mOKT3 bispecific Ab amino acid sequence (gy1-2):
```
MEFGLSWVFLVAILKGVQCEFQSVLTQPPSVSGAPGQSVIISCTGSSSNIGAGSHVHWYQ

QVPGTAPKLLIYENTNRPSGVPDRFSGSKSGTSGSLAITGLQPEDEADYYCATWDDSLNG

VIFGGGTKATVLGGSSRSSSSGGGGSGGGGEVQLVESGGALAKPGGSLRLSCAASGFTLS

GYAMHWVRQAPGKGLEWVAVISYDGSNKYYADSVKGRFTVSRDNSKNTLFLQMNSLRPED

TAVYYCAKGLTWGLGDNDALDIWGPGTTVTVSSASGGGGSQVQLQQSGAELARPGASVKM

SCKASGYTFTRYTMHWVKQRPGQGLEWIGYINPSRGYTNYNQKFKDKATLTTDKSSSTAY

MQLSSLTSEDSAVYYCARYYDDHYCLDYWGQGTTLTVSSGGGGSGGGGSGGGGSQIVLTQ

SPAIMSASPGEKVTMTCSASSSVSYMNWYQQKSGTSPKRWIYDTSKLASGVPAHFRGSGS

GTSYSLTISGMEAEDAATYYCQQWSSNPFTFGSGTKLEINRLEPKSADKTHTCPPCPAPE

FLGGPSVFLFPPKPKDTLMISRTPEVTCVVVDVSQEDPEVQFNWYVDGVEVHNAKTKPRE

EQFASTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVD

KSRWQEGNVFSCSVMHEALHNHYTQKSLSLSLGK
```

SEQ ID NO: 109 anti-PSMA & mOKT3 bispecific Ab amino acid sequence (gy1-2):
```
EFQSVLTQPPSVSGAPGQSVIISCTGSSSNIGAGSHVHWYQQVPGTAPKLLIYENTNRPS

GVPDRFSGSKSGTSGSLAITGLQPEDEADYYCATWDDSLNGVIFGGGTKATVLGGSSRSS

SSGGGGSGGGGEVQLVESGGALAKPGGSLRLSCAASGFTLSGYAMHWVRQAPGKGLEWVA

VISYDGSNKYYADSVKGRFTVSRDNSKNTLFLQMNSLRPEDTAVYYCAKGLTWGLGDNDA

LDIWGPGTTVTVSSASGGGGSQVQLQQSGAELARPGASVKMSCKASGYTFTRYTMHWVKQ

RPGQGLEWIGYINPSRGYTNYNQKFKDKATLTTDKSSSTAYMQLSSLTSEDSAVYYCARY

YDDHYCLDYWGQGTTLTVSSGGGGSGGGGSGGGGSQIVLTQSPAIMSASPGEKVTMTCSA

SSSVSYMNWYQQKSGTSPKRWIYDTSKLASGVPAHFRGSGSGTSYSLTISGMEAEDAATY

YCQQWSSNPFTFGSGTKLEINRLEPKSADKTHTCPPCPAPEFLGGPSVFLFPPKPKDTLM

ISRTPEVTCVVVDVSQEDPEVQFNWYVDGVEVHNAKTKPREEQFASTYRVVSVLTVLHQD

WLNGKEYKCKVSNKGLPSSIEKTISKAKGQPREPQVYTLPPSQEEMTKNQVSLTCLVKGF

YPSDIAVEWESNGQPENNYKTTPPVLDSDGSFFLYSRLTVDKSRWQEGNVFSCSVMHEAL

HNHYTQKSLSLSLGK
```

SEQ ID NO: 110 EF1a promoter sequence:
```
CGTGAGGCTCCGGTGCCCGTCAGTGGGCAGAGCGCACATCGCCCACAGTCCCCGAGAAGT

TGGGGGGAGGGGTCGGCAATTGAACCGGTGCCTAGAGAAGGTGGCGCGGGGTAAACTGGG

AAAGTGATGTCGTGTACTGGCTCCGCCTTTTTCCCGAGGGTGGGGGAGAACCGTATATAA

GTGCAGTAGTCGCCGTGAACGTTCTTTTTCGCAACGGGTTTGCCGCCAGAACACAGGTAA

GTGCCGTGTGTGGTTCCCGCGGGCCTGGCCTCTTTACGGGTTATGGCCCTTGCGTGCCTT

GAATTACTTCCACCTGGCTGCAGTACGTGATTCTTGATCCCGAGCTTCGGGTTGGAAGTG

GGTGGGAGAGTTCGAGGCCTTGCGCTTAAGGAGCCCCTTCGCCTCGTGCTTGAGTTGAGG

CCTGGCCTGGGCGCTGGGGCCGCCGCGTGCGAATCTGGTGGCACCTTCGCGCCTGTCTCG
```

-continued

```
CTGCTTTCGATAAGTCTCTAGCCATTTAAAATTTTTGATGACCTGCTGCGACGCTTTTTT
TCTGGCAAGATAGTCTTGTAAATGCGGGCCAAGATCTGCACACTGGTATTTCGGTTTTTG
GGGCCGCGGGCGGCGACGGGGCCCGTGCGTCCCAGCGCACATGTTCGGCGAGGCGGGGCC
TGCGAGCGCGGCCACCGAGAATCGGACGGGGGTAGTCTCAAGCTGGCCGGCCTGCTCTGG
TGCCTGGCCTCGCGCCGCCGTGTATCGCCCCGCCCTGGGCGGCAAGGCTGGCCCGGTCGG
CACCAGTTGCGTGAGCGGAAAGATGGCCGCTTCCCGGCCCTGCTGCAGGGAGCTCAAAAT
GGAGGACGCGGCGCTCGGGAGAGCGGGCGGGTGAGTCACCCACACAAAGGAAAAGGGCCT
TTCCGTCCTCAGCCGTCGCTTCATGTGACTCCACGGAGTACCGGGCGCCGTCCAGGCACC
TCGATTAGTTCTCGAGCTTTTGGAGTACGTCGTCTTTAGGTTGGGGGGAGGGGTTTTATG
CGATGGAGTTTCCCCACACTGAGTGGGTGGAGACTGAAGTTAGGCCAGCTTGGCACTTGA
TGTAATTCTCCTTGGAATTTGCCCTTTTTGAGTTTGGATCTTGGTTCATTCTCAAGCCTC
AGACAGTGGTTCAAAGTTTTTTTCTTCCATTTCAGGTGTCGTGA
```

Exemplary Embodiments

In addition to the embodiments described elsewhere in this disclosure, exemplary embodiments of the present invention include, without being limited to, the following:

1. A composition comprising an antibody or antibody fragment, wherein the antibody or antibody fragment comprises one or more of:

a.) a light chain variable region FR1 comprising an amino acid sequence selected from the group consisting of the amino acid sequence of SEQ ID NO: 7, and an amino acid sequence having greater than about 90% homology to SEQ ID NO: 7;

b.) a light chain CDR1 comprising an amino acid sequence selected from the group consisting of the amino acid sequence of SEQ ID NO: 9, and an amino acid sequence having greater than about 90% homology to SEQ ID NO: 9;

c.) a light chain variable region FR2 comprising an amino acid sequence selected from the group consisting of SEQ ID NO: 11, an amino acid sequence having greater than about 90% homology to SEQ ID NO: 11, SEQ ID NO: 39, and an amino acid sequence having greater than about 90% homology to SEQ ID NO: 39;

d.) a light chain CDR2 comprising an amino acid sequence selected from the group consisting of SEQ ID NO: 13, an amino acid sequence having greater than about 90% homology to SEQ ID NO: 13, SEQ ID NO: 41, and an amino acid sequence having greater than about 90% homology to SEQ ID NO: 41;

e.) a light chain variable region FR3 comprising an amino acid sequence selected from the group consisting of the amino acid sequence of SEQ ID NO: 15, and an amino acid sequence having greater than about 90% homology to SEQ ID NO: 15;

f.) a light chain CDR3 comprising an amino acid sequence selected from the group consisting of the amino acid sequence of SEQ ID NO: 17, and an amino acid sequence having greater than about 90% homology to SEQ ID NO: 17;

g.) a light chain variable region FR4 comprising an amino acid sequence selected from the group consisting of SEQ ID NO: 19, an amino acid sequence having greater than about 90% homology to SEQ ID NO: 19, SEQ ID NO: 43, and an amino acid sequence having greater than about 90% homology to SEQ ID NO: 43;

h.) a heavy chain variable region FR1 comprising an amino acid sequence selected from the group consisting of the amino acid sequence of SEQ ID NO: 23, and an amino acid sequence having greater than about 90% homology to SEQ ID NO: 23;

i.) a heavy chain CDR1 comprising an amino acid sequence selected from the group consisting of SEQ ID NO: 25, an amino acid sequence having greater than about 90% homology to SEQ ID NO: 25, SEQ ID NO: 45, and an amino acid sequence having greater than about 90% homology to SEQ ID NO: 45;

j.) a heavy chain variable region FR2 comprising an amino acid sequence selected from the group consisting of the amino acid sequence of SEQ ID NO: 27, and an amino acid sequence having greater than about 90% homology to SEQ ID NO: 27;

k.) a heavy chain CDR2 comprising an amino acid sequence selected from the group consisting of the amino acid sequence of SEQ ID NO: 29, and an amino acid sequence having greater than about 90% homology to SEQ ID NO: 29;

l.) a heavy chain variable region FR3 comprising an amino acid sequence selected from the group consisting of SEQ ID NO: 31, an amino acid sequence having greater than about 90% homology to SEQ ID NO: 31, SEQ ID NO: 47, and an amino acid sequence having greater than about 90% homology to SEQ ID NO: 47;

m.) a heavy chain CDR3 comprising an amino acid sequence selected from the group consisting of SEQ ID NO: 33, an amino acid sequence having greater than about 90% homology to SEQ ID NO: 33, SEQ ID NO: 49, and an amino acid sequence having greater than about 90% homology to SEQ ID NO: 49;

n.) a heavy chain variable region FR4 comprising an amino acid sequence selected from the group consisting of SEQ ID NO: 35, an amino acid sequence having greater than about 90% homology to SEQ ID NO: 35, SEQ ID NO: 51, and an amino acid sequence having greater than about 90% homology to SEQ ID NO: 51; and o.) a linker domain comprising an amino acid sequence selected from the group consisting of the amino acid sequence of SEQ ID NO: 37, and an amino acid sequence having greater than about 90% homology to SEQ ID NO: 37.

2. The composition of embodiment 1, wherein the antibody or antibody fragment comprises a light chain comprising an amino acid sequence of SEQ ID NO: 5 and a heavy chain comprising an amino acid sequence of SEQ ID NO: 21.

3. The composition of embodiment 1, wherein the antibody or antibody fragment comprises the amino acid sequence of SEQ ID NO: 3.

4. The composition of embodiment 1, wherein the antibody or antibody fragment comprises SEQ ID NO: 39, SEQ ID NO: 45, and SEQ ID NO: 51.

5. The composition of embodiment 1, wherein the antibody or antibody fragment comprises SEQ ID NO: 41, SEQ ID NO: 43, SEQ ID NO: 45, and SEQ ID NO: 47.

6. The composition of embodiment 1, wherein the antibody or antibody fragment comprises SEQ ID NO: 45 and SEQ ID NO: 49.

7. A composition comprising an antibody or antibody fragment, wherein the antibody or antibody fragment comprises one or more of
  a.) a heavy chain signal peptide comprising an amino acid sequence selected from the group consisting of the amino acid sequence of SEQ ID NO: 55, and an amino acid sequence having greater than about 90% homology to SEQ ID NO: 55;
  b). a heavy chain variable region comprising an amino acid sequence selected from the group consisting of the amino acid sequence of SEQ ID NO: 57, and an amino acid sequence having greater than about 90% homology to SEQ ID NO: 57;
  c.) a heavy chain constant region comprising an amino acid sequence selected from the group consisting of the amino acid sequence of SEQ ID NO: 59, and an amino acid sequence having greater than about 90% homology to SEQ ID NO: 59;
  d.) a light chain signal peptide comprising an amino acid sequence selected from the group consisting of the amino acid sequence of SEQ ID NO: 63, and an amino acid sequence having greater than about 90% homology to SEQ ID NO: 63;
  e.) a light chain variable region comprising an amino acid sequence selected from the group consisting of the amino acid sequence of SEQ ID NO: 65, and an amino acid sequence having greater than about 90% homology to SEQ ID NO: 65; and
  f.) a light chain constant region comprising an amino acid sequence selected from the group consisting of the amino acid sequence of SEQ ID NO: 67, and an amino acid sequence having greater than about 90% homology to SEQ ID NO: 67.

8. The composition of embodiment 7, wherein the antibody or antibody fragment comprises a heavy chain comprising the amino acid sequence of SEQ ID NO: 68 and a light chain comprising the amino acid sequence of SEQ ID NO: 69.

9. The composition of embodiment 7, wherein the antibody or antibody fragment comprises a heavy chain comprising the amino acid sequence of SEQ ID NO: 53 and a light chain comprising the amino acid sequence of SEQ ID NO: 61.

10. The composition of any of embodiments 1-9, wherein said antibody or antibody fragment thereof is selected from the group consisting of IgG1, IgG2, IgG3, IgG4, IgM, IgA1, IgA2, IgAsec, IgD, IgE or has immunoglobulin constant and/or variable domain of IgG1, IgG2, IgG3, IgG4, IgM, IgA1, IgA2, IgAsec, IgA or IgE.

11. The composition of any of embodiments 1-9, wherein said antibody or antigen-binding fragment comprises a part or a full light chain constant region of lambda, kappa or a variant thereof.

12. The composition of any of embodiments 1-11, wherein the antibody or antibody fragment is a recombinant antibody.

13. The composition of any of embodiments 1-11, wherein the antibody or antibody fragment is a monoclonal antibody.

14. The composition of any of embodiments 1-11, wherein the antibody or antibody fragment is a polyclonal antibody.

15. The composition of any of embodiments 1-11, wherein the antibody or antibody fragment is a mixture of monoclonal and/or polyclonal antibodies.

16. The composition of any of embodiments 1-11, wherein the antibody or antibody fragment is a human antibody.

17. The composition of any of embodiments 1-11, wherein the antibody or antibody fragment is a humanized antibody.

18. The composition of any of embodiments 1-11, wherein the antibody or antibody fragment is a chimeric antibody.

19. A composition comprising an isolated nucleic acid molecule encoding an antibody or antibody fragment, wherein the isolated nucleic acid molecule comprises one or more of:
  a.) a nucleotide sequence encoding a light chain variable region FR1 comprising an amino acid sequence selected from the group consisting of the amino acid sequence of SEQ ID NO: 7, and an amino acid sequence having greater than about 90% homology to SEQ ID NO: 7;
  b.) a nucleotide sequence encoding a light chain CDR1 comprising an amino acid sequence selected from the group consisting of the amino acid sequence of SEQ ID NO: 9, and an amino acid sequence having greater than about 90% homology to SEQ ID NO: 9;
  c.) a nucleotide sequence encoding a light chain variable region FR2 comprising an amino acid sequence selected from the group consisting of SEQ ID NO: 11, an amino acid sequence having greater than about 90% homology to SEQ ID NO: 11, SEQ ID NO: 39, and an amino acid sequence having greater than about 90% homology to SEQ ID NO: 39;
  d.) a nucleotide sequence encoding a nucleotide sequence encoding a light chain CDR2 comprising an amino acid sequence selected from the group consisting of SEQ ID NO: 13, an amino acid sequence having greater than about 90% homology to SEQ ID NO: 13, SEQ ID NO: 41, and an amino acid sequence having greater than about 90% homology to SEQ ID NO: 41;
  e.) a nucleotide sequence encoding a light chain variable region FR3 comprising an amino acid sequence selected from the group consisting of the amino acid sequence of SEQ ID NO: 15, and an amino acid sequence having greater than about 90% homology to SEQ ID NO: 15;
  f.) a nucleotide sequence encoding a light chain CDR3 comprising an amino acid sequence selected from the group consisting of the amino acid sequence of SEQ ID NO: 17, and an amino acid sequence having greater than about 90% homology to SEQ ID NO: 17;
  g.) a nucleotide sequence encoding a light chain variable region FR4 comprising an amino acid sequence selected from the group consisting of SEQ ID NO: 19, an amino acid sequence having greater than about 90% homology to SEQ ID NO: 19, SEQ ID NO: 43, and an amino acid sequence having greater than about 90% homology to SEQ ID NO: 43;

h.) a nucleotide sequence encoding a heavy chain variable region FR1 comprising an amino acid sequence selected from the group consisting of the amino acid sequence of SEQ ID NO: 23, and an amino acid sequence having greater than about 90% homology to SEQ ID NO: 23;

i.) a nucleotide sequence encoding a heavy chain CDR1 comprising an amino acid sequence selected from the group consisting of SEQ ID NO: 25, an amino acid sequence having greater than about 90% homology to SEQ ID NO: 25, SEQ ID NO: 45, and an amino acid sequence having greater than about 90% homology to SEQ ID NO: 45;

j.) a nucleotide sequence encoding a heavy chain variable region FR2 comprising an amino acid sequence selected from the group consisting of the amino acid sequence of SEQ ID NO: 27, and an amino acid sequence having greater than about 90% homology to SEQ ID NO: 27;

k.) a nucleotide sequence encoding a heavy chain CDR2 comprising an amino acid sequence selected from the group consisting of the amino acid sequence of SEQ ID NO: 29, and an amino acid sequence having greater than about 90% homology to SEQ ID NO: 29;

l.) a nucleotide sequence encoding a heavy chain variable region FR3 comprising an amino acid sequence selected from the group consisting of SEQ ID NO: 31, an amino acid sequence having greater than about 90% homology to SEQ ID NO: 31, SEQ ID NO: 47, and an amino acid sequence having greater than about 90% homology to SEQ ID NO: 47;

m.) a nucleotide sequence encoding a heavy chain CDR3 comprising an amino acid sequence selected from the group consisting of SEQ ID NO: 33, an amino acid sequence having greater than about 90% homology to SEQ ID NO: 33, SEQ ID NO: 49, and an amino acid sequence having greater than about 90% homology to SEQ ID NO: 49;

n.) a nucleotide sequence encoding a heavy chain variable region FR4 comprising an amino acid sequence selected from the group consisting of SEQ ID NO: 35, an amino acid sequence having greater than about 90% homology to SEQ ID NO: 35, SEQ ID NO: 51, and an amino acid sequence having greater than about 90% homology to SEQ ID NO: 51; and o.) a nucleotide sequence encoding a linker domain comprising an amino acid sequence selected from the group consisting of the amino acid sequence of SEQ ID NO: 37, an amino acid sequence having greater than about 90% homology to SEQ ID NO: 37.

20. The composition of embodiment 19, wherein the isolated nucleic acid molecule comprises a nucleotide sequence encoding a light chain comprising an amino acid sequence of SEQ ID NO: 5 and a nucleotide sequence encoding a heavy chain comprising an amino acid sequence of SEQ ID NO: 21.

21. The composition of embodiment 19, wherein the isolated nucleic acid molecule comprises a nucleotide sequence encoding the amino acid sequence of SEQ ID NO: 3.

22. The composition of embodiment 19, wherein the isolated nucleic acid molecule comprises a nucleotide sequence encoding SEQ ID NO: 39, a nucleotide sequence encoding SEQ ID NO: 45, and a nucleotide sequence encoding SEQ ID NO: 51.

23. The composition of embodiment 19, wherein the isolated nucleic acid molecule comprises a nucleotide sequence encoding SEQ ID NO: 41, a nucleotide sequence encoding SEQ ID NO: 43, a nucleotide sequence encoding SEQ ID NO: 45, and a nucleotide sequence encoding SEQ ID NO: 47.

24. The composition of embodiment 19, wherein the isolated nucleic acid molecule comprises a nucleotide sequence encoding SEQ ID NO: 45 and a nucleotide sequence encoding SEQ ID NO: 49.

25. A composition comprising an isolated nucleic acid molecule encoding an antibody or antibody fragment, wherein the isolated nucleic acid molecule comprises one or more of:

a.) a nucleotide sequence encoding a light chain variable region FR1 selected from the group consisting of the nucleotide sequence of SEQ ID NO: 6, and a nucleotide sequence having greater than about 90% homology to SEQ ID NO: 6;

b.) a nucleotide sequence encoding a light chain CDR1 selected from the group consisting of the nucleotide sequence of SEQ ID NO: 8, and a nucleotide sequence having greater than about 90% homology to SEQ ID NO: 8;

c.) a nucleotide sequence encoding a light chain variable region FR2 selected from the group consisting of SEQ ID NO: 10, a nucleotide sequence having greater than about 90% homology to SEQ ID NO: 10, SEQ ID NO: 38, and a nucleotide sequence having greater than about 90% homology to SEQ ID NO: 38;

d.) a nucleotide sequence encoding a nucleotide sequence encoding a light chain CDR2 selected from the group consisting of SEQ ID NO: 12, a nucleotide sequence having greater than about 90% homology to SEQ ID NO: 12, SEQ ID NO: 40, and a nucleotide sequence having greater than about 90% homology to SEQ ID NO: 40;

e.) a nucleotide sequence encoding a light chain variable region FR3 selected from the group consisting of the nucleotide sequence of SEQ ID NO: 14, and a nucleotide sequence having greater than about 90% homology to SEQ ID NO: 14;

f.) a nucleotide sequence encoding a light chain CDR3 selected from the group consisting of the nucleotide sequence of SEQ ID NO: 16, and a nucleotide sequence having greater than about 90% homology to SEQ ID NO: 16;

g.) a nucleotide sequence encoding a light chain variable region FR4 selected from the group consisting of SEQ ID NO: 18, a nucleotide sequence having greater than about 90% homology to SEQ ID NO: 18, SEQ ID NO: 42, and a nucleotide sequence having greater than about 90% homology to SEQ ID NO: 42;

h.) a nucleotide sequence encoding a heavy chain variable region FR1 selected from the group consisting of the nucleotide sequence of SEQ ID NO: 22, and a nucleotide sequence having greater than about 90% homology to SEQ ID NO: 22;

i.) a nucleotide sequence encoding a heavy chain CDR1 selected from the group consisting of SEQ ID NO: 24, a nucleotide sequence having greater than about 90% homology to SEQ ID NO: 24, SEQ ID NO: 44, and a nucleotide sequence having greater than about 90% homology to SEQ ID NO: 44;

j.) a nucleotide sequence encoding a heavy chain variable region FR2 selected from the group consisting of the nucleotide sequence of SEQ ID NO: 26, and a nucleotide sequence having greater than about 90% homology to SEQ ID NO: 26;

k.) a nucleotide sequence encoding a heavy chain CDR2 selected from the group consisting of the nucleotide sequence of SEQ ID NO: 28, and a nucleotide sequence having greater than about 90% homology to SEQ ID NO: 28;

l.) a nucleotide sequence encoding a heavy chain variable region FR3 selected from the group consisting of SEQ ID NO: 30, a nucleotide sequence having greater than about 90% homology to SEQ ID NO: 30, SEQ ID NO: 46, and a nucleotide sequence having greater than about 90% homology to SEQ ID NO: 46;

m.) a nucleotide sequence encoding a heavy chain CDR3 selected from the group consisting of SEQ ID NO: 32, a nucleotide sequence having greater than about 90% homology to SEQ ID NO: 32, SEQ ID NO: 48, and a nucleotide sequence having greater than about 90% homology to SEQ ID NO: 48;

n.) a nucleotide sequence encoding a heavy chain variable region FR4 selected from the group consisting of SEQ ID NO: 34, a nucleotide sequence having greater than about 90% homology to SEQ ID NO: 34, SEQ ID NO: 50, and a nucleotide sequence having greater than about 90% homology to SEQ ID NO: 50; and o.) a nucleotide sequence encoding a linker domain selected from the group consisting of the nucleotide sequence of SEQ ID NO: 36, a nucleotide sequence having greater than about 90% homology to SEQ ID NO: 36.

26. The composition of embodiment 25, wherein the isolated nucleic acid molecule comprises the nucleotide sequence of SEQ ID NO: 4 and the nucleotide sequence of SEQ ID NO: 20.

27. The composition of embodiment 25, wherein the isolated nucleic acid molecule comprises the nucleotide sequence of SEQ ID NO: 2.

28. The composition of embodiment 25, wherein the isolated nucleic acid molecule comprises the nucleotide sequence of SEQ ID NO: 38, the nucleotide sequence of SEQ ID NO: 44, and the nucleotide sequence of SEQ ID NO: 50.

29. The composition of embodiment 25, wherein the isolated nucleic acid molecule comprises the nucleotide sequence of SEQ ID NO: 40, the nucleotide sequence of SEQ ID NO: 42, the nucleotide sequence of SEQ ID NO: 44, and the nucleotide sequence of SEQ ID NO: 46.

30. The composition of embodiment 25, wherein the isolated nucleic acid molecule comprises the nucleotide sequence of SEQ ID NO: 44 and the nucleotide sequence of SEQ ID NO: 48.

31. A composition comprising an isolated nucleic acid molecule encoding an antibody or antibody fragment, wherein the isolated nucleic acid molecule comprises one or more of a.) a nucleotide sequence encoding a heavy chain signal peptide comprising an amino acid sequence selected from the group consisting of the amino acid sequence of SEQ ID NO: 55, and an amino acid sequence having greater than about 90% homology to SEQ ID NO: 55;

b). a nucleotide sequence encoding a heavy chain variable region comprising an amino acid sequence selected from the group consisting of the amino acid sequence of SEQ ID NO: 57, and an amino acid sequence having greater than about 90% homology to SEQ ID NO: 57;

c.) a nucleotide sequence encoding a heavy chain constant region comprising an amino acid sequence selected from the group consisting of the amino acid sequence of SEQ ID NO: 59, and an amino acid sequence having greater than about 90% homology to SEQ ID NO: 59;

d.) a nucleotide sequence encoding a light chain signal peptide comprising an amino acid sequence selected from the group consisting of the amino acid sequence of SEQ ID NO: 63, and an amino acid sequence having greater than about 90% homology to SEQ ID NO: 63;

e.) a nucleotide sequence encoding a light chain variable region comprising an amino acid sequence selected from the group consisting of the amino acid sequence of SEQ ID NO: 65, and an amino acid sequence having greater than about 90% homology to SEQ ID NO: 65; and f.) a nucleotide sequence encoding a light chain constant region comprising an amino acid sequence selected from the group consisting of the amino acid sequence of SEQ ID NO: 67, and an amino acid sequence having greater than about 90% homology to SEQ ID NO: 67.

32. The composition of embodiment 31, wherein the isolated nucleic acid molecule comprises a nucleotide sequence encoding a heavy chain comprising the amino acid sequence of SEQ ID NO: 68 and a nucleotide sequence encoding a light chain comprising the amino acid sequence of SEQ ID NO: 69.

33. The composition of embodiment 31, wherein the isolated nucleic acid molecule comprises a nucleotide sequence encoding a heavy chain comprising the amino acid sequence of SEQ ID NO: 53 and a nucleotide sequence encoding a light chain comprising the amino acid sequence of SEQ ID NO: 61.

34. A composition comprising an isolated nucleic acid molecule encoding an antibody or antibody fragment, wherein the isolated nucleic acid molecule comprises one or more of a.) a nucleotide sequence encoding a heavy chain signal peptide selected from the group consisting of the nucleotide sequence of SEQ ID NO: 54, and a nucleotide sequence having greater than about 90% homology to SEQ ID NO: 54;

b). a nucleotide sequence encoding a heavy chain variable region selected from the group consisting of the nucleotide sequence of SEQ ID NO: 56, and a nucleotide sequence having greater than about 90% homology to SEQ ID NO: 56;

c.) a nucleotide sequence encoding a heavy chain constant region selected from the group consisting of the nucleotide sequence of SEQ ID NO: 58, and a nucleotide sequence having greater than about 90% homology to SEQ ID NO: 58;

d.) a nucleotide sequence encoding a light chain signal peptide selected from the group consisting of the nucleotide sequence of SEQ ID NO: 62, and a nucleotide sequence having greater than about 90% homology to SEQ ID NO: 62;

e.) a nucleotide sequence encoding a light chain variable region selected from the group consisting of the nucleotide sequence of SEQ ID NO: 64, and a nucleotide sequence having greater than about 90% homology to SEQ ID NO: 64; and f.) a nucleotide sequence encoding a light chain constant region selected from the group consisting of the nucleotide sequence of SEQ ID NO: 66, and a nucleotide sequence having greater than about 90% homology to SEQ ID NO: 66.

35. The composition of embodiment 34, wherein the isolated nucleic acid molecule comprises the nucleotide sequence of SEQ ID NO: 52 and the nucleotide sequence of SEQ ID NO: 60.

36. The composition of any of embodiments 19-35, wherein the composition is a vector comprising the isolated nucleic acid molecule.

37. The composition of embodiment 36, wherein the vector is selected from the group consisting of a DNA, a RNA, a plasmid, a lentivirus vector, adenoviral vector, or a retrovirus vector.

38. The composition of any of embodiments 1-18, wherein the composition is a cell comprising the antibody or antibody fragment.

39. The composition of any of embodiments 19-35, wherein the composition is a cell comprising the isolated nucleic acid molecule.

40. The composition of any of embodiments 38-39, wherein the cell is a phage, an *E. coli*, a yeast cell, an insect cells or a mammalian cell such as CHO, HEK293, or PER.C6.

41. The composition of any of embodiments 38-40, wherein the cell is an in vitro or in vivo expression system, such as an engineered animal for protein expression.

42. A method of treating a subject having a disease associated with expression of PSMA comprising administering to the subject an effective amount of the composition of any of embodiments 1-41.

43. The composition of any of embodiments 1-18, wherein the composition is an antibody drug conjugate comprising the antibody or antibody fragment operably linked, covalently or non-covalently, to a biologically active agent, wherein said agent is a toxin, a radioisotope, a nanoparticle, an enzyme, a bio-active peptide or nucleotide.

44. The composition of embodiment 43, wherein the antibody drug conjugate has the following formula:

Ab-(LU-D)p or a pharmaceutically acceptable salt or solvate thereof, wherein:
Ab is the antibody or antibody fragment, and
(LU-D) is a Linker unit-Drug unit moiety, wherein:
LU- is a Linker unit, and
-D is a drug unit representing toxin, radioisotope, nanoparticle, enzyme, bio-active peptide or nucleotide; and
p is an integer from 1 to 20.

45. The composition of embodiment 43, wherein antibody drug conjugate has the following formula:

or a pharmaceutically acceptable salt or solvate thereof, wherein:
Ab is the Antibody or antibody fragment; and
-$A_a$-$W_w$—$Y_y$- is a Linker unit (LU), wherein:
-A- is a Stretcher unit,
a is 0 or 1,
each —W— is independently an Amino Acid unit,
w is an integer ranging from 0 to 12,
—Y— is a self-immolative spacer unit,
y is 0, 1 or 2;
-D is a drug units representing toxin, radioisotope, nanoparticle, enzyme, bio-active peptide or nucleotide; and
p is an integer from 1 to 20.

46. The composition of embodiment 43, wherein the toxin, radioisotope, nanoparticle, bio-active peptide or nucleotide is labeled to the antibody or antibody fragment indirectly via a carrier, which has the following formulas,

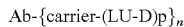

Or

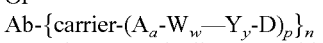

or a pharmaceutically acceptable salt or solvate thereof, wherein:
Ab is the Antibody or antibody fragment; and
(LU-D) is a Linker unit-Drug unit moiety, wherein:
LU- is a Linker unit, and
-$A_a$-$W_w$—$Y_y$— is a Linker unit (LU), wherein:
-A- is a Stretcher unit,
a is 0 or 1,
each —W— is independently an Amino Acid unit,
w is an integer ranging from 0 to 12,
—Y— is a self-immolative spacer unit,
y is 0, 1 or 2;
-D is a drug unit representing toxin, radioisotope, nanoparticle, enzyme, bio-active peptide or nucleotide; and
p is an integer from 1 to 20,
Carrier is a polymer, a PEG, a peptide, a sugar, a compound or a nucleotide that is used to load drug unit(s) for indirect antibody conjugation with drug units; and
N is an integer from 1 to 20.

47. The composition of any of embodiments 43-46, wherein the linker(s) is(are) cleavable, or non-cleavable, stable or acid-liable 48. The composition of any of embodiments 43-46, wherein the linker(s) is(are) peptide(s), polymer(s), PEG, sugar(s), compound(s), nucleotide(s)

49. The composition of any of embodiments 43-46, wherein the linker is SMCC, MC, MP, val-cit (VC), ala-phe, PAB, SPP, SPDB, SIAB, MC-vc, MC-vc-PAB, hydrazone or maleimidocaproyl 50. The composition of any of embodiments 43-46, wherein the said toxin is maytansinoids, auristatins, calicheamicins, dolastatins, doxorubicin or a combination thereof, such as DM1, DM4, MMAE, MMAF, dolastatin 10, dolastatin 15, calicheamicin, or doxorubicin.

51. The composition of any of embodiments 43-46, wherein the said toxin is a partial, a unit or a full toxin of saporin, diphtheria toxin, diphtheria toxin A, *Pseudomonas* exotoxin, *Pseudomonas* exotoxin PE38, caspase-3, caspase-9, granzyme B, Lymphotoxin, perforin, apoptosis inducing factor, DNAse, DNAse A, cytochrome C, botulinum, angiogenin, colicin, ricin A, or a combination thereof.

52. The composition of any of embodiments 43-46, wherein the said radioisotope emits α, β, γ or positron radiations 53. The composition of any of embodiments 43-46, wherein the said radioisotope is selected from the group consisting of Molybdenum-99, Technetium-99m, Bismuth-213, Chromium-51, Cobalt-60, Copper-64, Dysprosium-165, Erbium-169, Holmium-166, Iodine-125, Iridium-192, Iron-59, Lutetium-177, Palladium-103, Phosphorus-32, Potassium-42, Rhenium-186, Rhenium-188, Samarium-153, Selenium-75, Sodium-24 (15 h), Strontium-89, Xenon-133, Ytterbium-169, Yttrium-90, Carbon-11, Nitrogen-13, Oxygen-15, Cobalt-57, Gallium-67, Indium-111, Iodine-123, Iodine-131, Krypton-81m, Rubidium-82, Strontium-92, Thallium-201, Rhodium-86, Rhodium-188, Copper-67, Bromine-77, Lead-212, Radium-224, Radium-223Ra, Bromine-76, Iodine-124, Yttrium-86, Technetium-94m, Gallium-68, Gallium-66, Copper-60, Zirconium-89, Carbon-11, Nitrogen13, Oxgen-15, Fluorine-18, Rubidium-82

54. The composition of any of embodiments 43-46, wherein the said nanoparticle is a diagnostic, therapeutic or theranostic, containing imaging probe, imaging contrast, gene, drug, pre-drug or a combination thereof.

55. The composition of any of embodiments 43-46, wherein the said bio-active peptide is one or a combination of several cytokines, such as alpha interferons, beta interferons, gamma interferons, Interleukin-1, Interleukin-2, Interleukin-3, Interleukin-4, Interleukin-5, Interleukin-6, Interleukin-7, Interleukin-8, Interleukin-10, Interleukin-12, Interleukin-15, Interleukin-18, Interleukin-21, Interleukin-23, Gamma TNF, beta TGF, GM-CSF, G-CSF.

56. A composition of any of embodiments 1-18, wherein the composition comprises a multiple specific antibody that binds two or more different epitopes on the same or different antigens, wherein one of the epitopes is on human prostate specific membrane antigen (PSMA).

57. The composition of embodiment 56, wherein the multiple specific antibody is a bispecific antibody.

58. The composition of embodiment 57, wherein the bispecific antibody comprises
(a) a polypeptide chain comprising an amino acid sequence having the following formula: V1-L1-V2-L2-V3-L3-V4-L4-Fc; wherein Fc is a human IgG Fc polypeptide chain; wherein two of VI, V2, V3, and V4 are immunoglobulin heavy chain variable (VH) regions and the other two are immunoglobulin light chain variable (VL) regions; wherein LI, L2, L3, and L4 are linkers; and wherein L2 can be present or absent; and L4 is a IgG1 hinge with mutation at C220;
(b) a polypeptide chain comprising an amino acid sequence having the following formula: Fc-L4-V1-L1-V2-L2-V3-L3-V4; wherein Fc is a human IgG Fc polypeptide chain; wherein the disulfide bonds of Fc can be at the N or C terminus of Fc; wherein two of VI, V2, V3, and V4 are VH regions and the other two are VL regions; wherein LI, L2, L3, and L4 are linkers; and wherein L2 can be present or absent; and L4 is a IgG1 hinge with mutation at C220;
(c) a polypeptide chain comprising an amino acid sequence having the following formula: targeting moiety-L4-Fc; wherein Fc is a human IgG Fc polypeptide chain; wherein L4 is a IgG1 hinge with mutation at C220; or
(d) a polypeptide chain comprising an amino acid sequence having the following formula: Fc-L4-targeting moiety; wherein Fc is a human IgG Fc polypeptide chain; wherein L4 is a IgG1 hinge with mutation at C220
wherein the bispecific antibody binds to a target cell and an immune effector cell and/or mediates cytolysis of a target cell by an immune effector cell, and
wherein the bispecific antibody is a dimer.

59. The composition of embodiment 58, wherein the Fc polypeptide chain of (a) or (b) is an IgG1, IgG2, IgG3 or IgG4 Fc polypeptide chain.

60. The composition of embodiment 58, wherein the Fc polypeptide chain of (a) or (b) is an IgG1, IgG2, IgG3 or IgG4 Fc polypeptide chain with one or more of the following mutations: L234A, L235A, N297A.

61. The composition of embodiment 58, wherein the Fc polypeptide chain of (a) or (b) is an IgG4 Fc with one or more of the following mutations: L234A, L235A, N297A.

62. The composition of embodiment 58, wherein the L4 is a IgG1 hinge with mutation at C220, such as C220A, C220G, C220S.

63. The composition of any of embodiment 58-62, wherein the bispecific antibody comprising a first antigen-binding region and a second antigen-binding region, which second antigen-binding region binds an epitope on human CD3 and the first antigen-binding region comprises the antibody or antigen fragment and binds an epitope on human prostate specific membrane antigen (PSMA).

64. The composition of any of embodiments 58-62, wherein the bispecific antibody is bivalent, trivalent, or tetravalent.

66. The composition of any of embodiments 58-62, wherein the bispecific antibody is selected from the group consisting of a tandem scFv (taFv or scFv2), diabody, dAb2A/HH2, knob-into-holes derivates, SEED-IgG, heteroFc-scFv, Fab-scFv, scFv-Jun/Fos, Fab'-Jun/Fos, tribody, DNL-F(ab)3, scFv3-CH1/CL, Fab-scFv2, IgG-scFab, IgG-scFv, scFv-IgG, scFv2-Fc, F(ab')$_2$-scFv2, scDB-Fc, scDb-CH3, Db-Fc, scFv2-H/L, DVD-lg, tandAb, scFv-dhlx-scFv, dAb2-IgG, dAb-IgG, dAb-Fc-dAb, and combinations thereof.

67. The composition of any of embodiments 58-62, wherein the bispecific antibody is a diabody or a tribody.

68. The composition of any of embodiments 58-67, wherein the bispecific antibody comprises a first antigen-binding region and a second antigen-binding region, which second antigen-binding region binds an epitope on human CD3 and the first antigen-binding region binds an epitope on human prostate specific membrane antigen (PSMA), wherein the second antigen-binding region selected from the group consisting of:
a) an antibody comprising a variable heavy region (VH) comprising the amino acid sequence of SEQ ID NO: 85 and a VL region comprising the sequence of SEQ ID NO: 87, and
b) an antibody comprising a variable heavy region(VH) comprising the sequence of SEQ ID NO: 91 and a variable light (VL) region comprising the sequence of SEQ ID NO: 93.

69. The composition of embodiment 68, wherein the antibody or antigen binding region for second antigen-binding region (human CD3) is selected from the group consisting of:
a) an antibody or antigen-binding region comprising an amino acid sequence of SEQ ID NO: 83, and
b) an antibody or antigen-binding region comprising an amino acid sequence of SEQ ID NO: 89.

70. The composition of embodiment 68, wherein the bispecific antibody comprising a signal peptide-scFv1-MCS-scFv2-IgG1 hinge-IgG4 Fc expression cassette encoding amino acid sequence of SEQ ID NO: 101; or an amino acid sequence of SEQ ID NO: 103.

71. The composition of embodiment 68, wherein the bispecific antibody comprising a signal peptide-scFV1-MCS-scFv2-IgG1 hinge-IgG4 Fc expression cassette comprising a nucleic acid sequence of SEQ ID NO: 100; or a nucleic acid sequence of SEQ ID NO: 102.

72. The composition of any of embodiment 56-71, wherein the bispecific antibody comprises an amino acid sequence selected from the group of a) the amino acid sequence of SEQ ID NO: 105; b) the amino acid sequence of SEQ ID NO: 106; c) the amino acid sequence of SEQ ID NO: 108; d) the amino acid sequence of SEQ ID NO: 109.

73. The composition of any of embodiment 56-71, wherein the bispecific antibody is encoded by a nucleotide sequence selected from the group of a) a nucleic acid sequence of SEQ ID NO: 104; b) a nucleic acid sequence of SEQ ID NO: 107.

74. A composition comprising a vector comprising a nucleotide sequence encoding a bispecific antibody recited in any of embodiments 56-73.

75. The composition of embodiment 74, wherein the vector is selected from the group consisting of a DNA, a RNA, a plasmid, a lentivirus vector, adenoviral vector, or a retrovirus vector.

76. The composition of any of embodiment 74, wherein the composition is a cell comprising the vector.

77. The composition of embodiment 76, wherein the cell is a phage, an *E. coli*, a yeast cell, an insect cells or a mammalian cell such as CHO, HEK293, PER.C6, or any cell derived from a human.

78. The composition of any of embodiments 76-77, wherein the cell is an in vitro or in vivo expression system, such as an engineered animal for protein expression.

79. A composition of any of embodiments 1-18, wherein the composition comprises an isolated chimeric antigen receptor (CAR), wherein the CAR comprises the antibody or antibody fragment, a transmembrane domain, and an intracellular signaling domain comprising one or more stimulatory domains.

80. The composition of embodiment 79, wherein the CAR comprises transmembrane domain that comprises a transmembrane domain of a protein selected from the group consisting of the alpha, beta or zeta chain of the T-cell receptor, CD28, CD3 epsilon, CD45, CD4, CDS, CD8, CD9, CD16, CD22, CD33, CD37, CD64, CD80, CD86, CD134, CD137 and CD154.

81. The composition of embodiment 80, wherein transmembrane domain comprises an amino acid sequence selected from the group consisting of SEQ ID NO: 75 and an amino acid sequence having greater than about 90% homology to SEQ ID NO: 75.

82. The composition of embodiment 79, wherein the antibody or antibody fragment is connected to the transmembrane domain by a hinge region.

83. The composition of embodiment 82, wherein the hinge region comprises an amino acid sequence selected from the group comprising SEQ ID NO:73, and an amino acid sequence having greater than about 90% homology to SEQ ID NO: 73.

84. The composition of embodiment 79, further comprising one or more costimulatory domains.

85. The composition of embodiment 84, wherein the one or more costimulatory domains are a functional signaling domain obtained from one or more proteins selected from the group consisting of OX40, CD2, CD27, CD28, CDS, ICAM-1, LFA-1 (CD11a/CD18), ICOS (CD278), and 4-1BB (CD137).

86. The composition of embodiment 84 or 85, wherein the costimulatory domain comprises an amino acid sequence selected from the group consisting of SEQ ID NO: 77, and an amino acid sequence having greater than about 90% homology to SEQ ID NO: 77.

87. The composition of embodiment 79, wherein intracellular signaling domain comprises a functional signaling domain of 4-1BB and/or a functional signaling domain of CD3 zeta.

88. The composition of embodiment 87, wherein the intracellular signaling domain comprises an amino acid sequence selected from the group consisting of SEQ ID NO: 77, an amino acid sequence having greater than about 90% homology to SEQ ID NO: 77, SEQ ID NO: 79, and an amino acid sequence having greater than about 90% homology to SEQ ID NO: 79.

89. The composition of embodiment 79, further comprising a leader sequence.

90. The composition of embodiment 89, wherein the leader sequence comprises SEQ ID NO: 71.

91. The composition of embodiment 79, wherein the CAR comprises an amino acid sequence selected from the group consisting of SEQ ID NO: 81 and an amino acid sequence having greater than about 90% homology to SEQ ID NO: 81.

92. A composition of any of embodiments 19-35, wherein the composition comprising an isolated nucleic acid molecule encoding a CAR wherein the CAR comprises the antibody or antibody fragment, a transmembrane domain, and an intracellular signaling domain comprising one or more stimulatory domains.

93. The composition of embodiment 92, wherein the composition is a vector comprising a nucleic acid molecule encoding the CAR.

94. The composition of embodiment 93, wherein the vector is selected from the group consisting of a DNA, a RNA, a plasmid, a lentivirus vector, adenoviral vector, or a retrovirus vector.

95. The composition of embodiment 93, wherein the vector further comprises a promoter.

96. The composition of embodiment 95, wherein the promoter is an EF-1 promoter.

97. The composition of embodiment 96, wherein the EF-1 promoter comprises a sequence of SEQ ID NO: 110.

98. The composition of embodiment 92, wherein the composition comprises a cell comprising an isolated nucleic acid molecule encoding a CAR wherein the CAR comprises the antibody or antibody fragment, a transmembrane domain, and an intracellular signaling domain comprising one or more stimulatory domains.

99. The composition of embodiment 98, wherein the cell is a human T cell.

100. The composition of embodiment 99, wherein the T cell is a CD8+ T cell.

101. A method of making a cell comprising transducing a T cell with a composition of any of embodiments 93-97.

102. A method of treating a subject having a disease associated with expression of PSMA comprising administering to the subject an effective amount of a composition of any of embodiments 79-100.

103. The method of embodiment 102, wherein the composition is an autologous T cell.

104. The method of embodiment 102, wherein the composition is an allogeneic T cell.

105. A method of treating a subject having a disease associated with expression of PSMA comprising administering to the subject an effective amount of a composition of any of embodiments 43-55.

106. A method of treating a subject having a disease associated with expression of PSMA comprising administering to the subject an effective amount of a composition of any of embodiments 56-78

107. A method of diagnosing the presence of a disease associated with the expression of PSMA in a mammal, said method comprising sampling a tissue sample isolated from said mammal with a composition comprising the composition of any of embodiments 1-18, whereby specific binding of the antibody or antibody fragment to said tissue sample is indicative of the presence of a disease associated with the expression of PSMA in said mammal.

108. The composition of any of embodiments 1-41, further comprising a pharmaceutically acceptable carrier, excipient, stabilizer, diluent, adjuvants, cytokines, chemokines, chemotherapy drug, other therapeutic drug or a combination thereof.

109. The composition of any of embodiments 43-55 further comprising a pharmaceutically acceptable carrier, excipient, stabilizer, diluent, adjuvants, cytokines, chemokines, chemotherapy drug, other therapeutic drug or a combination thereof.

110. The composition of any of embodiments 56-78 further comprising pharmaceutically acceptable carrier, excipient, stabilizer, diluent, adjuvants, cytokines, chemokines, chemotherapy drug, other therapeutic drug or a combination thereof.

111. The composition of any of embodiments 79-100 further comprising a pharmaceutically acceptable carrier, excipient, stabilizer, diluent, adjuvants, cytokines, chemokines, chemotherapy drug, other therapeutic drug or a combination thereof.

112. A method of imaging a disease associated with the expression of PSMA in a subject, said method comprising the step of applying the composition of any of embodiments 1-18, wherein the antibody or antibody fragment is operably linked to a reagent.

113. The method of embodiment 112, wherein said reagent is a photoactivatable agent, a fluorophore, a radioisotope, a bioluminescent protein, a bioluminescent peptide, a fluorescent tag, a fluorescent protein, a fluorescent peptide, a imaging contrast, an enzyme, a nuclear magnetic resonance active reagent, or a nanoparticle.

114. The method any of embodiments of 42, 102, 105-107, and 112, wherein the disease associated with PSMA expression is selected from a proliferative disease such as a cancer or malignancy or a precancerous condition such as a prostate cancer, or other solid tumors with PSMA high expression on tumor cells or neovasculature, or is a non-cancer related indication associated with expression of PSMA, wherein the solid tumors include malignant epithelial tumors, lymphoma, blastoma, sarcoma (including liposarcoma), neuroendocrine tumors, mesothelioma, schwannoma, meningioma, malignant adenoma, melanoma, and leukemia or malignant lymphoproliferative disorders, in particular for example, sarcoma, ovarian cancer, breast cancer, glioblastoma, gastric cancer, colon cancer, colorectal cancer, lung cancer, liver cancer, thyroid cancer, lymphoma, nasopharyngeal cancer, maxillary sinus cancer, kidney cancer, prostate cancer, bladder cancer, pancreatic cancer, gallbladder cancer, bile duct cancer.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An antibody or antigen-binding fragment thereof that specifically binds to prostate specific membrane antigen (PSMA), the antibody or antigen-binding fragment comprising:
   (i) a light chain region that comprises SEQ ID NO: 9 (LCDR1), SEQ ID NO: 13 or 41 (LCDR2) and SEQ ID NO: 17 (LCDR3) and
   (ii) a heavy chain region that comprises SEQ ID NO: 25 or 45 (HCDR1), SEQ ID NO: 29 (HCDR2), and SEQ ID NO: 33 or 49 (HCDR3).

2. The antibody or antigen-binding fragment of claim 1, wherein the light chain region comprises one of SEQ ID NOs: 5, 7, 11, 15, 19, 39, 43, 61, 63, 65, 67, and 69.

3. The antibody or antigen-binding fragment of claim 1, wherein the heavy chain region comprises one of SEQ ID NOs: 21, 23, 27, 31, 35, 47, 51, 53, 55, 57, 59, and 68.

4. The antibody or antigen-binding fragment of claim 3, wherein the antibody or antigen-binding fragment comprises
   (i) a heavy chain comprising the amino acid sequence of SEQ ID NO: 68 and a light chain comprising the amino acid sequence of SEQ ID NO: 69, or
   (ii) a heavy chain comprising the amino acid sequence of SEQ ID NO: 53 and a light chain comprising the amino acid sequence of SEQ ID NO: 61.

5. The antibody or antibody antigen-binding fragment or variant of claim 1, wherein said antibody or antibody antigen-binding fragment thereof is selected from the group consisting of IgG1, IgG2, IgG3, IgG4, IgM, IgA1, IgA2, IgAsec, IgD, IgE or has immunoglobulin constant and/or variable domain of IgG1, IgG2, IgG3, IgG4, IgM, IgA1, IgA2, IgAsec, IgA or IgE.

6. The antibody or antigen-binding fragment of claim 1, wherein said antibody or antigen-binding fragment comprises a part or a full light chain constant region of lambda, kappa or a variant thereof.

7. The antibody or antigen-binding fragment of claim 1, wherein the antibody or antigen-binding fragment is a recombinant antibody, a monoclonal antibody, a human antibody, a humanized antibody, or a chimeric antibody.

8. A multiple specific antibody that binds two or more different epitopes on the same or different antigens, wherein one of the epitopes is on human prostate specific membrane antigen (PSMA) and the multiple specific antibody comprises the light chain region and the heavy chain region of the antibody or antigen-binding fragment of claim 1.

9. An isolated chimeric antigen receptor (CAR), wherein the CAR comprises the antibody or antigen-binding fragment of claim 1, a transmembrane domain, and an intracellular signaling domain comprising one or more stimulatory domains.

10. An isolated nucleic acid molecule encoding the antibody or antigen-binding fragment of claim 1.

11. A vector comprising the nucleic acid molecule of claim 10.

12. A cultured host cell comprising the vector of claim 11.

13. A composition comprising the antibody or antigen-binding fragment of claim 1.

14. The composition of claim 13, which is a pharmaceutical composition further comprising a pharmaceutically acceptable carrier.

15. A method of diagnosing the presence of a disease associated with the expression of PSMA in a mammal, said method comprising sampling a tissue sample isolated from said mammal with a composition comprising the composition of claim 13, whereby specific binding of the antibody or antigen-binding fragment to said tissue sample is indicative of the presence of a disease associated with the expression of PSMA in said mammal.

16. A method of imaging a disease associated with the expression of PSMA in a subject, said method comprising the step of applying the composition of claim 13, wherein the antibody or antibody fragment is operably linked to a reagent.

17. The antibody or antigen-binding fragment of claim 1, wherein the antibody or antigen-binding fragment comprises one or more of SEQ ID NOs: 3 and 37.

18. A composition comprising the CAR of claim 9.

19. The composition of claim 18, which is a pharmaceutical composition further comprising a pharmaceutically acceptable carrier.

* * * * *

SEQUENCE LISTING

```
<160> NUMBER OF SEQ ID NOS: 116

<210> SEQ ID NO 1
<211> LENGTH: 707
<212> TYPE: PRT
<213> ORGANISM: Homo sapiens

<400> SEQUENCE: 1

Lys Ser Ser Asn Glu Ala Thr Asn Ile Thr Pro Lys His Asn Met Lys
1               5                   10                  15

Ala Phe Leu Asp Glu Leu Lys Ala Glu Asn Ile Lys Lys Phe Leu Tyr
            20                  25                  30

Asn Phe Thr Gln Ile Pro His Leu Ala Gly Thr Glu Gln Asn Phe Gln
        35                  40                  45

Leu Ala Lys Gln Ile Gln Ser Gln Trp Lys Glu Phe Gly Leu Asp Ser
    50                  55                  60

Val Glu Leu Ala His Tyr Asp Val Leu Leu Ser Tyr Pro Asn Lys Thr
65                  70                  75                  80

His Pro Asn Tyr Ile Ser Ile Ile Asn Glu Asp Gly Asn Glu Ile Phe
                85                  90                  95

Asn Thr Ser Leu Phe Glu Pro Pro Pro Gly Tyr Glu Asn Val Ser
            100                 105                 110

Asp Ile Val Pro Pro Phe Ser Ala Phe Ser Pro Gln Gly Met Pro Glu
        115                 120                 125

Gly Asp Leu Val Tyr Val Asn Tyr Ala Arg Thr Glu Asp Phe Phe Lys
    130                 135                 140

Leu Glu Arg Asp Met Lys Ile Asn Cys Ser Gly Lys Ile Val Ile Ala
145                 150                 155                 160

Arg Tyr Gly Lys Val Phe Arg Gly Asn Lys Val Lys Asn Ala Gln Leu
                165                 170                 175

Ala Gly Ala Lys Gly Val Ile Leu Tyr Ser Asp Pro Ala Asp Tyr Phe
            180                 185                 190
```

```
Ala Pro Gly Val Lys Ser Tyr Pro Asp Gly Trp Asn Leu Pro Gly Gly
            195                 200                 205
Gly Val Gln Arg Gly Asn Ile Leu Asn Leu Asn Gly Ala Gly Asp Pro
        210                 215                 220
Leu Thr Pro Gly Tyr Pro Ala Asn Glu Tyr Ala Tyr Arg Arg Gly Ile
225                 230                 235                 240
Ala Glu Ala Val Gly Leu Pro Ser Ile Pro Val His Pro Ile Gly Tyr
                245                 250                 255
Tyr Asp Ala Gln Lys Leu Leu Glu Lys Met Gly Gly Ser Ala Pro Pro
            260                 265                 270
Asp Ser Ser Trp Arg Gly Ser Leu Lys Val Pro Tyr Asn Val Gly Pro
        275                 280                 285
Gly Phe Thr Gly Asn Phe Ser Thr Gln Lys Val Lys Met His Ile His
        290                 295                 300
Ser Thr Asn Glu Val Thr Arg Ile Tyr Asn Val Ile Gly Thr Leu Arg
305                 310                 315                 320
Gly Ala Val Glu Pro Asp Arg Tyr Val Ile Leu Gly His Arg Asp
                325                 330                 335
Ser Trp Val Phe Gly Gly Ile Asp Pro Gln Ser Gly Ala Ala Val Val
            340                 345                 350
His Glu Ile Val Arg Ser Phe Gly Thr Leu Lys Lys Glu Gly Trp Arg
            355                 360                 365
Pro Arg Arg Thr Ile Leu Phe Ala Ser Trp Asp Ala Glu Glu Phe Gly
        370                 375                 380
Leu Leu Gly Ser Thr Glu Trp Ala Glu Glu Asn Ser Arg Leu Leu Gln
385                 390                 395                 400
Glu Arg Gly Val Ala Tyr Ile Asn Ala Asp Ser Ser Ile Glu Gly Asn
                405                 410                 415
Tyr Thr Leu Arg Val Asp Cys Thr Pro Leu Met Tyr Ser Leu Val His
            420                 425                 430
Asn Leu Thr Lys Glu Leu Lys Ser Pro Asp Glu Gly Phe Glu Gly Lys
            435                 440                 445
Ser Leu Tyr Glu Ser Trp Thr Lys Lys Ser Pro Ser Pro Glu Phe Ser
        450                 455                 460
Gly Met Pro Arg Ile Ser Lys Leu Gly Ser Gly Asn Asp Phe Glu Val
465                 470                 475                 480
Phe Phe Gln Arg Leu Gly Ile Ala Ser Gly Arg Ala Arg Tyr Thr Lys
                485                 490                 495
Asn Trp Glu Thr Asn Lys Phe Ser Gly Tyr Pro Leu Tyr His Ser Val
            500                 505                 510
Tyr Glu Thr Tyr Glu Leu Val Glu Lys Phe Tyr Asp Pro Met Phe Lys
        515                 520                 525
Tyr His Leu Thr Val Ala Gln Val Arg Gly Gly Met Val Phe Glu Leu
        530                 535                 540
Ala Asn Ser Ile Val Leu Pro Phe Asp Cys Arg Asp Tyr Ala Val Val
545                 550                 555                 560
Leu Arg Lys Tyr Ala Asp Lys Ile Tyr Ser Ile Ser Met Lys His Pro
                565                 570                 575
Gln Glu Met Lys Thr Tyr Ser Val Ser Phe Asp Ser Leu Phe Ser Ala
            580                 585                 590
Val Lys Asn Phe Thr Glu Ile Ala Ser Lys Phe Ser Glu Arg Leu Gln
        595                 600                 605
Asp Phe Asp Lys Ser Asn Pro Ile Val Leu Arg Met Met Asn Asp Gln
```

```
                610             615              620
Leu Met Phe Leu Glu Arg Ala Phe Ile Asp Pro Leu Gly Leu Pro Asp
625                 630                 635                 640

Arg Pro Phe Tyr Arg His Val Ile Tyr Ala Pro Ser Ser His Asn Lys
                645                 650                 655

Tyr Ala Gly Glu Ser Phe Pro Gly Ile Tyr Asp Ala Leu Phe Asp Ile
            660                 665                 670

Glu Ser Lys Val Asp Pro Ser Lys Ala Trp Gly Glu Val Lys Arg Gln
        675                 680                 685

Ile Tyr Val Ala Ala Phe Thr Val Gln Ala Ala Glu Thr Leu Ser
    690                 695                 700

Glu Val Ala
705

<210> SEQ ID NO 2
<211> LENGTH: 756
<212> TYPE: DNA
<213> ORGANISM: Artificial Sequence
<220> FEATURE:
<223> OTHER INFORMATION: scFv

<400> SEQUENCE: 2
cagtctgtgc tgactcagcc gccctcagtg tctggggccc cagggcagag tgtcattatc      60
tcctgcactg ggagcagctc caacatcggg gcaggttctc atgtacactg gtaccagcag     120
gttccaggaa cagcccccaa actcctcatc tatggaaaca ccaatcggcc ctcaggggtc     180
cctgaccgat tctctggctc caagtctggc acctcaggtt ccctggccat cactggactc     240
cagcctgagg atgaggctga ttattattgt gcaacatggg atgacagtct gaatggtgta     300
atattcggcg gagggaccaa ggtcaccgtc ctaggcggat cctctaggtc aagttccagc     360
ggcggcggtg gcagcggagg cggcggtgag gtgcagctgg tggagtctgg gggagccctg     420
gccaagcctg gggggtccct gagactctcc tgtgcagcct ctggatccac cctcagtggc     480
tatgctatgc actgggtccg ccaggctcca ggcaaggggc tggagtgggt ggcagttata     540
tcatatgatg gaagcaataa atactacgca gactccgtga agggccgatt caccatctcc     600
agagacaatt ccaagaacac gctgtttctg caaatgaaca gcctgagacc tgaggacacg     660
gctgtgtact attgtgctaa aggccttact tggggactcg gtgacaatga tgctctcgat     720
atctggggcc ccgggaccac ggtcaccgtc tcctca                                756

<210> SEQ ID NO 3
<211> LENGTH: 252
<212> TYPE: PRT
<213> ORGANISM: Artificial Sequence
<220> FEATURE:
<223> OTHER INFORMATION: scFv

<400> SEQUENCE: 3

Gln Ser Val Leu Thr Gln Pro Pro Ser Val Ser Gly Ala Pro Gly Gln
1               5                   10                  15

Ser Val Ile Ile Ser Cys Thr Gly Ser Ser Asn Ile Gly Ala Gly
            20                  25                  30

Ser His Val His Trp Tyr Gln Gln Val Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Gly Ser Leu Ala Ile Thr Gly Leu
```

```
                65                  70                  75                  80
Gln Pro Glu Asp Glu Ala Asp Tyr Tyr Cys Ala Thr Trp Asp Ser
                    85                  90                  95
Leu Asn Gly Val Ile Phe Gly Gly Gly Thr Lys Val Thr Val Leu Gly
                100                 105                 110
Gly Ser Ser Arg Ser Ser Ser Gly Gly Gly Ser Gly Gly Gly
            115                 120                 125
Gly Glu Val Gln Leu Val Glu Ser Gly Gly Ala Leu Ala Lys Pro Gly
        130                 135                 140
Gly Ser Leu Arg Leu Ser Cys Ala Ala Ser Gly Ser Thr Leu Ser Gly
145                 150                 155                 160
Tyr Ala Met His Trp Val Arg Gln Ala Pro Gly Lys Gly Leu Glu Trp
                165                 170                 175
Val Ala Val Ile Ser Tyr Asp Gly Ser Asn Lys Tyr Tyr Ala Asp Ser
                180                 185                 190
Val Lys Gly Arg Phe Thr Ile Ser Arg Asp Asn Ser Lys Asn Thr Leu
            195                 200                 205
Phe Leu Gln Met Asn Ser Leu Arg Pro Glu Asp Thr Ala Val Tyr Tyr
        210                 215                 220
Cys Ala Lys Gly Leu Thr Trp Gly Leu Gly Asp Asn Asp Ala Leu Asp
225                 230                 235                 240
Ile Trp Gly Pro Gly Thr Thr Val Thr Val Ser Ser
                245                 250

<210> SEQ ID NO 4
<211> LENGTH: 333
<212> TYPE: DNA
<213> ORGANISM: Homo sapiens

<400> SEQUENCE: 4
cagtctgtgc tgactcagcc gcccctcagtg tctggggccc cagggcagag tgtcattatc     60
tcctgcactg ggagcagctc caacatcggg gcaggttctc atgtacactg gtaccagcag    120
gttccaggaa cagcccccaa actcctcatc tatggaaaca ccaatcgccc tcagggggtc    180
cctgaccgat tctctggctc caagtctggc acctcaggtt ccctggccat cactggactc    240
cagcctgagg atgaggctga ttattattgt gcaacatggg atgacagtct gaatggtgta    300
atattcggcg agggaccaa ggtcaccgtc cta                                  333

<210> SEQ ID NO 5
<211> LENGTH: 111
<212> TYPE: PRT
<213> ORGANISM: Homo sapiens

<400> SEQUENCE: 5

Gln Ser Val Leu Thr Gln Pro Pro Ser Val Ser Gly Ala Pro Gly Gln
1               5                   10                  15
Ser Val Ile Ile Ser Cys Thr Gly Ser Ser Ser Asn Ile Gly Ala Gly
            20                  25                  30
Ser His Val His Trp Tyr Gln Gln Val Pro Gly Thr Ala Pro Lys Leu
        35                  40                  45
Leu Ile Tyr Gly Asn Thr Asn Arg Pro Ser Gly Val Pro Asp Arg Phe
    50                  55                  60
Ser Gly Ser Lys Ser Gly Thr Ser Gly Ser Leu Ala Ile Thr Gly Leu
65                  70                  75                  80
Gln Pro Glu Asp Glu Ala Asp Tyr Tyr Cys Ala Thr Trp Asp Asp Ser
```

85                  90                  95
Leu Asn Gly Val Ile Phe Gly Gly Gly Thr Lys Val Thr Val Leu
                100                 105                 110

<210> SEQ ID NO 6
<211> LENGTH: 75
<212> TYPE: DNA
<213> ORGANISM: Homo sapiens

<400> SEQUENCE: 6
cagtctgtgc tgactcagcc gccctcagtg tctggggccc cagggcagag tgtcattatc    60
tcctgcactg ggagc                                                    75

<210> SEQ ID NO 7
<211> LENGTH: 25
<212> TYPE: PRT
<213> ORGANISM: Homo sapiens

<400> SEQUENCE: 7

Gln Ser Val Leu Thr Gln Pro Pro Ser Val Ser Gly Ala Pro Gly Gln
1               5                   10                  15

Ser Val Ile Ile Ser Cys Thr Gly Ser
            20                  25

<210> SEQ ID NO 8
<211> LENGTH: 27
<212> TYPE: DNA
<213> ORGANISM: Homo sapiens

<400> SEQUENCE: 8
agctccaaca tcggggcagg ttctcat                                       27

<210> SEQ ID NO 9
<211> LENGTH: 9
<212> TYPE: PRT
<213> ORGANISM: Homo sapiens

<400> SEQUENCE: 9

Ser Ser Asn Ile Gly Ala Gly Ser His
1               5

<210> SEQ ID NO 10
<211> LENGTH: 51
<212> TYPE: DNA
<213> ORGANISM: Homo sapiens

<400> SEQUENCE: 10
gtacactggt accagcaggt tccaggaaca gccccccaaac tcctcatcta t            51

<210> SEQ ID NO 11
<211> LENGTH: 17
<212> TYPE: PRT
<213> ORGANISM: Homo sapiens

<400> SEQUENCE: 11

Val His Trp Tyr Gln Gln Val Pro Gly Thr Ala Pro Lys Leu Leu Ile
1               5                   10                  15

Tyr

<210> SEQ ID NO 12
<211> LENGTH: 9
<212> TYPE: DNA

```
<213> ORGANISM: Homo sapiens

<400> SEQUENCE: 12 ggaaacacc                                                                  9

<210> SEQ ID NO 13
<211> LENGTH: 3
<212> TYPE: PRT
<213> ORGANISM: Homo sapiens

<400> SEQUENCE: 13

Gly Asn Thr
1

<210> SEQ ID NO 14
<211> LENGTH: 108
<212> TYPE: DNA
<213> ORGANISM: Homo sapiens

<400> SEQUENCE: 14
aatcggccct cagggtccc tgaccgattc tctggctcca agtctggcac ctcaggttcc      60
ctggccatca ctggactcca gcctgaggat gaggctgatt attattgt                 108

<210> SEQ ID NO 15
<211> LENGTH: 36
<212> TYPE: PRT
<213> ORGANISM: Homo sapiens

<400> SEQUENCE: 15

Asn Arg Pro Ser Gly Val Pro Asp Arg Phe Ser Gly Ser Lys Ser Gly
1               5                   10                  15

Thr Ser Gly Ser Leu Ala Ile Thr Gly Leu Gln Pro Glu Asp Glu Ala
            20                  25                  30

Asp Tyr Tyr Cys
        35

<210> SEQ ID NO 16
<211> LENGTH: 33
<212> TYPE: DNA
<213> ORGANISM: Homo sapiens

<400> SEQUENCE: 16
gcaacatggg atgacagtct gaatggtgta ata                                  33

<210> SEQ ID NO 17
<211> LENGTH: 11
<212> TYPE: PRT
<213> ORGANISM: Homo sapiens

<400> SEQUENCE: 17

Ala Thr Trp Asp Asp Ser Leu Asn Gly Val Ile
1               5                   10

<210> SEQ ID NO 18
<211> LENGTH: 30
<212> TYPE: DNA
<213> ORGANISM: Homo sapiens

<400> SEQUENCE: 18
ttcggcggag ggaccaaggt caccgtccta                                      30

<210> SEQ ID NO 19
```

```
<211> LENGTH: 10
<212> TYPE: PRT
<213> ORGANISM: Homo sapiens

<400> SEQUENCE: 19

Phe Gly Gly Gly Thr Lys Val Thr Val Leu
1               5                   10

<210> SEQ ID NO 20
<211> LENGTH: 369
<212> TYPE: DNA
<213> ORGANISM: Homo sapiens

<400> SEQUENCE: 20
gaggtgcagc tggtggagtc tgggggagcc ctggccaagc ctgggggtc cctgagactc      60 tcctgtgcag cctctggatc caccctcagt ggctatgcta tgcactgggt ccgccaggct    120
ccaggcaagg ggctggagtg ggtggcagtt atatcatatg atggaagcaa taaatactac    180
gcagactccg tgaagggccg attcaccatc tccagagaca attccaagaa cacgctgttt    240
ctgcaaatga acagcctgag acctgaggac acggctgtgt actattgtgc taaaggcctt    300
acttggggac tcggtgacaa tgatgctctc gatatctggg gccccgggac cacggtcacc    360
gtctcctca                                                            369

<210> SEQ ID NO 21
<211> LENGTH: 123
<212> TYPE: PRT
<213> ORGANISM: Homo sapiens

<400> SEQUENCE: 21

Glu Val Gln Leu Val Glu Ser Gly Gly Ala Leu Ala Lys Pro Gly Gly
1               5                   10                  15

Ser Leu Arg Leu Ser Cys Ala Ala Ser Gly Ser Thr Leu Ser Gly Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Pro Glu Asp Thr Ala Val Tyr Tyr Cys
                85                  90                  95

Ala Lys Gly Leu Thr Trp Gly Leu Gly Asp Asn Asp Ala Leu Asp Ile
            100                 105                 110

Trp Gly Pro Gly Thr Thr Val Thr Val Ser Ser
        115                 120

<210> SEQ ID NO 22
<211> LENGTH: 75
<212> TYPE: DNA
<213> ORGANISM: Homo sapiens

<400> SEQUENCE: 22
gaggtgcagc tggtggagtc tgggggagcc ctggccaagc ctgggggtc cctgagactc      60 tcctgtgcag cctct                                                      75

<210> SEQ ID NO 23
<211> LENGTH: 25
<212> TYPE: PRT
```

<210> SEQ ID NO 23
<211> LENGTH: (not shown)
<212> TYPE: PRT
<213> ORGANISM: Homo sapiens

<400> SEQUENCE: 23

Glu Val Gln Leu Val Glu Ser Gly Gly Ala Leu Ala Lys Pro Gly Gly
1               5                   10                  15
Ser Leu Arg Leu Ser Cys Ala Ala Ser
            20                  25

<210> SEQ ID NO 24
<211> LENGTH: 24
<212> TYPE: DNA
<213> ORGANISM: Homo sapiens

<400> SEQUENCE: 24
ggatccaccc tcagtggcta tgct                                          24

<210> SEQ ID NO 25
<211> LENGTH: 8
<212> TYPE: PRT
<213> ORGANISM: Homo sapiens

<400> SEQUENCE: 25

Gly Ser Thr Leu Ser Gly Tyr Ala
1               5

<210> SEQ ID NO 26
<211> LENGTH: 51
<212> TYPE: DNA
<213> ORGANISM: Homo sapiens

<400> SEQUENCE: 26
atgcactggg tccgccaggc tccaggcaag gggctggagt gggtggcagt t            51

<210> SEQ ID NO 27
<211> LENGTH: 17
<212> TYPE: PRT
<213> ORGANISM: Homo sapiens

<400> SEQUENCE: 27

Met His Trp Val Arg Gln Ala Pro Gly Lys Gly Leu Glu Trp Val Ala
1               5                   10                  15
Val

<210> SEQ ID NO 28
<211> LENGTH: 24
<212> TYPE: DNA
<213> ORGANISM: Homo sapiens

<400> SEQUENCE: 28
atatcatatg atggaagcaa taaa                                          24

<210> SEQ ID NO 29
<211> LENGTH: 8
<212> TYPE: PRT
<213> ORGANISM: Homo sapiens

<400> SEQUENCE: 29

Ile Ser Tyr Asp Gly Ser Asn Lys
1               5

<210> SEQ ID NO 30
<211> LENGTH: 114
<212> TYPE: DNA

<210> SEQ ID NO 30 (continued)
<213> ORGANISM: Homo sapiens

<400> SEQUENCE: 30

```
tactacgcag actccgtgaa gggccgattc accatctcca gagacaattc caagaacacg    60
ctgtttctgc aaatgaacag cctgagacct gaggacacgg ctgtgtacta ttgt          114
```

<210> SEQ ID NO 31
<211> LENGTH: 38
<212> TYPE: PRT
<213> ORGANISM: Homo sapiens

<400> SEQUENCE: 31

Tyr Tyr Ala Asp Ser Val Lys Gly Arg Phe Thr Ile Ser Arg Asp Asn
1               5                   10                  15

Ser Lys Asn Thr Leu Phe Leu Gln Met Asn Ser Leu Arg Pro Glu Asp
            20                  25                  30

Thr Ala Val Tyr Tyr Cys
        35

<210> SEQ ID NO 32
<211> LENGTH: 48
<212> TYPE: DNA
<213> ORGANISM: Homo sapiens

<400> SEQUENCE: 32

```
gctaaaggcc ttacttgggg actcggtgac aatgatgctc tcgatatc                  48
```

<210> SEQ ID NO 33
<211> LENGTH: 16
<212> TYPE: PRT
<213> ORGANISM: Homo sapiens

<400> SEQUENCE: 33

Ala Lys Gly Leu Thr Trp Gly Leu Gly Asp Asn Asp Ala Leu Asp Ile
1               5                   10                  15

<210> SEQ ID NO 34
<211> LENGTH: 33
<212> TYPE: DNA
<213> ORGANISM: Homo sapiens

<400> SEQUENCE: 34

```
tggggccccg ggaccacggt caccgtctcc tca                                  33
```

<210> SEQ ID NO 35
<211> LENGTH: 11
<212> TYPE: PRT
<213> ORGANISM: Homo sapiens

<400> SEQUENCE: 35

Trp Gly Pro Gly Thr Thr Val Thr Val Ser Ser
1               5                   10

<210> SEQ ID NO 36
<211> LENGTH: 54
<212> TYPE: DNA
<213> ORGANISM: Artificial Sequence
<220> FEATURE:
<223> OTHER INFORMATION: linker

<400> SEQUENCE: 36

```
ggcggatcct ctaggtcaag ttccagcggc ggcggtggca gcggaggcgg cggt           54
```

```
<210> SEQ ID NO 37
<211> LENGTH: 18
<212> TYPE: PRT
<213> ORGANISM: Artificial Sequence
<220> FEATURE:
<223> OTHER INFORMATION: linker

<400> SEQUENCE: 37

Gly Gly Ser Ser Arg Ser Ser Ser Ser Gly Gly Gly Gly Ser Gly Gly
1               5                   10                  15

Gly Gly

<210> SEQ ID NO 38
<211> LENGTH: 51
<212> TYPE: DNA
<213> ORGANISM: Artificial Sequence
<220> FEATURE:
<223> OTHER INFORMATION: mutant

<400> SEQUENCE: 38
gtacactggt accagcaggc tccaggaaca gcccccaaac tcctcatcta t            51

<210> SEQ ID NO 39
<211> LENGTH: 17
<212> TYPE: PRT
<213> ORGANISM: Artificial Sequence
<220> FEATURE:
<223> OTHER INFORMATION: mutant

<400> SEQUENCE: 39

Val His Trp Tyr Gln Gln Ala Pro Gly Thr Ala Pro Lys Leu Leu Ile
1               5                   10                  15

Tyr

<210> SEQ ID NO 40
<211> LENGTH: 9
<212> TYPE: DNA
<213> ORGANISM: Artificial Sequence
<220> FEATURE:
<223> OTHER INFORMATION: mutant

<400> SEQUENCE: 40 gaaaacacc                                                            9

<210> SEQ ID NO 41
<211> LENGTH: 3
<212> TYPE: PRT
<213> ORGANISM: Artificial Sequence
<220> FEATURE:
<223> OTHER INFORMATION: mutant

<400> SEQUENCE: 41

Glu Asn Thr
1

<210> SEQ ID NO 42
<211> LENGTH: 30
<212> TYPE: DNA
<213> ORGANISM: Artificial Sequence
<220> FEATURE:
<223> OTHER INFORMATION: mutant

<400> SEQUENCE: 42
ttcggcggag ggaccaaggc caccgtccta                                    30
```

<210> SEQ ID NO 43
<211> LENGTH: 10
<212> TYPE: PRT
<213> ORGANISM: Artificial Sequence
<220> FEATURE:
<223> OTHER INFORMATION: mutant

<400> SEQUENCE: 43

Phe Gly Gly Gly Thr Lys Ala Thr Val Leu
1               5                   10

<210> SEQ ID NO 44
<211> LENGTH: 24
<212> TYPE: DNA
<213> ORGANISM: Artificial Sequence
<220> FEATURE:
<223> OTHER INFORMATION: mutant

<400> SEQUENCE: 44
ggattcaccc tcagtggcta tgct                                              24

<210> SEQ ID NO 45
<211> LENGTH: 8
<212> TYPE: PRT
<213> ORGANISM: Artificial Sequence
<220> FEATURE:
<223> OTHER INFORMATION: mutant

<400> SEQUENCE: 45

Gly Phe Thr Leu Ser Gly Tyr Ala
1               5

<210> SEQ ID NO 46
<211> LENGTH: 114
<212> TYPE: DNA
<213> ORGANISM: Artificial Sequence
<220> FEATURE:
<223> OTHER INFORMATION: mutant

<400> SEQUENCE: 46
tactacgcag actccgtgaa gggccgattc accgtctcca gagacaattc caagaacacg       60
ctgtttctgc aaatgaacag cctgagacct gaggacacgg ctgtgtacta ttgt            114

<210> SEQ ID NO 47
<211> LENGTH: 38
<212> TYPE: PRT
<213> ORGANISM: Artificial Sequence
<220> FEATURE:
<223> OTHER INFORMATION: mutant

<400> SEQUENCE: 47

Tyr Tyr Ala Asp Ser Val Lys Gly Arg Phe Thr Val Ser Arg Asp Asn
1               5                   10                  15

Ser Lys Asn Thr Leu Phe Leu Gln Met Asn Ser Leu Arg Pro Glu Asp
            20                  25                  30

Thr Ala Val Tyr Tyr Cys
        35

<210> SEQ ID NO 48
<211> LENGTH: 48
<212> TYPE: DNA
<213> ORGANISM: Artificial Sequence
<220> FEATURE:
<223> OTHER INFORMATION: mutant

```
<400> SEQUENCE: 48
gctaaaggcc ttacttgggg actcggtgac aatgatgctc tcggtatc         48

<210> SEQ ID NO 49
<211> LENGTH: 16
<212> TYPE: PRT
<213> ORGANISM: Artificial Sequence
<220> FEATURE:
<223> OTHER INFORMATION: mutant

<400> SEQUENCE: 49

Ala Lys Gly Leu Thr Trp Gly Leu Gly Asp Asn Asp Ala Leu Gly Ile
1               5                   10                  15

<210> SEQ ID NO 50
<211> LENGTH: 33
<212> TYPE: DNA
<213> ORGANISM: Artificial Sequence
<220> FEATURE:
<223> OTHER INFORMATION: mutant

<400> SEQUENCE: 50 tggggcccg agaccacggt caccgtctcc tca                          33

<210> SEQ ID NO 51
<211> LENGTH: 11
<212> TYPE: PRT
<213> ORGANISM: Artificial Sequence
<220> FEATURE:
<223> OTHER INFORMATION: mutant

<400> SEQUENCE: 51

Trp Gly Pro Glu Thr Thr Val Thr Val Ser Ser
1               5                   10

<210> SEQ ID NO 52
<211> LENGTH: 1419
<212> TYPE: DNA
<213> ORGANISM: Homo sapiens

<400> SEQUENCE: 52
atggagtttg ggctgagctg ggttttcctc gttgctcttt taagaggtgt ccagtgtgag    60
gtgcagctgg tggagtctgg gggagccctg gccaagcctg gggggtccct gagactctcc   120
tgtgcagcct ctggattcac cctcagtggc tatgctatgc actgggtccg ccaggctcca   180
ggcaaggggc tggagtgggt ggcagttata tcatatgatg gaagcaataa atactacgca   240
gactccgtga agggccgatt caccgtctcc agagacaatt ccaagaacac gctgtttctg   300
caaatgaaca gcctgagacc tgaggacacg gctgtgtact attgtgctaa aggccttacc   360
tggggactcg gtgacaatga tgctctcgat atctggggcc ccgggaccac ggtcaccgtc   420
tcctcagcct ccaccaaggg cccatcggtc ttccccctgg cacccctcct caagagcacc   480
tctgggggca cagcggccct gggctgcctg gtcaaggact acttccccga accggtgacg   540
gtgtcgtgga actcaggcgc cctgaccagc ggcgtgcaca ccttcccggc tgtcctacag   600
tcctcaggac tctactccct cagcagcgtg gtgaccgtgc cctccagcag cttgggcacc   660
cagacctaca tctgcaacgt gaatcacaag cccagcaaca ccaaggtgga caagaaagtt   720
gagcccaaat cttgtgacaa aactcacaca tgcccaccgt gcccagcacc tgaactcctg   780
gggggaccgt cagtcttcct cttccccca aaacccaagg acaccctcat gatctcccgg    840
acccctgagg tcacatgcgt ggtggtggac gtgagccacg aagaccctga ggtcaagttc   900
```

-continued

```
aactggtacg tggacggcgt ggaggtgcat aatgccaaga caaagccgcg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga caactacaa gaccacgcct   1260 cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaatga                           1419
```

<210> SEQ ID NO 53
<211> LENGTH: 472
<212> TYPE: PRT
<213> ORGANISM: Homo sapiens

<400> SEQUENCE: 53

```
Met Glu Phe Gly Leu Ser Trp Val Phe Leu Val Ala Leu Leu Arg Gly
1               5                   10                  15

Val Gln Cys Glu Val Gln Leu Val Glu Ser Gly Gly Ala Leu Ala Lys
            20                  25                  30

Pro Gly Gly Ser Leu Arg Leu Ser Cys Ala Ala Ser Gly Phe Thr Leu
        35                  40                  45

Ser Gly Tyr Ala Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Val Ser Arg Asp Asn Ser Lys Asn
                85                  90                  95

Thr Leu Phe Leu Gln Met Asn Ser Leu Arg Pro Glu Asp Thr Ala Val
            100                 105                 110

Tyr Tyr Cys Ala Lys Gly Leu Thr Trp Gly Leu Gly Asp Asn Asp Ala
        115                 120                 125

Leu Asp Ile Trp Gly Pro Gly Thr Thr Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
```

```
                275                 280                 285
Val Asp Val Ser His Glu Asp Pro Glu Val Lys Phe Asn Trp Tyr Val
            290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
                355                 360                 365
Arg Glu Pro Gln Val Tyr Thr Leu Pro Pro Ser Arg Asp Glu Leu Thr
370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
                435                 440                 445
Ser Cys Ser Val Met His Glu Ala Leu His Asn His Tyr Thr Gln Lys
            450                 455                 460
Ser Leu Ser Leu Ser Pro Gly Lys
465                 470

<210> SEQ ID NO 54
<211> LENGTH: 57
<212> TYPE: DNA
<213> ORGANISM: Homo sapiens

<400> SEQUENCE: 54
atggagtttg ggctgagctg ggttttcctc gttgctcttt taagaggtgt ccagtgt       57

<210> SEQ ID NO 55
<211> LENGTH: 19
<212> TYPE: PRT
<213> ORGANISM: Homo sapiens

<400> SEQUENCE: 55

Met Glu Phe Gly Leu Ser Trp Val Phe Leu Val Ala Leu Leu Arg Gly
1               5                   10                  15

Val Gln Cys

<210> SEQ ID NO 56
<211> LENGTH: 369
<212> TYPE: DNA
<213> ORGANISM: Homo sapiens

<400> SEQUENCE: 56
gaggtgcagc tggtggagtc tgggggagcc ctggccaagc ctgggggtc cctgagactc       60 tcctgtgcag cctctggatt caccctcagt ggctatgcta tgcactgggt ccgccaggct      120
ccaggcaagg ggctggagtg ggtggcagtt atatcatatg atggaagcaa taaatactac      180
gcagactccg tgaagggccg attcaccgtc tccagagaca attccaagaa cacgctgttt      240
ctgcaaatga acagcctgag acctgaggac acggctgtgt actattgtgc taaaggcctt      300
```

```
acctggggac tcggtgacaa tgatgctctc gatatctggg ccccgggac cacggtcacc      360 gtctcctca                                                              369
```

<210> SEQ ID NO 57
<211> LENGTH: 123
<212> TYPE: PRT
<213> ORGANISM: Homo sapiens

<400> SEQUENCE: 57

```
Glu Val Gln Leu Val Glu Ser Gly Gly Ala Leu Ala Lys Pro Gly Gly
1               5                   10                  15

Ser Leu Arg Leu Ser Cys Ala Ala Ser Gly Phe Thr Leu Ser Gly Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Val Ser Arg Asp Asn Ser Lys Asn Thr Leu Phe
65                  70                  75                  80

Leu Gln Met Asn Ser Leu Arg Pro Glu Asp Thr Ala Val Tyr Tyr Cys
                85                  90                  95

Ala Lys Gly Leu Thr Trp Gly Leu Gly Asp Asn Asp Ala Leu Asp Ile
            100                 105                 110

Trp Gly Pro Gly Thr Thr Val Thr Val Ser Ser
        115                 120
```

<210> SEQ ID NO 58
<211> LENGTH: 990
<212> TYPE: DNA
<213> ORGANISM: Homo sapiens

<400> SEQUENCE: 58

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggga     360 ccgtcagtct tcctcttccc cccaaaaccc aaggacaccc tcatgatctc ccggaccct      420 gaggtcacat gcgtggtggt ggacgtgagc cacgaagacc ctgaggtcaa gttcaactgg     480
tacgtggacg gcgtggaggt gcataatgcc aagacaaagc cgcggggagga gcagtacaac    540 agcacgtacc gggtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 59
<211> LENGTH: 330
<212> TYPE: PRT
<213> ORGANISM: Homo sapiens

<400> SEQUENCE: 59

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 60
<211> LENGTH: 711
<212> TYPE: DNA
<213> ORGANISM: Homo sapiens

<400> SEQUENCE: 60
atggcctggt ctcctctcct cctcactctc ctcgctcact gcacagggtc ctgggcccag    60

```
tctgtgctga ctcagccgcc ctcagtgtct ggggccccag ggcagagtgt cattatctcc      120
tgcactggga gcagctccaa catcggggca ggttctcatg tacactggta ccagcaggtt      180
ccaggaacag cccccaaact cctcatctat gaaaacacca atcggccctc agggGtccct      240
gaccgattct ctggctccaa gtctggcacc tcaggttccc tggccatcac tggactccag      300
cctgaggatg aggctgatta ttattgtgca acatgggatg acagtctgaa tggtgtaata      360
ttcggcggag ggaccaaggc caccgtccta ggtcagccca aggctgcccc ctcggtcact      420
ctgttcccgc cctcctctga ggagcttcaa gccaacaagg ccacactggt gtgtctcata      480
agtgacttct acccgggagc cgtgacagtg gcctggaagg cagatagcag ccccgtcaag      540
gcgggagtgg agaccaccac accctccaaa caaagcaaca caagtacgc ggccagcagc      600 tatctgagcc tgacgcctga gcagtggaag tcccacagaa gctacagctg ccaggtcacg      660
catgaaggga gcaccgtgga agacagtg gcccctacag aatgttcatg a                 711
```

<210> SEQ ID NO 61
<211> LENGTH: 236
<212> TYPE: PRT
<213> ORGANISM: Homo sapiens
<400> SEQUENCE: 61

```
Met Ala Trp Ser Pro Leu Leu Thr Leu Leu Ala His Cys Thr Gly
1               5                   10                  15

Ser Trp Ala Gln Ser Val Leu Thr Gln Pro Ser Val Ser Gly Ala
            20                  25                  30

Pro Gly Gln Ser Val Ile Ile Ser Cys Thr Gly Ser Ser Asn Ile
        35                  40                  45

Gly Ala Gly Ser His Val His Trp Tyr Gln Gln Val Pro Gly Thr Ala
    50                  55                  60

Pro Lys Leu Leu Ile Tyr Glu Asn Thr Asn Arg Pro Ser Gly Val Pro
65                  70                  75                  80

Asp Arg Phe Ser Gly Ser Lys Ser Gly Thr Ser Gly Ser Leu Ala Ile
                85                  90                  95

Thr Gly Leu Gln Pro Glu Asp Glu Ala Asp Tyr Tyr Cys Ala Thr Trp
            100                 105                 110

Asp Asp Ser Leu Asn Gly Val Ile Phe Gly Gly Gly Thr Lys Ala Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235
```

<210> SEQ ID NO 62
<211> LENGTH: 57

```
<212> TYPE: DNA
<213> ORGANISM: Homo sapiens

<400> SEQUENCE: 62
atggcctggt ctcctctcct cctcactctc ctcgctcact gcacagggtc ctgggcc        57

<210> SEQ ID NO 63
<211> LENGTH: 19
<212> TYPE: PRT
<213> ORGANISM: Homo sapiens

<400> SEQUENCE: 63

Met Ala Trp Ser Pro Leu Leu Leu Thr Leu Leu Ala His Cys Thr Gly
 1               5                  10                  15

Ser Trp Ala

<210> SEQ ID NO 64
<211> LENGTH: 333
<212> TYPE: DNA
<213> ORGANISM: Homo sapiens

<400> SEQUENCE: 64
cagtctgtgc tgactcagcc gccctcagtg tctggggccc cagggcagag tgtcattatc        60
tcctgcactg ggagcagctc caacatcggg gcaggttctc atgtacactg gtaccagcag       120
gttccaggaa cagcccccaa actcctcatc tatgaaaaca ccaatcggcc ctcaggggtc       180
cctgaccgat tctctggctc caagtctggc acctcaggtt ccctggccat cactggactc       240
cagcctgagg atgaggctga ttattattgt gcaacatggg atgacagtct gaatggtgta       300
atattcggcg gagggaccaa ggccaccgtc cta                                    333

<210> SEQ ID NO 65
<211> LENGTH: 111
<212> TYPE: PRT
<213> ORGANISM: Homo sapiens

<400> SEQUENCE: 65

Gln Ser Val Leu Thr Gln Pro Pro Ser Val Ser Gly Ala Pro Gly Gln
 1               5                  10                  15

Ser Val Ile Ile Ser Cys Thr Gly Ser Ser Asn Ile Gly Ala Gly
                20                  25                  30

Ser His Val His Trp Tyr Gln Gln Val Pro Gly Thr Ala Pro Lys Leu
                35                  40                  45

Leu Ile Tyr Glu Asn Thr Asn Arg Pro Ser Gly Val Pro Asp Arg Phe
    50                  55                  60

Ser Gly Ser Lys Ser Gly Thr Ser Gly Ser Leu Ala Ile Thr Gly Leu
65                  70                  75                  80

Gln Pro Glu Asp Glu Ala Asp Tyr Tyr Cys Ala Thr Trp Asp Ser
                85                  90                  95

Leu Asn Gly Val Ile Phe Gly Gly Gly Thr Lys Ala Thr Val Leu
                100                 105                 110

<210> SEQ ID NO 66
<211> LENGTH: 318
<212> TYPE: DNA
<213> ORGANISM: Homo sapiens

<400> SEQUENCE: 66
ggtcagccca aggctgcccc ctcggtcact ctgttcccgc cctcctctga ggagcttcaa        60
```

```
gccaacaagg ccacactggt gtgtctcata agtgacttct acccgggagc cgtgacagtg      120
gcctggaagg cagatagcag ccccgtcaag gcgggagtgg agaccaccac accctccaaa      180
caaagcaaca caagtacgc ggccagcagc tatctgagcc tgacgcctga gcagtggaag       240
tcccacagaa gctacagctg ccaggtcacg catgaaggga gcaccgtgga agacagtg        300 gccccatacag aatgttca                                                   318
```

<210> SEQ ID NO 67
<211> LENGTH: 106
<212> TYPE: PRT
<213> ORGANISM: Homo sapiens

<400> SEQUENCE: 67

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 68
<211> LENGTH: 453
<212> TYPE: PRT
<213> ORGANISM: Homo sapiens

<400> SEQUENCE: 68

```
Glu Val Gln Leu Val Glu Ser Gly Gly Ala Leu Ala Lys Pro Gly Gly
1               5                   10                  15

Ser Leu Arg Leu Ser Cys Ala Ala Ser Gly Phe Thr Leu Ser Gly Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Val Ser Arg Asp Asn Ser Lys Asn Thr Leu Phe
65                  70                  75                  80

Leu Gln Met Asn Ser Leu Arg Pro Glu Asp Thr Ala Val Tyr Tyr Cys
                85                  90                  95

Ala Lys Gly Leu Thr Trp Gly Leu Gly Asp Asn Asp Ala Leu Asp Ile
            100                 105                 110

Trp Gly Pro Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

Pro Ala Val Leu Gln Ser Ser Gly Leu Tyr Ser Leu Ser Val Val
              180                 185                 190

Thr Val Pro Ser Ser Leu Gly Thr Gln Thr Tyr Ile Cys Asn Val
          195                 200                 205

Asn His Lys Pro Ser Asn Thr Lys Val Asp Lys Val Glu Pro Lys
      210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                  245                 250                 255

Leu Met Ile Ser Arg Thr Pro Glu Val Thr Cys Val Val Val Asp Val
              260                 265                 270

Ser His Glu Asp Pro Glu Val Lys Phe Asn Trp Tyr Val Asp Gly Val
          275                 280                 285

Glu Val His Asn Ala Lys Thr Lys Pro Arg Glu Glu Gln Tyr Asn Ser
      290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                  325                 330                 335

Pro Ile Glu Lys Thr Ile Ser Lys Ala Lys Gly Gln Pro Arg Glu Pro
              340                 345                 350

Gln Val Tyr Thr Leu Pro Pro Ser Arg Asp Glu Leu Thr Lys Asn Gln
          355                 360                 365

Val Ser Leu Thr Cys Leu Val Lys Gly Phe Tyr Pro Ser Asp Ile Ala
      370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                  405                 410                 415

Thr Val Asp Lys Ser Arg Trp Gln Gln Gly Asn Val Phe Ser Cys Ser
              420                 425                 430

Val Met His Glu Ala Leu His Asn His Tyr Thr Gln Lys Ser Leu Ser
          435                 440                 445

Leu Ser Pro Gly Lys
        450

<210> SEQ ID NO 69
<211> LENGTH: 217
<212> TYPE: PRT
<213> ORGANISM: Homo sapiens

<400> SEQUENCE: 69

Gln Ser Val Leu Thr Gln Pro Pro Ser Val Ser Gly Ala Pro Gly Gln
1               5                   10                  15

Ser Val Ile Ile Ser Cys Thr Gly Ser Ser Ser Asn Ile Gly Ala Gly
              20                  25                  30

Ser His Val His Trp Tyr Gln Gln Val Pro Gly Thr Ala Pro Lys Leu
          35                  40                  45

Leu Ile Tyr Glu Asn Thr Asn Arg Pro Ser Gly Val Pro Asp Arg Phe
      50                  55                  60

Ser Gly Ser Lys Ser Gly Thr Ser Gly Ser Leu Ala Ile Thr Gly Leu
65                  70                  75                  80

Gln Pro Glu Asp Glu Ala Asp Tyr Tyr Cys Ala Thr Trp Asp Asp Ser

```
                    85                  90                  95

Leu Asn Gly Val Ile Phe Gly Gly Thr Lys Ala Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 70
<211> LENGTH: 63
<212> TYPE: DNA
<213> ORGANISM: Homo sapiens

<400> SEQUENCE: 70
atggccttac cagtgaccgc cttgctcctg ccgctggcct tgctgctcca cgccgccagg    60
ccg                                                                 63

<210> SEQ ID NO 71
<211> LENGTH: 21
<212> TYPE: PRT
<213> ORGANISM: Homo sapiens

<400> SEQUENCE: 71

Met Ala Leu Pro Val Thr Ala Leu Leu Leu Pro Leu Ala Leu Leu Leu
1               5                  10                  15

His Ala Ala Arg Pro
            20

<210> SEQ ID NO 72
<211> LENGTH: 135
<212> TYPE: DNA
<213> ORGANISM: Homo sapiens

<400> SEQUENCE: 72
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                   135

<210> SEQ ID NO 73
<211> LENGTH: 45
<212> TYPE: PRT
<213> ORGANISM: Homo sapiens

<400> SEQUENCE: 73

Thr Thr Thr Pro Ala Pro Arg Pro Pro Thr Pro Ala Pro Thr Ile Ala
1               5                  10                  15

Ser Gln Pro Leu Ser Leu Arg Pro Glu Ala Cys Arg Pro Ala Ala Gly
            20                  25                  30
```

```
Gly Ala Val His Thr Arg Gly Leu Asp Phe Ala Cys Asp
        35                  40                  45

<210> SEQ ID NO 74
<211> LENGTH: 72
<212> TYPE: DNA
<213> ORGANISM: Homo sapiens

<400> SEQUENCE: 74
atctacatct gggcgccctt ggccgggact tgtggggtcc ttctcctgtc actggttatc    60 acccttact  gc                                                       72

<210> SEQ ID NO 75
<211> LENGTH: 24
<212> TYPE: PRT
<213> ORGANISM: Homo sapiens

<400> SEQUENCE: 75

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 76
<211> LENGTH: 126
<212> TYPE: DNA
<213> ORGANISM: Homo sapiens

<400> SEQUENCE: 76
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 77
<211> LENGTH: 42
<212> TYPE: PRT
<213> ORGANISM: Homo sapiens

<400> SEQUENCE: 77

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 78
<211> LENGTH: 336
<212> TYPE: DNA
<213> ORGANISM: Homo sapiens

<400> SEQUENCE: 78
agagtgaagt tcagcaggag cgcagacgcc cccgcgtaca gcagggcca gaaccagctc    60 tataacgagc tcaatctagg acgaagagag gagtacgatg tttggacaa gagacgtggc   120 cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
```

```
tacgacgccc ttcacatgca ggccctgccc cctcgc                              336
```

<210> SEQ ID NO 79
<211> LENGTH: 112
<212> TYPE: PRT
<213> ORGANISM: Homo sapiens

<400> SEQUENCE: 79

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 80
<211> LENGTH: 1503
<212> TYPE: DNA
<213> ORGANISM: Artificial Sequence
<220> FEATURE:
<223> OTHER INFORMATION: construct

<400> SEQUENCE: 80

```
atggccttac cagtgaccgc cttgctcctg ccgctggcct tgctgctcca cgccgccagg    60
ccgtctagac agtctgtgct gactcagccg ccctcagtgt ctggggcccc agggcagagt   120
gtcattatct cctgcactgg gagcagctcc aacatcgggg caggttctca tgtacactgg   180
taccagcagg ttccaggaac agccccccaaa ctcctcatct atgaaaacac caatcggccc   240
tcaggggtcc ctgaccgatt ctctggctcc aagtctggca cctcaggttc cctggccatc   300
actggactcc agcctgagga tgaggctgat tattattgtg caacatggga tgacagtctg   360
aatggtgtaa tattcggcgg agggaccaag gccaccgtcc taggcggatc ctctaggtca   420
agttccagcg gcggcggtgg cagcggaggc ggcggtgagg tgcagctggt ggagtctggg   480
ggagccctgg ccaagcctgg ggggtccctg agactctcct gtgcagcctc tggattcacc   540
ctcagtggct atgctatgca ctgggtccgc caggctccag gcaaggggct ggagtgggtg   600
gcagttatat catatgatgg aagcaataaa tactacgcag actccgtgaa gggccgattc   660
accgtctcca gagacaattc caagaacacg ctgtttctgc aaatgaacag cctgagacct   720
gaggacacgg ctgtgtacta ttgtgctaaa ggccttacct ggggactcgg tgacaatgat   780
gctctcgata tctggggccc cgggaccacg gtcaccgtct cctcaagatc caccacgacg   840
ccagcgccgc gaccaccaac accggcgccc accatcgcgt cgcagcccct gtccctgcgc   900
ccagaggcgt gccggccagc ggcggggggc gcagtgcaca cgaggggggct ggacttcgcc   960 tgtgatatct acatctgggc gcccttggcc gggacttgtg gggtccttct cctgtcactg  1020
gttatcaccc tttactgcaa acggggcaga aagaaactcc tgtatatatt caaacaacca  1080
tttatgagac cagtacaaac tactcaagag gaagatggct gtagctgccg atttccagaa  1140
```

```
gaagaagaag gaggatgtga actgagagtg aagttcagca ggagcgcaga cgcccccgcg    1200
taccagcagg gccagaacca gctctataac gagctcaatc taggacgaag agaggagtac    1260
gatgttttgg acaagagacg tggccgggac cctgagatgg ggggaaagcc gagaaggaag    1320
aaccctcagg aaggcctgta caatgaactg cagaaagata gatggcggaa ggcctacagt    1380
gagattggga tgaaggcga gcgccggagg ggcaaggggc acgatggcct ttaccagggt    1440
ctcagtacag ccaccaagga cacctacgac gcccttcaca tgcaggccct gccccctcgc    1500
taa                                                                  1503

<210> SEQ ID NO 81
<211> LENGTH: 500
<212> TYPE: PRT
<213> ORGANISM: Artificial Sequence
<220> FEATURE:
<223> OTHER INFORMATION: construct

<400> SEQUENCE: 81
```

Met Ala Leu Pro Val Thr Ala Leu Leu Pro Leu Ala Leu Leu Leu
1               5                   10                  15

His Ala Ala Arg Pro Ser Arg Gln Ser Val Leu Thr Gln Pro Pro Ser
            20                  25                  30

Val Ser Gly Ala Pro Gly Gln Ser Val Ile Ile Ser Cys Thr Gly Ser
        35                  40                  45

Ser Ser Asn Ile Gly Ala Gly Ser His Val His Trp Tyr Gln Gln Val
    50                  55                  60

Pro Gly Thr Ala Pro Lys Leu Leu Ile Tyr Glu Asn Thr Asn Arg Pro
65                  70                  75                  80

Ser Gly Val Pro Asp Arg Phe Ser Gly Ser Lys Ser Gly Thr Ser Gly
                85                  90                  95

Ser Leu Ala Ile Thr Gly Leu Gln Pro Glu Asp Glu Ala Asp Tyr Tyr
            100                 105                 110

Cys Ala Thr Trp Asp Asp Ser Leu Asn Gly Val Ile Phe Gly Gly Gly
        115                 120                 125

Thr Lys Ala Thr Val Leu Gly Gly Ser Ser Arg Ser Ser Ser Ser Gly
    130                 135                 140

Gly Gly Gly Ser Gly Gly Gly Gly Glu Val Gln Leu Val Glu Ser Gly
145                 150                 155                 160

Gly Ala Leu Ala Lys Pro Gly Gly Ser Leu Arg Leu Ser Cys Ala Ala
                165                 170                 175

Ser Gly Phe Thr Leu Ser Gly Tyr Ala Met His Trp Val Arg Gln Ala
            180                 185                 190

Pro Gly Lys Gly Leu Glu Trp Val Ala Val Ile Ser Tyr Asp Gly Ser
        195                 200                 205

Asn Lys Tyr Tyr Ala Asp Ser Val Lys Gly Arg Phe Thr Val Ser Arg
    210                 215                 220

Asp Asn Ser Lys Asn Thr Leu Phe Leu Gln Met Asn Ser Leu Arg Pro
225                 230                 235                 240

Glu Asp Thr Ala Val Tyr Tyr Cys Ala Lys Gly Leu Thr Trp Gly Leu
                245                 250                 255

Gly Asp Asn Asp Ala Leu Asp Ile Trp Gly Pro Gly Thr Thr Val Thr
            260                 265                 270

Val Ser Ser Arg Ser Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys

```
            290                 295                 300
Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Lys Arg Gly Arg Lys Lys
            340                 345                 350

Leu Leu Tyr Ile Phe Lys Gln Pro Phe Met Arg Pro Val Gln Thr Thr
        355                 360                 365

Gln Glu Glu Asp Gly Cys Ser Cys Arg Phe Pro Glu Glu Glu Glu Gly
    370                 375                 380

Gly Cys Glu Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415

Arg Glu Glu Tyr Asp Val Leu Asp Lys Arg Arg Gly Arg Asp Pro Glu
            420                 425                 430

Met Gly Gly Lys Pro Arg Arg Lys Asn Pro Gln Glu Gly Leu Tyr Asn
        435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
                485                 490                 495

Leu Pro Pro Arg
        500

<210> SEQ ID NO 82
<211> LENGTH: 723
<212> TYPE: DNA
<213> ORGANISM: Artificial Sequence
<220> FEATURE:
<223> OTHER INFORMATION: scFv

<400> SEQUENCE: 82
caggtgcagc tgcagcagag cggcgcggaa ctggcgcgcc cgggcgcgag cgtgaaaatg      60
agctgcaaag cgagcggcta cctttacc cgctatacca tgcattgggt gaaacagcgc      120
ccgggccagg gcctggaatg gattggctat attaacccga ccgcggcta taccaactat     180 aaccagaaat taaagataa agcgaccctg accaccgata aaagcagcag caccgcgtat     240
atgcagctga gcagcctgac cagcgaagat agcgcggtgt attattgcgc gcgctattat     300
gatgatcatt attgcctgga ttattggggc cagggcacca ccctgaccgt gagcagcggc     360
ggcggcggca gcggcggcgg cggcagcggc ggcggcggca gccagattgt gctgacccag     420
agcccggcga ttatgagcgc gagccccggc gaaaaagtga ccatgacctg cagcgcgagc     480
agcagcgtga gctatatgaa ctggtatcag cagaaaagcg gcaccagccc gaaacgctgg     540
atttatgata ccagcaaact ggcgagcggc gtgccggcgc attttcgcgg cagcggcagc     600
ggcaccagct atagcctgac cattagcggc atggaagcgg aagatgcggc gacctattat     660
tgccagcagt ggagcagcaa cccgtttacc tttggcagcg gcaccaaact ggaaattaac     720
cgc                                                                   723

<210> SEQ ID NO 83
```

<211> LENGTH: 241
<212> TYPE: PRT
<213> ORGANISM: Artificial Sequence
<220> FEATURE:
<223> OTHER INFORMATION: scFv

<400> SEQUENCE: 83

Gln Val Gln Leu Gln Gln Ser Gly Ala Glu Leu Ala Arg Pro Gly Ala
1               5                   10                  15
Ser Val Lys Met Ser Cys Lys Ala Ser Gly Tyr Thr Phe Thr Arg Tyr
                20                  25                  30
Thr Met His Trp Val Lys Gln Arg Pro Gly Gln Gly Leu Glu Trp Ile
            35                  40                  45
Gly Tyr Ile Asn Pro Ser Arg Gly Tyr Thr Asn Tyr Asn Gln Lys Phe
        50                  55                  60
Lys Asp Lys Ala Thr Leu Thr Thr Asp Lys Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Tyr Tyr Asp Asp His Tyr Cys Leu Asp Tyr Trp Gly Gln Gly
                100                 105                 110
Thr Thr Leu Thr Val Ser Ser Gly Gly Gly Ser Gly Gly Gly
            115                 120                 125
Ser Gly Gly Gly Ser Gln Ile Val Leu Thr Gln Ser Pro Ala Ile
        130                 135                 140
Met Ser Ala Ser Pro Gly Glu Lys Val Thr Met Thr Cys Ser Ala Ser
145                 150                 155                 160
Ser Ser Val Ser Tyr Met Asn Trp Tyr Gln Gln Lys Ser Gly Thr Ser
                165                 170                 175
Pro Lys Arg Trp Ile Tyr Asp Thr Ser Lys Leu Ala Ser Gly Val Pro
            180                 185                 190
Ala His Phe Arg Gly Ser Gly Ser Gly Thr Ser Tyr Ser Leu Thr Ile
        195                 200                 205
Ser Gly Met Glu Ala Glu Asp Ala Ala Thr Tyr Tyr Cys Gln Gln Trp
210                 215                 220
Ser Ser Asn Pro Phe Thr Phe Gly Ser Gly Thr Lys Leu Glu Ile Asn
225                 230                 235                 240
Arg

<210> SEQ ID NO 84
<211> LENGTH: 357
<212> TYPE: DNA
<213> ORGANISM: Mus musculus

<400> SEQUENCE: 84
caggtgcagc tgcagcagag cggcgcggaa ctggcgcgcc cgggcgcgag cgtgaaaatg    60
agctgcaaag cgagcggcta cctttacc cgctatacca tgcattgggt gaaacagcgc    120
ccgggccagg gcctggaatg gattggctat attaacccga gccgcggcta taccaactat    180
aaccagaaat ttaaagataa agcgacctg accaccgata aaagcagcag caccgcgtat    240
atgcagctga gcagcctgac cagcgaagat agcgcggtgt attattgcgc gcgctattat    300
gatgatcatt attgcctgga ttattgggc agggcacca ccctgaccgt gagcagc        357

<210> SEQ ID NO 85
<211> LENGTH: 119
<212> TYPE: PRT

<213> ORGANISM: Mus musculus

<400> SEQUENCE: 85

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115

<210> SEQ ID NO 86
<211> LENGTH: 321
<212> TYPE: DNA
<213> ORGANISM: Mus musculus

<400> SEQUENCE: 86

```
cagattgtgc tgacccagag cccggcgatt atgagcgcga gcccgggcga aaaagtgacc    60
atgacctgca gcgcgagcag cagcgtgagc tatatgaact ggtatcagca gaaaagcggc   120
accagcccga aacgctggat ttatgatacc agcaaactgg cgagcggcgt gccggcgcat   180
tttcgcggca gcggcagcgg caccagctat agcctgacca ttagcggcat ggaagcggaa   240
gatgcggcga cctattattg ccagcagtgg agcagcaacc cgtttacctt tggcagcggc   300
accaaactgg aaattaaccg c                                             321
```

<210> SEQ ID NO 87
<211> LENGTH: 107
<212> TYPE: PRT
<213> ORGANISM: Mus musculus

<400> SEQUENCE: 87

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 88

<211> LENGTH: 723
<212> TYPE: DNA
<213> ORGANISM: Artificial Sequence
<220> FEATURE:
<223> OTHER INFORMATION: humanized scFv

<400> SEQUENCE: 88

```
caggtgcagc tggtgcagag cggcggcggc gtggtgcagc cgggccgcag cctgcgcctg      60
agctgcaaag cgagcggcta cctttacc cgctatacca tgcattgggt gcgccaggcg      120
ccgggcaaag gcctggaatg gattggctat attaacccga gccgcggcta taccaactat      180
aaccagaaaa tgaaagatcg ctttaccatt agcaccgata aaagcaaaag caccgcgttt      240
ctgcagatgg atagcctgcg cccggaagat accggcgtgt attttgcgc gcgctattat      300
gatgatcatt attgcctgga ttattgggc agggcacca ccctgaccgt gagcagcggc      360
ggcggcggca gcggcggcgg cggcagcggc ggcggcggca gcgatattca gatgacccag      420
agcccgagca gcctgagcgc gagcgtgggc gatcgcgtga ccattacctg cagcgcgagc      480
agcagcgtga gctatatgaa ctggtatcag cagacccccgg gcaaagcgcc gaaacgctgg      540
atttatgata ccagcaaaact ggcgagcggc gtgccgagcc gctttagcgg cagcggcagc      600
ggcaccgatt taccttac cattagcagc ctgcagccgg aagatattgc gacctattat      660
tgccagcagt ggagcagcaa cccgtttacc tttggccagg gcaccaaact gcagattacc      720
cgc                                                                   723
```

<210> SEQ ID NO 89
<211> LENGTH: 241
<212> TYPE: PRT
<213> ORGANISM: Artificial Sequence
<220> FEATURE:
<223> OTHER INFORMATION: humanized scFv

<400> SEQUENCE: 89

```
Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Ser Ala Ser
145                 150                 155                 160

Ser Ser Val Ser Tyr Met Asn Trp Tyr Gln Gln Thr Pro Gly Lys Ala
                165                 170                 175

Pro Lys Arg Trp Ile Tyr Asp Thr Ser Lys Leu Ala Ser Gly Val Pro
            180                 185                 190
```

-continued

```
Ser Arg Phe Ser Gly Ser Gly Ser Gly Thr Asp Tyr Thr Phe Thr Ile
        195                 200                 205

Ser Ser Leu Gln Pro Glu Asp Ile Ala Thr Tyr Tyr Cys Gln Gln Trp
        210                 215                 220

Ser Ser Asn Pro Phe Thr Phe Gly Gln Gly Thr Lys Leu Gln Ile Thr
225                 230                 235                 240

Arg

<210> SEQ ID NO 90
<211> LENGTH: 357
<212> TYPE: DNA
<213> ORGANISM: Homo sapiens

<400> SEQUENCE: 90
caggtgcagc tggtgcagag cggcggcggc gtggtgcagc cgggccgcag cctgcgcctg      60
agctgcaaag cgagcggcta cctttacc cgctatacca tgcattgggt gcgccaggcg      120
ccgggcaaag gcctggaatg gattggctat attaacccga gccgcggcta taccaactat     180
aaccagaaag tgaaagatcg ctttaccatt agcaccgata aaagcaaaag caccgcgttt     240
ctgcagatgg atagcctgcg cccggaagat accggcgtgt attttgcgc gcgctattat     300 gatgatcatt attgcctgga ttattggggc cagggcacca ccctgaccgt gagcagc       357

<210> SEQ ID NO 91
<211> LENGTH: 119
<212> TYPE: PRT
<213> ORGANISM: Homo sapiens

<400> SEQUENCE: 91

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 92
<211> LENGTH: 321
<212> TYPE: DNA
<213> ORGANISM: Homo sapiens

<400> SEQUENCE: 92
gatattcaga tgacccagag cccgagcagc ctgagcgcga gcgtgggcga tcgcgtgacc      60
attacctgca gcgcgagcag cagcgtgagc tatatgaact ggtatcagca gccccgggc     120 aaagcgccga aacgctggat ttatgatacc agcaaactgg cgagcggcgt gccgagccgc     180
tttagcggca gcggcagcgg caccgattat acctttacca ttagcagcct gcagccggaa     240
```

```
gatattgcga cctattattg ccagcagtgg agcagcaacc cgtttacctt tggccagggc    300
accaaactgc agattacccg c                                              321
```

<210> SEQ ID NO 93
<211> LENGTH: 107
<212> TYPE: PRT
<213> ORGANISM: Homo sapiens

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105
```

<210> SEQ ID NO 94
<211> LENGTH: 45
<212> TYPE: DNA
<213> ORGANISM: Artificial Sequence
<220> FEATURE:
<223> OTHER INFORMATION: mutant

<400> SEQUENCE: 94

```
gagcccaaat ctgctgacaa aactcacaca tgcccaccgt gccca                     45
```

<210> SEQ ID NO 95
<211> LENGTH: 15
<212> TYPE: PRT
<213> ORGANISM: Artificial Sequence
<220> FEATURE:
<223> OTHER INFORMATION: mutated IgG1 hinge amino acid sequence

<400> SEQUENCE: 95

```
Glu Pro Lys Ser Ala Asp Lys Thr His Thr Cys Pro Pro Cys Pro
1               5                   10                  15
```

<210> SEQ ID NO 96
<211> LENGTH: 651
<212> TYPE: DNA
<213> ORGANISM: Artificial Sequence
<220> FEATURE:
<223> OTHER INFORMATION: mutated IgG4 Fc (N297A) nucleic acid sequence

<400> SEQUENCE: 96

```
gcacctgagt tcctgggggg accatcagtc ttcctgttcc ccccaaaacc caaggacact    60
ctcatgatct cccggacccc tgaggtcacg tgcgtggtgg tggacgtgag ccaggaagac   120
cccgaggtcc agttcaactg gtacgtggat ggcgtggagg tgcataatgc caagacaaag   180
ccgcgggagg agcagttcgc tagcacgtac cgtgtggtca gcgtcctcac cgtcctgcac   240
caggactggc tgaacggcaa ggagtacaag tgcaaggtct ccaacaaagg cctcccgtcc   300
```

-continued

```
tccatcgaga aaaccatctc caaagccaaa gggcagcccc gagagccaca ggtgtacacc    360
ctgcccccat cccaggagga gatgaccaag aaccaggtca gcctgacctg cctggtcaaa    420
ggcttctacc ccagcgacat cgccgtggag tgggagagca atgggcagcc ggagaacaac    480
tacaagacca cgcctcccgt gctggactcc gacggctcct tcttcctcta cagcaggcta    540
accgtggaca agagcaggtg gcaggagggg aatgtcttct catgctccgt gatgcatgag    600
gctctgcaca accactacac acagaagagc ctctccctgt ctctgggtaa a             651
```

<210> SEQ ID NO 97
<211> LENGTH: 217
<212> TYPE: PRT
<213> ORGANISM: Artificial Sequence
<220> FEATURE:
<223> OTHER INFORMATION: mutated IgG4 Fc (N297A) amino acid sequence

<400> SEQUENCE: 97

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215
```

<210> SEQ ID NO 98
<211> LENGTH: 696
<212> TYPE: DNA
<213> ORGANISM: Artificial Sequence
<220> FEATURE:
<223> OTHER INFORMATION: mutated IgG1 Hinge-IgG4 Fc nucleic acid
      sequence

<400> SEQUENCE: 98

```
gagcccaaat ctgctgacaa aactcacaca tgcccaccgt gcccagcacc tgagttcctg     60
gggggaccat cagtcttcct gttccccccca aaacccaagg acactctcat gatctcccgg    120
```

```
accccctgagg tcacgtgcgt ggtggtggac gtgagccagg aagaccccga ggtccagttc    180
aactggtacg tggatggcgt ggaggtgcat aatgccaaga caaagccgcg ggaggagcag    240
ttcgctagca cgtaccgtgt ggtcagcgtc ctcaccgtcc tgcaccagga ctggctgaac    300
ggcaaggagt acaagtgcaa ggtctccaac aaaggcctcc cgtcctccat cgagaaaacc    360
atctccaaag ccaaagggca gccccgagag ccacaggtgt acaccctgcc cccatcccag    420
gaggagatga ccaagaacca ggtcagcctg acctgcctgg tcaaaggctt ctaccccagc    480
gacatcgccg tggagtggga gagcaatggg cagccggaga caactacaa gaccacgcct     540
cccgtgctgg actccgacgg ctccttcttc ctctacagca ggctaaccgt ggacaagagc    600
aggtggcagg aggggaatgt cttctcatgc tccgtgatgc atgaggctct gcacaaccac    660
tacacacaga gagcctctc cctgtctctg ggtaaa                                696
```

<210> SEQ ID NO 99
<211> LENGTH: 232
<212> TYPE: PRT
<213> ORGANISM: Artificial Sequence
<220> FEATURE:
<223> OTHER INFORMATION: mutated IgG1 Hinge-IgG4 Fc amino acid sequence

<400> SEQUENCE: 99

```
Glu Pro Lys Ser Ala Asp Lys Thr His Thr Cys Pro Pro Cys Pro Ala
1               5                   10                  15

Pro Glu Phe Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser Gln Glu Asp Pro Glu Val Gln Phe Asn Trp Tyr Val
    50                  55                  60

Asp Gly Val Glu Val His Asn Ala Lys Thr Lys Pro Arg Glu Glu Gln
65                  70                  75                  80

Phe Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Gly
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Gln Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Arg Leu Thr Val Asp Lys Ser Arg Trp Gln Glu Gly Asn Val Phe
        195                 200                 205

Ser Cys Ser Val Met His Glu Ala Leu His Asn His Tyr Thr Gln Lys
    210                 215                 220

Ser Leu Ser Leu Ser Leu Gly Lys
225                 230
```

<210> SEQ ID NO 100
<211> LENGTH: 1547
<212> TYPE: DNA

<213> ORGANISM: Artificial Sequence
<220> FEATURE:
<223> OTHER INFORMATION: scFv1 MCS-G4S-hOKT3 scFv-IgG1 hinge - IgG4 Fc
      expression cassette nucleic acid sequence

<400> SEQUENCE: 100

```
actagtgcca ccatggagtt tgggctgagc tgggtcttcc tggtggctat cttgaagggt    60
gtccagtgtg aattcaagct ttctagaagc gctgctagcg gtggaggtgg atcccaggtc   120
cagctggtgc agtcagggggg gggagtcgtg cagcccggtc ggtctctgcg tctgtcttgt   180
aaggcatccg gttatacttt taccaggtac acaatgcact gggtgcggca ggctcctggc   240
aagggcctgg agtggatcgg ctatatcaac ccatccaggg gctacaccaa ctataatcag   300
aaggtgaagg accggttcac catctctaca gataagagca agtctacagc ctttctgcag   360
atggactccc tgagacctga ggataccggc gtgtacttct gcgctcgcta ctatgacgat   420
cattactgtc tggactattg gggccagggc accacactga cagtgtccag cggaggagga   480
ggctccggag gaggaggcag cggcggcggc ggctctgaca tccagatgac ccagagccca   540
tcttccctgt ccgccagcgt gggcgataga gtgaccatca catgctccgc ctcctcctcc   600
gtgtcctaca tgaactggta tcagcagaca cccggcaagg cccctaagag atggatctac   660
gatacctcca agctggcctc cggagtgccc tctcgcttct ctggctccgg cagcggcaca   720
gactatacct ttacaatcag ctctctgcag cctgaggata tcgctaccta ctattgtcag   780
cagtggtcca gcaatccatt cacctttggc cagggcacaa gctgcagat caccaggctc   840
gagccaaaga cgccgacaa acccacaca tgcccccctt gtccagctcc cgagtttctg   900
ggcggcccat ccgtgttcct gtttccaccc aagcccaagg atacactgat gatcagccgg   960
acccccagagg tgacatgcgt ggtggtggac gtgtctcagg aggacccgga ggtgcagttc  1020
aactggtacg tggacggcgt ggaggtgcac aatgccaaga ccaagcccag ggaggagcag  1080
tttgcttcta catccgggt ggtgtccgtc ctgaccgtgc tgcatcagga ttggctgaac  1140
ggcaaggagt ataagtgcaa ggtgtccaat aagggcctgc cttcttccat cgagaagaca  1200
atcagcaagg ctaagggaca gcctcgcgag ccacaggtgt acaccctgcc tccatctcag  1260
gaggagatga caaagaacca ggtgtccctg acctgtctgg tgaagggctt ctatccctcc  1320
gacatcgctg tggagtggga gagcaatggc cagcctgaga caattacaa gaccacaccc  1380
cctgtgctgg acagcgatgg ctctttcttt ctgtatagca gactgaccgt ggataagtct  1440
cgctggcagg agggcaacgt gttctcctgt tccgtgatgc acgaggcact gcacaaccac  1500
tacactcaga atcactgtc actgtccctg ggcaagtagg cggccgc             1547
```

<210> SEQ ID NO 101
<211> LENGTH: 496
<212> TYPE: PRT
<213> ORGANISM: Artificial Sequence
<220> FEATURE:
<223> OTHER INFORMATION: scFv1 MCS-G4S-hOKT3 scFv-IgG1 hinge - IgG4 Fc
      expression cassette amino acid sequence

<400> SEQUENCE: 101

```
Met Glu Phe Gly Leu Ser Trp Val Phe Leu Val Ala Ile Leu Lys Gly
1               5                   10                  15

Val Gln Cys Met Cys Ser Gln Val Gln Leu Val Gln Ser Gly Gly Gly
            20                  25                  30

Val Val Gln Pro Gly Arg Ser Leu Arg Leu Ser Cys Lys Ala Ser Gly
        35                  40                  45
```

-continued

```
Tyr Thr Phe Thr Arg Tyr Thr Met His Trp Val Arg Gln Ala Pro Gly
 50                  55                  60

Lys Gly Leu Glu Trp Ile Gly Tyr Ile Asn Pro Ser Arg Gly Tyr Thr
 65                  70                  75                  80

Asn Tyr Asn Gln Lys Val Lys Asp Arg Phe Thr Ile Ser Thr Asp Lys
                 85                  90                  95

Ser Lys Ser Thr Ala Phe Leu Gln Met Asp Ser Leu Arg Pro Glu Asp
            100                 105                 110

Thr Gly Val Tyr Phe Cys Ala Arg Tyr Tyr Asp His Tyr Cys Leu
        115                 120                 125

Asp Tyr Trp Gly Gln Gly Thr Thr Leu Thr Val Ser Ser Gly Gly Gly
130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Val Gly Asp Arg Val Thr
                165                 170                 175

Ile Thr Cys Ser Ala Ser Ser Val Ser Tyr Met Asn Trp Tyr Gln
        180                 185                 190

Gln Thr Pro Gly Lys Ala Pro Lys Arg Trp Ile Tyr Asp Thr Ser Lys
        195                 200                 205

Leu Ala Ser Gly Val Pro Ser Arg Phe Ser Gly Ser Gly Ser Gly Thr
210                 215                 220

Asp Tyr Thr Phe Thr Ile Ser Ser Leu Gln Pro Glu Asp Ile Ala Thr
225                 230                 235                 240

Tyr Tyr Cys Gln Gln Trp Ser Ser Asn Pro Phe Thr Phe Gly Gln Gly
                245                 250                 255

Thr Lys Leu Gln Ile Thr Arg Leu Glu Pro Lys Ser Ala Asp Lys Thr
        260                 265                 270

His Thr Cys Pro Pro Cys Pro Ala Pro Glu Phe Leu Gly Gly Pro Ser
        275                 280                 285

Val Phe Leu Phe Pro Pro Lys Pro Lys Asp Thr Leu Met Ile Ser Arg
        290                 295                 300

Thr Pro Glu Val Thr Cys Val Val Val Asp Val Ser Gln Glu Asp Pro
305                 310                 315                 320

Glu Val Gln Phe Asn Trp Tyr Val Asp Gly Val Glu Val His Asn Ala
                325                 330                 335

Lys Thr Lys Pro Arg Glu Glu Gln Phe Ala Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Gly Leu Pro Ser Ser Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Gln Glu Glu Met Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Tyr Lys Thr Thr Pro Pro Val Leu Asp
        435                 440                 445

Ser Asp Gly Ser Phe Phe Leu Tyr Ser Arg Leu Thr Val Asp Lys Ser
    450                 455                 460

Arg Trp Gln Glu Gly Asn Val Phe Ser Cys Ser Val Met His Glu Ala
```

Leu His Asn His Tyr Thr Gln Lys Ser Leu Ser Leu Ser Leu Gly Lys
    485                 490                 495

<210> SEQ ID NO 102
<211> LENGTH: 1547
<212> TYPE: DNA
<213> ORGANISM: Artificial Sequence
<220> FEATURE:
<223> OTHER INFORMATION: scFv1 MCS-G4S-mOKT3 scFv-IgG1 hinge - IgG4 Fc
      expression cassette nucleic acid sequence

<400> SEQUENCE: 102

| | |
|---|---|
| actagtgcca ccatggagtt tgggctgagc tgggtcttcc tggtggctat cttgaagggt | 60 |
| gtccagtgtg aattcaagct ttctagaagc gctgctagcg gtggaggtgg atcccaggtc | 120 |
| cagctgcagc agagcggtgc cgaactggcc cgtcccggag caagcgtgaa aatgtcctgt | 180 |
| aaagcaagtg gctataccct taccaggtac acaatgcact gggtgaagca gaggccagga | 240 |
| cagggcctgg agtggatcgg ctatatcaac ccctctaggg gctacacaaa ctataatcag | 300 |
| aagttcaagg acaaggccac cctgaccacc gataagtcca gctctacagc ttacatgcag | 360 |
| ctgtccagcc tgaccagcga ggactctgcc gtgtactatt gcgctagata ctatgacgat | 420 |
| cattactgtc tggattattg gggccagggc accacactga cagtgtcttc cggaggagga | 480 |
| ggcagcggag gaggaggctc tggcggcggc ggctcccaga tcgtgctgac ccagtcccca | 540 |
| gctatcatgt ccgcctcccc tggagagaag gtgaccatga catgcagcgc cagctcttcc | 600 |
| gtgtcttaca tgaattggta tcagcagaag tccggcacaa gccctaagag atggatctac | 660 |
| gacacctcta gctggcctc cggagtgcca gctcactttc gcggctccgg cagcggcacc | 720 |
| tcttattccc tgacaatcag cggcatggag gctgaggatg ccgctaccta ctattgtcag | 780 |
| cagtggtcat caaatccttt caccttcggt tcagggacaa aactggagat caataggctc | 840 |
| gagccaaaga gcgccgacaa gacccacaca tgccccccct tgtccagctcc cgagtttctg | 900 |
| ggcggcccat ccgtgttcct gtttccaccc aagcccaagg atacactgat gatcagccgg | 960 |
| acccagagg tgacatgcgt ggtggtggac gtgtctcagg aggacccga ggtgcagttc | 1020 |
| aactggtacg tggacggcgt ggaggtgcac aatgccaaga ccaagcccag ggaggagcag | 1080 |
| tttgcttcta catccggt ggtgtccgtg ctgaccgtgc tgcatcagga ttggctgaac | 1140 |
| ggcaaggagt ataagtgcaa ggtgtccaat aagggcctgc cttcttccat cgagaagaca | 1200 |
| atcagcaagg ctaagggaca gcctcgcgag ccacaggtgt acaccctgcc tccatctcag | 1260 |
| gaggagatga caaagaacca ggtgtccctg acctgtctgg tgaagggctt ctatccctcc | 1320 |
| gacatcgctg tggagtggga gagcaatggc cagcctgaga acaattacaa gaccacaccc | 1380 |
| cctgtgctgg acagcgatgg ctctttcttt ctgtatagca gactgaccgt ggataagtct | 1440 |
| cgctggcagg agggcaacgt gttctcctgt tccgtgatgc acgaggcact gcacaaccac | 1500 |
| tacactcaga aatcactgtc actgtccctg ggcaagtagg cggccgc | 1547 |

<210> SEQ ID NO 103
<211> LENGTH: 496
<212> TYPE: PRT
<213> ORGANISM: Artificial Sequence
<220> FEATURE:
<223> OTHER INFORMATION: scFv1 MCS-G4S-mOKT3 scFv-IgG1 hinge - IgG4 Fc
      expression cassette amino acid sequence

<400> SEQUENCE: 103

```
Met Glu Phe Gly Leu Ser Trp Val Phe Leu Val Ala Ile Leu Lys Gly
1               5                   10                  15

Val Gln Cys Met Cys Ser Gln Val Gln Leu Gln Gln Ser Gly Ala Glu
            20                  25                  30

Leu Ala Arg Pro Gly Ala Ser Val Lys Met Ser Cys Lys Ala Ser Gly
        35                  40                  45

Tyr Thr Phe Thr Arg Tyr Thr Met His Trp Val Lys Gln Arg Pro Gly
    50                  55                  60

Gln Gly Leu Glu Trp Ile Gly Tyr Ile Asn Pro Ser Arg Gly Tyr Thr
65                  70                  75                  80

Asn Tyr Asn Gln Lys Phe Lys Asp Lys Ala Thr Leu Thr Thr Asp Lys
                85                  90                  95

Ser Ser Ser Thr Ala Tyr Met Gln Leu Ser Ser Leu Thr Ser Glu Asp
            100                 105                 110

Ser Ala Val Tyr Tyr Cys Ala Arg Tyr Tyr Asp Asp His Tyr Cys Leu
            115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Gln Ile Val Leu
145                 150                 155                 160

Thr Gln Ser Pro Ala Ile Met Ser Ala Ser Pro Gly Glu Lys Val Thr
                165                 170                 175

Met Thr Cys Ser Ala Ser Ser Ser Val Ser Tyr Met Asn Trp Tyr Gln
            180                 185                 190

Gln Lys Ser Gly Thr Ser Pro Lys Arg Trp Ile Tyr Asp Thr Ser Lys
        195                 200                 205

Leu Ala Ser Gly Val Pro Ala His Phe Arg Gly Ser Gly Ser Gly Thr
    210                 215                 220

Ser Tyr Ser Leu Thr Ile Ser Gly Met Glu Ala Glu Asp Ala Ala Thr
225                 230                 235                 240

Tyr Tyr Cys Gln Gln Trp Ser Ser Asn Pro Phe Thr Phe Gly Ser Gly
                245                 250                 255

Thr Lys Leu Glu Ile Asn Arg Leu Glu Pro Lys Ser Ala Asp Lys Thr
            260                 265                 270

His Thr Cys Pro Pro Cys Pro Ala Pro Glu Phe Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser Gln Glu Asp Pro
305                 310                 315                 320

Glu Val Gln Phe Asn Trp Tyr Val Asp Gly Val Glu Val His Asn Ala
                325                 330                 335

Lys Thr Lys Pro Arg Glu Glu Gln Phe Ala Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Gly Leu Pro Ser Ser Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Gln Glu Glu Met Thr Lys Asn Gln Val Ser Leu Thr Cys
                405                 410                 415

Leu Val Lys Gly Phe Tyr Pro Ser Asp Ile Ala Val Glu Trp Glu Ser
```

```
            420             425             430
Asn Gly Gln Pro Glu Asn Asn Tyr Lys Thr Thr Pro Pro Val Leu Asp
        435             440             445

Ser Asp Gly Ser Phe Phe Leu Tyr Ser Arg Leu Thr Val Asp Lys Ser
    450             455             460

Arg Trp Gln Glu Gly Asn Val Phe Ser Cys Ser Val Met His Glu Ala
465             470             475             480

Leu His Asn His Tyr Thr Gln Lys Ser Leu Ser Leu Ser Leu Gly Lys
            485             490             495

<210> SEQ ID NO 104
<211> LENGTH: 2265
<212> TYPE: DNA
<213> ORGANISM: Artificial Sequence
<220> FEATURE:
<223> OTHER INFORMATION: anti-PSMA & hOKT3 bispecific Ab nucleic acid
      sequence (gy1-2)

<400> SEQUENCE: 104
atggagtttg gctgagctg ggtcttcctg gtggctatct tgaagggtgt ccagtgtgaa      60
ttccagtctg tgctgactca gccgccctca gtgtctgggg ccccagggca gagtgtcatt    120
atctcctgca ctgggagcag ctccaacatc ggggcaggtt ctcatgtaca ctggtaccag    180
caggttccag gaacagcccc caaactcctc atctatgaaa acaccaatcg gccctcaggg    240
gtccctgacc gattctctgg ctccaagtct ggcacctcag gttccctggc catcactgga    300
ctccagcctg aggatgaggc tgattattat tgtgcaacat gggatgacag tctgaatggt    360
gtaatattcg gcggagggac caaggccacc gtcctaggcg atcctctag gtcaagttcc    420 agcggcggcg gtgcagcgg aggcggcggt gaggtgcagc tggtggagtc tgggggagcc    480
ctggccaagc tgggggtgc cctgagactc tcctgtgcag cctctggatt caccctcagt    540
ggctatgcta tgcactgggt ccgccaggct ccaggcaagg gctgagtg ggtggcagtt    600 atatcatatg atggaagcaa taaatactac gcagactccg tgaagggccg attcaccgtc    660
tccagagaca attccaagaa cacgctgttt ctgcaaatga acagcctgag acctgaggac    720
acggctgtgt actattgtgc taaaggcctt acctgggac tcggtgacaa tgatgctctc    780
gatatctggg gccccgggac cacggtcacc gtctcctcag ctagcggtgg aggtggatcc    840
caggtccagc tggtgcagtc aggggggga gtcgtgcagc ccggtcggtc tctgcgtctg    900
tcttgtaagg catccggtta tactttacc aggtacacaa tgcactgggt gcggcaggct    960
cctggcaagg gctggagtg atcggctat atcaacccat ccaggggcta caccaactat   1020
aatcagaagg tgaaggaccg gttcaccatc tctacagata gagcaagtc tacagccttt   1080 ctgcagatgg actccctgag acctgaggat accggcgtgt acttctgcgc tgctactat   1140 gacgatcatt actgtctgga ctattgggc cagggcacca cactgacagt gtccagcgga   1200
ggaggaggct ccgaggagg aggcagcgg ggcggcggct tgacatcca gatgacccag   1260 agcccatctt ccctgtccgc cagcgtgggc gatagagtga ccatcacatg ctccgcctcc   1320
tcctccgtgt cctacatgaa ctggtatcag cagacacccg gcaaggcccc taagagatgg   1380
atctacgata cctccaagct ggcctccgga gtgccctctc gcttctctgg ctccggcagc   1440
ggcacagact atacctttac aatcagctct ctgcagcctg aggatatcgc tacctactat   1500
tgtcagcagt ggtccagcaa tccattcacc tttggccagg gcacaaagct gcagatcacc   1560
aggctcgagc caaagagcgc cgacaagacc cacacatgcc ccccttgtcc agctcccgag   1620
```

```
tttctgggcg gcccatccgt gttcctgttt ccacccaagc ccaaggatac actgatgatc    1680
agccggaccc cagaggtgac atgcgtggtg gtggacgtgt ctcaggagga ccccgaggtg    1740
cagttcaact ggtacgtgga cggcgtggag gtgcacaatg ccaagaccaa gcccagggag    1800
gagcagtttg cttctacata ccgggtggtg tccgtgctga ccgtgctgca tcaggattgg    1860
ctgaacggca aggagtataa gtgcaaggtg tccaataagg gcctgccttc ttccatcgag    1920
aagacaatca gcaaggctaa gggacagcct cgcgagccac aggtgtacac cctgcctcca    1980
tctcaggagg agatgacaaa gaaccaggtg tccctgacct gtctggtgaa gggcttctat    2040
ccctccgaca tcgctgtgga gtgggagagc aatggccagc ctgagaacaa ttacaagacc    2100 acacccctg tgctggacag cgatggctct ttctttctgt atagcagact gaccgtggat    2160
aagtctcgct ggcaggaggg caacgtgttc tcctgttccg tgatgcacga ggcactgcac    2220
aaccactaca ctcagaaatc actgtcactg tccctgggca gtag                    2265
```

<210> SEQ ID NO 105
<211> LENGTH: 754
<212> TYPE: PRT
<213> ORGANISM: Artificial Sequence
<220> FEATURE:
<223> OTHER INFORMATION: anti-PSMA & hOKT3 bispecific Ab amino acid
      sequence (gy1-2)

<400> SEQUENCE: 105

```
Met Glu Phe Gly Leu Ser Trp Val Phe Leu Val Ala Ile Leu Lys Gly
1               5                   10                  15

Val Gln Cys Glu Phe Gln Ser Val Leu Thr Gln Pro Pro Ser Val Ser
            20                  25                  30

Gly Ala Pro Gly Gln Ser Val Ile Ile Ser Cys Thr Gly Ser Ser Ser
        35                  40                  45

Asn Ile Gly Ala Gly Ser His Val His Trp Tyr Gln Gln Val Pro Gly
    50                  55                  60

Thr Ala Pro Lys Leu Leu Ile Tyr Glu Asn Thr Asn Arg Pro Ser Gly
65                  70                  75                  80

Val Pro Asp Arg Phe Ser Gly Ser Lys Ser Gly Thr Ser Gly Ser Leu
                85                  90                  95

Ala Ile Thr Gly Leu Gln Pro Glu Asp Glu Ala Asp Tyr Tyr Cys Ala
            100                 105                 110

Thr Trp Asp Asp Ser Leu Asn Gly Val Ile Phe Gly Gly Gly Thr Lys
        115                 120                 125

Ala Thr Val Leu Gly Gly Ser Ser Arg Ser Ser Ser Gly Gly Gly Gly
    130                 135                 140

Gly Ser Gly Gly Gly Gly Glu Val Gln Leu Val Glu Ser Gly Gly Ala
145                 150                 155                 160

Leu Ala Lys Pro Gly Gly Ser Leu Arg Leu Ser Cys Ala Ala Ser Gly
                165                 170                 175

Phe Thr Leu Ser Gly Tyr Ala Met His Trp Val Arg Gln Ala Pro Gly
            180                 185                 190

Lys Gly Leu Glu Trp Val Ala Val Ile Ser Tyr Asp Gly Ser Asn Lys
        195                 200                 205

Tyr Tyr Ala Asp Ser Val Lys Gly Arg Phe Thr Val Ser Arg Asp Asn
    210                 215                 220

Ser Lys Asn Thr Leu Phe Leu Gln Met Asn Ser Leu Arg Pro Glu Asp
225                 230                 235                 240

Thr Ala Val Tyr Tyr Cys Ala Lys Gly Leu Thr Trp Gly Leu Gly Asp
```

```
                    245                 250                 255
Asn Asp Ala Leu Asp Ile Trp Gly Pro Gly Thr Thr Val Thr Val Ser
            260                 265                 270

Ser Ala Ser Gly Gly Gly Gly Ser Gln Val Gln Leu Val Gln Ser Gly
            275                 280                 285

Gly Gly Val Val Gln Pro Gly Arg Ser Leu Arg Leu Ser Cys Lys Ala
        290                 295                 300

Ser Gly Tyr Thr Phe Thr Arg Tyr Thr Met His Trp Val Arg Gln Ala
305                 310                 315                 320

Pro Gly Lys Gly Leu Glu Trp Ile Gly Tyr Ile Asn Pro Ser Arg Gly
                325                 330                 335

Tyr Thr Asn Tyr Asn Gln Lys Val Lys Asp Arg Phe Thr Ile Ser Thr
            340                 345                 350

Asp Lys Ser Lys Ser Thr Ala Phe Leu Gln Met Asp Ser Leu Arg Pro
        355                 360                 365

Glu Asp Thr Gly Val Tyr Phe Cys Ala Arg Tyr Tyr Asp Asp His Tyr
    370                 375                 380

Cys Leu Asp Tyr Trp Gly Gln Gly Thr Thr Leu Thr Val Ser Ser Gly
385                 390                 395                 400

Gly Gly Gly Ser Gly Gly Gly Ser Gly Gly Gly Ser Asp Ile
                405                 410                 415

Gln Met Thr Gln Ser Pro Ser Ser Leu Ser Ala Ser Val Gly Asp Arg
            420                 425                 430

Val Thr Ile Thr Cys Ser Ala Ser Ser Val Ser Tyr Met Asn Trp
        435                 440                 445

Tyr Gln Gln Thr Pro Gly Lys Ala Pro Lys Arg Trp Ile Tyr Asp Thr
    450                 455                 460

Ser Lys Leu Ala Ser Gly Val Pro Ser Arg Phe Ser Gly Ser Gly Ser
465                 470                 475                 480

Gly Thr Asp Tyr Thr Phe Thr Ile Ser Ser Leu Gln Pro Glu Asp Ile
                485                 490                 495

Ala Thr Tyr Tyr Cys Gln Gln Trp Ser Ser Asn Pro Phe Thr Phe Gly
            500                 505                 510

Gln Gly Thr Lys Leu Gln Ile Thr Arg Leu Glu Pro Lys Ser Ala Asp
        515                 520                 525

Lys Thr His Thr Cys Pro Pro Cys Pro Ala Pro Glu Phe Leu Gly Gly
    530                 535                 540

Pro Ser Val Phe Leu Phe Pro Pro Lys Pro Lys Asp Thr Leu Met Ile
545                 550                 555                 560

Ser Arg Thr Pro Glu Val Thr Cys Val Val Val Asp Val Ser Gln Glu
                565                 570                 575

Asp Pro Glu Val Gln Phe Asn Trp Tyr Val Asp Gly Val Glu Val His
            580                 585                 590

Asn Ala Lys Thr Lys Pro Arg Glu Glu Gln Phe Ala Ser Thr Tyr Arg
        595                 600                 605

Val Val Ser Val Leu Thr Val Leu His Gln Asp Trp Leu Asn Gly Lys
    610                 615                 620

Glu Tyr Lys Cys Lys Val Ser Asn Lys Gly Leu Pro Ser Ser Ile Glu
625                 630                 635                 640

Lys Thr Ile Ser Lys Ala Lys Gly Gln Pro Arg Glu Pro Gln Val Tyr
                645                 650                 655

Thr Leu Pro Pro Ser Gln Glu Glu Met Thr Lys Asn Gln Val Ser Leu
            660                 665                 670
```

```
Thr Cys Leu Val Lys Gly Phe Tyr Pro Ser Asp Ile Ala Val Glu Trp
            675                 680                 685

Glu Ser Asn Gly Gln Pro Glu Asn Asn Tyr Lys Thr Thr Pro Pro Val
        690                 695                 700

Leu Asp Ser Asp Gly Ser Phe Phe Leu Tyr Ser Arg Leu Thr Val Asp
705                 710                 715                 720

Lys Ser Arg Trp Gln Glu Gly Asn Val Phe Ser Cys Ser Val Met His
                725                 730                 735

Glu Ala Leu His Asn His Tyr Thr Gln Lys Ser Leu Ser Leu Ser Leu
            740                 745                 750

Gly Lys

<210> SEQ ID NO 106
<211> LENGTH: 735
<212> TYPE: PRT
<213> ORGANISM: Artificial Sequence
<220> FEATURE:
<223> OTHER INFORMATION: anti-PSMA & hOKT3 bispecific Ab amino acid
      sequence (gy1-2) without signal peptide

<400> SEQUENCE: 106

Glu Phe Gln Ser Val Leu Thr Gln Pro Pro Ser Val Ser Gly Ala Pro
1               5                   10                  15

Gly Gln Ser Val Ile Ile Ser Cys Thr Gly Ser Ser Ser Asn Ile Gly
            20                  25                  30

Ala Gly Ser His Val His Trp Tyr Gln Gln Val Pro Gly Thr Ala Pro
        35                  40                  45

Lys Leu Leu Ile Tyr Glu Asn Thr Asn Arg Pro Ser Gly Val Pro Asp
50                  55                  60

Arg Phe Ser Gly Ser Lys Ser Gly Thr Ser Gly Ser Leu Ala Ile Thr
65                  70                  75                  80

Gly Leu Gln Pro Glu Asp Glu Ala Asp Tyr Tyr Cys Ala Thr Trp Asp
                85                  90                  95

Asp Ser Leu Asn Gly Val Ile Phe Gly Gly Gly Thr Lys Ala Thr Val
            100                 105                 110

Leu Gly Gly Ser Ser Arg Ser Ser Ser Gly Gly Gly Gly Ser Gly
        115                 120                 125

Gly Gly Gly Glu Val Gln Leu Val Glu Ser Gly Gly Ala Leu Ala Lys
        130                 135                 140

Pro Gly Gly Ser Leu Arg Leu Ser Cys Ala Ala Ser Gly Phe Thr Leu
145                 150                 155                 160

Ser Gly Tyr Ala Met His Trp Val Arg Gln Ala Pro Gly Lys Gly Leu
                165                 170                 175

Glu Trp Val Ala Val Ile Ser Tyr Asp Gly Ser Asn Lys Tyr Tyr Ala
            180                 185                 190

Asp Ser Val Lys Gly Arg Phe Thr Val Ser Arg Asp Asn Ser Lys Asn
        195                 200                 205

Thr Leu Phe Leu Gln Met Asn Ser Leu Arg Pro Glu Asp Thr Ala Val
        210                 215                 220

Tyr Tyr Cys Ala Lys Gly Leu Thr Trp Gly Leu Gly Asp Asn Asp Ala
225                 230                 235                 240

Leu Asp Ile Trp Gly Pro Gly Thr Thr Val Thr Val Ser Ser Ala Ser
                245                 250                 255

Gly Gly Gly Gly Ser Gln Val Gln Leu Val Gln Ser Gly Gly Gly Val
            260                 265                 270
```

```
Val Gln Pro Gly Arg Ser Leu Arg Leu Ser Cys Lys Ala Ser Gly Tyr
            275                 280                 285

Thr Phe Thr Arg Tyr Thr Met His Trp Val Arg Gln Ala Pro Gly Lys
        290                 295                 300

Gly Leu Glu Trp Ile Gly Tyr Ile Asn Pro Ser Arg Gly Tyr Thr Asn
305                 310                 315                 320

Tyr Asn Gln Lys Val Lys Asp Arg Phe Thr Ile Ser Thr Asp Lys Ser
                325                 330                 335

Lys Ser Thr Ala Phe Leu Gln Met Asp Ser Leu Arg Pro Glu Asp Thr
            340                 345                 350

Gly Val Tyr Phe Cys Ala Arg Tyr Tyr Asp Asp His Tyr Cys Leu Asp
            355                 360                 365

Tyr Trp Gly Gln Gly Thr Thr Leu Thr Val Ser Ser Gly Gly Gly Gly
        370                 375                 380

Ser Gly Gly Gly Gly Ser Gly Gly Gly Ser Asp Ile Gln Met Thr
385                 390                 395                 400

Gln Ser Pro Ser Ser Leu Ser Ala Ser Val Gly Asp Arg Val Thr Ile
                405                 410                 415

Thr Cys Ser Ala Ser Ser Ser Val Ser Tyr Met Asn Trp Tyr Gln Gln
            420                 425                 430

Thr Pro Gly Lys Ala Pro Lys Arg Trp Ile Tyr Asp Thr Ser Lys Leu
        435                 440                 445

Ala Ser Gly Val Pro Ser Arg Phe Ser Gly Ser Gly Ser Gly Thr Asp
450                 455                 460

Tyr Thr Phe Thr Ile Ser Ser Leu Gln Pro Glu Asp Ile Ala Thr Tyr
465                 470                 475                 480

Tyr Cys Gln Gln Trp Ser Ser Asn Pro Phe Thr Phe Gly Gln Gly Thr
                485                 490                 495

Lys Leu Gln Ile Thr Arg Leu Glu Pro Lys Ser Ala Asp Lys Thr His
            500                 505                 510

Thr Cys Pro Pro Cys Pro Ala Pro Glu Phe Leu Gly Gly Pro Ser Val
        515                 520                 525

Phe Leu Phe Pro Pro Lys Pro Lys Asp Thr Leu Met Ile Ser Arg Thr
530                 535                 540

Pro Glu Val Thr Cys Val Val Val Asp Val Ser Gln Glu Asp Pro Glu
545                 550                 555                 560

Val Gln Phe Asn Trp Tyr Val Asp Gly Val Glu Val His Asn Ala Lys
                565                 570                 575

Thr Lys Pro Arg Glu Glu Gln Phe Ala Ser Thr Tyr Arg Val Val Ser
            580                 585                 590

Val Leu Thr Val Leu His Gln Asp Trp Leu Asn Gly Lys Glu Tyr Lys
        595                 600                 605

Cys Lys Val Ser Asn Lys Gly Leu Pro Ser Ser Ile Glu Lys Thr Ile
610                 615                 620

Ser Lys Ala Lys Gly Gln Pro Arg Glu Pro Gln Val Tyr Thr Leu Pro
625                 630                 635                 640

Pro Ser Gln Glu Glu Met Thr Lys Asn Gln Val Ser Leu Thr Cys Leu
                645                 650                 655

Val Lys Gly Phe Tyr Pro Ser Asp Ile Ala Val Glu Trp Glu Ser Asn
            660                 665                 670

Gly Gln Pro Glu Asn Asn Tyr Lys Thr Thr Pro Val Leu Asp Ser
        675                 680                 685
```

```
Asp Gly Ser Phe Phe Leu Tyr Ser Arg Leu Thr Val Asp Lys Ser Arg
    690                 695                 700

Trp Gln Glu Gly Asn Val Phe Ser Cys Ser Val Met His Glu Ala Leu
705                 710                 715                 720

His Asn His Tyr Thr Gln Lys Ser Leu Ser Leu Ser Leu Gly Lys
                725                 730                 735

<210> SEQ ID NO 107
<211> LENGTH: 2265
<212> TYPE: DNA
<213> ORGANISM: Artificial Sequence
<220> FEATURE:
<223> OTHER INFORMATION: anti-PSMA & mOKT3 bispecific Ab nucleic acid
      sequence (gy1-2)

<400> SEQUENCE: 107
```

| | |
|---|---|
| atggagtttg ggctgagctg ggtcttcctg gtggctatct tgaagggtgt ccagtgtgaa | 60 |
| ttccagtctg tgctgactca gccgccctca gtgtctgggg ccccagggca gagtgtcatt | 120 |
| atctcctgca ctgggagcag ctccaacatc ggggcaggtt ctcatgtaca ctggtaccag | 180 |
| caggttccag gaacagcccc caaactcctc atctatgaaa acaccaatcg ccctcaggg | 240 |
| gtccctgacc gattctctgg ctccaagtct ggcacctcag gttccctggc catcactgga | 300 |
| ctccagcctg aggatgaggc tgattattat tgtgcaacat gggatgacag tctgaatggt | 360 |
| gtaatattcg gcgagggac caaggccacc gtcctaggcg atcctctag gtcaagttcc | 420 |
| agcggcggcg gtggcagcgg aggcggcggt gaggtgcagc tggtggagtc tgggggagcc | 480 |
| ctggccaagc tggggggtc cctgagactc tcctgtgcag cctctggatt cacccctcagt | 540 |
| ggctatgcta tgcactgggt ccgccaggct ccaggcaagg gctggagtg gtggcagtt | 600 |
| atatcatatg atggaagcaa taaatactac gcagactccg tgaagggccg attcaccgtc | 660 |
| tccagagaca attccaagaa cacgctgttt ctgcaaatga acagcctgag acctgaggac | 720 |
| acggctgtgt actattgtgc taaaggcctt acctggggac tcggtgacaa tgatgctctc | 780 |
| gatatctggg gccccgggac cacggtcacc gtctcctcag ctagcggtgg aggtggatcc | 840 |
| caggtccagc tgcagcagag cggtgccgaa ctggcccgtc ccggagcaag cgtgaaaatg | 900 |
| tcctgtaaag caagtggcta ccttcacc aggtacacaa tgcactgggt gaagcagagg | 960 |
| ccaggacagg gcctggagtg gatcggctat atcaacccct ctaggggcta cacaaactat | 1020 |
| aatcagaagt tcaaggacaa ggccaccctg accaccgata gtccagctc tacagcttac | 1080 |
| atgcagctgt ccagcctgac cagcgaggac tctgccgtgt actattgcgc tagatactat | 1140 |
| gacgatcatt actgtctgga ttattgggc cagggcacca cactgacagt gtcttccgga | 1200 |
| ggaggaggca gcggaggagg aggctctggc ggcggcggct cccagatcgt gctgacccag | 1260 |
| tccccagcta tcatgtccgc ctcccctgga gagaaggtga ccatgacatg cagcgccagc | 1320 |
| tcttccgtgt cttacatgaa ttggtatcag cagaagtccg gcacaagccc taagagatgg | 1380 |
| atctacgaca cctctaagct ggcctccgga gtgccagctc actttcgcgg ctccggcagc | 1440 |
| ggcacctctt attccctgac aatcagcggc atggaggctg aggatgccgc tacctactat | 1500 |
| tgtcagcagt ggtcatcaaa tcctttcacc ttcggttcag gacaaaaact ggagatcaat | 1560 |
| aggctcgagc caaagagcgc cgacaagacc cacacatgcc cccttgtcc agctcccgag | 1620 |
| tttctgggcg gccatccgt gttcctgttt ccacccaagc ccaaggatac actgatgatc | 1680 |
| agccggaccc cagaggtgac atgcgtggtg gtggacgtgt ctcaggagga ccccgaggtg | 1740 |
| cagttcaact ggtacgtgga cggcgtggag gtgcacaatg ccaagaccaa gcccagggag | 1800 |

-continued

```
gagcagtttg cttctacata ccgggtggtg tccgtgctga ccgtgctgca tcaggattgg   1860
ctgaacggca aggagtataa gtgcaaggtg tccaataagg cctgccttc ttccatcgag    1920 aagacaatca gcaaggctaa gggacagcct cgcgagccac aggtgtacac cctgcctcca   1980
tctcaggagg agatgacaaa gaaccaggtg tccctgacct gtctggtgaa gggcttctat   2040
ccctccgaca tcgctgtgga gtgggagagc aatggccagc ctgagaacaa ttacaagacc   2100 acacccctg tgctggacag cgatggctct ttctttctgt atagcagact gaccgtggat    2160
aagtctcgct ggcaggaggg caacgtgttc cctgttccg tgatgcacga ggcactgcac    2220
aaccactaca ctcagaaatc actgtcactg tccctgggca agtag                   2265
```

<210> SEQ ID NO 108
<211> LENGTH: 754
<212> TYPE: PRT
<213> ORGANISM: Artificial Sequence
<220> FEATURE:
<223> OTHER INFORMATION: anti-PSMA & mOKT3 bispecific Ab amino acid sequence (gy1-2)

<400> SEQUENCE: 108

```
Met Glu Phe Gly Leu Ser Trp Val Phe Leu Val Ala Ile Leu Lys Gly
1               5                   10                  15

Val Gln Cys Glu Phe Gln Ser Val Leu Thr Gln Pro Pro Ser Val Ser
            20                  25                  30

Gly Ala Pro Gly Gln Ser Val Ile Ile Ser Cys Thr Gly Ser Ser Ser
        35                  40                  45

Asn Ile Gly Ala Gly Ser His Val His Trp Tyr Gln Gln Val Pro Gly
    50                  55                  60

Thr Ala Pro Lys Leu Leu Ile Tyr Glu Asn Thr Asn Arg Pro Ser Gly
65                  70                  75                  80

Val Pro Asp Arg Phe Ser Gly Ser Lys Ser Gly Thr Ser Gly Ser Leu
                85                  90                  95

Ala Ile Thr Gly Leu Gln Pro Glu Asp Glu Ala Asp Tyr Tyr Cys Ala
            100                 105                 110

Thr Trp Asp Asp Ser Leu Asn Gly Val Ile Phe Gly Gly Gly Thr Lys
        115                 120                 125

Ala Thr Val Leu Gly Gly Ser Ser Arg Ser Ser Ser Ser Gly Gly Gly
    130                 135                 140

Gly Ser Gly Gly Gly Gly Glu Val Gln Leu Val Glu Ser Gly Gly Ala
145                 150                 155                 160

Leu Ala Lys Pro Gly Gly Ser Leu Arg Leu Ser Cys Ala Ala Ser Gly
                165                 170                 175

Phe Thr Leu Ser Gly Tyr Ala Met His Trp Val Arg Gln Ala Pro Gly
            180                 185                 190

Lys Gly Leu Glu Trp Val Ala Val Ile Ser Tyr Asp Gly Ser Asn Lys
        195                 200                 205

Tyr Tyr Ala Asp Ser Val Lys Gly Arg Phe Thr Val Ser Arg Asp Asn
    210                 215                 220

Ser Lys Asn Thr Leu Phe Leu Gln Met Asn Ser Leu Arg Pro Glu Asp
225                 230                 235                 240

Thr Ala Val Tyr Tyr Cys Ala Lys Gly Leu Thr Trp Gly Leu Gly Asp
                245                 250                 255

Asn Asp Ala Leu Asp Ile Trp Gly Pro Gly Thr Thr Val Thr Val Ser
            260                 265                 270
```

```
Ser Ala Ser Gly Gly Gly Ser Gln Val Gln Leu Gln Ser Gly
            275             280             285

Ala Glu Leu Ala Arg Pro Gly Ala Ser Val Lys Met Ser Cys Lys Ala
        290                 295                 300

Ser Gly Tyr Thr Phe Thr Arg Tyr Thr Met His Trp Val Lys Gln Arg
305                 310                 315                 320

Pro Gly Gln Gly Leu Glu Trp Ile Gly Tyr Ile Asn Pro Ser Arg Gly
                325                 330                 335

Tyr Thr Asn Tyr Asn Gln Lys Phe Lys Asp Lys Ala Thr Leu Thr Thr
            340                 345                 350

Asp Lys Ser Ser Ser Thr Ala Tyr Met Gln Leu Ser Ser Leu Thr Ser
        355                 360                 365

Glu Asp Ser Ala Val Tyr Tyr Cys Ala Arg Tyr Tyr Asp Asp His Tyr
    370                 375                 380

Cys Leu Asp Tyr Trp Gly Gln Gly Thr Thr Leu Thr Val Ser Ser Gly
385                 390                 395                 400

Gly Gly Gly Ser Gly Gly Gly Gly Ser Gly Gly Gly Gly Ser Gln Ile
                405                 410                 415

Val Leu Thr Gln Ser Pro Ala Ile Met Ser Ala Ser Pro Gly Glu Lys
            420                 425                 430

Val Thr Met Thr Cys Ser Ala Ser Ser Ser Val Ser Tyr Met Asn Trp
        435                 440                 445

Tyr Gln Gln Lys Ser Gly Thr Ser Pro Lys Arg Trp Ile Tyr Asp Thr
    450                 455                 460

Ser Lys Leu Ala Ser Gly Val Pro Ala His Phe Arg Gly Ser Gly Ser
465                 470                 475                 480

Gly Thr Ser Tyr Ser Leu Thr Ile Ser Gly Met Glu Ala Glu Asp Ala
                485                 490                 495

Ala Thr Tyr Tyr Cys Gln Gln Trp Ser Ser Asn Pro Phe Thr Phe Gly
            500                 505                 510

Ser Gly Thr Lys Leu Glu Ile Asn Arg Leu Glu Pro Lys Ser Ala Asp
        515                 520                 525

Lys Thr His Thr Cys Pro Pro Cys Pro Ala Pro Glu Phe Leu Gly Gly
    530                 535                 540

Pro Ser Val Phe Leu Phe Pro Pro Lys Pro Lys Asp Thr Leu Met Ile
545                 550                 555                 560

Ser Arg Thr Pro Glu Val Thr Cys Val Val Val Asp Val Ser Gln Glu
                565                 570                 575

Asp Pro Glu Val Gln Phe Asn Trp Tyr Val Asp Gly Val Glu Val His
            580                 585                 590

Asn Ala Lys Thr Lys Pro Arg Glu Glu Gln Phe Ala Ser Thr Tyr Arg
        595                 600                 605

Val Val Ser Val Leu Thr Val Leu His Gln Asp Trp Leu Asn Gly Lys
    610                 615                 620

Glu Tyr Lys Cys Lys Val Ser Asn Lys Gly Leu Pro Ser Ser Ile Glu
625                 630                 635                 640

Lys Thr Ile Ser Lys Ala Lys Gly Gln Pro Arg Glu Pro Gln Val Tyr
                645                 650                 655

Thr Leu Pro Pro Ser Gln Glu Glu Met Thr Lys Asn Gln Val Ser Leu
            660                 665                 670

Thr Cys Leu Val Lys Gly Phe Tyr Pro Ser Asp Ile Ala Val Glu Trp
        675                 680                 685

Glu Ser Asn Gly Gln Pro Glu Asn Asn Tyr Lys Thr Thr Pro Pro Val
```

```
              690             695             700
Leu Asp Ser Asp Gly Ser Phe Phe Leu Tyr Ser Arg Leu Thr Val Asp
705             710             715             720

Lys Ser Arg Trp Gln Glu Gly Asn Val Phe Ser Cys Ser Val Met His
            725             730             735

Glu Ala Leu His Asn His Tyr Thr Gln Lys Ser Leu Ser Leu Ser Leu
            740             745             750

Gly Lys

<210> SEQ ID NO 109
<211> LENGTH: 735
<212> TYPE: PRT
<213> ORGANISM: Artificial Sequence
<220> FEATURE:
<223> OTHER INFORMATION: anti-PSMA & mOKT3 bispecific Ab amino acid
      sequence (gy1-2)

<400> SEQUENCE: 109

Glu Phe Gln Ser Val Leu Thr Gln Pro Pro Ser Val Ser Gly Ala Pro
1               5                   10                  15

Gly Gln Ser Val Ile Ile Ser Cys Thr Gly Ser Ser Ser Asn Ile Gly
            20                  25                  30

Ala Gly Ser His Val His Trp Tyr Gln Gln Val Pro Gly Thr Ala Pro
        35                  40                  45

Lys Leu Leu Ile Tyr Glu Asn Thr Asn Arg Pro Ser Gly Val Pro Asp
50                  55                  60

Arg Phe Ser Gly Ser Lys Ser Gly Thr Ser Gly Ser Leu Ala Ile Thr
65                  70                  75                  80

Gly Leu Gln Pro Glu Asp Glu Ala Asp Tyr Tyr Cys Ala Thr Trp Asp
                85                  90                  95

Asp Ser Leu Asn Gly Val Ile Phe Gly Gly Gly Thr Lys Ala Thr Val
            100                 105                 110

Leu Gly Gly Ser Ser Arg Ser Ser Ser Gly Gly Gly Gly Ser Gly
        115                 120                 125

Gly Gly Gly Glu Val Gln Leu Val Glu Ser Gly Gly Ala Leu Ala Lys
    130                 135                 140

Pro Gly Gly Ser Leu Arg Leu Ser Cys Ala Ala Ser Gly Phe Thr Leu
145                 150                 155                 160

Ser Gly Tyr Ala Met His Trp Val Arg Gln Ala Pro Gly Lys Gly Leu
                165                 170                 175

Glu Trp Val Ala Val Ile Ser Tyr Asp Gly Ser Asn Lys Tyr Tyr Ala
            180                 185                 190

Asp Ser Val Lys Gly Arg Phe Thr Val Ser Arg Asp Asn Ser Lys Asn
        195                 200                 205

Thr Leu Phe Leu Gln Met Asn Ser Leu Arg Pro Glu Asp Thr Ala Val
    210                 215                 220

Tyr Tyr Cys Ala Lys Gly Leu Thr Trp Gly Leu Gly Asp Asn Asp Ala
225                 230                 235                 240

Leu Asp Ile Trp Gly Pro Gly Thr Thr Val Thr Val Ser Ser Ala Ser
                245                 250                 255

Gly Gly Gly Gly Ser Gln Val Gln Leu Gln Ser Gly Ala Glu Leu
            260                 265                 270

Ala Arg Pro Gly Ala Ser Val Lys Met Ser Cys Lys Ala Ser Gly Tyr
        275                 280                 285

Thr Phe Thr Arg Tyr Thr Met His Trp Val Lys Gln Arg Pro Gly Gln
```

```
            290                 295                 300
Gly Leu Glu Trp Ile Gly Tyr Ile Asn Pro Ser Arg Gly Tyr Thr Asn
305                 310                 315                 320

Tyr Asn Gln Lys Phe Lys Asp Lys Ala Thr Leu Thr Thr Asp Lys Ser
                325                 330                 335

Ser Ser Thr Ala Tyr Met Gln Leu Ser Ser Leu Thr Ser Glu Asp Ser
                340                 345                 350

Ala Val Tyr Tyr Cys Ala Arg Tyr Tyr Asp Asp His Tyr Cys Leu Asp
                355                 360                 365

Tyr Trp Gly Gln Gly Thr Thr Leu Thr Val Ser Ser Gly Gly Gly Gly
        370                 375                 380

Ser Gly Gly Gly Gly Ser Gly Gly Gly Gly Ser Gln Ile Val Leu Thr
385                 390                 395                 400

Gln Ser Pro Ala Ile Met Ser Ala Ser Pro Gly Glu Lys Val Thr Met
                405                 410                 415

Thr Cys Ser Ala Ser Ser Ser Val Ser Tyr Met Asn Trp Tyr Gln Gln
                420                 425                 430

Lys Ser Gly Thr Ser Pro Lys Arg Trp Ile Tyr Asp Thr Ser Lys Leu
                435                 440                 445

Ala Ser Gly Val Pro Ala His Phe Arg Gly Ser Gly Ser Gly Thr Ser
450                 455                 460

Tyr Ser Leu Thr Ile Ser Gly Met Glu Ala Glu Asp Ala Ala Thr Tyr
465                 470                 475                 480

Tyr Cys Gln Gln Trp Ser Ser Asn Pro Phe Thr Phe Gly Ser Gly Thr
                485                 490                 495

Lys Leu Glu Ile Asn Arg Leu Glu Pro Lys Ser Ala Asp Lys Thr His
                500                 505                 510

Thr Cys Pro Pro Cys Pro Ala Pro Glu Phe Leu Gly Gly Pro Ser Val
                515                 520                 525

Phe Leu Phe Pro Pro Lys Pro Lys Asp Thr Leu Met Ile Ser Arg Thr
                530                 535                 540

Pro Glu Val Thr Cys Val Val Val Asp Val Ser Gln Glu Asp Pro Glu
545                 550                 555                 560

Val Gln Phe Asn Trp Tyr Val Asp Gly Val Glu Val His Asn Ala Lys
                565                 570                 575

Thr Lys Pro Arg Glu Glu Gln Phe Ala Ser Thr Tyr Arg Val Val Ser
                580                 585                 590

Val Leu Thr Val Leu His Gln Asp Trp Leu Asn Gly Lys Glu Tyr Lys
                595                 600                 605

Cys Lys Val Ser Asn Lys Gly Leu Pro Ser Ser Ile Glu Lys Thr Ile
        610                 615                 620

Ser Lys Ala Lys Gly Gln Pro Arg Glu Pro Gln Val Tyr Thr Leu Pro
625                 630                 635                 640

Pro Ser Gln Glu Glu Met Thr Lys Asn Gln Val Ser Leu Thr Cys Leu
                645                 650                 655

Val Lys Gly Phe Tyr Pro Ser Asp Ile Ala Val Glu Trp Glu Ser Asn
                660                 665                 670

Gly Gln Pro Glu Asn Asn Tyr Lys Thr Thr Pro Pro Val Leu Asp Ser
                675                 680                 685

Asp Gly Ser Phe Phe Leu Tyr Ser Arg Leu Thr Val Asp Lys Ser Arg
        690                 695                 700

Trp Gln Glu Gly Asn Val Phe Ser Cys Ser Val Met His Glu Ala Leu
705                 710                 715                 720
```

His Asn His Tyr Thr Gln Lys Ser Leu Ser Leu Ser Leu Gly Lys
            725                 730                 735

<210> SEQ ID NO 110
<211> LENGTH: 1184
<212> TYPE: DNA
<213> ORGANISM: Homo sapiens

<400> SEQUENCE: 110
cgtgaggctc cggtgcccgt cagtgggcag agcgcacatc gcccacagtc cccgagaagt      60
tgggggggagg ggtcggcaat tgaaccggtg cctagagaag gtggcgcggg gtaaactggg    120
aaagtgatgt cgtgtactgg ctccgccttt ttcccgaggg tgggggagaa ccgtatataa    180
gtgcagtagt cgccgtgaac gttctttttc gcaacgggtt tgccgccaga acacaggtaa    240
gtgccgtgtg tggttcccgc gggcctggcc tctttacggg ttatggccct tgcgtgcctt    300
gaattacttc cacctggctg cagtacgtga ttcttgatcc cgagcttcgg gttggaagtg    360
ggtgggagag ttcgaggcct tgcgcttaag gagccccttc gcctcgtgct tgagttgagg    420
cctggcctgg gcgctgggggc cgccgcgtgc gaatctggtg gcaccttcgc gcctgtctcg    480
ctgctttcga taagtctcta gccatttaaa attttgatg acctgctgcg acgctttttt     540
tctggcaaga tagtcttgta aatgcgggcc aagatctgca cactggtatt tcggtttttg    600
gggccgcggg cggcgacggg gcccgtgcgt cccagcgcac atgttcggcg aggcggggcc    660
tgcgagcgcg gccaccgaga atcggacggg ggtagtctca agctggccgg cctgctctgg    720
tgcctggcct cgccgccgcg tgtatcgccc gccctgggc ggcaaggctg gcccggtcgg     780
caccagttgc gtgagcggaa agatggccgc ttcccggccc tgctgcaggg agctcaaaat    840
ggaggacgcg gcgctcggga gagcgggcgg gtgagtcacc cacacaaagg aaaagggcct    900
ttccgtcctc agccgtcgct tcatgtgact ccacggagta ccgggcgccg tccaggcacc    960
tcgattagtt ctcgagcttt tggagtacgt cgtctttagg ttgggggggag gggttttatg   1020
cgatggagtt tccccacact gagtgggtgg agactgaagt taggccagct tggcacttga   1080
tgtaattctc cttggaattt gccctttttg agtttggatc ttggttcatt ctcaagcctc   1140
agacagtggt tcaaagtttt tttcttccat ttcaggtgtc gtga                    1184

<210> SEQ ID NO 111
<211> LENGTH: 21
<212> TYPE: DNA
<213> ORGANISM: Artificial Sequence
<220> FEATURE:
<223> OTHER INFORMATION: primer

<400> SEQUENCE: 111
gactacaagg acgacgatga c                                                21

<210> SEQ ID NO 112
<211> LENGTH: 25
<212> TYPE: DNA
<213> ORGANISM: Artificial Sequence
<220> FEATURE:
<223> OTHER INFORMATION: primer

<400> SEQUENCE: 112
agtagaatca agacctagta gaggg                                            25

<210> SEQ ID NO 113
<211> LENGTH: 19

```
<212> TYPE: DNA
<213> ORGANISM: Artificial Sequence
<220> FEATURE:
<223> OTHER INFORMATION: primer

<400> SEQUENCE: 113
ctattgccag cattgctgc                                                  19

<210> SEQ ID NO 114
<211> LENGTH: 20
<212> TYPE: DNA
<213> ORGANISM: Artificial Sequence
<220> FEATURE:
<223> OTHER INFORMATION: primer

<400> SEQUENCE: 114
atagggacct agacttcagg                                                 20

<210> SEQ ID NO 115
<211> LENGTH: 20
<212> TYPE: DNA
<213> ORGANISM: Artificial Sequence
<220> FEATURE:
<223> OTHER INFORMATION: primer

<400> SEQUENCE: 115
ccttctactc ctcctacacc                                                 20

<210> SEQ ID NO 116
<211> LENGTH: 19
<212> TYPE: DNA
<213> ORGANISM: Artificial Sequence
<220> FEATURE:
<223> OTHER INFORMATION: primer

<400> SEQUENCE: 116
ggagggcgtg aatgtaagc                                                  19
```